(12) United States Patent
Jakobsen et al.

(10) Patent No.: US 9,279,122 B2
(45) Date of Patent: Mar. 8, 2016

(54) T CELL RECEPTOR DISPLAY

(71) Applicants: ADAPTIMMUNE LIMITED, Oxford (GB); IMMUNOCORE LIMITED, Abingdon, Oxfordshire (GB)

(72) Inventors: Bent Karsten Jakobsen, Oxfordshire (GB); Peter Eamon Molloy, Oxfordshire (GB); Yi Li, Oxfordshire (GB)

(73) Assignees: ADAPTIMMUNE LIMITED, Oxford (GB); IMMUNOCORE LIMITED, Oxford (GB)

( * ) Notice: Subject to any disclaimer, the term of this patent is extended or adjusted under 35 U.S.C. 154(b) by 0 days.

(21) Appl. No.: 14/248,919

(22) Filed: Apr. 9, 2014

(65) Prior Publication Data
US 2014/0371085 A1 Dec. 18, 2014

Related U.S. Application Data

(62) Division of application No. 12/603,255, filed on Oct. 21, 2009, now Pat. No. 8,741,814, which is a division of application No. 10/532,879, filed as application No. PCT/GB03/04636 on Oct. 30, 2003, now abandoned.

(60) Provisional application No. 60/463,046, filed on Apr. 16, 2003.

(30) Foreign Application Priority Data

| Nov. 9, 2002 | (GB) | 0226227.7 |
| Jan. 25, 2003 | (GB) | 0301814.0 |
| Feb. 22, 2003 | (GB) | 0304067.2 |
| May 16, 2003 | (GB) | 0311397.4 |
| Jul. 11, 2003 | (GB) | 0316356.5 |

(51) Int. Cl.
C40B 40/10 (2006.01)
C12N 15/10 (2006.01)
(Continued)

(52) U.S. Cl.
CPC ........ *C12N 15/1037* (2013.01); *C07K 14/7051* (2013.01); *C12N 7/00* (2013.01);
(Continued)

(58) Field of Classification Search
None
See application file for complete search history.

(56) References Cited

U.S. PATENT DOCUMENTS

2002/0058253 A1 5/2002 Kranz et al.
2002/0142389 A1 10/2002 Jakobsen et al.

FOREIGN PATENT DOCUMENTS

EP 1 118 661 A 7/2001
WO WO 98 39482 A 9/1998
(Continued)

OTHER PUBLICATIONS

Weidanz et al. "Display of Functional Alphabeta Single-Chain T-Cell Receptor Molecules on the Surface of Bacteriophage", Journal of Immunological Methods, vol. 221, No. 1-2, Dec. 1998, pp. 59-76, XP004153560.
(Continued)

*Primary Examiner* — Christian Boesen
(74) *Attorney, Agent, or Firm* — Vedder Price P.C.; Thomas J. Kowalski; Deborah L. Lu

(57) ABSTRACT

A proteinaceous particle, for example a bacteriophage, ribosome or cell, displaying on its surface a T-cell receptor (TCR). The displayed TCR is preferably a heterodimer having a non-native disulfide bond between constant domain residues. Such display particles may be used for the creation of diverse TCR libraries for the identification of high affinity TCRs. Several high affinities are disclosed.

5 Claims, 55 Drawing Sheets

Schematic diagram of the A6 scTCR-C-Kappa ribosome display construct

(51) Int. Cl.
*C07K 14/725* (2006.01)
*C12N 7/00* (2006.01)
*C40B 40/02* (2006.01)
*A61K 38/00* (2006.01)

(52) U.S. Cl.
CPC ........ *C12N 15/1041* (2013.01); *C12N 15/1058* (2013.01); *C40B 40/02* (2013.01); *A61K 38/00* (2013.01); *C12N 2795/18121* (2013.01); *C12N 2795/18143* (2013.01); *C40B 40/10* (2013.01)

(56) References Cited

FOREIGN PATENT DOCUMENTS

| WO | WO 98 48008 A | 10/1998 |
|----|---------------|---------|
| WO | WO 99 18129 A | 4/1999 |
| WO | WO 99 36569 A | 7/1999 |
| WO | WO 00 24782 A | 5/2000 |
| WO | WO 01 62908 A | 8/2001 |
| WO | WO 01 92291 A | 12/2001 |
| WO | WO 02 092780 A | 11/2002 |
| WO | WO 03 020763 A | 3/2003 |

OTHER PUBLICATIONS

Reiter et al. "Construction of a Functional Disulfide-Stabilized TCR FV Indicates that Antibody and TCR FV Frameworks are Very Similar in Structure", Immunity, vol. 2, No. 3, Mar. 1995, p. 281-287, XP0009004075.

Boulter et al. "Stable soluble T-cell receptor molecules for crystallization and therapeutics." Protein Engineering, Sep. 2003, vol. 16, No. 9, Sep. 2003, pp. 707-711, XP002275339.

Holler et al. "CD8-T Cell Transfectants that Express a High Affinity T Cell Receptor Exhibit Enhanced Peptide-Dependent Activation", Journal of Experimental Medicine, vol. 194, No. 8, Oct. 15, 2001, pp. 1043-1052, XP002287143.

Saito et al. "In vivo selection of T-Cell Receptor Junctional Region Sequences by HLA-A2 Human T-Cell Lymphotropic Virus Type 1 Tax11-19 Peptide Complexes", Journal of Virology, vol. 75, No. 2, Jan. 2001, pp. 1065-1071, XP002287144.

Utz et al. "Analysis of the T-Cell Receptor Repertoire of Human T-Cell Leukemia Virus Type 1 (HTLV-1) tax-specific CD8+cytotoxic T Lymphocytes from Patients with HTLV-1-Associated Disease: Evidence for Oligoclonal Expansion", Journal of Virology, vol. 70, No. 2, 1996, pp. 843-851, XP002287145.

Hausmann et al. "Peptide Recognition by Two HLA-A2/Tax11-19-Specific T Cell Clones in Relationship to Their MHC/Peptide/TCR Crystal Structures", Journal of Immunology. May 1, 1999, vol. 162, No. 9, May 1, 1999, pp. 5389-5397, XP002287146.

Xu et al., "Diversity in the CDR3 Region of $V_H$ is Sufficient for Most Antibody Specificities", Immunity, 13, 37-45, Jul. 2000.

LeFranc & LeFranc, *The T Cell Receptor Facts Book*, pp. 76-78 and pp. 188-191, Academic Press, NY, 2001.

Chang et al., "A general method for facilitating heterodimeric pairing between two proteins: application to expression of alpha and beta T-cell receptor extracellular segments," *Proc. Natl. Acad. Sci. USA* 91, 11408-22, 1994.

Pecorari et al., "Folding, heterodimeric association and specific peptide recognition of a murine alphabeta T-cell receptor expressed in *Escherichia coli*," *J. Mol. Biol. 285*, 1831-43, 1999.

Li et al., Structural mutations in the constant region of the T-cell antigen receptor (TCR) β chain and their effect on TCRα and β chain interaction; Immunology, 1996, 88, 524-30.

Verhaert et al., "Processing and functional display of the 86 kDa heterodimeric penicillin G acylase on the surface of phage fd", J. Biochem 342, pp. 415-422, 1999.

Figure 1A

Atgcagaaggaagtggagcagaactctggacccctcagtgttccagagggagccatt
gcctctctcaactgcacttacagtgaccgaggttcccagtccttcttctggtacaga
caatattctgggaaaagccctgagttgataatgtccatactccaatggtgacaaa
gaagatggaaggtttacagcacagctcaataaagccagccagtatgtttctctgctc
atcagagactccagcccagtgattcagccacctacctctgtgccgttacaactgac
agctgggggaaattgcagtttggagcagggacccaggttgtggtcacccagatatc
cagaaccctgaccctgccgtgtaccagctgagagactctaaatccagtgacaagtct
gtctgcctattcaccgattttgattctcaaacaaatgtgtcacaaagtaaggattct
gatgtgtatatcacagacaaagtgtgctagacatgaggtctatggacttcaagagc
aacagtgctgtggcctggagcaacaaatctgactttgcatgtgcaaacgccttcaac
aacagcattattccagaagacaccttcttccccagcccagaaagttcctaa (SEQ ID 147)

Figure 1B atgaacgctggtgtcactcagaccccaaaattccaggtcctgaagacaggacagagc
atgacactgcagtgtgcccaggatatgaaccatgaatacatgtcctggtatcgacaa
gacccaggcatggggctgaggctgattcattactcagttggtgctggtatcactgac
caaggagaagtccccaatggctacaatgtctccagatcaaccacagaggatttcccg
ctcaggctgctgtcggctgctccctcccagacatctgtgtacttctgtgccagcagg
ccgggactagcgggagggcgaccagagcagtactcgggccgggcaccaggctcacg
gtcacagaggacctgaaaaacgtgttcccacccgaggtcgctgtgtttgagccatca
gaagcagagatctcccacacccaaaaggccacactggtgtgcctggccacaggcttc
taccccgaccacgtggagctgagctggtgggtgaatgggaaggaggtgcacagtggg
gtctgcacagacccgcagcccctcaaggagcagcccgccctcaatgactccagatac
gctctgagcagccgcctgagggtctcggccaccttctggcaggaccccgcaaccac
ttccgctgtcaagtccagttctacgggctctcggagaatgacgagtggacccaggat
agggccaaacccgtcacccagatcgtcagcgccgaggcctggggtagagcagactaa (SEQ ID 148)

Figure 2A

MQ
KEVEQNSGPL SVPEGAIASL NCTYSDRGSQ SFFWYRQYSG KSPELIMSIY
SNGDKEDGRF TAQLNKASQY VSLLIRDSQP SDSATYLCAV TTDSWGKLQF
GAGTQVVVTP DIQNPDPAVY QLRDSKSSDK SVCLFTDFDS QINVSQSKDS
DVYITDKCVL DMRSMDFKSN SAVAWSNKSD PACANAFNNS IIPEDTFFPS
PESS*

(SEQ ID 149)

Figure 2B

M
NAGVTQTPKF QVLKTGQSMT LQCAQDMNHE YMSWYRQDPG MGLRLIHYSV
GAGITDQGEV PNGYNVSRST TEDFPLRLLS AAPSQTSVYF CASRPGLAGG
RPEQYFGPGT RLTVTEDLKN VFPPEVAVFE PSEAEISHTQ KATLVCLATG
FYPDHVELSW WVNGKEVHSG VCTDPQPLKE QPALNDSRYA LSSRLRVSAT
FWQDPRNHFR CQVQFYGLSE NDEWTQDRAK PVTQIVSAEA WGRAD*
(SEQ ID 150)

Figure 4

```
   1 gttaactacg tcaggtggca cttttcgggg aaatgtgcgc ggaacccta tttgtttatt
  61 tttctaaata cattcaaata tgtatccgct catgagacaa taaccctgat aaatgcttca
 121 ataatattga aaaaggaaga gtatgagtat tcaacatttc cgtgtcgccc ttattccctt
 181 ttttgcggca ttttgccttc ctgttttgc tcacccagaa acgctggtga aagtaaaaga
 241 tgctgaagat cagttgggtg cacgagtggg ttacatcgaa ctggatctca acagcggtaa
 301 gatccttgag agttttcgcc ccgaagaacg ttctccaatg atgagcactt taaagttct
 361 gctatgtggc gcggtattat cccgtgttga cgccgggcaa gagcaactcg gtcgccgcat
 421 acactattct cagaatgact tggttgagta ctcaccagtc acagaaaagc atcttacgga
 481 tggcatgaca gtaagagaat tatgcagtgc tgccataacc atgagtgata acactgcggc
 541 caacttactt ctgacaacga tcggaggacc gaaggagcta accgcttttt tgcacaacat
 601 gggggatcat gtaactcgcc ttgatcgttg ggaaccggag ctgaatgaag ccataccaaa
 661 cgacgagcgt gacaccacga tgcctgtagc aatggcaaca acgttgcgca aactattaac
 721 tggcgaacta cttactctag cttcccggca acaattaata gactggatgg aggcggataa
 781 agttgcagga ccacttctgc gctcggccct tccggctggc tggtttattg ctgataaatc
 841 tggagccggt gagcgtgggt ctcgcggtat cattgcagca ctggggccag atggtaagcc
 901 ctcccgtatc gtagttatct acacgacggg gagtcaggca actatggatg aacgaaatag
 961 acagatcgct gagataggtg cctcactgat taagcattgg taactgtcag accaagttta
1021 ctcatatata cttagattg atttaccccg gttgataatc agaaaagccc caaaaacagg
1081 aagattgtat aagcaaatat ttaaattgta aacgttaata ttttgttaaa attcgcgtta
1141 aatttttgtt aaatcagctc attttttaac caataggccg aaatcggcaa aatcccttat
1201 aaatcaaaag aatagcccga gatagggttg agtgttgttc cagtttggaa caagagtcca
1261 ctattaaaga acgtggactc caacgtcaaa gggcgaaaaa ccgtctatca gggcgatggc
1321 ccactacgtg aaccatcacc caaatcaagt tttttggggt cgaggtgccg taaagcacta
1381 aatcggaacc ctaaagggag cccccgattt agagcttgac ggggaaagcg aacgtggcga
1441 gaaggaagg gaagaaagcg aaaggagcgg gcgctagggc gctggcaagt gtagcggtca
1501 cgctgcgcgt aaccaccaca cccgccgcgc ttaatgcgcc gctacagggc gcgtaaaagg
1561 atctaggtga agatccttt tgataatctc atgaccaaaa tcccttaacg tgagttttcg
1621 ttccactgag cgtcagaccc cgtagaaaag atcaaaggat cttcttgaga tcctttttt
1681 ctgcgcgtaa tctgctgctt gcaaacaaaa aaaccaccgc taccagcggt ggtttgtttg
1741 ccggatcaag agctaccaac tcttttccg aaggtaactg gcttcagcag agcgcagata
1801 ccaaatactg ttcttctagt gtagccgtag ttaggccacc acttcaagaa ctctgtagca
1861 ccgcctacat acctcgctct gctaatcctg ttaccagtgg ctgctgccag tggcgataag
1921 tcgtgtctta ccgggttgga ctcaagacga tagttaccgg ataaggcgca gcggtcgggc
1981 tgaacggggg gttcgtgcac acagcccagc ttggagcgaa cgacctacac cgaactgaga
2041 tacctacagc gtgagctatg agaaagcgcc acgcttcccg aagggagaaa ggcggacagg
2101 tatccggtaa cggcagggt cggaacagga gagcgcacga gggagcttcc agggggaaac
2161 gcctggtatc tttatagtcc tgtcgggttt cgccacctct gacttgagcg tcgatttttg
2221 tgatgctcgt caggggggcg gagcctatgg aaaaacgcca gcaacgcggc ctttttacgg
2281 ttcctggcct tttgctggcc ttttgctcac atgtaatgtg agttagctca ctcattaggc
2341 accccaggct ttacacttta tgcttccggc tcgtatgttg tgtggaattg tgagcggata
2401 acaatttcac acaggaaaca gctatgacca tgattacgcc aagctacgta taataatatt
2461 ctatttcaag gagacagtca taatgaaata cctattgcct acggcagccg ctggattgtt
2521 attactcgcg gcccagccgg ccatggccca gaaggaagtg gagcagaact ctggacccct
2581 cagtgttcca gagggagcca ttgcctctct caactgcact tacagtgacc gaggttccca
2641 gtccttcttc tggtacagac aatattctgg gaaagccct gagttgataa tgtccatata
2701 ctccaatggt gacaaagaag atggaaggtt tacagcacag ctcaataaag ccagccagta
2761 tgtttctctg ctcatcagag actcccagcc cagtgattca gccacctacc tctgtgccgt
2821 tacaactgac agctggggga aattgcagtt ggagcaggg acccaggttg tggtcacccc
2881 agatatccag aaccctgacc ctgccgtgta ccagctgaga gactctaaat ccagtgacaa
2941 gtctgtctgc ctattcaccg attttgattc tcaaacaaat gtgtcacaaa gtaaggattc
3001 tgatgtgtat atcacagaca aatgtgtgct agacatgagg tctatggact tcaagagcaa
3061 cagtgctgtg gcctggagca acaaatctga ctttgcatgt gcaaacgcct tcaacaacag
3121 cattattcca gaagacacct tcttccccag cccagaaagt tcctaataac ctaggttaat
3181 taagaattct ttaagaagga gatatacata tgaaaaaatt attattcgca attcctttag
3241 ttgttccttt ctattctcac agcgcgcagg ctggtgtcac tcagccccca aaattccagg
3301 tcctgaagac aggacagagc atgacactgc agtgtgccca ggatatgaac catgaataca
3361 tgtcctggta tcgacaagac ccaggcatgg ggctgaggct gattcattac tcagttggtg
```

Figure 4 (continued)

```
3421 ctggtatcac tgaccaagga gaagtcccca atggctacaa tgtctccaga tcaaccacag
3481 aggatttccc gctcaggctg ctgtcggctg ctccctccca gacatctgtg tacttctgtg
3541 ccagcaggcc gggactagcg ggagggcgac cagagcagta cttcgggccg ggcaccaggc
3601 tcacggtcac agaggacctg aaaaacgtgt tcccacccga ggtcgctgtg tttgagccat
3661 cagaagcaga gatctcccac acccaaaagg ccacactggt gtgcctggcc acaggcttct
3721 accccgacca cgtggagctg agctggtggg tgaatgggaa ggaggtgcac agtggggtct
3781 gcacagaccc gcagcccctc aaggagcagc ccgccctcaa tgactccaga tacgctctga
3841 gcagccgcct gagggtctcg gccaccttct ggcaggaccc ccgcaaccac ttccgctgtc
3901 aagtccagtt ctacgggctc tcggagaatg acgagtggac ccaggatagg gccaaacccg
3961 tcacccagat cgtcagcgcc gaggcctggg gtagagcaga cgcggccgca tctagacatc
4021 atcaccatca tcactagact gttgaaagtt gtttagcaaa accccataca gaaaattcat
4081 ttactaacgt ctggaaagac gacaaaactt tagatcgtta cgctaactat gagggttgtc
4141 tgtggaatgc tacaggcgtt gtagtttgta ctggtgacga aactcagtgt tacggtacat
4201 gggttcctat tgggcttgct atccctgaaa atgagggtgg tggctctgag ggtggcggtt
4261 ctgagggtgg cggttctgag ggtggcggta ctaaacctcc tgagtacggt gatacaccta
4321 ttccgggcta tacttatatc aaccctctcg acggcactta tccgcctggt actgagcaaa
4381 accccgctaa tcctaatcct tctcttgagg agtctcagcc tcttaatact ttcatgtttc
4441 agaataatag gttccgaaat aggcaggggg cattaactgt ttatacgggc actgttactc
4501 aaggcactga ccccgttaaa acttattacc agtacactcc tgtatcatca aaagccatgt
4561 atgacgctta ctggaacggt aaattcagag actgcgcttt ccattctggc tttaatgagg
4621 atccattcgt ttgtgaatat caaggccaat cgtctgacct gcctcaacct cctgtcaatg
4681 ctggcggcgg ctctggtggt ggttctggtg gcggctctga gggtggtggc tctgagggtg
4741 gcggttctga gggtggcggc tctgagggag gcggttccgg tggtggctct ggttccggtg
4801 attttgatta tgaaaagatg gcaaacgcta ataaggggc tatgaccgaa aatgccgatg
4861 aaaacgcgct acagtctgac gctaaaggca aacttgattc tgtcgctact gattacggtg
4921 ctgctatcga tggtttcatt ggtgacgttt ccggccttgc taatggtaat ggtgctactg
4981 gtgattttgc tggctctaat tcccaaatgg ctcaagtcgg tgacggtgat aattcacctt
5041 taatgaataa tttccgtcaa tatttacctt ccctccctca atcggttgaa tgtcgccctt
5101 ttgtctttag cgctggtaaa ccatatgaat tttctattga ttgtgacaaa ataaacttat
5161 tccgtggtgt cttttgcgtt cttttatatg ttgccacctt tatgtatgta ttttctacgt
5221 ttgctaacat actgcgtaat aaggagtctt aataaggtac cctctagtca aggcctatag
5281 tgagtcgtat tacggactgg ccgtcgtttt acaacgtcgt gactgggaaa accctggcgt
5341 tacccaactt aatcgccttg cagcacatcc ccctttcgcc agctggcgta atagcgaaga
5401 ggcccgcacc gatcgccctt cccaacagtt gcgcagcctg aatggcgaat ggcgcttcgc
5461 ttggtaataa agcccgcttc ggcgggcttt ttttt
```

(SEQ ID 151)

Schematic diagram of the A6 scTCR-C-Kappa ribosome display construct

Figure 7B

```
agctgcagct aatacgactc actataggaa caggccacca tgggccagaa
ggaagtggag cagaactctg gacccctcag tgttccagag ggagccattg
cctctctcaa ctgcacttac agtgaccgag gttcccagtc cttcttctgg
tacagacaat attctggaa aagccctgag ttgataatgt ccatatactc
caatggtgac aaagaagatg gaaggtttac agcacagctc aataaagcca
gccagtatgt ttctctgctc atcagagact cccagcccag tgattcagcc
acctacctct gtgccgttac aactgacagc tgggggaaat tgcagtttgg
agcagggacc caggttgtgg tcaccggtgg aggcggttca ggcggaggtg
gatccggcgg tggcgggtcg aacgctggtg tcactcagac cccaaaattc
caggtcctga agacaggaca gagcatgaca ctgcagtgtg cccaggatat
gaaccatgaa tacatgtcct ggtatcgaca agacccaggc atggggctga
ggctgattca ttactcagtt ggtgctggta tcactgacca aggagaagtc
cccaatggct acaatgtctc cagatcaacc acagaggatt tcccgctcag
gctgctgtcg gctgctccct cccagacatc tgtgtacttc tgtgccagca
ggcgggact agcgggaggg cgaccagagc agtacttcgg gccgggcacc
aggctcacgg tcacagagga cctgaaaaac gtgttccacc ccgaggtcgc
tgtgtttgag ccatcagaag cagagatctc ccacacccaa aaggccacac
tggtgtgcct ggccacaggc ttctacccg accacgtgga gctgagctgg
tgggtgaatg ggaaggaggt gcacagtggg gtcagcacag acccgcagcc
cctcaaggag cagcccgccc tcaatgactc cagatacgct ctgagcagcc
gcctgagggt ctcggccacc ttctggcagg accccgcaa ccacttccgc
tgtcaagtcc agttctacgg gctctcggag aatgacgagt ggacccagga
tagggccaaa cccgtcaccc agatcgtcag cgccgaggcc tggggtagag
cagacggtgg aggcggttca ctcagcagca ccctgacgct gagcaaagca
gactacgaga aacacaaagt ctacgcctgc gaagtcaccc atcagggcct
gagttcgccc gtcacaaaga gcttcaaccg cggagagtca taagaattct
cag
```

(SEQ ID 152)

(SEQ ID: 153)

Figure 8 pUC19-T7 sequence

```
   1 ctgctttccc ggagcactat gcggataaaa atatccaatt acagtactat tattaccaaa gaatctgcag
  71 tccaccgtga aaagcccctt tacacgcgcc ttggggataa acaaataaaa agatttatgt aagtttatac
 141 ataggcgagt actctgttat tggactatt tacgaagtta ttataacttt ttccttctca tactcataag
 211 ttgtaaaggc acagcgggaa taaggaaaa aacgccgtaa aacggaagga caaaaacgag tgggtctttg
 281 cgaccacttt catttctac gacttctagt caaccacgt gctcaccaa tgtagcttga cctagagttg
 351 tcgccattct aggaactctc aaaagcgggg cttcttgca aaggttacta ctcgtgaaaa tttcaagacg
 421 atacacgcg ccataatagg gcataactgc ggccgttct cgttgagcca gcggcgtatg tgataagagt
 491 cttactgaac caactcatga gtggtcagtg tcttttcgta gaatgcctac cgtactgtca ttctcttaat
 561 acgtcacgac ggtattggta ctcactattg tgagcggt tgaatgaaga ctgttgctag cctcctggct
 631 tcctcgattg gcgaaaaaac gtgttgtacc ccctagtaca ttgagcggaa ctagcaaccc ttggcctga
 701 cttacttcgg tatggttgc tgctcgcact gtggtgctac ggacatcgtt acgttgttg caacgcgtt
 771 gataattgac cgcttgatga atgagatcga agggcgttg ttaattatct gcctaccctc cgcctattc
 841 aacgtcctgg tgaagacgcg agccggaag gcgaccgac caaataacga ctatttagac ctcggcaact
 911 cgcaccagaa gcgccatagt aacgtcgtga cccggtcta ccattcggga gggcatagca tcaatagatg
 981 tgctgcccct cagtccgttg ataactactt gctttatctg tctagcgact ctatccacgg agtgactaat
1051 tcgtaaccat tgacagtctg gttcaaatga gtatatatga aatctaacta aatttgaag taaaaattaa
1121 attttcctag atccacttct aggaaaaact attagagtac tggttttagg gaatttgcact caaaagcaag
1191 gtgactcgca gtctggggca tctttctag tttcctagaa gaactctagg aaaaaaagac gcgcattaga
1261 cgacgaacgt ttgttttttt ggtggcgatg gtcgccacca aacaaacgc ctagttctcg atggttgaga
1331 aaaaggcttc cattgaccga agtcgtctcg cgtctatggt ttatgacagg aagatcacat cggcatcaat
1401 ccggtggtga agttcttgag acatcgtggc ggatgtatgg agcgagacga ttaggacaat ggtcacgac
1471 gcaggtcacc gctattcga acagaatggc ccaacctgag ttctgctatc aatggcctat tccgcgtcgc
1541 cagccgact tgcccccaa gcacgtgtgt cgggtcgaac ctgcttgct ggatgtggct tgactctatg
1611 gatgtcgcac tcgatactct ttgcgggtgc gaagggcttc cctctttccg cctgtccata ggccattcgc
1681 cgtcccagcc ttgtcctctc gcgtgctccc tgaaggtcc ccctttgcgg accatagaaa tatcaggaca
1751 gccaaaagcg gtggagacg aactcgcagc taaaaacact acgagcagtc ccccgcctc ggatacctt
1821 ttgcgtcgt tgcgccggaa aaatgccaag gaccggaaaa cgaccggaaa acgagtgtac aagaaaggac
1891 gcaatagggg actaagacac ctattggcat aatggcggaa actcactcga ctatggcgag cggcgtcggc
1961 ttgctggctc gcgtcgtca gtcactcgct cctgcctt ctgcggggtt atgcgttggg cggagagggg
2031 cgcgcaaccg gctaagtaat tacgtcgacc gtgctgtcca aagggctgac ctttcgcccg tcactcgcgt
2101 tgcgttaatt acactcaatc gagtgagtaa tccgtggggt ccgaaatgtg aaatacgaag gccgagcata
2171 caacacacct taacactcgc ctattgttaa agtgtgtcct ttgtcgatac tggtactaat gcggttcgac
2241 gtcgattatg ctgagtgata tccttgtccg gtggtaccct aggggcccat ggctcgagct taagtaccg
2311 gcagcaaaat gttgcagcac tgaccctttt gggaccgcaa tggttgaat tagcgaacg tcgtgtaggg
2381 ggaaagcggt cgaccgcatt atcgcttctc cggggcgtcg tagcgggaag ggttgtcaac gcgtcggact
2451 taccgttac cgcggactac gccataaaag aggaatgcgt agacacgcca taaagtgtgg cgtataccac
2521 gtgagagtca tgttagacga gactacggcg tatcaattcg gtcgggctg tgggcggttg tgggcgactg
2591 cgcgggactg cccgaacaga cgagggcgt aggcgaatgt ctgttcgaca ctggcagagg ccctcgacgt
2661 acacagtctc caaaagtggc agtagtggct ttgcgcgct
```

(SEQ ID 154)

A6 scTCR-C-kappa cloned into pUC19-T7

```
   1 ccatgggcca gaaggaagtg gagcagaact ctggacccct cagtgttcca
  51 gagggagcca ttgcctctct caactgcact tacagtgacc gaggttcca
 101 gtccttcttc tggtacagac aatattctgg gaaaagccct gagttgataa
 151 tgtccatata ctccaatggt gacaaagaag atggaaggtt tacagcacag
 201 ctcaataaag ccagccagta tgtttctctg ctcatcagag actccagcc
 251 cagtgattca gccacctacc tctgtgccgt tacaactgac agctggggga
 301 aattgcagtt tggagcaggg acccaggttg tggtcaccgg tggaggcggt
 351 tcaggcggag gtggatcggg cggtggcggg tgaaacgctg gtgtcactca
 401 gaccccaaaa ttccaggtcc tgaagacagg acagagcatg acactgcagt
 451 gtgcccagga tatgaaccat gaatacatgt cctggtatcg acaagaccca
 501 ggcatggggc tgaggctgat tcattactca gttggtgctg gtatcactga
 551 ccaaggagaa gtccccaatg gctacaatgt ctccagatca accacagagg
 601 atttcccgct caggctgctg tcggctgctc cctccagac atctgtgtac
 651 ttctgtgcca gcagccggg actagcggga gggcgaccag agcagtactt
 701 cgggccggga accaggctca cggtcacaga ggacctgaaa aacgtgttcc
 751 caccccgaggt cgctgtgttt gagccatcag aagcagagat ctcccacacc
 801 caaaaggcca cactggtgtg cctggccaca ggcttctacc ccgaccacgt
 851 ggagctgagc tggtgggtga atgggaagga ggtgcacagt ggggtcagca
 901 cagacccgca gcccctcaag gagcagcccg ccctcaatga ctccagatac
 951 gctctgagca gccgcctgag ggtctcggcc accttctggc aggacccg
1001 caaccacttc cgctgtcaag tccagttcta cgggctctcg gagaatgacg
1051 agtggaccca ggatagggcc aaaccgtca cccagatcgt cagcgccgag
1101 gctgggggta gagcagacgg tggaggcggt tcactcagca gcaccctgac
1151 gctgagcaaa gcagactacg agaaacacaa agtctacgcc tgcgaagtca
1201 cccatcaggg cctgagttcg cccgtcacaa agagcttcaa ccgcggagag
1251 tcataagaat tc
```

(SEQ ID 155)

The A6 scTCR-C-Kappa protein is shown in the above western blot with an arrow.

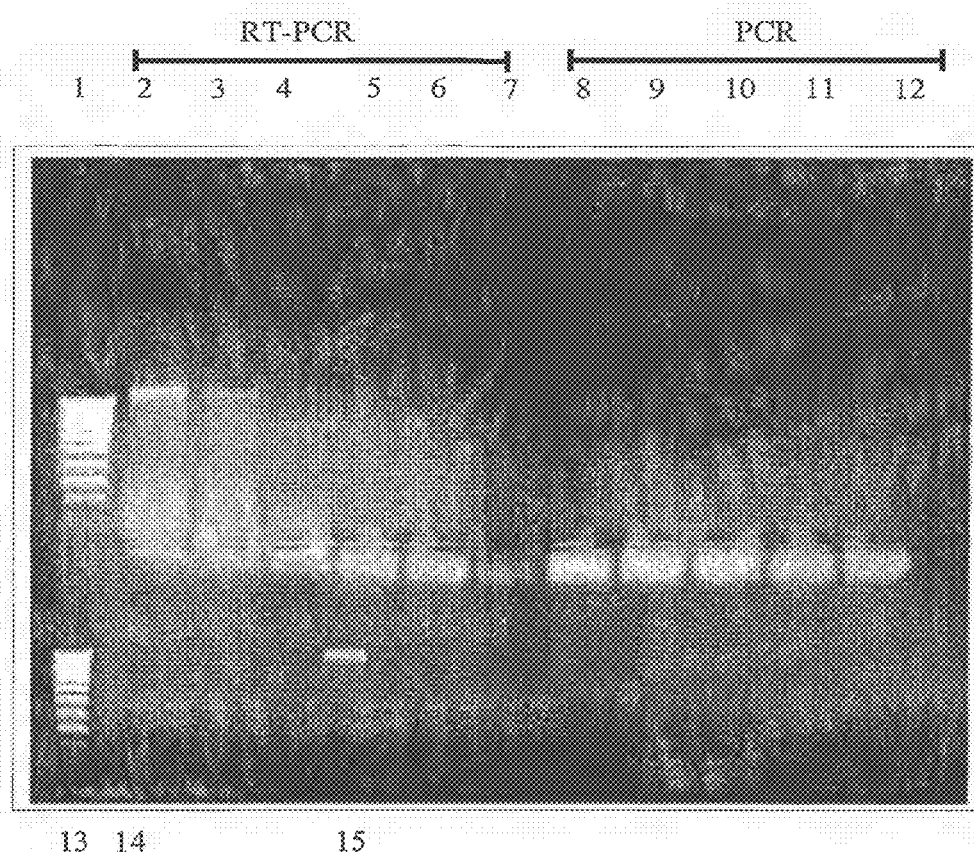

Figure 11

Lane 1 Bioline 100bp DNA marker
Lane 2 A6scTCR-C-Kappa reaction selected againt HLA-A2 TAX beads
Lane 3 A6scTCR-C-Kappa reaction selected againt HLA-A2 TAX beads in the presence of 10 microgrammes of soluble A6scTCR
Lane 4 A6scTCR-C-Kappa reaction selected against control beads
Lane 5 Control no DNA reaction selected against HLA-A2-TAX beads
Lane 6 Control no DNA reaction selected against HLA-A2 TAX beads in the presence of 10 microgrammes of soluble A6scTCR
Lane 7 Control no DNA reaction selected against control beads
Lanes 8-12 and lane 13 are as lanes 2-7 except no rerverse transcriptase was added just Roche high fidelity taq. These are the DNA contamination controls.
Lane 13 RT-PCR positive control.

Figure 12A

Clone 9 Mutated A6 TCR β chain DNA sequence
gctggtgtcactcagaccccaaaattccaggtcctgaagacaggacagagcatgacactgcagtgtgcccaggatatgaaccat
gaatacatgtcctggtatcgacaagacccaggcatggggctgaggctgattcattactcagttggtgctggtatcactgaccaagga
gaagtccccaatggctacaatgtctccagatcaaccacagaggatttccgctcaggctgctgtcggctgctccctccagacatct
gtgtacttctgtgccagcaggcgggactagcgggaggtgaccagagcagtacttcgggccgggcaccaggctcacggtcac
agaggacctgaaaaacgtgttcccacccgaggtcgctgtgtttgagccatcagaagcagagatctcccacacccaaaaggcca
cactggtgtgcctggccacaggcttctaccccgaccacgtgagctgagctggtgggtgaatgggaaggaggtgcacagtgggg
tctgcacagacccgcagcccctcaaggagcagcccgccctcaatgactccagatacgctctgagcagccgcctgagggtctcgg
ccacctctggcaggacccccgcaaccacttccgctgtcaagtccagttctacgggctctcggagaatgacgagtggacccagga
tagggccaaacccgtcacccagatcgtcagcgccgaggcctgggtagagcagac
(SEQ ID 156)

Figure 12B

Clone 9 Mutated A6 TCR β chain amino acid sequence

AGVTQTPKFQVLKTGQSMTLQCAQDMNHEYMSWYRQDPGMGLRLIHYSVGAGITDQGEVP
NGYNVSRSTTEDFPLRLLSAAPSQTSVYFCASRPGLAGGXPEQYFGPGTRLTVTEDLKNVF
PPEVAVFEPSEAEISHTQKATLVCLATGFYPDHVELSWWVNGKEVHSGVCTDPQPLKEQPA
LNDSRYALSSRLRVSATFWQDPRNHFRCQVQFYGLSENDEWTQDRAKPVTQIVSAEAWGR
AD
(SEQ ID 157)

X - Denotes the position of the amino acid corresponding to the introduced 'opal' stop codon, this will generally result in the substitution of a tryptophan (w) residue into the TCR β chain at this point.

Figure 13

Clone 49 Mutated A6 TCR β chain DNA sequence
gctggtgtcactcagaccccaaaattccaggtcctgaagacaggacagagcatgacactgtagtgtgcccaggatatgaaccat
gaatacatgcctggtatcgacaagacccaggcatggggctgaggctgattcattactcagttggtgctggtatcactgaccaagga
gaagtccccaatggctacaatgtctccagatcaaccacagaggatttcccgctcaggctgcigtcggctgctccctcccagacatct
gtgtacttctgtgccagcaggccgggactagcgggagggcgaccagagcagtacttgggccgggcaccaggctcacggtcac
agaggacctgaaaaacgtgttcccacccgaggtcgctgtgtttgagccatcagaagcagagatctcccacacccaaaaggcca
cactggtgtgcctggccacaggcttctaccccgaccacgtggagctgagctggtgggtgaatgggaaggaggtgcacagtgggg
tctgcacagacccgcagccctcaaggagcagcccgccctcaatgactccagatacgctctgagcagccgcctgagggtctcgg
ccaccttctggcaggacccccgcaaccactccgctgtcaagtccagttctacgggctctcggagaatgacgagtggacccagga
tagggccaaaacccgtcaccagatcgtcagcgccgaggcctggggtagagcagac
(SEQ ID 158)

Figure 14A

Clone 134 Mutated A6 TCR β chain DNA sequence
gctggtgtcactcagacccccaaaattccaggtcctgaagacaggacagagcatgacactgcagtgtgcccaggatatgaaccat
gaatacatgtcctggtatcgacaagacccaggcatggggctgaggctgattcattactcagttggtgctggtatcactgaccaagga
gaagtccccaatggctacaatgtctccagatcaaccacagaggatttcccgctcaggctgctgtcggctgctccctcccagacatct
gtgtactctgtgcctcgaggccggggctgatgagtgcggaaccagagcagtacttcgggccgggcaccaggctcacggtcac
agaggacctgaaaaacgtgttcccacccgaggtcgctgtgtttgagccatcagaagcagagatctcccacacccaaaaggcca
cactggtgtgcctggccaccggtttctaccccgaccacgtggagctgagctggtgggtgaatgggaaggaggtgcacagtgggt
ctgcacagacccgcagccctcaaggagcagccgccctcaatgactcccagatacgctctgagcagccgcctgagggtctcgg
ccacccttctggcaggacccccgcaaccacttccgctgtcaagtccagtctacgggctctggagaatgacgagtggacccagga
tagggccaaacccgtcacccagatcgtcagcgccgaggcctggggtagagcagactaagcttgaattc
(SEQ ID 159)

Figure 14B

Clone 134A Mutated A6 TCR β chain amino acid sequence (BIAcore)
MNAGVTQTPKFQVLKTGQSMTLQCAQDMNHEYMSWYRQDPGMGLRLIHYSVGAGITDQG
EVPNGYNVSRSTTEDFPLRLLSAAPSQTSVYFCASRPGLMSAEPEQYFGPGTRLTVTEDLK
NVFPPEVAVFEPSEAEISHTQKATLVCLATGFYPDHVELSWWVNGKEVHSGVCTDPQPLKE
QPALNDSRYALSSRLRVSATFWQDPRNHFRCQVQFYGLSENDEWTQDRAKPVTQIVSAEA
WGRAD*
(SEQ ID 160)

Figure 14C

Clone 134 Mutated A6 TCR β chain amino acid sequence (ELISA)
AGVTQTPKFQVLKTGQSMTLQCAQDMNHEYMSWYRQDPGMGLRLIHYSVGAGITDQGEVP
NGYNVSRSTTEDFPLRLLSAAPSQTSVYFCASRPGLMSAQPEQYFGPGTRLTVTEDLKNVF
PPEVAVFEPSEAEISHTQKATLVCLATGFYPDHVELSWWVNGKEVHSGVCTDPQPLKEQPA
LNDSRYALSSRLRVSATFWQDPRNHFRCQVQFYGLSENDEWTQDRAKPVTQIVSAEAWGR
AD
(SEQ ID 161)

Figure 17A atgcaggaggtgacacagattcctgcagctctgagtgtcccagaaggagaaaacttggttctcaactgcagtttcactgata
gcgctatttacaacctccagtggtttaggcaggaccctgggaaaggtctcacatctctgttgcttattcagtcaagtcagaga
gagcaaacaagtggaagacttaatgcctcgctggataaatcatcaggacgtagtactttatacattgcagcttctcagcctgg
tgactcagccacctacctctgtgctgtgaggcccacatcaggaggaagctacatacctacattggaagaggaaccagcct
tattgttcatccgtatatccagaaccctgaccctgccgtgtaccagctgagagactctaaatccagtgacaagtctgtctgcct
attcaccgattttgattctcaaacaaatgtgtcacaaagtaaggattctgatgtgtatatcacagacaaatgtgtgctagacatg
aggtctatggacttcaagagcaacagtgctgtggcctggagcaacaaatctgactttgcatgtgcaaacgccttcaacaaca
gcattattccagaagacaccttcttccccagcccagaaagttcctaa
(SEQ ID 162)

Figure 17B atgggtgtcactcagaccccaaaattccaggtcctgaagacaggacagagcatgacactgcagtgtgcccaggatatgaa
ccatgaatacatgtcctggtatcgacaagacccaggcatgggctgaggctgattcattactcagttggtgctggtatcactg
accaaggagaagtccccaatggctacaatgtctccagatcaaccacagaggatttcccgctcaggctgctgtcggctgctc
cctcccagacatctgtgtacttctgtgccagcagttacgtcgggaacaccggggagctgtttttggagaaggctctaggctg
accgtactggaggacctgaaaaacgtgttcccacccgaggtcgctgtgtttgagccatcagaagcagagatctcccacacc
caaaaggccacactggtgtgcctggccacaggcttctacccegaccacgtggagctgagctggtgggtgaatgggaagg
aggtgcacagtggggtctgcacagacccgcagccctcaaggagcagcccgccctcaatgactccagatacgctctgag
cagccgcctgagggtctcggccaccttctggcaggaccccgcaaccactccgctgtcaagtccagttctacgggctctc
ggagaatgacgagtggacccaggatagggccaaaccgtcacccagatcgtcagcgccgaggcctgggglagagcag
actaa
(SEQ ID 163)

Figure 18A

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRPTSGGSYIPTFGRGTSLIVHPYI
QNPDPAVYQLRDSKSSDKSVCLFTDFDSQTNVSQSKDS
DVYITDKCVLDMRSMDFKSNSAVAWSNKSDFACANAF
NNSIIPEDTFFPSPESS Stop
(SEQ ID 164)

Figure 18B

MGVTQTPKFQVLKTGQSMTLQCAQDMNHEYMSWYRQ
DPGMGLRLIHYSVGAGITDQGEVPNGYNVSRSTTEDFP
LRLLSAAPSQTSVYFCASSYVGNTGELFFGEGSRLTVLE
DLKNVFPPEVAVFEPSEAEISHTQKATLVCLATGFYPDH
VELSWWVNGKEVHSGVCTDPQPLKEQPALNDSRYALS
SRLRVSATFWQDPRNHFRCQVQFYGLSENDEWTQDRA
KPVTQIVSAEAWGRAD Stop (SEQ ID 165)

Figure 19A

```
TTCCTGGCCT TTTGCTGGCC TTTTGCTCAC ATGTAATGTG AGTTAGCTCA
AAGGACCGGA AAACGACCGG AAAACGAGTG TACATTACAC TCAATCGAGT
CTCATTAGGC ACCCCAGGCT TTACACTTTA TCCTTCCGGC TCGTAAGTTG
GAGTAATCCG TGGGGTCCGA AATGTGAAAT ACGAAGGCCG AGCATACAAC
TGTGGAATTG TGAGCGGATA ACAATTTCAC ACAGGAAACA GCTATGACCA
ACACCTTAAC ACTCGCCTAT TGTTAAAGTG TGTCCTTTGT CGATACTGGT
TGATTACGCC AAGCTACGTA CTTAAGTATT CTATTTCAAG GAGACAGTCA
ACTAATGCGG TTCGATGCAT GAATTCATAA GATAAAGTTC CTCTGTCAGT
TAATGAAATA CCTATTGCCT ACGGCAGCCG CTGGATTGTT ATTACTCGCG
ATTACTTTAT GGATAACGGA TGCCGTCGGC GACCTAACAA TAATGAGCGC
GCCCAGCCGG CCATGGCCAA ACAGGAGGTG ACGCAGATTC CTGCAGCTCT
CGGGTCGGCC GGTACCGGTT TGTCCTCCAC TGCGTCTAAG GACGTCGAGA
GAGTGTCCCA GAAGGAGAAA ACTTGGTTCT CAACTGCAGT TTCACTGATA
CTCACAGGGT CTTCCTCTTT TGAACCAAGA GTTGACGTCA AAGTGACTAT
GCCCTATTTA CAACCTCCAG TGGTTTAGGC AGGACCCTGG GAAAGGTCTC
CGCGATAAAT GTTGGAGGTC ACCAAATCCG TCCTGGGACC CTTTCCAGAG
ACATCTCTGT TGCTTATTCA GTCAAGTCAG AGAGAGCAAA CAAGTGGAAG
TGTAGAGACA ACGAATAAGT CAGTTCAGTC TCTCTCGTTT GTTCACCTTC
ACTTAATGCC TGCCTGGATA AATTATCAGG ACGTAGTACT TTATACATTG
TGAATTACCG AGCGACCTAT TTAGTAGTCC TGCATCATGA AATATGTAAC
CAGCTTCTCA GCCTGGTGAC TCAGCCACCT ACCTCTGTGC TGTGAGGCCC
GTCGAAGAGT CGGACCACTG AGTCGGTGGA TGGAGACACG ACACTCCGGG
ACATCAGGAG GAAGCTACAT ACCTACATTT GGAAGAGGAA CCAGCCTTAT
TGTAGTCCTC CTTCGATGTA TGGATGTAAA CCTTCTCCTT GGTCGGAATA
TGTTCATCCG TATATCCAGA ACCCGGATCC TGCCGTGTAC CAGCTGAGAG
ACAAGTAGGC ATATAGGTCT TGGCCTAGG ACGGACATG GTCGACTCTC
ACTCTAAATC CAGTGACAAG TCTGTCTGCC TATTCACCGA TTTTGATTCT
TGAGATTTAG GTCACTGTTC AGACAGACGG ATAAGTGGCT AAAACTAAGA
CAAACAAATG TGTCACAAAG TAAGGATTCT GATGTGTATA TCACAGACAA
GTTGTTTAC ACAGTGTTTC ATTCCTAAGA CTACACATAT AGTGTCTGTT
ATGTGTGCTA GACATGAGGT CTATGGACTT CAAGAGCAAC AGTGCTGTGG
TACACACGAT CTGTACTCCA GATACCTGAA GTTCTCGTTG TCACGACACC
CCTGGAGCAA CAAATCTGAC TTTGCATGTG CAAACGCCTT CAACAACAGC
GGACCTCGTT GTTTAGACTG AAACGTACAC GTTTGCGGAA GTTGTTGTCG
ATTATTCCAG AAGACACCTT CTTCCCCAGC CCAGAAAGTT CCTAATAACC
TAATAAGGTC TTCTGTGGAA GAAGGGGTCG GGTCTTTCAA GGATTATTGG
TAGGTTAATT AAGAATTCTT TAAGAAGGGG ATATACATAT GAAAAAATTA
ATCCAATTAA TTCTTAAGAA ATTCTTCCGC TATATGTATA CTTTTTTAAT
TTATTCGCAA TTCCTTTAGT TGTTCCTTTC TATTCTCACA GCGCGCACGC
AATAAGCGTT AAGGAAATCA ACAAGGAAAG ATAAGAGTGT CGCGCGTCCG
TGGTGTCACT CAGACCCCAA AAGTTCCAGG CCTGAAGACA GGACAGAGCA
ACCACAGTGA GTCTGGGGTT TTAAGGTCCA GGACTTCTGT CCTGTCTCGT
TGACACTGCA GTGTGCCCAG GATATGAACC ATGAATACAT GTCCTGGTAT
ACTGTGACGT CACACGGGTC CTATACTTGG TACTTATGTA CAGGACCATA
CGACAAGACC CAGGCATGGG GCTGAGGCTG ATTCATTACT CAGTTGGTGC
GCTGTTCTGG GTCCGACCC CGACTCCGAC TAAGTAATGA GTCAACCACG
TGGTATCACT GACCAAGGAG AAGTCCCAA TGGCTACAAT GTCTCCAGAT
ACCATAGTGA CTGTTCCTC TTCAGGGGTT ACCGATGTTA CAGAGGTCTA
CAACCACAGA GGATTTCCCG CTCAGGCTGC TGTCGGCTGC TCCCTCCCAG
GTTGGTGTCT CCTAAAGGGC GAGTCCGACG ACAGCCGACG AGGGAGGGTC
ACATCTGTGT ACTTCTGTGC CAGCAGTTAC GTCGGGAACA CCGGGGAGCT
TGTAGACACA TGAACACACG GTCGTCAATG CAGCCCTTGT GCCCCTTCCA
GTTTTTTGGA GAAGGCTCTA GGCTGACCGT ACTGGAGGAC CTGAAAAACG
CAAAAAACCT CTTCCGAGAT CCGACTGGCA TGACCTCCTG GACTTTTTGC
TGTTCCCACC CGAGGTCGCT GTGTTGAGC CATCAGAAGC AGAGATCTCC
ACAGGGTGG GCTCCAGCA CACAAACTCG GTAGTCTTCG TCTCTAGAGG
CACACCCAAA AGTCCACACT GGTGTGCCTG GCCACAGGCT TCTACCCCGA
GTGTGGGTTT TCCGGTGTGA CCACACGGAC CGGTGTCCGA AGATCGGGCT
CCACGTGGAG CTGAGCTCGT GGGTGAATGG GAAGGAGGTG CACAGTGGGG
GGTGCACCTC GACTCGACCA CCCACTTACC CTTCCTCCAC GTGTCACCCC
TCTGCACAGA CCCGCAGCCC CTCAAGGAGC AGCCCGCCCT CAATGACTCC
AGACGTGTCT GGGCGTCGGG GAGTTCCTCG TCGGGCGGGA GTTACGAGG
AGATACGCTC TGAGCAGCCG CCTGAGGGTC TCGGCCACCT TCTGGCACGA
TCTATGCGAG ACTCGTCGGC GGACTCCCAG AGCCGGTGGA AGACCGTCCT
CCCCCGCAAC CACTTCCGCT GTCAAGTCCA GTTCTACGGG CTCTCGGAGA
GGGGCGTTG GTGAAGGCGA CAGTTCAGGT CAAGATGCCC GAGAGCCTCT
ATGACGAGTG GACCCAGGAT AGGGCCAAAC CGGTCACCCA GATCGTCAGC
TACTGCTCAC CTGGGTCCTA TCCCGGTTTG GGCAGTGGGT CTAGCACTCG
GCCGAGGCCT GGGGTAGAGC AGACGCGGCC GCA
CGGCTCCGGA CCCCATCTCG TCTGCGCCGG CGT
```

(SEQ ID 166)

(SEQ ID 167)

Figure 21

DRA0101

```
  1 ggatccatgg ccataagtgg agtccctgtg ctaggatttt tcatcatagc tgtgctgatg
 61 agcgctcagg aatcatgggc tatcaaagaa gaacatgtga tcatccaggc cgagttctat
121 ctgaatcctg accaatcagg cgagtttatg tttgactttg atggtgatga gattttccat
181 gtggatatgg caaagaagga gacggtctgg cggcttgaag aatttggacg atttgccagc
241 tttgaggctc aaggtgcatt ggccaacata gctgtggaca aagccaacct ggaaatcatg
301 acaaagcgct ccaactatac tccgatcacc aatgtacctc cagaggtaac tgtgctcacg
361 aacagccctg tggaactgag agagccaaac gtcctcatct gtttcatcga caagttcacc
421 ccaccagtgg tcaatgtcac gtggcttcga aatggaaaac ctgtcaccac aggagtgtca
481 gagacagtct tcctgcccag ggaagaccac ctttttcgca gttccacta tctccccttc
541 ctgccctcaa ctgaggacgt ttacgactgc agggtggagc actgggggct ggatgagcct
601 cttctcaagc actgggagtt tgatgctcca agccctctcc cagagactac agagaacgtg
661 gatggggtc tgactgaac atctaagcg gagacagatc aactgaaga caagaagc
721 gggttgaaga cgagattc caatctactg aagagaaag aaaactaga gttcattctc
781 gcagctagg gatctggtgg tggtctgaac gatattttg aagctcagaa aatcgaatgg
841 catgagtagg atcc
```

(SEQ ID 168)

xxx  -  Fos Leucine zipper codons
xxx  -  Biotinylation tag codons

Figure 22A

```
   1 aattctactc gtaaagcgag ttgaaggatc atatttagtt gcgtttatga gataagattg
  61 aaagcacgtg taaaatgttt cccgcgcgtt ggcacaacta tttacaatgc ggccaagtta
 121 taaaagattc taatctgata tgttttaaaa cacctttgcg gcccgagttg tttgcgtacg
 181 tgactagcga agaagatgtg tggaccgcag aacagatagt aaaacaaaac cctagtattg
 241 gagcaataat cgatttaacc aacacgtcta aatattatga tggtgtgcat ttttttgcggg
 301 cgggcctgtt atacaaaaaa attcaagtac ctggccagac tttgccgcct gaaagcatag
 361 ttcaagaatt tattgacacg gtaaaagaat ttacagaaaa gtgtcccggc atgttggtgg
 421 gcgtgcactg cacacacggt attaatcgca ccggttacat ggtgtgcaga tatttaatgc
 481 acacctgggg tattgcgccg caggaagcca tagatagatt cgaaaaagcc agaggtcaca
 541 aaattgaaag acaaaattac gttcaagatt tattaattta attaatatta tttgcattct
 601 ttaacaaata ctttatccta ttttcaaatt gttgcgcttc ttccagcgaa ccaaaactat
 651 gcttgcttg ctccgtttag cttgtagccg atcagtggcg ttgttccaat cgacggtagg
 721 attaggcgg atattctcca ccacaatgtt ggcaacgttg atgttacgtt tatgcttttg
 781 gttttccacg tacgtctttt ggccggtaat agccgtaaac gtagtgccgt cgcgcgtcac
 841 gcacaacacc ggatgtttgc gcttgtccgc ggggtattga accgcgcgat ccgacaaatc
 901 caccactttg gcaactaaat cggtgacctg cgcgtctttt ttctgcatta tttcgtcttt
 961 cttttgcatg gtttcctgga agccggtgta catgcggttt agatcagtca tgacgcgcgt
1021 gacctgcaaa tctttggcct cgatctgctt gtccttgatg gcaacgatgc gttcaataaa
1081 ctcttgtttt ttaacaagtt cctcggtttt ttgcgccacc accgcttgca gcgcgtttgt
1141 gtgctcggtg aatgtcgcaa tcagcttagt caccaactgt ttgctctcct cctcccgttg
1201 tttgatcgcg ggatcgtact tgccggtgca gagcacttga ggaattactt cttctaaaag
1261 ccattcttgt aattctatgg cgtaaggcaa tttggacttc ataatcagct gaatcacgcc
1321 ggattagta atgagcactg tatgcggctg caaatacagc gggtcgccc ttttcacgac
1381 gctgttagag gtagggcccc catttttgat ggtctgctca aataacgatt tgtatttatt
1441 gtctacatga acacgtatag ctttatcaca aactgtatat tttaaactgt tagcgacgtc
1501 cttggccacg aaccggacct gttggtcgcg ctctagcacg tacgcaggt tgaagtatc
1561 ctctccaaat ttaaattctc caatttttaac gcgagccatt ttgatacacg tgtgtcgatt
1621 ttgcaacaac tattgttttt taacgcaaac taaactatt gtggtaagca ataattaaat
1683 atggggaac atgcgccgct acaacactcg tcgttatgaa cgcagacggc gccggtctcg
1741 gcgcaagcgg ctaaaacgtg ttgcgcgttc aacgcggcaa acatgcaaa agccaatagt
1801 acagttttga tttgcatatt aacggcgatt ttttaaatta tcttatttaa taaatagtta
1861 tgacgcctac aactcccgc ccgcgttgac tcgtgcacc tgagcagtt cgttgacgcc
1921 ttcctccgtc tggccgaaca cgtcgagcgg gtggtcgatg accagcgcg tgccgcacgc
1981 gacgcacaag tatctgtaca ccgaatgatc gtcgggcgaa ggcacgtcgg cctccaagtg
2041 gcaatattgg caaattcgaa aatatataca gttgggttgt ttgcgcatat ctatcgtggc
2101 gttgggcatg tacgtccgaa cgttgatttg catgcaagcc gaaattaaat cattgcgatt
2161 agtgcgatta aaacgttgta catcctcgct tttaatcatg ccgtcgatta aatcgcgcaa
2221 tcgagtcaag tgatcaaagt gtggaataat gttttctttg tattcccgag tcaagcgcag
2281 cgcgtatttt aacaaactag ccatcttgta agttagttc atttaatgca actttatcca
2341 ataatatatt atgtatcgca cgtcaagaat taacaatgcg cccgttgcg catctcaaca
2401 cgactatgat agagatcaaa taaagcgcga attaaatagc ttgcgacgca acgtgcacga
2461 tctgtgcacg cgttccggca cgagctttga ttgtaataag ttttttacgaa gcgatgacat
2521 gaccccgta gtgacaacga tcagcccaa aagaactgcc gactacaaaa ttaccgagta
2581 tgtcggtgac gttaaaacta ttaagccatc caatcgaccg ttagtcgaat caggaccgct
2641 ggtgcgagaa gccgcgaagt atggcgaatg catcgtataa cgtgtggagt ccgctcatta
2701 gagcgtcatg tttagacaag aaagctacat atttaattga tcccgatgat tttattgata
2761 aattgaccct aactccatac acggtattct acaatggcgg ggttttggtc aaaattccg
2821 gactgcgatt gtacatgctg ttaacggctc cgcccactat taatgaaatt aaaaattcca
2881 atttaaaaa acgcagcaag agaaacattt gtatgaaaga atgcgtagaa ggaaagaaa
2941 atgtcgtcga catgctgaac aacaagatta atatgcctcc gtgtataaaa aaatattga
3001 acgatttgaa agaaaacaat gtaccgcgcg gcggtatgta caggaagagg tttatactaa
3061 actgttacat tgcaaacgtg gtttcgtgtg ccaagtgtga aaaccgatgt ttaatcaagg
3121 ctctgacgca tttctacaac cacgactcca agtgtgtggg tgaagtcatg catcttttaa
3181 tcaaatccca agatgtgtat aaaccaccaa actgccaaaa aatgaaaact gtcgacaagc
```

Figure 22B

```
3241 tctgtccgtt tgctggcaac tgcaagggtc tcaatcctat ttgtaattat tgaataataa
3301 aacaattata aatgctaaat ttgttttta ttaacgatac aaaccaaacg caacaagaac
3361 atttgtagta ttatctataa ttgaaaacgc gtagttataa tcgctgaggt aatatttaaa
3421 atcatttca aatgattcac agttaatttg cgacaatata attttatttt cacataaact
3481 agacgccttg tcgtcttctt cttcgtattc cttctctttt tcattttct cctcataaaa
3541 attaacatag ttattatcgt atccatatat gtatctatcg tatagagtaa atttttgtt
3601 gtcataaata tatatgtctt ttttaatggg gtgtatagta ccgctgcgca tagtttttct
3661 gtaatttaca acagtgctat tttctggtag ttcttcggag tgtgttgctt taattattaa
3721 atttatataa tcaatgaatt tgggatcgtc ggttttgtac aatatgttgc cggcatagta
3781 cgcagcttct tctagttcaa ttacaccatt tttagcagc accggattaa cataactttc
3841 caaaatgttg tacgaaccgt taaacaaaaa cagttcacct ccctttcta tactattgtc
3901 tgcgagcagt tgtttgtgt aaaaataac agccattgta atgagacgca caaactaata
3961 tcacaaactg gaaatgtcta tcaatatata gttgctgatg atccagcatg ataagataca
4021 tgatgagtt tggacaaacc acaactagaa tgcagtgaaa aaaatgcttt attgtgaaa
4081 ttgtgatgc tattgcttta tttgtaacca ttataagctg caataaacaa gttccgagtt
4141 tgtcagaaag cagaccaaac agcggttgga ataatagcga gaacagagaa atagcggcaa
4201 aaataatacc cgtatcactt ttgctgatat ggttgatgtc atgtagccaa atcgggaaaa
4261 acggaagta ggctccatg ataaaaagt aaaagaaaaa gaataaaccg aacatccaaa
4321 agtttgtgtt ttttaaatag tacataatgg attttccttac gcgaaatacg ggcagacatg
4381 gcctgcccgg ttattattat tttgacacc agaccaactg gtaatggtag cgaccggcgc
4441 tcagctggaa ttcagatctg tgattgtaaa taaaatgtaa tttacagtat agtatttaa
4501 ttaatataca aatgatttga taataattct tatttaacta taatatattg tgttgggttg
4561 aattaaaggt cccggcatcc tcaaatgcat aatttcatag tccccttgt tgtaagtgat
4621 gcgtatttct gaatctttgt aaaatagcac acaagactcc aacgcgtttg gcgtttatt
4681 ttcttgctcg actctagttt attaggcctc tagagatccg tatttatagg ttttttatt
4741 acaaaactgt tacgaaaaca gtaaatact tatttatttg cgagatggtt atcatttaa
4801 ttatctccat gatccaataa acctagaata aagggcccga cctttaatt aaccaacac
4861 aatatattat agttaaataa gaattattat caaatcattt gtatattaat taaaatacta
4921 tactgtaaat tacatttat ttacaatcac agatcccggg gatccggtta ttagtacatt
4981 tattaagcgc tagattctgt gcgttgttga tttacagaca attgttgtac gtattttaat
5041 aattcattaa atttataatc tttagggtgg tatgttagag cgaaaatcaa atgattttca
5101 gcgtcttat atctgaattt aaatattaaa tctcaatag atttgtaaaa taggtttcga
5161 ttagtttcaa acaagggttg ttttttccgaa ccgatggctg gactatctaa tggatttcg
5221 ctcaacgcca caaaacttgc caaatcttgt agcagcaatc tagctttgtc gatattcgtt
5281 tgtgttttgt tttgtaataa aggttcgacg tcgttcaaaa tattatgcgc tttgtattt
5341 ctttcatcac tgtcgttagt gtacaattga ctcgacgtaa acacgttaaa taaagcttgg
5401 acatatttaa catcgggcgt gttagcttta ttaggccgat tatcgtcgtc gtccaaccc
5461 tcgtcgttag aagttgcttc cgaagacgat tttgccatag ccacacgacg cctattaatt
5521 gtgtcggcta acacgtccgc gatcaaattt gtagttgagc ttttggaat tatttctgat
5581 tgcgggcgtt tttgggcggg tttcaatcta actgtgcccg attttaattc agacaacacg
5641 ttagaaagcg atggtcagg cggtggtaac atttcagacg gcaaatctac taatggcggc
5701 ggtggtggag ctgatgataa atctaccatc ggtggaggcg caggcggggc tggcggcgga
5761 ggcggaggcg gaggtggtgg cggtgatgca gacggcggtt taggctcaaa tgtctcttta
5821 ggcaacacag tggcacctc aactattgta ctggtttcgg gcgccgtttt tggtttgacc
5881 ggtctgagac gagtgcgatt ttttcgtttt ctaatagctt ccaacaattg ttgtctgtcg
5941 tctaaaggtg cagcgggttg aggttccgtc ggcattggtg gagcgggcgg caattcagac
6001 atcgatggtg gtggtggtgg tggaggcgct ggaatgttag gcacgggaga aggtggtggc
6061 ggcggtgccg ccggtataat ttgttctggt ttagtttgtt cgcgcacgat tgtgggcacc
6121 ggcggcaggcg gcggtggctg cacacggaca ggtcgtctgc ttcgagcgga cgcttgggt
6181 ggtggcaatt caatattata attggaatac aaatcgtaaa aatcgctat aagcattgta
6241 atttcgctat cgtttaccgt gccgatattt aacaaccgct caatgtaagc aattgtattg
6301 taaagagatt gtctcaagct cggatcgatc ccgcacgccg ataacaagcc tttcattt
6361 tactacagca ttgtagtggc gagacttcc gctgtcgtcg acgtacatgt atgctttgtt
6421 gtcaaaaacg tcgttggcaa gctttaaaat atttaaaaga acatctctgt tcagcaccac
6481 tgtgttgtcg taaatgttgt ttttgataat ttgcgcttcc gcagtatcga cacgttcaaa
```

Figure 22C

```
6541 aaattgatgc gcatcaattt tgttgttcct attattgaat aaataagatt gtacagattc
6601 atatctacga ttcgtcatgg ccaccacaaa tgctacgctg caaacgctgg tacaattta
6661 cgaaaactgc aaaacgtca aaactgggta taaaataatc aacgggcgct tggcaaaat
6721 atctatttta tcgcacaagc ccactagcaa attgtatttg cagaaaacaa tttcggcgca
6781 caattttaac gctgacgaaa taaaagttca ccagttaatg agcgaccacc caaattttat
6841 aaaaatctat tttaatcacg gttccatcaa caaccaagtg atcgtgatgg actacattga
6901 ctgtccgat ttatttgaaa cactacaaat taaagcgag ctttcgtacc aacttgttag
6961 caatattatt agacagctgt gtgaagcgct caacgatttg cacaagcaca attcataca
7021 caacgacata aaactcgaaa atgtcttata tttcgaagca cttgatcgcg tgtatgttg
7081 cgattacgga ttgtgaaaac acgaaaacto acttagcgtg cacgacggca cgttggagta
7141 tttagtccg gaaaaattc gacacacaac tatgcacgtt tcgtttgact ggtacgcggc
7201 gtgttaacat acaagttgct aacggcggc cgacacccat ttgaaaaag cgaagacgaa
7261 atgttggact tgaatagcat gaagcgtgt cagcaataca atgacattgg cgttttaaaa
7321 cacgttcgta acgttaacgc tcgtgacttt gtgtactgcc taacaagata caacatagat
7381 tgtagactca caaattacaa acaaattata aaacatgagt tttgtcgta aaaatgccac
7441 ttgtttacg agtagaattc ccagcttggc actggcgtc gttttacaac gtcgtgactg
7501 ggaaaaccct ggcgttaccc aacttaatcg ccttgcagca catccccttt tgccagctg
7561 gcgtaatagc gaagaggccc gcaccgatcg cccttcccaa cagttgcgca gcctgaatgg
7621 cgaatggcgc ctgatgcggt attttctct tacgcatctg tgcggtattt cacaccgcat
7681 atggtgcact ctcagtacaa tctgtctga tgccgcatag ttaagccagc ccgacaccc
7741 gccaacaccc gctgacgcgc cctgacgggc ttgtctgctc ccggcatccg cttacagaca
7801 agctgtgacc gtctccggga gctgcatgtg tcagaggttt tcaccgtcat caccgaaacg
7861 cgcggacgaa agggcctcgt gatacgccta ttttatagg ttaatgtcat gataataatg
7921 gtttcttaga cgtcaggtgg cactttggg ggaaatgtgc gcggaacccc tatttgttta
7981 tttttctaaa tacattcaaa tatgtatccg ctcatgagac aataaccctg ataaatgctt
8041 caataatatt gaaaaggaa gagtatgagt attcaacatt tccgtgtcgc ccttattccc
8101 ttttttgcgg cattttgcct tcctgttttt gctcacccag aaacgctggt gaaagtaaaa
8161 gatgctgaag atcagttggg tgcacgagtg ggttacatcg aactggatct caacagcggt
8221 aagatccttg agagttttcg ccccgaagaa cgttttccaa tgatgagcac ttttaaagtt
8281 ctgctatgtg gcgcggtatt atcccgtatt gacgccggc aagagcaact cggtcgccgc
8341 atacactatt ctcagaatga cttggttgag tactcaccag tcacagaaaa gcatcttacg
8401 gatggcatga cagtaagaga attatgcagt gctgccataa ccatgagtga taacactgcg
8461 gccaacttac ttctgacaac gatcggagga ccgaaggagc taaccgcttt tttgcacaac
8521 atgggggatc atgtaactcg ccttgatcgt tgggaaccgg agctgaatga agccatacca
8581 aacgacgagc gtgacaccac gatgcctgta gcaatggcaa caacgttgcg caaactatta
8641 actggcgaac tacttactct agcttccgg caacaattaa tagactggat ggaggcggat
8701 aaagttgcag gaccacttct gcgctcggcc cttccggctg gctggtttat tgctgataaa
8761 tctggagccg gtgagcgtg gtctcgcggt atcattgcag cactggggcc agatggtaag
8821 ccctcccgta tcgtagttat ctacacgacg gggagtcagg caactatgga tgaacgaaat
8881 agacagatcg ctgagatagg tgcctcactg attaagcatt ggtaactgtc agaccaagtt
8941 tactcatata ctttagat tgatttaaaa cttcatttt aatttaaaag gatctaggtg
9001 aagatccttt tgataatct catgaccaaa atcccttaac gtgagttttc gttccactga
9061 gcgtcagacc ccgtagaaaa gatcaaagga tcttcttgag atcctttt tctgcgcgta
9121 atctgctgct tgcaaacaaa aaaaccaccg ctaccagcgg tggtttgttt gccggatcaa
9181 gagctaccaa ctctttttcc gaaggtaact ggcttcagca gagcgcagat accaaatact
9241 gtccttctag tgtagccgta gttaggccac cacttcaaga actctgtagc accgcctaca
9301 tacctcgctc tgctaatcct gttaccagtg gctgctgcca gtggcgataa gtcgtgtctt
9361 accgggttgg actcaagacg atagttaccg gataaggcgc agcggtcggg ctgaacgggg
9421 ggttcgtgca cacagcccag cttggagcga acgacctaca ccgaactgag atacctacag
9481 cgtgagcatt gagaaagcgc cacgcttccc gaagggagaa aggcggacag gtatccggta
9541 agcggcaggg tcgaacagg agagcgcacg agggagcttc caggggggaaa cgcctggtat
9601 ctttatagtc ctgtcgggtt tcgccacctc tgacttgagc gtcgattct gtgatgctcg
9661 tcaggggggc ggagcctatg gaaaaacgcc agcaacgcgg cctttttacg gttcctggcc
9721 ttttgctggc cttttgctca catgttcttt cctgcgttat cccctgattc tgtggataac
9781 cgtattaccg cctttgagtg agctgatacc gctcgccgca gccgaacgac cgagcgcagc
9841 gagtcagtga gcgaggaagc ggaagagcgc ccaatacgca aaccgcctct ccccgcgcgt
9901 tggccgattc attaatgcag ctggcacgac aggtttcccg actggaaagc gggcagtgag
9961 cgcaacgcaa ttaatgtgag ttagctcact cattaggcac cccaggcttt acactttatg
```

```
10021 cttccggctc gtatgttgtg tggaattgtg agcggataac aatttcacac aggaaacagc
10081 tatgaccatg attacg
```

(SEQ ID 169)

- Restriction enzyme sites

Figure 23

```
  1 ggtacggat ccagcatggt gtgtctgaag ctccctggag gctcctgcat gacagcgctg
 61 acagtgacac tgatggtgct gagctccca ctggctttgt ccggagacac cggacctaag
121 tacgtcaagc agaacacact gaaactggct tccggtggcg gatctctagt tccacgcggt
181 agtggaggcg gtggttccgg agacacgcgt ccacgtttct tgtggcagct taagtttgaa
241 tgtcatttct tcaatgggac ggagcgggtg cggttgctgg aaagatgcat ctataaccaa
301 gaggagtccg tgcgcttcga cagcgacgtg ggggagtacc gggcggtgac ggagctgggg
361 cggcctgatg ccgagtactg gaacagccag aaggacctcc tggagcagag gcgggccgcg
421 gtggacacct actgcagaca caactacggg gttggtgaga gcttcacagt gcagcggcga
481 gttgagccta aggtgactgt gtatccttca aagacccagc ccctgcagca ccacaacctc
541 ctggtctgct ctgtgagtgg tttctatcca ggcagcattg aagtcaggtg gttccggaac
601 ggccaggaag agaaggctgg ggtggtgtcc acaggcctga tccagaatgg agattggacc
661 ttccagaccc tggtgatgct ggaaacagtt cctcggagtg gagaggttta cacctgccaa
721 gtggagcacc caagtgtgac gagccctctc acagtggaat ggagagcacg gtctgaatct
781 gcacagagca aggtcgacgg aggcggtggg ggtagaatcg cccggctgga ggaaaaagtg
841 aaaactttga aagctcagaa ctcggagctg gcgtccacgg cgaatatgct gagggaagtg
901 gtggcacagc taaaacagaa agtcatgaac tagtaggatc c
```

(SEQ ID 170)

xxx  - Jun Leucine zipper codons
xxx  - HLA-loaded peptide

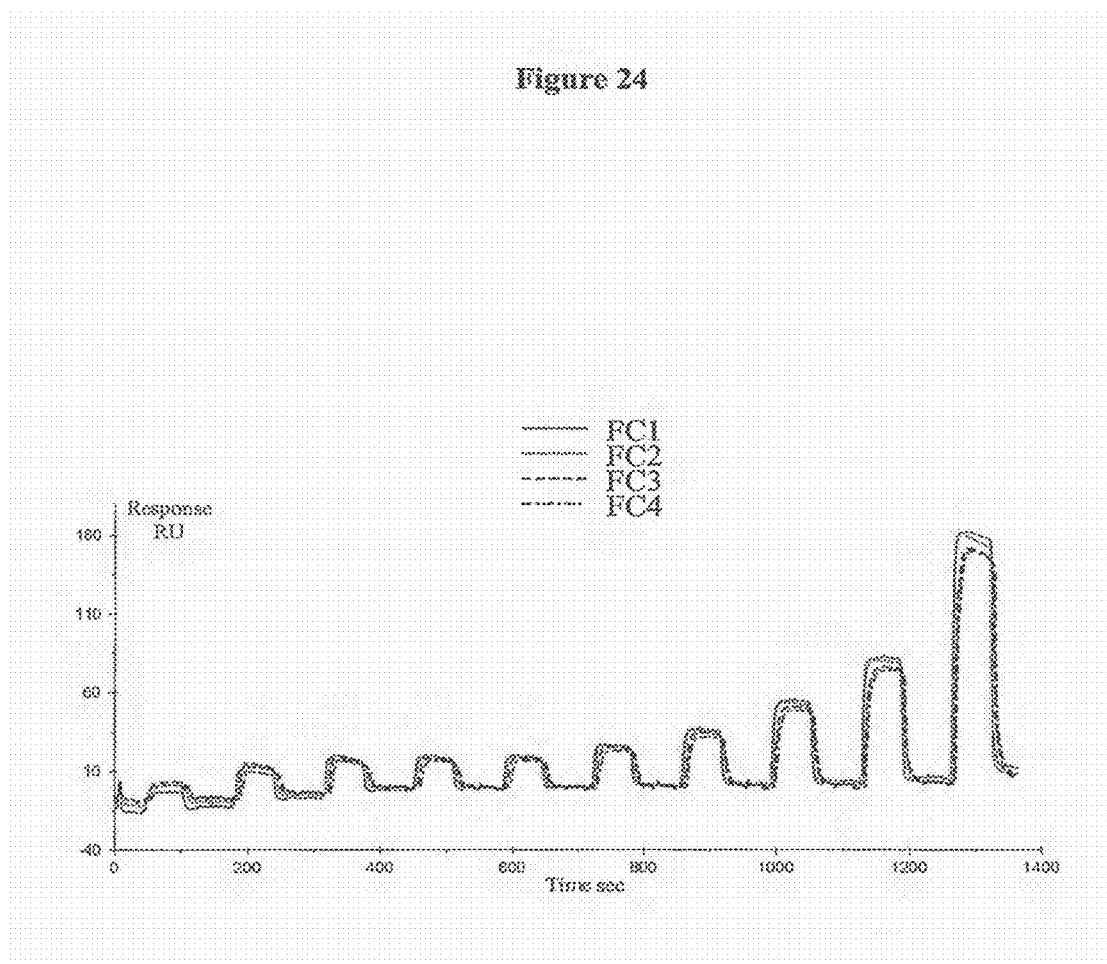

Response RU

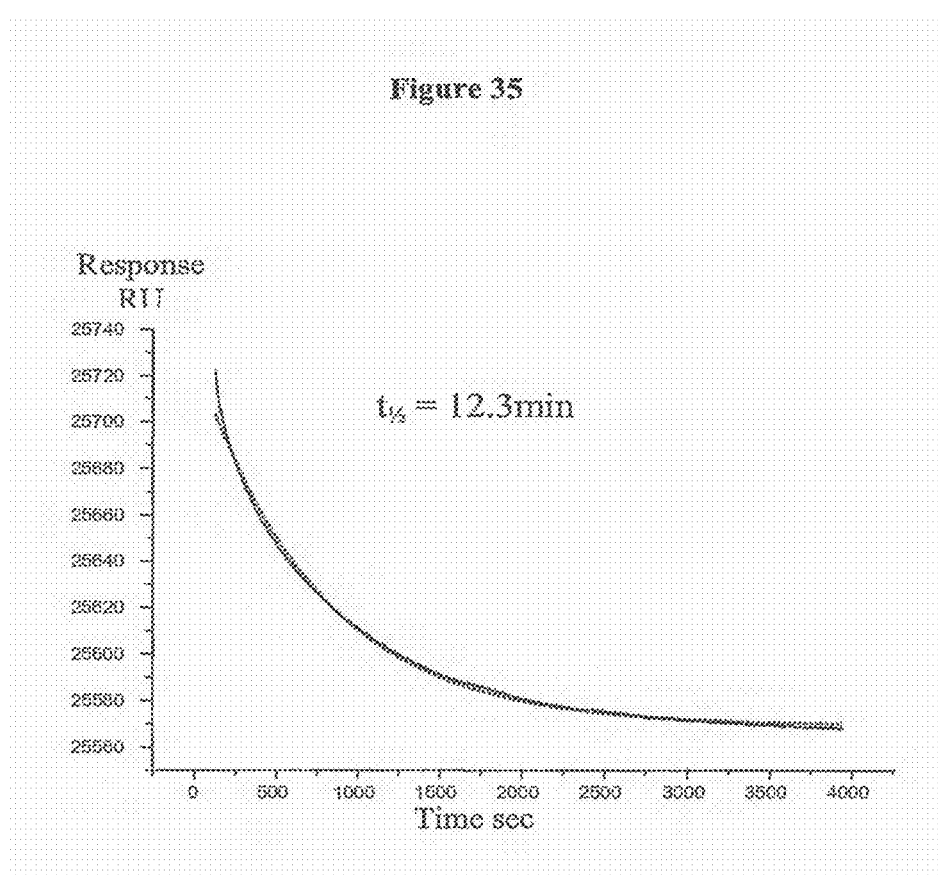

Figure 38A

MNAGVTQTPKF QVLKTGQSMT LQCAQDMNHE YMSWYRQDPG
MGLRLIHYSV GAGITDQGEV PNGYNVSRST TEDFPLRLLS AAPSQTSVYF
CASRPGLAGG RPEQYFGPGT RLTVT (SEQ ID 171)

Figure 38B

MNAGVTQTPKF QVLKTGQSMT LQCAQDMNHE YMSWYRQDPG
MGLRLIHYSV GAGITDQGEV PNGYNVSRST TEDFPLRLLS AAPSQTSVYF
CASRPGLMSAXPEQYFGPGT RLTVT (SEQ ID 172)

X denotes a position at which amino acids E, Q or R can be inserted.

Figure 38C

MNAGVTQTPKF QVLKTGQSMT LQCAQDMNHE YMSWYRQDPG
MGLRLIHYSV GAGITDQGEV PNGYNVSRST TEDFPLRLLS AAPSQTSVYF
CASRPGLAGG RPEDQYFGPGT RLTVT (SEQ ID 173)

Figure 38D

MNAGVTQTPKF QVLKTGQSMT LQCAQDMNHE YMSWYRQDPG
MGLRLIHYSV GAGITDQGEV PNGYNVSRST TEDFPLRLLS AAPSQTSVYF
CASRPGLVPG RPEQQFGPGT RLTVT (SEQ ID 174)

Figure 38E

MNAGVTQTPKF QVLKTGQSMT LQCAQDMNHE YMSWYRQDPG
MGLRLIHYSV GAGITDQGEV PNGYNVSRST TEDFPLRLLS AAPSQTSVYF
CASRPGLAGG RPHPQFGPGT RLTVT (SEQ ID 175)

T CELL RECEPTOR DISPLAY

CROSS REFERENCE TO RELATED APPLICATION

This application is a divisional of U.S. application Ser. No. 12/603,255 filed Oct. 21, 2009, which is a divisional of U.S. application Ser. No. 10/532,879 filed Apr. 25, 2006, now abandoned, which is a U.S. National Stage application of co-pending PCT application PCT/GB2003/04636 filed Oct. 30, 2003, which claims the priority of Great Britain Patent Application No. 0226227.7, filed Nov. 9, 2002; Great Britain Patent Application No. 0301814.0, filed Jan. 25, 2003; Great Britain Patent Application No. 0304067.2, filed Feb. 22, 2003; U.S. Provisional Patent Application No. 60/463,046, filed Apr. 16, 2003; Great Britain Patent Application No. 0311397.4, filed May 16, 2003; and Great Britain Patent Application No. 0316356.5, filed Jul. 11, 2003. These applications are incorporated herein by reference in their entireties.

SEQUENCE LISTING

This application incorporates by reference the contents of a 97.9 kb text file created on Jun. 23, 2011 and named 12603255.txt which is the sequence listing for this application.

The present invention relates to proteinaceous particles, for example phage or ribosome particles, displaying T cell receptors (TCRs), and diverse libraries thereof.

BACKGROUND TO THE INVENTION

Native TCRs

As is described in, for example, WO 99/60120 TCRs mediate the recognition of specific Major Histocompatibility Complex (MHC)-peptide complexes by T cells and, as such, are essential to the functioning of the cellular arm of the immune system.

Antibodies and TCRs are the only two types of molecules which recognise antigens in a specific manner, and thus the TCR is the only receptor for particular peptide antigens presented in MHC, the alien peptide often being the only sign of an abnormality within a cell. T cell recognition occurs when a T-cell and an antigen presenting cell (APC) are in direct physical contact, and is initiated by ligation of antigen-specific TCRs with pMHC complexes.

The native TCR is a heterodimeric cell surface protein of the immunoglobulin superfamily which is associated with invariant proteins of the CD3 complex involved in mediating signal transduction. TCRs exist in αβ and γδ forms, which are structurally similar but have quite distinct anatomical locations and probably functions. The MHC class I and class II ligands are also immunoglobulin superfamily proteins but are specialised for antigen presentation, with a highly polymorphic peptide binding site which enables them to present a diverse array of short peptide fragments at the APC cell surface.

Two further classes of proteins are known to be capable of functioning as TCR ligands. (1) CD1 antigens are MHC class I-related molecules whose genes are located on a different chromosome from the classical MHC class I and class II antigens. CD1 molecules are capable of presenting peptide and non-peptide (e.g, lipid, glycolipid) moieties to T cells in a manner analogous to conventional class I and class II-MHC-pep complexes. See, for example (Barclay et al, (1997) The Leucocyte Antigen Factsbook 2nd Edition, Academic Press) and (Bauer (1997) Eur J Immunol 27 (6) 1366-1373)) (2) Bacterial superantigens are soluble toxins which are capable of binding both class II MHC molecules and a subset of TCRs. (Fraser (1989) Nature 339 221-223) Many superantigens exhibit specificity for one or two Vbeta segments, whereas others exhibit more promiscuous binding. In any event, superantigens are capable of eliciting an enhanced immune response by virtue of their ability to stimulate subsets of T cells in a polyclonal fashion.

The extracellular portion of native heterodimeric αβ and γδ TCRs consist of two polypeptides each of which has a membrane-proximal constant domain, and a membrane-distal variable domain. Each of the constant and variable domains includes an intra-chain disulfide bond. The variable domains contain the highly polymorphic loops analogous to the complementarity determining regions (CDRs) of antibodies.

CDR3 of αβ TCRs interact with the peptide presented by MHC, and CDRs 1 and 2 of αβ TCRs interact with the peptide and the MHC. The diversity of TCR sequences is generated via somatic rearrangement of linked variable (V), diversity (D), joining (J), and constant genes Functional α and γ chain polypeptides are formed by rearranged V-J-C regions, whereas β and δ chains consist of V-D-J-C regions. The extracellular constant domain has a membrane proximal region and an immunoglobulin region. There are single α and δ chain constant domains, known as TRAC and TRDC respectively. The β chain constant domain is composed of one of two different β constant domains, known as TRBC1 and TRBC2 (IMGT nomenclature). There are four amino acid changes between these β constant domains, three of which are within the domains used to produce the single-chain TCRs displayed on phage particles of the present invention. These changes are all within exon 1 of TRBC1 and TRBC2: $N_4K_5$->$K_4N_5$ and $F_{37}$->$Y$ (IMGT numbering, differences TRBC1->TRBC2), the final amino acid change between the two TCR β chain constant regions being in exon 3 of TRBC1 and TRBC2: $V_1$->$E$. The constant γ domain is composed of one of either TRGC1, TRGC2(2×) or TRGC2(3×). The two TRGC2 constant domains differ only in the number of copies of the amino acids encoded by exon 2 of this gene that are present.

The extent of each of the TCR extracellular domains is somewhat variable. However, a person skilled in the art can readily determine the position of the domain boundaries using a reference such as The T Cell Receptor Facts Book, Lefranc & Lefranc, Publ. Academic Press 2001.

Recombinant TCRs

The production of recombinant TCRs is beneficial as these provide soluble TCR analogues suitable for the following purposes:

Studying the TCR/ligand interactions (e.g. pMHC for αβ TCRs)

Screening for inhibitors of TCR-associated interactions

Providing the basis for potential therapeutics

A number of constructs have been devised to date for the production of recombinant TCRs. These constructs fall into two broad classes, single-chain TCRs and dimeric TCRs, the literature relevant to these constructs is summarized below.

Single-chain TCRs (scTCRs) are artificial constructs consisting of a single amino acid strand, which like native heterodimeric TCRs bind to MHC-peptide complexes. Unfortunately, attempts to produce functional alpha/beta analogue scTCRs by simply linking the alpha and beta chains such that both are expressed in a single open reading frame have been unsuccessful, presumably because of the natural instability of the alpha-beta soluble domain pairing.

Accordingly, special techniques using various truncations of either or both of the alpha and beta chains have been necessary for the production of scTCRs. These formats appear to be applicable only to a very limited range of scTCR sequences. Soo Hoo et al (1992) PNAS. 89 (10): 4759-63 report the expression of a mouse TCR in single chain format from the 2C T cell clone using a truncated beta and alpha chain linked with a 25 amino acid linker and bacterial periplasmic expression (see also Schodin et al (1996) Mol. Immunol. 33 (9): 819-29). This design also forms the basis of the m6 single-chain TCR reported by Holler et al (2000) PNAS. 97 (10): 5387-92 which is derived from the 2C scTCR and binds to the same H2-Ld-restricted alloepitope. Shusta et al (2000) Nature Biotechnology 18: 754-759 and U.S. Pat. No. 6,423,538 report using a murine single-chain 2C TCR constructs in yeast display experiments, which produced mutated TCRs with, enhanced thermal stability and solubility. This report also demonstrated the ability of these displayed 2C TCRs to selectively bind cells expressing their cognate pMHC. Khandekar et al (1997) J. Biol. Chem. 272 (51): 32190-7 report a similar design for the murine D10 TCR, although this scTCR was fused to MBP and expressed in bacterial cytoplasm (see also Hare et al (1999) Nat. Struct. Biol. 6 (6): 574-81). Hilyard et al (1994) PNAS. 91 (19): 9057-61 report a human scTCR specific for influenza matrix protein-HLA-A2, using a Vα-linker-Vβ design and expressed in bacterial periplasm.

Chung et al (1994) PNAS. 91 (26) 12654-8 report the production of a human scTCR using a Vα-linker-Vβ-Cβ design and expression on the surface of a mammalian cell line. This report does not include any reference to peptide-HLA specific binding of the scTCR. Plaksin et al (1997) J. Immunol. 158 (5): 2218-27 report a similar Vα-linker-Vβ-Cβ design for producing a murine scTCR specific for an HIV gp120-H-2D$^d$ epitope. This scTCR is expressed as bacterial inclusion bodies and refolded in vitro.

A number of papers describe the production of TCR heterodimers which include the native disulphide bridge which connects the respective subunits (Garboczi, et al., (1996), Nature 384(6605): 134-41; Garboczi, et al., (1996), J Immunol 157(12): 5403-10; Chang et al., (1994), PNAS USA 91: 11408-11412; Davodeau et al., (1993), *J. Biol. Chem.* 268 (21): 15455-15460; Golden et al., (1997), J. Imm. Meth. 206: 163-169; U.S. Pat. No. 6,080,840). However, although such TCRs can be recognised by TCR-specific antibodies, none were shown to recognise its native ligand at anything other than relatively high concentrations and/or were not stable.

In WO 99/60120, a soluble TCR is described which is correctly folded so that it is capable of recognising its native ligand, is stable over a period of time, and can be produced in reasonable quantities. This TCR comprises a TCR α or γ chain extracellular domain dimerised to a TCR β or δ chain extracellular domain respectively, by means of a pair of C-terminal dimerisation peptides, such as leucine zippers. This strategy of producing TCRs is generally applicable to all TCRs.

Reiter et al, Immunity, 1995, 2:281-287, details the construction of a soluble molecule comprising disulphide-stabilised TCR α and β variable domains, one of which is linked to a truncated form of *Pseudomonas* exotoxin (PE38). One of the stated reasons for producing this molecule was to overcome the inherent instability of single-chain TCRs. The position of the novel disulphide bond in the TCR variable domains was identified via homology with the variable domains of antibodies, into which these have previously been introduced (for example see Brinkmann, et al. (1993), Proc. Natl. Acad. Sci. USA 90: 7538-7542, and Reiter, et al. (1994) Biochemistry 33: 5451-5459). However, as there is no such homology between antibody and TCR constant domains, such a technique could not be employed to identify appropriate sites for new inter-chain disulphide bonds between TCR constant domains.

As mentioned above Shusta et at (2000) Nature Biotechnology 18: 754-759 report using single-chain 2 C TCR constructs in yeast display experiments. The principle of displaying scTCRs on phage particles has previously been discussed. For example, WO 99/19129 details the production of scT-CRs, and summarise a potential method for the production of phage particles displaying scTCRs of the Vα-Linker-VβCβ format. However, this application contains no exemplification demonstrating the production of said phage particles displaying TCR. The application does however refer to a co-pending application:

"The construction of DNA vectors including a DNA segment encoding a sc-TCR molecules fused to a bacteriophage coat protein (gene II or gene VIII) have been described in said pending U.S. application Ser. No. 08/813,781."

Furthermore, this application relies on the ability of anti-TCR antibodies or superantigen MHC complexes to recognise the soluble, non-phage displayed, scTCRs produced to verify their correct conformation. Therefore, true peptide-MHC binding specificity of the scTCRs, in any format, is not conclusively demonstrated.

Finally, a further study (Onda et al., (1995) Molecular Immunology 32 (17-18) 1387-1397) discloses the phage display of two murine TCR α chains in the absence of their respective β chains. This study demonstrated that phage particles displaying one of the TCR α chains (derived from the A1.1 murine hybridoma) bound preferentially to the same peptides immobilised in microtitre wells that the complete TCR would normally respond to when there were presented by the murine Class I MHC I-A$^d$.

Screening Use

A number of important cellular interactions and cell responses, including the TCR-mediated immune synapse, are controlled by contacts made between cell surface receptors and ligands presented on the surfaces of other cells. These types of specific molecular contacts are of crucial importance to the correct biochemical regulation in the human body and are therefore being studied intensely. In many cases, the objective of such studies is to devise a means of modulating cellular responses in order to prevent or combat disease.

Therefore, methods with which to identify compounds that bind with some degree of specificity to human receptor or ligand molecules are important as leads for the discovery and development of new disease therapeutics. In particular, compounds that interfere with certain receptor-ligand interactions have immediate potential as therapeutic agents or carriers.

Advances in combinatorial chemistry, enabling relatively easy and cost-efficient production of very large compound libraries have increased the scope for compound testing enormously. Now the limitations of screening programmes most often reside in the nature of the assays that can be employed, the production of suitable receptor and ligand molecules and how well these assays can be adapted to high throughput screening methods.

Display Methods

It is often desirable to present a given peptide or polypeptide on the surface of a proteinaceous particle. Such particles may serve as purification aids for the peptide or polypeptide (since the particles carrying the peptide or polypeptide may be separated from unwanted contaminants by sedimentation or other methods). They may also serve as particulate vaccines, the immune response to the surface displayed peptide or polypeptide being stimulated by the particulate presentation. Protein p24 of the yeast retrotransposon, and the hepatitis B surface coat protein are examples of proteins which self assemble into particles. Fusion of the peptide or polypeptide of interest to these particle-forming proteins is a recognised way of presenting the peptide or polypeptide on the surface of the resultant particles.

However, particle display methods have primarily been used to identify proteins with desirable properties such as enhanced expression yields, binding and/or stability characteristics. These methods involve creating a diverse pool or 'library' of proteins or polypeptides expressed on the surface of proteinaceous particles. These particles have two key features, firstly each particle presents a single variant protein or polypeptide, and secondly the genetic material encoding the expressed protein or polypeptide is associated with that of the particle. This library is then subjected to one or more rounds of selection. For example, this may consist of contacting a ligand with a particle-display library of mutated receptors and identifying which mutated receptors bind the ligand with the highest affinity. Once the selection process has been completed the receptor or receptors with the desired properties can be isolated, and their genetic material can be amplified in order to allow the receptors to be sequenced. These display methods fall into two broad categories, in-vitro and in-vivo display.

All in-vivo display methods rely on a step in which the library, usually encoded in or with the genetic nucleic acid of a replicable particle such as a plasmid or phage replicon is transformed into cells to allow expression of the proteins or polypeptides. (Plückthun (2001) Adv Protein Chem 55 367-403). There are a number of replicon/host systems that have proved suitable for in-vivo display of protein or polypeptides. These include the following
  Phage/bacterial cells
  plasmid/CHO cells
  Vectors based on the yeast 2 μm plasmid/yeast cells
  bacculovirus/insect cells
  plasmid/bacterial cells In-vivo display methods include cell-surface display methods in which a plasmid is introduced into the host cell encoding a fusion protein consisting of the protein or polypeptide of interest fused to a cell surface protein or polypeptide. The expression of this fusion protein leads to the protein or polypeptide of interest being displayed on the surface of the celL The cells displaying these proteins or polypeptides of interest can then be subjected to a selection process such as FACS and the plasmids obtained from the selected cell or cells can be isolated and sequenced. Cell surface display systems have been devised for mammalian cells (Higuschi (1997) J. Immunol. Methods 202 193-204), yeast cells (Shusta (1999) J Mol Biol 292 949-956) and bacterial cells (Sameulson (2002) J. Biotechnol 96 (2) 129-154).

Numerous reviews of the various in-vivo display techniques have been published. For example, (Hudson (2002) Expert Opin Biol Ther (2001) 1 (5) 845-55) and (Schmitz (2000) 21 (Supp A) S106-S112).

In-vitro display methods are based on the use of ribosomes to translate libraries of mRNA into a diverse array of protein or polypeptide variants. The linkage between the proteins or polypeptides formed and the mRNA encoding these molecules is maintained by one of two methods. Conventional ribosome display utilises mRNA sequences that encode a short (typically 40-100 amino acid) linker sequence and the protein or polypeptide to be displayed. The linker sequence allow the displayed protein or polypeptide sufficient space to re-fold without being sterically hindered by the ribosme. The mRNA sequence lacks a 'stop' codon, this ensures that the expressed protein or polypeptide and the RNA remain attached to the ribosome particle. The related mRNA display method is based on the preparation of mRNA sequences encoding the protein or polypeptide of interest and DNA linkers carrying a puromycin moiety. As soon as the ribosome reaches the mRNA/DNA junction translation is stalled and the puromycin forms a covalent linkage to the ribosome. For a recent review of these two related in-vitro display methods see (Amstutz (2001) Curr Opin Biotechnol 12 400-405).

Particularly preferred is the phage display technique which is based on the ability of bacteriophage particles to express a heterologous peptide or polypeptide fused to their surface proteins. (Smith (1985) Science 217 1315-1317). The procedure is quite general, and well understood in the art for the display of polypeptide monomers. However, in the case of polypeptides that in their native form associate as dimers, only the phage display of antibodies appears to have been thoroughly investigated.

For monomeric polypeptide display there are two main procedures:

Firstly (Method A) by inserting into a vector (phagemid) DNA encoding the heterologous peptide or polypeptide fused to the DNA encoding a bacteriophage coat protein. The expression of phage particles displaying the heterologous peptide or polypeptide is then carried out by transfecting bacterial cells with the phagemid, and then infecting the transformed cells with a 'helper phage'. The helper phage acts as a source of the phage proteins not encoded by the phagemid required to produce a functional phage particle.

Secondly (Method B), by inserting DNA encoding the heterologous peptide or polypeptide into a complete phage genome fused to the DNA encoding a bacteriophage coat protein. The expression of phage particles displaying the heterologous peptide or polypeptide is then carried out by infecting bacterial cells with the phage genome. This method has the advantage of the first method of being a 'single-step' process. However, the size of the heterologous DNA sequence that can be successfully packaged into the resulting phage particles is reduced. M13, T7 and Lambda are examples of suitable phages for this method.

A variation on (Method B) the involves adding a DNA sequence encoding a nucleotide binding domain to the DNA in the phage genome encoding the heterologous peptide be displayed, and further adding the corresponding nucleotide binding site to the phage genome. This causes the heterologous peptide to become directly attached to the phage genome. This peptide/genome complex is then packaged into a phage particle which displays the heterologous peptide. This method is fully described in WO 99/11785.

The phage particles can then be recovered and used to study the binding characteristics of the heterologous peptide or polypeptide. Once isolated, phagemid or phage DNA can be recovered from the peptide- or polypeptide-displaying phage particle, and this DNA can be replicated via PCR. The PCR product can be used to sequence the heterologous peptide or polypeptide displayed by a given phage particle.

The phage display of single-chain antibodies and fragments thereof, has become a routine means of studying the binding characteristics of these polypeptides. There are numerous books available that review phage display techniques and the biology of the bacteriophage. (See, for example, Phage Display—A Laboratory Manual, Barbas et al., (2001) Cold Spring Harbour Laboratory Press).

A third phage display method (Method C) relies on the fact that heterologous polypeptides having a cysteine residue at a desired location can be expressed in a soluble form by a phagemid or phage genome, and caused to associate with a modified phage surface protein also having a cysteine residue at a surface exposed position, via the formation of a disulphide linkage between the two cysteines. WO 01/05950 details the use of this alternative linkage method for the expression of single-chain antibody-derived peptides.

BRIEF DESCRIPTION OF THE INVENTION

Native TCR's are heterodimers which have lengthy transmembrane domains which are essential to maintain their stability as functional dimers. As discussed above, TCRs are useful for research and therapeutic purposes in their soluble forms so display of the insoluble native form has little utility. On the other hand, soluble stable forms of TCRs have proved difficult to design, and since most display methods appear to have been described only for monomeric peptides and polypeptides, display methods suitable for soluble dimeric TCRs have not been investigated. Furthermore, since the functionality of the displayed TCR depends on proper association of the variable domains of the TCR dimer, successful display of a functional dimeric TCR is not trivial.

WO 99/18129 contains the statement: "DNA constructs encoding the sc-TCR fusion proteins can be used to make a bacteriophage display library in accordance with methods described in pending U.S. application Ser. No. 08/813,781 filed on Mar. 7, 1997, the disclosure of which is incorporated herein by reference.", but no actual description of such display is included in this application. However, The inventors of this application published a paper (Weidanz (1998) J Immunol Methods 221 59-76) that demonstrates the display of two murine scTCRs on phage particles.

WO 01/62908 discloses methods for the phage display of scTCRs and scTCR/Ig fusion proteins. However, the functionality (specific pMHC binding) of the constructs disclosed was not assessed.

Finally, a retrovirus-mediated method for the display of diverse TCR libraries on the surface of immature T cells has been demonstrated for a murine TCR. The library of mutated TCRs displayed of the surface of the immature T cells was screened by flow cytometry using pMHC tetramers, and this lead to the identification TCR variants that were either specific for the cognate pMHC, or a variant thereof. (Helmut et al., (2000) PNAS 97 (26) 14578-14583)

This invention is based in part on the finding that single chain and dimeric TCRs can be expressed as surface fusions to proteinaceous particles, and makes available proteinaceous particles displaying alpha/beta-analogue and gamma/delta-analogue scTCR and dTCR constructs. The proteinaceous particles on which the TCRs are displayed include self-aggregating particle-forming proteins, phage, virus-derived, ribosome particles and cells with a cell surface protein or polypeptide molecules to which the TCR is covalently linked. Such proteinaceous particle-displayed TCRs are useful for purification and screening purposes, particularly as a diverse library of particle displayed TCRs for biopanning to identify TCRs with desirable characteristics such as high affinity for the target MHC-peptide complex. In the latter connection, particle-displayed scTCRs may be useful for identification of the desired TCR, but that information may be better applied to the construction of analogous dimeric TCRs for ultimate use in therapy. The invention also includes high affinity TCRs identifiable by these methods.

DETAILED DESCRIPTION OF THE INVENTION

In one broad aspect, he present invention provides a proteinaceous particle displaying on its surface a T-cell receptor (TCR), characterised in that (i) the proteinaceous particle is a ribosome and the TCR is a single chain TCR (scTCR) polypeptide, or dimeric TCR (dTCR) polypeptide pair, or (ii) the proteinaceous particle is a phage particle, or a cell with cell surface protein or polypeptide molecules to which the TCR is covalently linked, and the TCR is a human scTCR or a human dTCR polypeptide pair, or (iii) the proteinaceous particle is a phage particle, or a cell with cell surface protein or polypeptide molecules to which the TCR is covalently linked, and the TCR is a non-human dTCR polypeptide pair, or (iv) the proteinaceous particle is a phage particle, or a cell with cell surface protein or polypeptide molecules to which the TCR is covalently linked, and the TCR is a scTCR polypeptide comprising TCR amino acid sequences corresponding to extracellular constant and variable domain sequences present in native TCR chains and a linker sequence, the latter linking a variable domain sequence corresponding to that of one chain of a native TCR to a constant domain sequence corresponding to a constant domain sequence of another native TCR chain, and a disulfide bond which has no equivalent in native T cell receptors links residues of the constant domain sequences.

In one preferred embodiment, the invention provides A proteinaceous particle, displaying on its surface a dimeric T-cell receptor (dTCR) polypeptide pair, or a single chain T-cell receptor (scTCR) polypeptide wherein the dTCR polypeptide pair is constituted by TCR amino acid sequences corresponding to extracellular constant and variable domain sequences present in native TCR chains, and the scTCR is constituted by TCR amino acid sequences corresponding to extracellular constant and variable domain sequences present in native TCR chains and a linker sequence, the latter linking a variable domain sequence corresponding to that of one chain of a native TCR to a constant domain sequence corresponding to a constant domain sequence of another native TCR chain; wherein the variable domain sequences of the dTCR polypeptide pair or scTCR polypeptide are mutually orientated substantially as in native TCRs, and in the case of the scTCR polypeptide a disulfide bond which has no equivalent in native T cell receptors links residues of the polypeptide.

In the case of αβ scTCRs or dTCRs displayed according to the invention, a requirement that the variable domain sequences of the α and β segments are mutually orientated substantially as in native αβ T cell receptors is merely an alternative way of saying that the TCRs are functional, and this can be tested by confirming that the molecule binds to the relevant TCR ligand (pMHC complex, CD1-antigen complex, superantigen or superantigen/pMHC complex)—if it binds, then the requirement is met. Interactions with pMHC complexes can be measured using a Biacore 3000™ or Biacore2000™ instrument. WO99/6120 provides detailed descriptions of the methods required to analyse TCR binding to MHC-peptide complexes. These methods are equally applicable to the study of TCR/CD1 and TCR/superantigen interactions. In order to apply these methods to the study of TCR/CD1 interactions soluble forms of CD1 are required, the production of which are described in (Bauer (1997) Eur J Immunol 27 (6) 1366-1373). In the case of γδ TCRs of the present invention the cognate ligands for these molecules are unknown therefore secondary means of verifying their conformation such as recognition by antibodies can be employed. The monoclonal antibody MCA991T (available from Serotec), specific for the δ chain variable region, is an example of an antibody appropriate for this task.

The scTCRs or dTCRs of the present invention may be displayed on proteinaceous particles, for example phage particles, preferably filamentous phage particles, by, for example, the following two means:
  (i) The C-terminus of one member of the dTCR polypeptide pair, or the C-terminus of the scTCR polypeptide, or the C-terminus of a short peptide linker attached to the C-terminus of either, can be directly linked by a peptide bond to a surface exposed residue of the proteinaceous particle. For example, the said surface exposed residue is preferably at the N-terminus of the gene product of bacteriophage gene III or gene VIII; and
  (ii) The C-terminus of one member of the dTCR polypeptide pair, or the C-terminus of the scTCR polypeptide, or the C-terminus of a short peptide linker attached to the C-terminus of either, is linked by a disulfide bond to a surface exposed cysteine residue of the proteinaceous particle via an introduced cysteine residue. For example, the said surface exposed residue is again preferably at the N-terminus of the gene product of bacteriophage gene III or gene VIII.

Method (i) above is preferred. In the case of a scTCR, nucleic acid encoding the TCR may be fused to nucleic acid encoding the particle forming protein or a surface protein of the replicable particle such as a phage or cell. Alternatively, nucleic acid representing mRNA but without a stop codon, or fused to puromycin RNA may be translated by ribosome such that the TCR remains fused to the ribosome particle. In the case of a dTCR, nucleic acid encoding one chain of the TCR may be fused to nucleic acid encoding the particle forming protein or a cell surface protein of the replicable particle such as a phage or cell, and the second chain of the TCR polypeptide pair may be allowed to associate with the resultant expressed particle displaying the first chain. Proper functional association of the two chains may be assisted by the presence of cysteines in the constant domain of the two chains which are capable of forming an interchain disulfide bond, as more fully discussed below.

The Displayed scTCR

The displayed scTCR polypeptide may be, for example, one which has
  a first segment constituted by an amino acid sequence corresponding to a TCR α or β chain variable domain sequence fused to the N terminus of an amino acid sequence corresponding to α TCR a chain constant domain extracellular sequence,
  a second segment constituted by an amino acid sequence corresponding to a TCR β or γ chain variable domain fused to the N terminus of an amino acid sequence corresponding to TCR β chain constant domain extracellular sequence,
  a linker sequence linking the C terminus of the first segment to the N terminus of the second segment, or vice versa, and
  a disulfide bond between the first and second chains, said disulfide bond being one which has no equivalent in native αβ or γδ T cell receptors,
  the length of the linker sequence and the position of the disulfide bond being such that the variable domain sequences of the first and second segments are mutually orientated substantially as in native αβ or γδ T cell receptors.

Alternatively, the displayed scTCR may be one which has
  a first segment constituted by an amino acid sequence corresponding to a TCR α or δ chain variable domain
  a second segment constituted by an amino acid sequence corresponding to a TCR β or γ chain variable domain sequence fused to the N terminus of an amino acid sequence corresponding to a TCR β chain constant domain extracellular sequence, and
  a linker sequence linking the C terminus of the first segment to the N terminus of the second segment,
PROVIDED THAT where the proteinaceous particle is a phage, the scTCR corresponds to a human TCR; or
  One which has
    a first segment constituted by an amino acid sequence corresponding to a TCR β or γ chain variable domain
    a second segment constituted by an amino acid sequence corresponding to a TCR α or δ chain variable domain sequence fused to the N terminus of an amino acid sequence corresponding to a TCR α chain constant domain extracellular sequence, and
    a linker sequence linking the C terminus of the first segment to the N terminus of the second segment
PROVIDED THAT where the proteinaceous particle is a phage, the scTCR corresponds to a human TCR.

The Displayed dTCR

The dTCR which is displayed on the proteinaceous particle may be one which is constituted by
  a first polypeptide wherein a sequence corresponding to a TCR α or γ chain variable region sequence is fused to the N terminus of a sequence corresponding to a TCR β chain constant domain extracellular sequence, and
  a second polypeptide wherein a sequence corresponding to a TCR β or γ chain variable domain sequence fused to the N terminus a sequence corresponding to a TCR β chain constant domain extracellular sequence,
the first and second polypeptides being linked by a disulfide bond which has no equivalent in native αβ or γδ T cell receptors.

Preferably, the dTCR is displayed on a filamentous phage particle and is one which is constituted by
  a first polypeptide wherein a sequence corresponding to a TCR α chain variable domain sequence is fused to the N terminus of a sequence corresponding to a TCR α chain constant domain extracellular sequence, and
  a second polypeptide wherein a sequence corresponding to a TCR β chain variable domain sequence is fused to the N terminus a sequence corresponding to a TCR β chain constant domain extracellular sequence,
the first and second polypeptides being linked by a disulfide bond between cysteine residues substituted for Thr 48 of exon 1 of TRAC*01 and Ser 57 of exon 1 of TRBC1*01 or TRBC2*01 or the non-human equivalent thereof,
the C-terminus of one member of the dTCR polypeptide pair being linked by a peptide bond to a coat protein of the phage.

dTCR Polypeptide Pair and scTCR Polypeptide

The constant domain extracellular sequences present in the scTCRs or dTCRs preferably correspond to those of a human TCR, as do the variable domain sequences. However, the correspondence between such sequences need not be 1:1 on an amino acid level. N- or C-truncation, and/or amino acid deletion and/or substitution relative to the corresponding human TCR sequences is acceptable. In particular, because the constant domain extracellular sequences present in the first and second segments are not directly involved in contacts with the ligand to which the scTCR or dTCR binds, they may be shorter than, or may contain substitutions or deletions relative to, extracellular constant domain sequences of native TCRs.

The constant domain extracellular sequence present in one of the dTCR polypeptide pair, or in the first segment of a scTCR polypeptide may include a sequence corresponding to the extracellular constant Ig domain of a TCR α chain, and/or the constant domain extracellular sequence present in the other member of the pair or second segment may include a sequence corresponding to the extracellular constant Ig domain of a TCR β chain.

In one embodiment of the invention, one member of the dTCR polypeptide pair, or the first segment of the scTCR polypeptide, corresponds to substantially all the variable domain of a TCR α chain fused to the N terminus of substantially all the extracellular domain of the constant domain of an TCR α chain; and/or the other member of the pair or second segment corresponds to substantially all the variable domain of a TCR β chain fused to the N terminus of substantially all the extracellular domain of the constant domain of a TCR β chain.

In another embodiment, the constant domain extracellular sequences present in the dTCR polypeptide pair, or first and second segments of the scTCR polypeptide, correspond to the constant domains of the α and β chains of a native TCR truncated at their C termini such that the cysteine residues which form the native inter-chain disulfide bond of the TCR are excluded. Alternatively those cysteine residues may be substituted by another amino acid residue such as serine or alanine, so that the native disulfide bond is deleted. In addition, the native TCR β chain contains an unpaired cysteine residue and that residue may be deleted from, or replaced by a non-cysteine residue in, the β sequence of the scTCR of the invention.

In one particular embodiment of the invention, the TCR α and β chain variable domain sequences present in the dTCR polypeptide pair, or first and second segments of the scTCR polypeptide, may together correspond to the functional variable domain of a first TCR, and the TCR α and β chain constant domain extracellular sequences present in the dTCR polypeptide pair or first and second segments of the scTCR polypeptide may correspond to those of a second TCR, the first and second TCRs being from the same species. Thus, the α and β chain variable domain sequences present in dTCR polypeptide pair, or first and second segments of the scTCR polypeptide, may correspond to those of a first human TCR, and the α and β constant domain extracellular sequences may correspond to those of a second human TCR. For example, A6 Tax sTCR constant domain extracellular sequences can be used as a framework onto which heterologous α and β variable domains can be fused.

In another embodiment of the invention, the TCR δ and γ chain variable domain sequences present in the dTCR polypeptide pair or first and second segments of the scTCR polypeptide respectively, may together correspond to the functional variable domain of a first TCR, and the TCR α and β chain constant domain extracellular sequences present in the dTCR polypeptide pair or first and second segments of the scTCR polypeptide respectively, may correspond to those of a second TCR, the first and second TCRs being from the same species. Thus the δ and γ chain variable domain sequences present in the dTCR polypeptide pair or first and second segments of the scTCR polypeptide may correspond to those of a first human TCR, and the α and β chain constant domain extracellular sequences may correspond to those of a second human TCR. For example, A6 Tax sTCR constant domain extracellular sequences can be used as a framework onto which heterologous γ and δ variable domains can be fused.

In one particular embodiment of the invention, the TCR α and β, or δ and γ chain variable domain sequences present in the dTCR polypeptide pair or first and second segments of the scTCR polypeptide may together correspond to the functional variable domain of a first human TCR, and the TCR α and β chain constant domain extracellular sequences present in the dTCR polypeptide pair or first and second segments of the scTCR polypeptide may correspond to those of a second non-human TCR, Thus the α and β, or δ and γ chain variable domain sequences present dTCR polypeptide pair or first and second segments of the scTCR polypeptide may correspond to those of a first human TCR, and the α and β chain constant domain extracellular sequences may correspond to those of a second non-human TCR. For example, murine TCR constant domain extracellular sequences can be used as a framework onto which heterologous human α and β TCR variable domains can be fused.

Linker in the scTCR Polypeptide

For scTCR-displaying proteinaceous particles of the present invention, a linker sequence links the first and second TCR segments, to form a single polypeptide strand.

The linker sequence may, for example, have the formula —P-AA-P— wherein P is proline and AA represents an amino acid sequence wherein the amino acids are glycine and serine.

For the scTCR displayed by proteinaceous particles of the present invention to bind to a ligand, MHC-peptide complex in the case of αβ TCRs, the first and second segments are paired so that the variable domain sequences thereof are orientated for such binding. Hence the linker should have sufficient length to span the distance between the C terminus of the first segment and the N terminus of the second segment, or vice versa. On the other hand excessive linker length should preferably be avoided, in case the end of the linker at the N-terminal variable domain sequence blocks or reduces bonding of the scTCR to the target ligand.

For example, in the case where the constant domain extracellular sequences present in the first and second segments correspond to the constant domains of the α and β chains of a native TCR truncated at their C termini such that the cysteine residues which form the native interchain disulfide bond of the TCR are excluded, and the linker sequence links the C terminus of the first segment to the N terminus of the second segment.

The linker sequence may consist of, for example, from 26 to 41 amino acids, preferably 29, 30, 31 or 32 amino acids, or 33, 34, 35 or 36 amino acids. Particular linkers have the formula —PGGG-(SGGGG)$_5$-P— and —PGGG-(SGGGG)$_6$-P— wherein P is proline, G is glycine and S is serine.

Inter-Chain Disulfide Bond

A principle characterising feature of the preferred dTCRs and scTCRs displayed by proteinaceous particles of the present invention, is a disulfide bond between the constant domain extracellular sequences of the dTCR polypeptide pair or first and second segments of the scTCR polypeptide. That bond may correspond to the native inter-chain disulfide bond present in native dimeric αβ TCRs, or may have no counterpart in native TCRs, being between cysteines specifically incorporated into the constant domain extracellular sequences of dTCR polypeptide pair or first and second segments of the scTCR polypeptide. In some cases, both a native and a non-native disulfide bond may be desirable.

The position of the disulfide bond is subject to the requirement that the variable domain sequences of dTCR polypeptide pair or first and second segments of the scTCR polypeptide are mutually orientated substantially as in native αβ or γδ T cell receptors.

The disulfide bond may be formed by mutating non-cysteine residues on the first and second segments to cysteine, and causing the bond to be formed between the mutated residues. Residues whose respective β carbons are approximately 6 Å (0.6 nm) or less, and preferably in the range 3.5 Å

(0.35 nm) to 5.9 Å (0.59 nm) apart in the native TCR are preferred, such that a disulfide bond can be formed between cysteine residues introduced in place of the native residues. It is preferred if the disulfide bond is between residues in the constant immunoglobulin domain, although it could be between residues of the membrane proximal domain. Preferred sites where cysteines can be introduced to form the disulfide bond are the following residues in exon 1 of TRAC*01 for the TCR α chain and TRBC1*01 or TRBC2*01 for the TCR β chain:

| TCR α chain | TCR β chain | Native β carbon separation (nm) |
|---|---|---|
| Thr 48 | Ser 57 | 0.473 |
| Thr 45 | Ser 77 | 0.533 |
| Tyr 10 | Ser 17 | 0.359 |
| Thr 45 | Asp 59 | 0.560 |
| Ser 15 | Glu 15 | 0.59 |

The following motifs in the respective human TCR chains may be used to identify the residue to be mutated (the shaded residue is the residue for mutation to a cysteine).

α Chain Thr 48:
(SEQ ID 1)
DSDVYITDKTVLDMRSMDFK (amino acids 39-58 of exon 1 of the TRAC*01 gene)

α Chain Thr 45:
(SEQ ID 2)
QSKDSDVYITDKTVLDMRSM (amino acids 36-55 of exon 1 of the TRAC*01 gene)

α Chain Tyr 10:
(SEQ ID 3)
DIQNPDPAVYQLRDSKSSDK (amino acids 1-20 of exon 1 of the TRAC*01 gene)

α Chain Ser 15:
(SEQ ID 4)
DPAVYQLRDSKSSDKSVCLF (amino acids 6-25 of exon 1 of the TRAC*01 gene)

β Chain Ser 57:
(SEQ ID 5)
NGKEVHSGVSTDPQPLKEQP (amino acids 48-67 of exon 1 of the TRBC1*01 & TRBC2*01 genes)

β Chain Ser 77:
(SEQ ID 6)
ALNDSRYALSSRLRVSATFW (amino acids 68-87 of exon 1 of the TRBC1*01 & TRBC2*01 genes)

β Chain Ser 17:
(SEQ ID 7)
PPEVAVFEPSEAEISHTQKA (amino acids 8-27 of exon 1 of the TRBC1*01 & TRBC2*01 genes)

β Chain Asp 59:
(SEQ ID 8)
KEVHSGVSTDPQPLKEQPAL (amino acids 50-69 of exon 1 of the TRBC1*01 & TRBC2*01 genes gene)

β Chain Glu 15:
(SEQ ID 9)
VFPPEVAVFEPSEAEISHTQ (amino acids 6-25 of exon 1 of the TRBC1*01 & TRBC2*01 genes)

In other species, the TCR chains may not have a region which has 100% identity to the above motifs. However, those of skill in the art will be able to use the above motifs to identify the equivalent part of the TCR α or β chain and hence the residue to be mutated to cysteine. Alignment techniques may be used in this respect. For example, ClustalW, available on the European Bioinformatics Institute website (http://www.ebi.ac.uk/index.html) can be used to compare the motifs above to a particular TCR chain sequence in order to locate the relevant part of the TCR sequence for mutation.

The present invention includes within its scope proteinaceous particle-displayed αβ and γδ-analogue scTCRs, as well as those of other mammals, including, but not limited to, mouse, rat, pig, goat and sheep. As mentioned above, those of skill in the art will be able to determine sites equivalent to the above-described human sites at which cysteine residues can be introduced to form an inter-chain disulfide bond. For example, the following shows the amino acid sequences of the mouse Cα and Cβ soluble domains, together with motifs showing the murine residues equivalent to the human residues mentioned above that can be mutated to cysteines to form a TCR interchain disulfide bond (where the relevant residues are shaded):

Mouse Cα soluble domain:
(SEQ ID 10)
PYIQNPEPAVYQLKDPRSQDSTLCLFTDFDSQINVPKTMESGTFITDKTV
LDMKAMDSKSNGAIAWSNQTSFTCQDIFKETNATYPSSDVP Mouse Cβ soluble domain:
(SEQ ID 11)
EDLRNVTPPKVSLFEPSKAEIANKQKATLVCLARGFFPDHVELSWWVNGR
EVHSGVSTDPQAYKESNYSYCLSSRLRVSATFWHNPRNHFRCQVQFHGLS
EEDKWPEGSPKPVTQNISAEAWGRAD Murine equivalent of human α Chain Thr 48:
(SEQ ID 12)
ESGTFITDKTVLDMKAMDSK Murine equivalent of human α Chain Thr 45:
(SEQ ID 13)
KTMESGTFITDKTVLDMKAM Murine equivalent of human α Chain Tyr 10:
(SEQ ID 14)
YIQNPEPAVYQLKDPRSQDS Murine equivalent of human α Chain Ser 15:
(SEQ ID 15)
AVYQLKDPRSQDSTLCLFTD Murine equivalent of human β Chain Ser 57:
(SEQ ID 16)
NGREVHSGVSTDPQAYKESN Murine equivalent of human β Chain Ser 77:
(SEQ ID 17)
KESNYSYCLSSRLRVSATFW Murine equivalent of human β Chain Ser 17:
(SEQ ID 18)
PPKVSLFEPSKAEIANKQKA Murine equivalent of human β Chain Asp 59:
(SEQ ID 19)
REVHSGVSTDPQAYKESNYS Murine equivalent of human β Chain Glu 15:
(SEQ ID 20)
VTPPKVSLFEPSKAEIANKQ As discussed above, the A6 Tax sTCR extracellular constant domains can be used as framework onto which heterologous variable domains can be fused. It is preferred that the heterologous variable domain sequences are linked to the constant domain sequences at any point between the disulfide bond and the N termini of the constant domain sequences. In the case of the A6 Tax TCR α and β constant domain sequences, the disulfide bond may be formed between cysteine residues introduced at amino acid residues 158 and 172 respectively. Therefore it is preferred if the heterologous α and β chain variable domain sequence attachment points are between residues 159 or 173 and the N terminus of the α or β constant domain sequences respectively.

TCR Display

The preferred in-vivo TCR display method for biopanning to identify TCRs having desirable properties such as high affinity for a target peptide-MHC complex is phage display.

Firstly, a DNA library is constructed that encodes a diverse array of mutated scTCRs or dTCRs. This library is constructed by using DNA encoding a native TCR as the template for amplification. There are a number of suitable methods, known to those skilled in the art, for the introduction of the desired mutations into the TCR DNA, and hence the finally expressed TCR protein. For example error-prone PCR (EP-TCR), DNA shuffling techniques, and the use of bacterial mutator strains such as XL-1-Red are convenient means of introducing mutations into the TCR sequences. It is particularly preferred if these mutations are introduced into defined domain of the TCRs. For example, mutations in the variable domain, particularly the complementarity-determining regions (CDRs) and/or framework regions are likely to be the most appropriate sites for the introduction of mutations leading to the production of a diverse library of TCRs for the production of TCRs with enhanced ligand-binding properties. EP-PCR is an example of a method by which such 'region-specific' mutations can be introduced into the TCRs. EP-PCR primers are used that are complementary to DNA sequences bordering the region to be mutated to amplify multiple copies of this region of the TCR DNA that contain a controllable level of random mutations. These DNA sequences encoding mutated regions are inserted into the DNA sequences, which encode the non-mutagenised sections of the TCR, by ligation or overlapping PCR. The DNA encoding the TCR with mutated region can then be ligated onto DNA encoding a heterologous polypeptide in order to produce a fusion protein suitable for display. In the case of phage-display the expression vector utilised is either a phagemid or a phage gemone vector in which the TCR DNA can be ligated to DNA encoding a surface protein, preferably the gIII or gVIII surface protein. In the case of a scTCR such ligation is performed as for phage display of any monomeric peptide or polypeptide. In the case of dTCRs, only one of the TCR chains is ligated as aforesaid. The other chain is encoded in nucleic acid for co-expression with phagemid and helper phage nucleic acid, so that the expressed second chain finds and associates with the expressed phage with surface displayed first chain. In both cases, as discussed in more detail above, properly positioned cysteines in the constant domains are helpful in causing the variable domains of the TCR to adopt their functional positions, through the formation of a disulfide bond by those cysteines.

For expression, an expression vector comprising (a) nucleic acid encoding one chain of a dTCR polypeptide pair, and (b) the other chain of a dTCR polypeptide pair fused to a nucleic acid sequence encoding a particle forming protein, or a cell surface protein; or nucleic acid encoding a scTCR polypeptide fused to a nucleic acid sequence encoding a particle forming protein or a cell surface protein, the dTCR pair, or a composition comprising a first vector comprising nucleic acid (a) and a second vector comprising nucleic acid (b), are contacted with host cells capable of causing the expression of the encoded genetic material under conditions suitable to allow the transformation of said cells. Such expression vectors, expression systems comprising phagemid or phage genome vectors encoding dTCRs and scTCRs, and host cells harbouring them form additional aspects of the current invention. In a preferred embodiment of the invention the phagemid or phage genome vectors are derived from filamentous phage.

The transformed cells are then incubated to allow the expression of the TCR-displaying proteinaceous particles. These particles can then be used for screening or in assays to identify TCR variants with specific enhanced characteristics. Any particles that possess the enhanced characteristics under investigation can then be isolated. The DNA encoding these TCRs can then be amplified by PCR and the sequence determined.

It is known that high expression levels of an exogenous polypeptide may be toxic to the host cell. In such cases, either a host strain which is more tolerant of the exogenous polypeptide must be found, or the expression levels in the host cell must be limited to a level which is tolerated. For example (Beekwilder et al., (1999) Gene 228 (1-2) 23-31) report that only mutated forms of a potato protease inhibitor (PI2) which contained deletions or amber stop codons would be successfully selected from a phage display library. In the present case, an observation in the course of the work reported in the Examples herein suggests that it may be desirable to limit the expression levels of protein particle-displayed TCRs of the invention, at least in some strains of E. coli. Thus, the A6 TCR selected in Example 4 after repeated rounds of culture was shown to be derived from cells in which the phagemid had mutated relative to that introduced at the start. The mutation had created an 'opal' stop codon in the TCR β chain. This codon is 'read-through' with low frequency by ribosomes of the E. coli strain utilised resulting in the insertion of a tryptophan residue at this site and a much reduced overall level of full-length β chain expression.

There are several strategies for limiting the expression levels of an exogenous polypeptide from a given expression-system in a host which may be suitable for the limiting the expression levels of a scTCR, or one, or both TCR chains of a dTCR. For example:

Use of a weak promoter sequence—The level of expression obtained for a given gene product, such as the TCR α or β chain, can be tailored by using promoter sequences of varying strengths. The lambda phage $P_{RM}$ promoter is an example of a weak promoter.

Mutated ribosome binding sites (RBS's)—Mutating a single nucleic acid in the RBS associated with a gene product, such as the TCR α or β chain, can result in a reduced level of expression. For example, mutating a wild-type AGGA sequence to AGGG.

Mutated 'start codons'—Mutating a single nucleic acid in the start codon associated with a gene product, such as the TCR α or β chain, can also result in a reduced level of expression. For example, mutating a wild-type AUG start codon to GUG.

Miss-sense suppressor mutations—These are inserted within the TCR β chain coding regions. Examples include the 'opal' stop codon (UGA), this 'leaky' stop codon results in the low frequency insertion of a tryptophan amino acid and read-through of the rest of the coding sequence.

Metabolite-mediated modification of promoter strength—The level of expression of a gene product, such as the TCR α or β chain, under the control of certain promoters can be down-regulated by the addition of a relevant metabolite to the cells containing the promoter. For example, glucose additions can be used to down-regulate expression of a gene product under the control of a Lac promoter.

Codon usage—Bacterial cells and, for example, mammalian cells have different 'preferences' relating to the codons they use to encode certain amino acids. For example, bacterial cells most commonly use the CGU codon to encode arginine whereas eucaryotic cells most commonly use AGA. It is possible to reduce the level of expression of a gene product, such as the TCR α or β chain, by utilising DNA sequences that contain a number of codons less preferred by the expression system being utilised.

Details relating to the above means of down-regulating gene product expression can be found in (Glass (1982) Gene Function—E. coli and its heritable elements, Croom Helm) and (Rezinoff (1980) The Operon 2nd Edition, Cold Spring Harbor Laboratory).

It is also known that supplying bacterial cultures with a relatively high concentration of a sugar such as sucrose can increase periplasmic expression levels of soluble proteins. (See for example (Sawyer et al., (1994) Protein Engineering 7 (11) 1401-1406))

After expression, correct pairing of the scTCR polypeptide variable domain sequences is preferably assisted by the introduction of a disulfide bond in the extracellular constant domain of the scTCR. Without wanting to be limited by theory, the novel disulfide bond is believed to provide extra stability to the scTCR during the folding process and thereby facilitating correct pairing of the first and second segments.

Also as mentioned above, for dTCR phage display, one of the dTCR polypeptide pair is expressed as if it were eventually to be displayed as a monomeric polypeptide on the phage, and the other of the dTCR polypeptide pair is co-expressed in the same host cell. As the phage particle self assembles, the two polypeptides self associate for display as a dimer on the phage. Again, in the preferred embodiment of this aspect of the invention, correct folding during association of the polypeptide pair is assisted by a disulfide bond between the constant sequences, as discussed above. Further details of a procedure for phage display of a dTCR having an interchain disulfide bond appear in the Examples herein.

As an alternative, the phage displaying the first chain of the dTCR may be expressed first, and the second chain polypeptide may be contacted with the expressed phage in a subsequent step, for association as a functional dTCR on the phage surface.

The preferred in-vitro TCR display method for biopanning to identify TCRs having desirable properties such as high affinity for a target peptide-MHC complex is ribosomal display. Firstly, a DNA library is constructed that encodes a diverse array of mutated scTCRs or dTCR polypeptides using the techniques discussed above. The DNA library is then contacted with RNA polymerase in order to produce a complementary mRNA library. Optionally, for mRNA display techniques the mRNA sequences can then be ligated to a DNA sequence comprising a puromycin binding site. These genetic constructs are then contacted with ribosomes in-vitro under conditions allowing the translation of the scTCR polypeptide or the first polypeptide of the dTCR pair. In the case of the dTCR, the second of the polypeptide pairs is separately expressed and contacted with the ribosome-displayed first polypeptide, for association between the two, preferably assisted by the formation of the disulfide bond between constant domains. Alternatively, mRNA encoding both chains of the TCR may be contacted with ribosomes in-vitro under conditions allowing the translation of the TCR chains such that a ribosome displaying a dTCR is formed.

These scTCR- or dTCR-displaying ribosomes can then used for screening or in assays to identify TCR variants with specific enhanced characteristics. Any particles that possess the enhanced characteristics under investigation can then be isolated. The mRNA encoding these TCRs can then converted to the complementary DNA sequences using reverse transcriptase. This DNA can then be amplified by PCR and the sequence determined.

Additional Aspects

A proteinaceous particle displaying a scTCR or dTCR (which preferably is constituted by constant and variable sequences corresponding to human sequences) of the present invention may be provided in substantially pure form, or as a purified or isolated preparation. For example, it may be provided in a form which is substantially free of other proteins.

A phage particle displaying a plurality of scTCRs or dTCRs of the present invention may be provided in a multivalent complex. Thus, the present invention provides, in one aspect, a multivalent T cell receptor (TCR) complex, which comprises a phage particle displaying a plurality of scTCRs or dTCRs as described herein. Each of the plurality of said scTCRs or dTCRs is preferably identical.

In a further aspect, the invention provides a method for detecting TCR ligand complexes, which comprises:
 a. providing a TCR-displaying proteineaceous particle of the current invention
 b. contacting the TCR-displaying phage with the putative ligand complexes; and detecting binding of the TCR-displaying proteinaceous particle to the putative ligand complexes.

TCR ligands suitable for identification by the above method include, but are not limited to, peptide-MHC complexes.

Isolation of TCR Variants with Enhanced Characteristics

A further aspect of the invention is a method for the identification of TCRs with a specific characteristic, said method comprising subjecting a diverse library of TCRs displayed on proteinaceous particles to a selection process which selects for said characteristic, and isolating proteinaceous particles which display a TCR having said characteristic, and optionally to an amplification process to multiply the isolated particles, and/or a screening process which measures said characteristic, identifying those proteinaceous particles which display a TCR with the desired characteristic and isolating these proteinaceous particles, and optionally to an amplification process to multiply the isolated particles.

The DNA sequences encoding the variant TCRs can then be obtained and amplified by PCR to allow the sequences to be determined. The characteristics that can be enhanced include, but are not limited to, ligand binding affinity and construct stability.

Screening Use

The TCR-displaying proteinaceous particles of the present invention are capable of utilisation in screening methods designed to identify modulators, including inhibitors, of the TCR-mediated cellular immune synapse.

As is know to those skilled in the art there are a number of assay formats that provide a suitable basis for protein-protein interaction screens of this type.

Amplified Luminescent Proximity Homogeneous Assay systems such as the AlphaScreen™, rely on the use of "Donor" and "Acceptor" beads that are coated with a layer of hydrogel to which receptor and ligand proteins can be attached. The interaction between these receptor and ligand molecules brings the beads into proximity. When these beads are subject to laser light a photosensitizer in the "Donor" bead converts ambient oxygen to a more excited singlet state. The singlet state oxygen molecules diffuse across to react with a chemiluminescer in the "Acceptor" bead that further activates fluorophores contained within the same bead. The fluorophores subsequently emit light at 520-620 nm, this signals that the receptor-ligand interaction has occurred. The presence of an inhibitor of the receptor-ligand interaction causes this signal to be diminished.

Surface Plasmon Resonance (SPR) is an interfacial optical assay, in which one binding partner (normally the receptor) is immobilised on a 'chip' (the sensor surface) and the binding of the other binding partner (normally the ligand), which is soluble and is caused to flow over the chip, is detected. The binding of the ligand results in an increase in concentration of protein near to the chip surface which causes a change in the refractive index in that region. The surface of the chip is comprised such that the change in refractive index may be detected by surface plasmon resonance, an optical phenomenon whereby light at a certain angle of incidence on a thin metal film produces a reflected beam of reduced intensity due to the resonant excitation of waves of oscillating surface charge density (surface plasmons). The resonance is very sensitive to changes in the refractive index on the far side of the metal film, and it is this signal which is used to detect binding between the immobilised and soluble proteins. Systems which allow convenient use of SPR detection of molecular interactions, and data analysis, are commercially available. Examples are the Iasys™ machines (Fisons) and the Biacore™ machines.

Other interfacial optical assays include total internal reflectance fluorescence (TIRF), resonant mirror (RM) and optical grating coupler sensor (GCS), and are discussed in more detail in Woodbury and Venton (*J. Chromatog. B.* 725 113-137 (1999)).

The scintillation proximity assay (SPA) has been used to screen compound libraries for inhibitors of the low affinity interaction between CD28 and B7 ($K_d$ probably in the region of 4 µM (Van der Merwe et at J. Exp. Med. 185:393-403 (1997), Jenh et al, Anal Biochem 165(2) 287-93 (1998)). SPA is a radioactive assay making use of beta particle emission from certain radioactive isotopes which transfers energy to a scintillant immobilised on the indicator surface. The short range of the beta particles in solution ensures that scintillation only occurs when the beta particles are emitted in close proximity to the scintillant. When applied for the detection of protein-protein interactions, one interaction partner is labelled with the radioisotope, while the other is either bound to beads containing scintillant or coated on a surface together with scintillant. If the assay can be set up optimally, the radioisotope will be brought close enough to the scintillant for photon emission to be activated only when binding between the two proteins occurs.

A further aspect of the invention is a method of identifying an inhibitor of the interaction between a TCR-displaying proteinaceous particle of the invention, and a TCR-binding ligand comprising contacting the TCR-displaying proteinaceous particle with a TCR-binding ligand, in the presence of and in the absence of a test compound, and determining whether the presence of the test compound reduces binding of the TCR-displaying proteinaceous particle to the TCR-binding ligand, such reduction being taken as identifying an inhibitor.

A further aspect of the invention is a method of identifying a potential inhibitor of the interaction between an TCR-displaying proteinaceous particle of the invention, and a TCR-binding ligand, for example a MHC-peptide complex, comprising contacting the TCR-displaying proteinaceous particle or TCR-binding ligand partner with a test compound and determining whether the test compound binds to the TCR-displaying proteinaceous particle and/or the TCR-binding ligand, such binding being taken as identifying a potential inhibitor. This aspect of the invention may find particular utility in interfacial optical assays such as those carried out using the Biacore™ system.

High Affinity TCRs

The present invention also makes available mutated TCRs specific for a given TCR ligand with higher affinity for said TCR ligand than the wild-type TCR. These high affinity TCRs are expected to be particularly useful for the diagnosis and treatment of disease.

As used herein the term 'high affinity TCR' refers to a mutated scTCR or dTCR which interacts with a specific TCR ligand and either:has a Kd for the said TCR ligand less than that of a corresponding native TCR as measured by Surface Plasmon Resonance, or has an off-rate ($k_{off}$) for the said TCR ligand less than that of a corresponding native TCR as measured by Surface Plasmon Resonance.

High affinity scTCRs or dTCRs of the present invention are preferably mutated relative to the native TCR in at least one complementarity determining region and/or framework regions.

In one aspect of the present invention the TCR ligand for which a given high affinity TCR is specific is a peptide-MHC complex (pMHC).

In another aspect of the present invention the TCR ligand for which a given high affinity TCR is specific is an MHC type or types.

In a further aspect of the present invention the TCR ligand for which a given high affinity TCR is specific is the HLA-A2 tax peptide (LLFGYPVYV) (SEQ ID 21) complex.

In a further aspect of the present invention the TCR ligand for which a given high affinity TCR is specific is the HLA-A2 NY-ESO peptide (SLLMITQC) (SEQ ID 22) complex.

A high affinity scTCR or one or both of the high affinity dTCR chains may be labelled with an imaging compound, for example a label that is suitable for diagnostic purposes. Such labelled high affinity TCRs are useful in a method for detecting a TCR ligand selected from CD1-antigen complexes, bacterial superantigens, and MHC-peptide/superantigen complexes which method comprises contacting the TCR ligand with a high affinity TCR (or a multimeric high affinity TCR complex) which is specific for the TCR ligand; and detecting binding to the TCR ligand. In tetrameric high affinity TCR complexes (formed, for example) using biotinylated heterodimers) fluorescent streptavidin (commercially available) can be used to provide a detectable label. A fluorescently-labelled tetramer is suitable for use in FACS analysis, for example to detect antigen presenting cells carrying the peptide for which the high affinity TCR is specific.

Another manner in which the soluble high affinity TCRs of the present invention may be detected is by the use of TCR-specific antibodies, in particular monoclonal antibodies. There are many commercially available anti-TCR antibodies, such as αF1 and βF1, which recognise the constant domains of the α and β chains, respectively.

A high affinity TCR (or multivalent complex thereof) of the present invention may alternatively or additionally be associated with (e.g. covalently or otherwise linked to) a therapeutic agent which may be, for example, a toxic moiety for use in cell killing, or an immunostimulating agent such as an interleukin or a cytokine. A multivalent high affinity TCR complex of the present invention may have enhanced binding capability for a TCR ligand compared to a non-multimeric wild-type or high affinity T cell receptor heterodimer. Thus, the multivalent high affinity TCR complexes according to the invention are particularly useful for tracking or targeting cells presenting particular antigens in vitro or in vivo, and are also useful as intermediates for the production of further multivalent high affinity TCR complexes having such uses. The high affinity TCR or multivalent high affinity TCR complex may therefore be provided in a pharmaceutically acceptable formulation for use in vivo.

The invention also provides a method for delivering a therapeutic agent to a target cell, which method comprises contacting potential target cells with a high affinity TCR or multivalent high affinity TCR complex in accordance with the invention under conditions to allow attachment of the high affinity TCR or multivalent high affinity TCR complex to the target cell, said high affinity TCR or multivalent high affinity TCR complex being specific for the TCR ligand and having the therapeutic agent associated therewith.

In particular, the soluble high affinity TCR or multivalent high affinity TCR complex can be used to deliver therapeutic agents to the location of cells presenting a particular antigen. This would be useful in many situations and, in particular, against tumours. A therapeutic agent could be delivered such that it would exercise its effect locally but not only on the cell it binds to. Thus, one particular strategy envisages anti-tumour molecules linked to high affinity T cell receptors or multivalent high affinity TCR complexes specific for tumour antigens.

Many therapeutic agents could be employed for this use, for instance radioactive compounds, enzymes (perforin for example) or chemotherapeutic agents (cis-platin for example). To ensure that toxic effects are exercised in the desired location the toxin could be inside a liposome linked to streptavidin so that the compound is released slowly. This will prevent damaging effects during the transport in the body and ensure that the toxin has maximum effect after binding of the TCR to the relevant antigen presenting cells.

Other suitable therapeutic agents include:
  small molecule cytotoxic agents, i.e. compounds with the ability to kill mammalian cells having a molecular weight of less than 700 daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cis-platin, maytansine derivatives, rachelmycin, calicheamicin, docetaxel, etoposide, gemcitabine, ifosfamide, irinotecan, melphalan, mitoxantrone, sorfimer sodiumphotofrin II, temozolmide, topotecan, trimetreate glucuronate, auristatin E vincristine and doxorubicin;
  peptide cytotoxins, i.e. proteins or fragments thereof with the ability to kill mammalian cells. Examples include ricin, diphtheria toxin, pseudomonas bacterial exotoxin A, DNAase and RNAase;
  radio-nuclides, i.e. unstable isotopes of elements which decay with the concurrent emission of one or more of α or β particles, or γ rays. Examples include iodine 131, rhenium 186, indium 111, yttrium 90, bismuth 210 and 213, actinium 225 and astatine 213; chelating agents may be used to facilitate the association of these radio-nuclides to the high affinity TCRs, or multimers thereof;
  prodrugs, such as antibody directed enzyme pro-drugs;
  immuno-stimulants, i.e. moieties which stimulate immune response. Examples include cytokines such as IL-2, chemokines such as IL-8, platelet factor 4, melanoma growth stimulatory protein, etc, antibodies or fragments thereof, complement activators, xenogeneic protein domains, allogeneic protein domains, viral/bacterial protein domains and viral/bacterial peptides.

Soluble high affinity TCRs or multivalent high affinity TCR complexes of the invention may be linked to an enzyme capable of converting a prodrug to a drug. This allows the prodrug to be converted to the drug only at the site where it is required (i.e. targeted by the sTCR).

A multitude of disease treatments can potentially be enhanced by localizing the drug through the specificity of soluble high affinity TCRs. For example, it is expected that the high affinity HLA-A2-tax (LLFGYPVYV) (SEQ ID 21) specific A6 TCRs disclosed herein may be used in methods for the diagnosis and treatment of HTLV-1 and that the high affinity HLA-A2-NY-ESO (SLLMITQC) (SEQ ID 22) specific NY-ESO TCR disclosed herein may be used in methods for the diagnosis and treatment of cancer.

Viral diseases for which drugs exist, e.g. HIV, SIV, EBV, CMV, would benefit from the drug being released or activated in the near vicinity of infected cells. For cancer, the localisation in the vicinity of tumours or metastasis would enhance the effect of toxins or immunostimulants. In autoimmune diseases, immunosuppressive drugs could be released slowly, having more local effect over a longer time-span while minimally affecting the overall immune-capacity of the subject. In the prevention of graft rejection, the effect of immunosuppressive drugs could be optimised in the same way. For vaccine delivery, the vaccine antigen could be localised in the vicinity of antigen presenting cells, thus enhancing the efficacy of the antigen. The method can also be applied for imaging purposes.

The soluble high affinity TCRs of the present invention may be used to modulate T cell activation by binding to specific TCR ligand and thereby inhibiting T cell activation. Autoimmune diseases involving T cell-mediated inflammation and/or tissue damage would be amenable to this approach, for example type I diabetes. Knowledge of the specific peptide epitope presented by the relevant pMHC is required for this use.

Therapeutic or imaging high affinity TCRs in accordance with the invention will usually be supplied as part of a sterile, pharmaceutical composition which will normally include a pharmaceutically acceptable carrier. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, for example parenteral, transdermal or via inhalation, preferably a parenteral (including subcutaneous, intramuscular, or, most preferably intravenous) route. Such compositions may be prepared by any method known in the art of pharmacy, for example by admixing the active ingredient with the carrier(s) or excipient(s) under sterile conditions.

Dosages of the substances of the present invention can vary between wide limits, depending upon the disease or disorder to be treated, the age and condition of the individual to be treated, etc. and a physician will ultimately determine appropriate dosages to be used.

The invention also provides a method for obtaining a high affinity TCR chain, which method comprises incubating such a host cell under conditions causing expression of the high affinity TCR chain and then purifying the polypeptide.

Preferred features of each aspect of the invention are as for each of the other aspects mutatis mutandis. The prior art documents mentioned herein are incorporated to the fullest extent permitted by law.

EXAMPLES

The invention is further described in the following examples, which do not limit the scope of the invention in any way.

Reference is made in the following to the accompanying drawings in which:

BRIEF DESCRIPTION OF THE DRAWINGS

FIGS. 1A and 1B show respectively the nucleic acid sequences of a soluble A6 TCR α and β chains, mutated so as to introduce a cysteine codon. The shading indicates the introduced cysteine codons.

FIG. 2A shows the A6 TCR α chain extracellular amino acid sequence, including the $T_{48} \to C$ mutation (underlined) used to produce the novel disulphide inter-chain bond, FIG. 2B shows the A6 TCR β chain extracellular amino acid sequence, including the $S_{57} \to C$ mutation (underlined) used to produce the novel disulphide inter-chain bond.

FIG. 4 details the DNA sequence of phagemid pEX746: A6.

FIGS. 7B and 7C detail the complete DNA coding strand and amino acid sequence of the single-chain A6 TCR-C-Kappa DNA ribosome display construct encoded in pUC19 respectively.

FIG. 8 details the DNA sequence of pUC19-T7.

FIG. 9 details the DNA sequence of the single-chain A6 TCR-C-Kappa ribosome display construct that was cloned into pUC19-T7.

FIG. 11 RT-PCR of the single-chain A6 TCR-C-Kappa mRNA on beads rescued from the ribosome display reactions.

FIG. 12A details the DNA sequence of the A6 TCR Clone 9 mutated β chain; the mutated nucleic acid is indicated in bold.

FIG. 12B details the amino acid sequence of the A6 TCR Clone 9 mutated β chain, the position corresponding to the introduced opal stop codon is indicated with an *.

FIG. 13 details the DNA sequence of the A6 TCR Clone 49 mutated β chain; the mutated nucleic acid is indicated in bold. As this is a 'silent' mutation no change is introduced into the resulting amino acid sequence by this mutation.

FIG. 14A details the DNA sequence of the A6 TCR Clone 134 mutated A6 TCR β chain; the mutated nucleic acids are indicated in bold.

FIG. 14B details the amino acid sequence of the A6 TCR Clone 134 mutated A6 TCR β chain as tested by BIAcore assay; the mutated amino acids are indicated in bold.

FIG. 14C details the amino acid sequence of the A6 TCR Clone 134 mutated A6 TCR β chain as tested by phage ELISA assay; the mutated amino acids are indicated in bold.

FIGS. 17A and 17B show the DNA sequence of the mutated α and β chains of the NY-ESO TCR respectively FIGS. 18A and 18B show the amino acid sequences of the mutated α and β chains of the NY-ESO TCR respectively FIGS. 19A and 19B detail the DNA and amino acid sequence of the NY-ESO TCR β chain incorporated into the pEX746:NY-ESO phagemid respectively.

FIG. 21 shows the DNA sequence of the DR1α chain incorporating codons encoding the Fos dimerisation peptide attached to the 3' end of the DRA0101 sequence. Shading indicates the Fos codons and the biotinylation tag codons are indicated by in bold text.

FIG. 23 shows the DNA sequence of the DR1 β chain incorporating codons encoding the Jun dimerisation peptide attached to the 3' end of the DRB0401 sequence and codons encoding an HLA-loaded peptide attached to the 5' end of the DRB0401 sequence. Shading indicates the Jun codons, and the HLA-loaded Flu HA peptide codons are underlined.

FIG. 24 shows a BIAcore trace of the binding of the high affinity A6 TCR clone 134 to flowcells coated as follows:

```
Flow-cell 1 (FC 1)-Blank
                                          (SEQ ID 23)
Flow-cell 2 (FC 2)-HLA-A2 (LLGRNSFEV)
                                          (SEQ ID 24)
Flow-cell 3 (FC 3)-HLA-A2 (KLVALGINAV)
                                          (SEQ ID 25)
Flow-cell 4 (FC 4)-HLA-A2 (LLGDLFGV)
```

Figure 25:
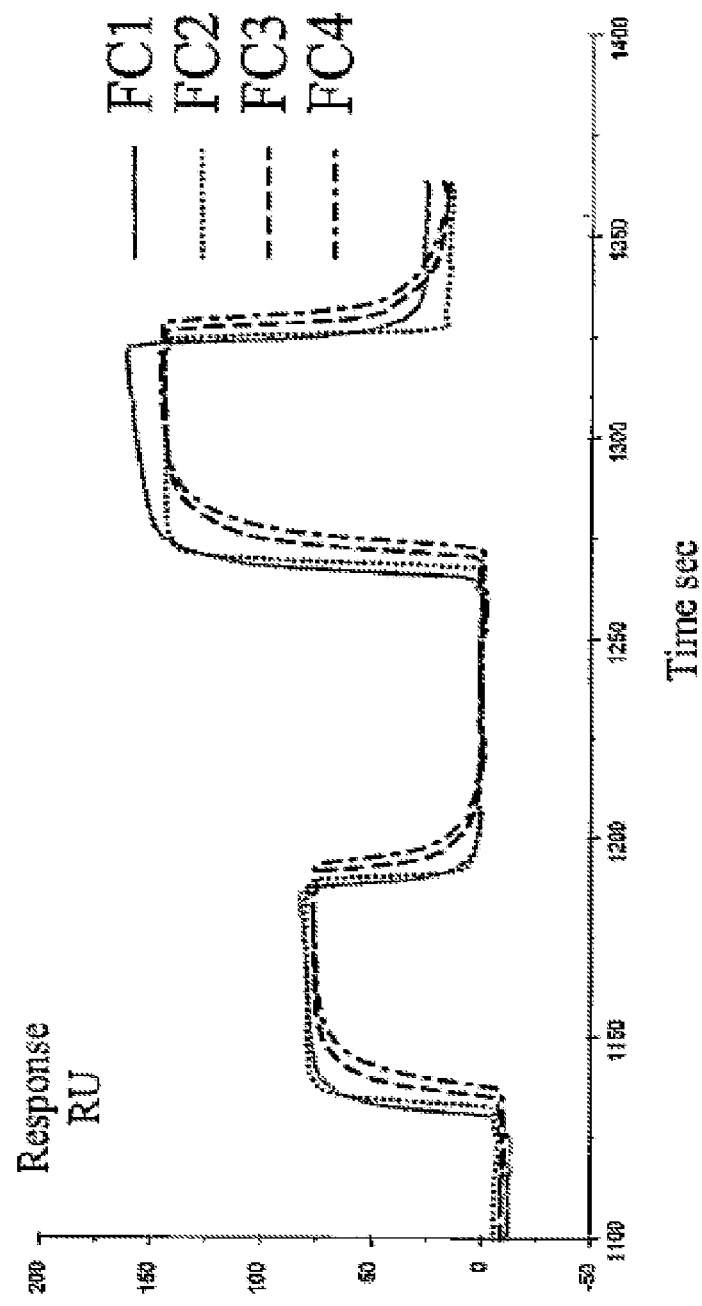

FIG. 25 shows a BIAcore trace of the binding of the high affinity A6 TCR clone 134 to flowcells coated as follows:

```
    Flow-cell 1 (FC 1)-Blank (SEQ ID 26)
    Flow-cell 2 (FC 2)-HLA-B8 (FLRGRAYGL)

(SEQ ID 27)
    Flow-cell 3 (FC 3)-HLA-B27 (HRCQAIRKK)

(SEQ ID 28)
    Flow-cell 4 (FC 4)-HLA-Cw6 (YRSGIIAVV)
```

Figure 26:
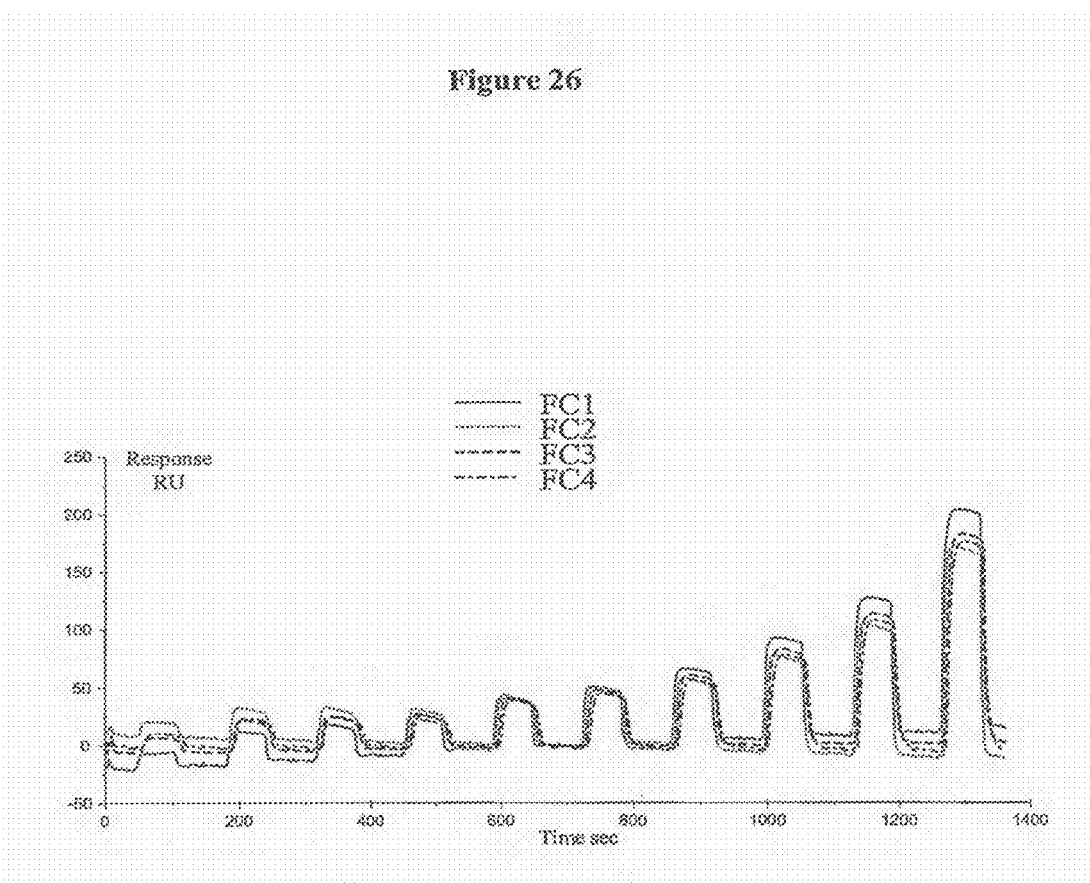

FIG. 26 shows a BIAcore trace of the binding of the high affinity A6 TCR clone 134 to flowcells coated as follows:

```
    Flow-cell 1 (FC 1)-Blank (SEQ ID 29)
    Flow-cell 2 (FC 2)-HLA-A24 (VYGFVRACL)

(SEQ ID 30)
    Flow-cell 3 (FC 3)-HLA-A2 (ILAKFLHWL)

(SEQ ID 31)
    Flow-cell 4 (FC 4)-HLA-A2 (LTLGEFLKL)
```

Figure 27:
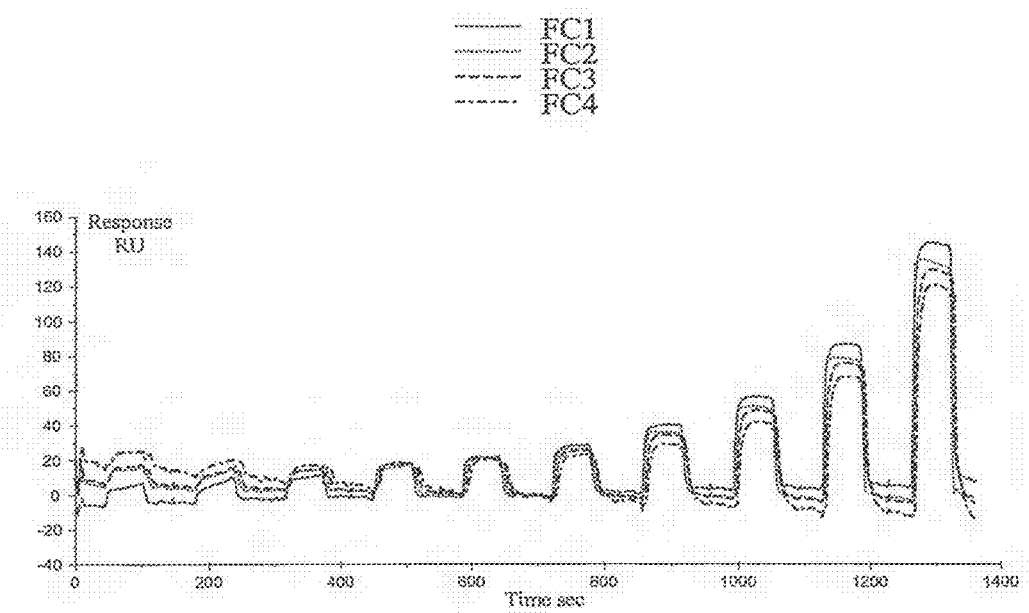

FIG. 27 shows a BIAcore trace of the binding of the high affinity A6 TCR clone 134 to flowcells coated as follows:

```
    Flow-cell 1 (FC 1)-Blank (SEQ ID 32)
    Flow-cell 2 (FC 2)-HLA-DR1 (PKYVKQNTLKLA)

(SEQ ID 33)
    Flow-cell 3 (FC 3)-HLA-A2 (GILGFVFTL)

(SEQ ID 34)
    Flow-cell 4 (FC 4)-HLA-A2 (SLYNTVATL)
```

Figure 28:
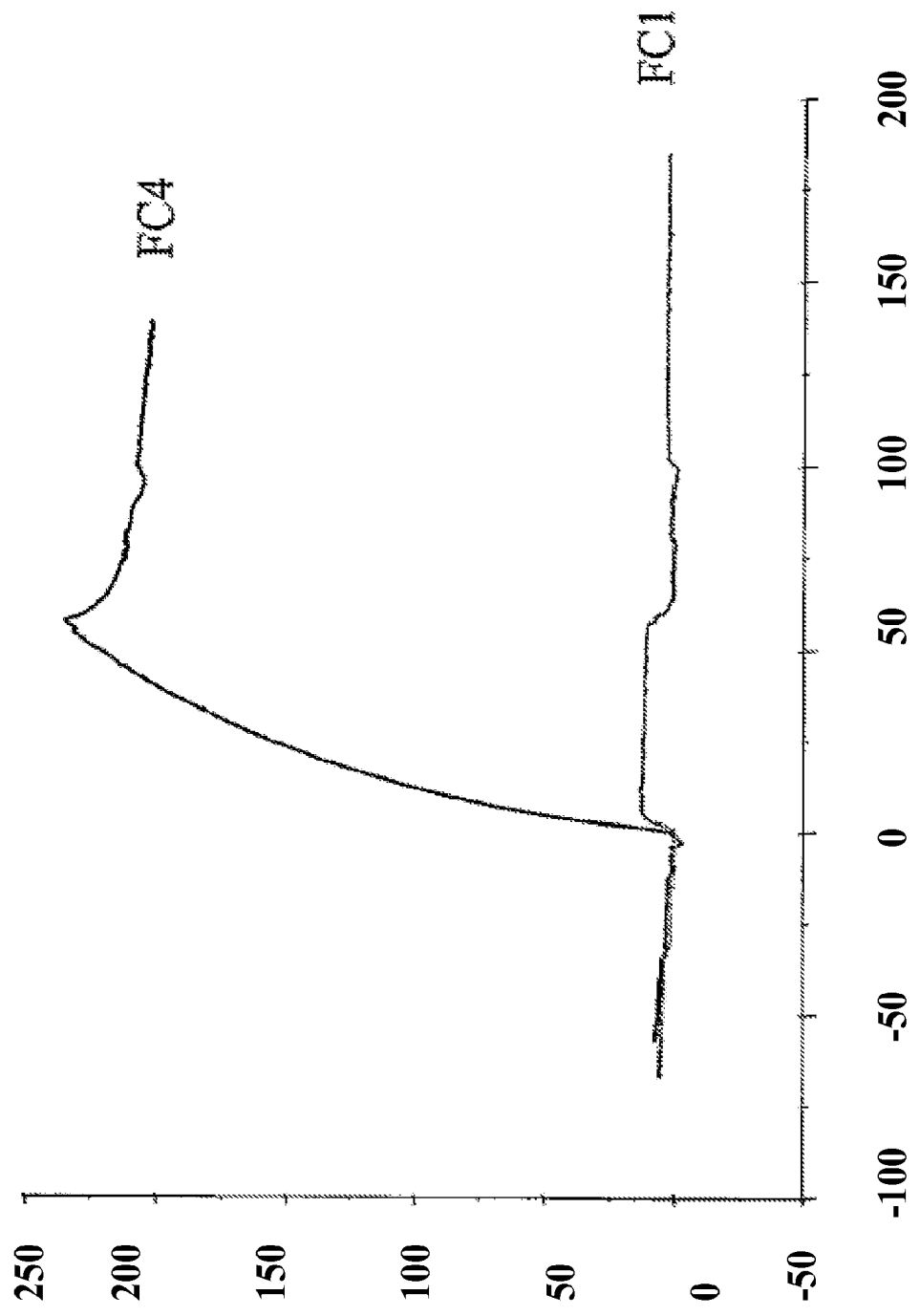

FIG. 28 shows a BIAcore trace of the binding of the high affinity A6 TCR clone 134 to flowcells coated as follows:

```
    Flow-cell 1 (FC 1)-Blank (SEQ ID 21)
    Flow-cell 4 (FC 4)-HLA-A2 (LLFGYPVYV)
```

Figure 29A:
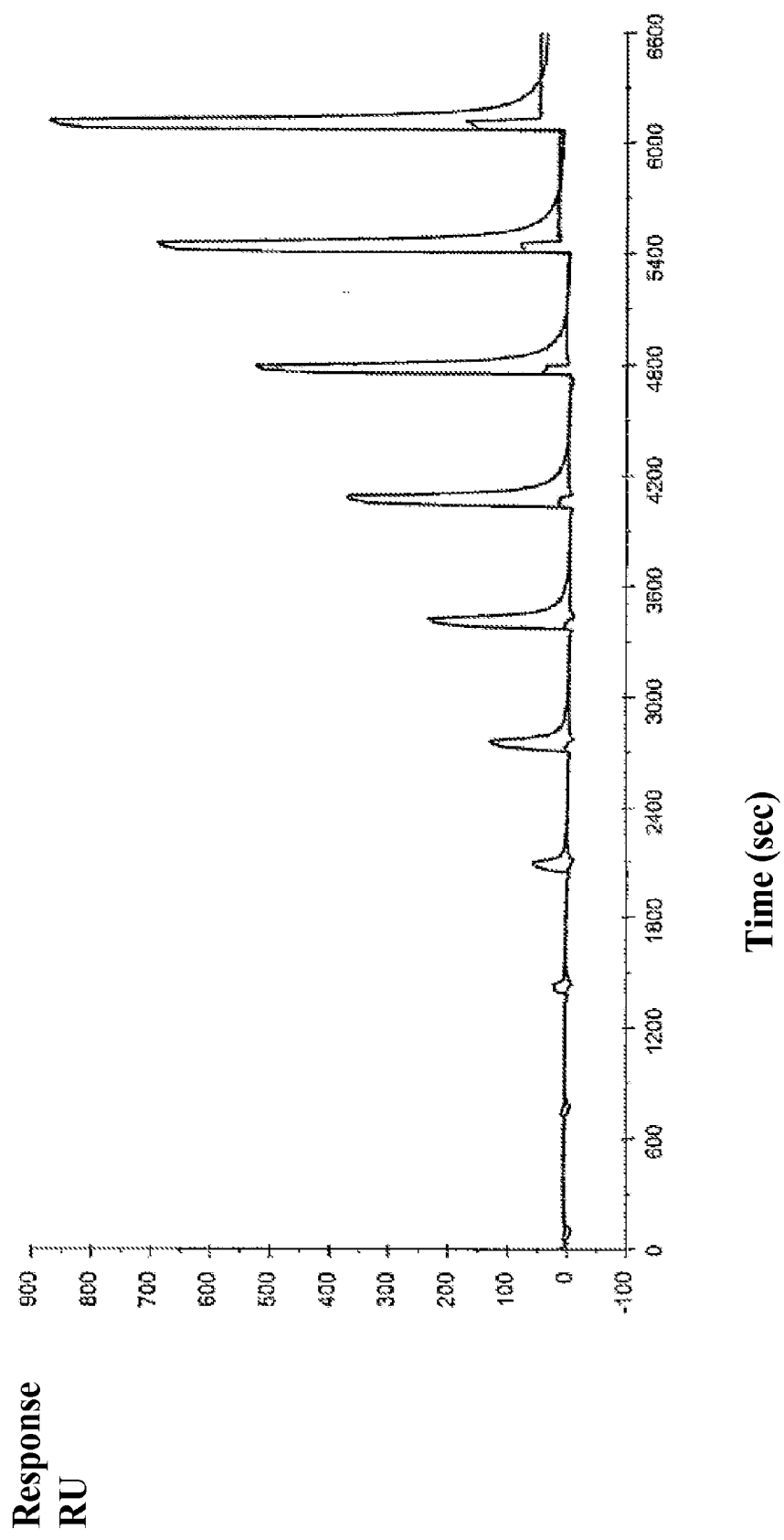
Figure 29B:
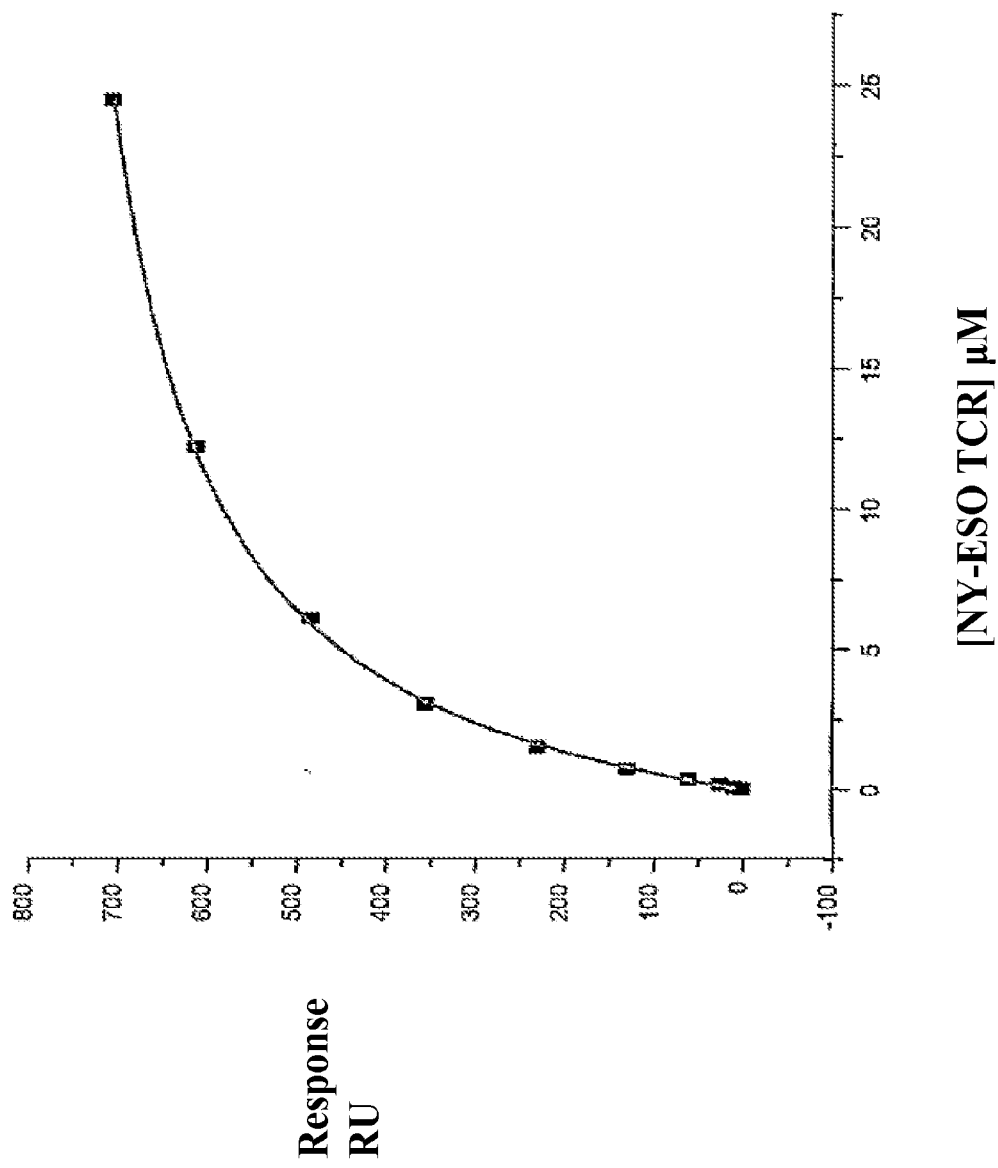

FIGS. 29A and 29B show Biacore plots of the interaction between the soluble high affinity NY-ESO TCR and HLA-A2 NY-ESO.

Figure 30A:
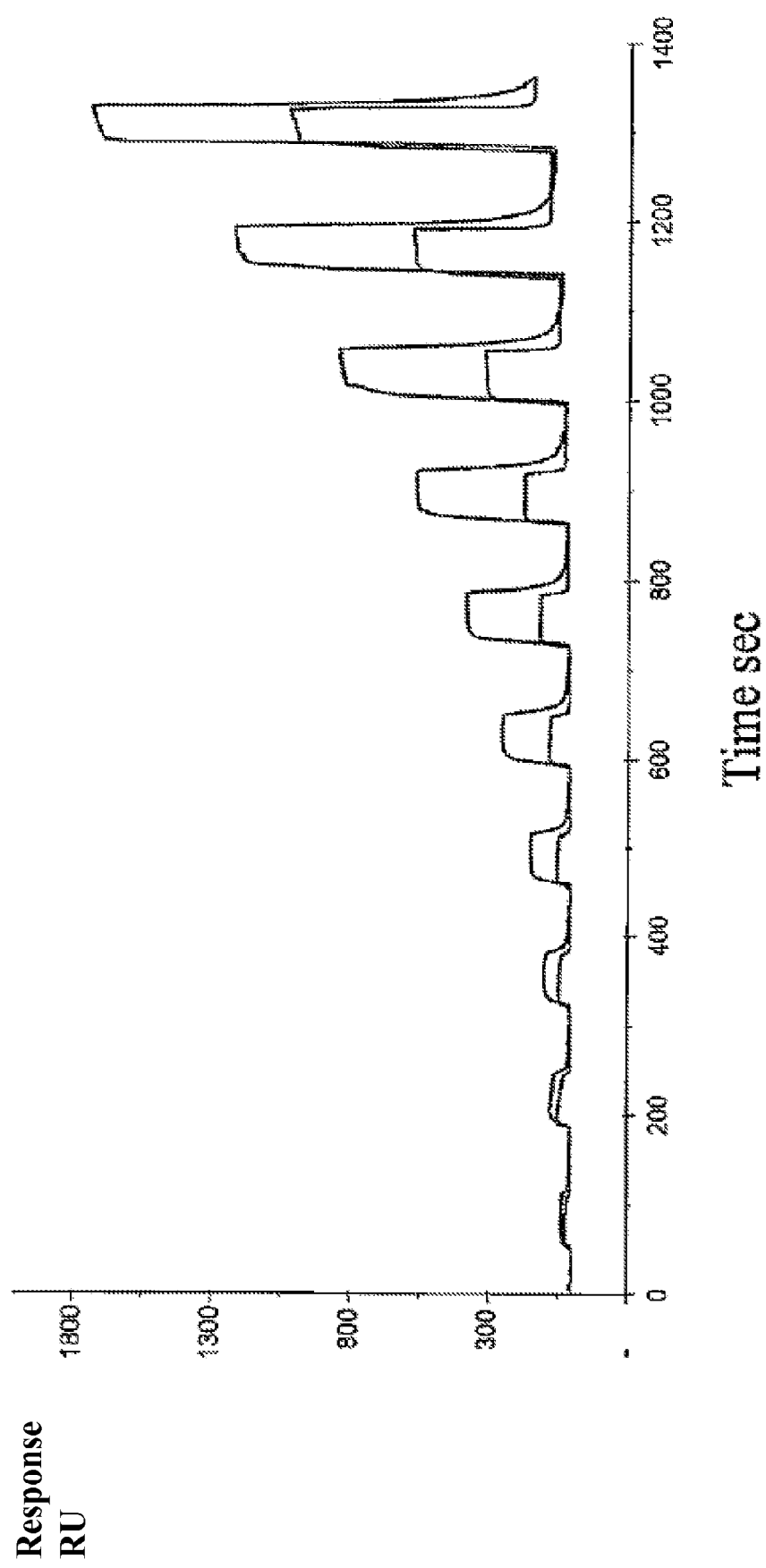
Figure 30B:
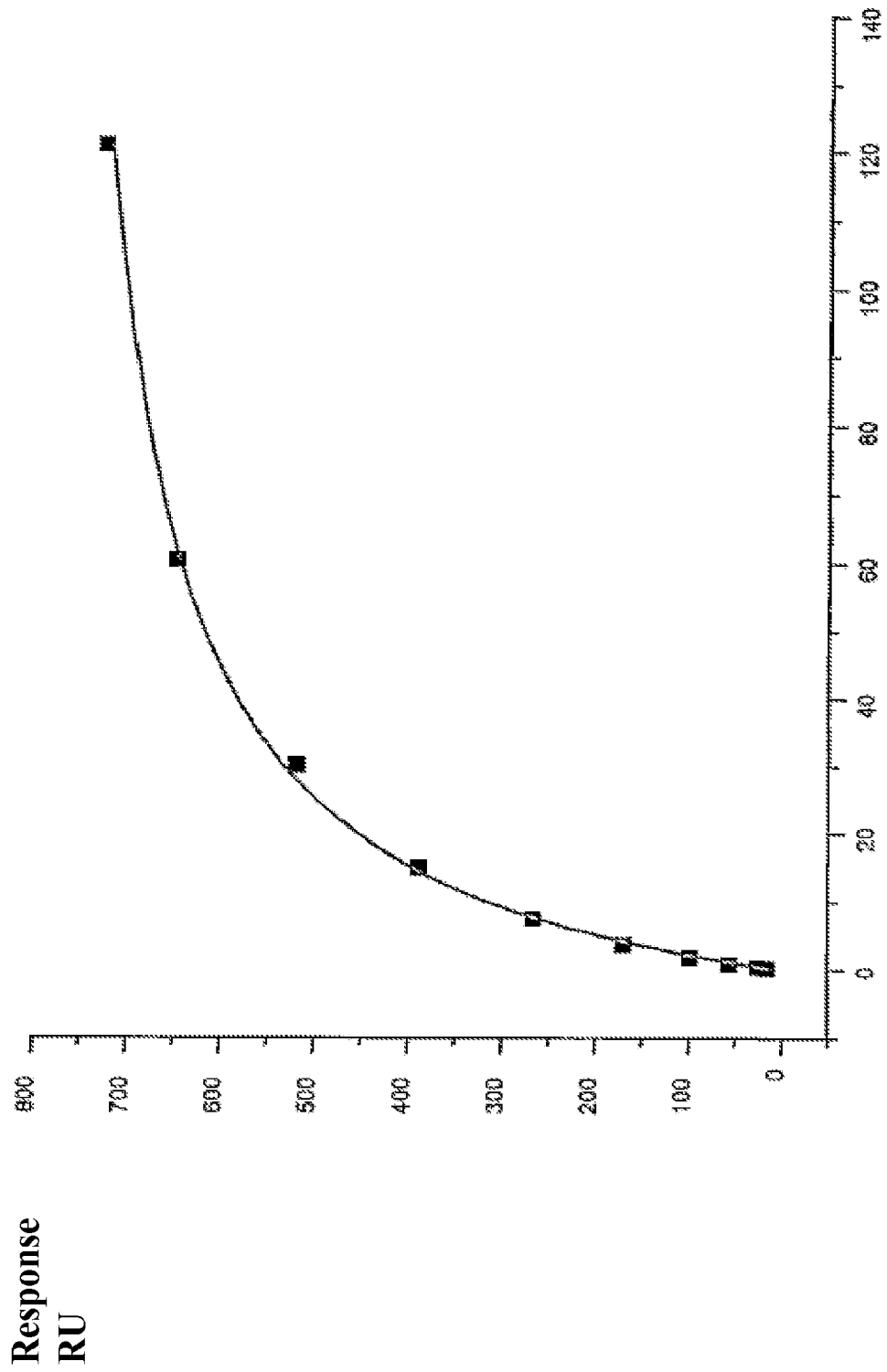

FIGS. 30A and 30B show Biacore plots of the interaction between the soluble "wild-type" NY-ESO TCR and HLA-A2 NY-ESO.

Figure 31A:
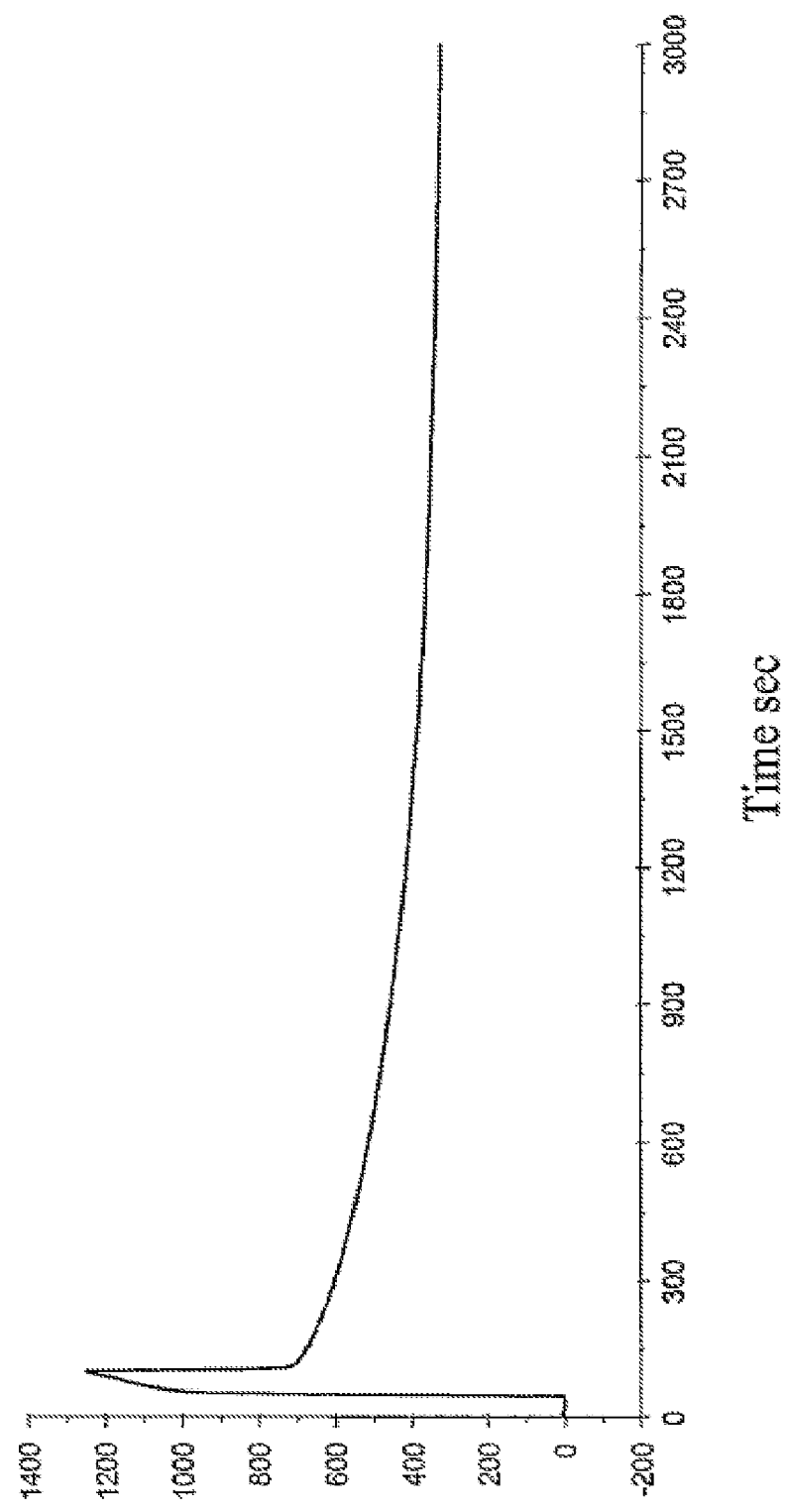
Figure 31B:
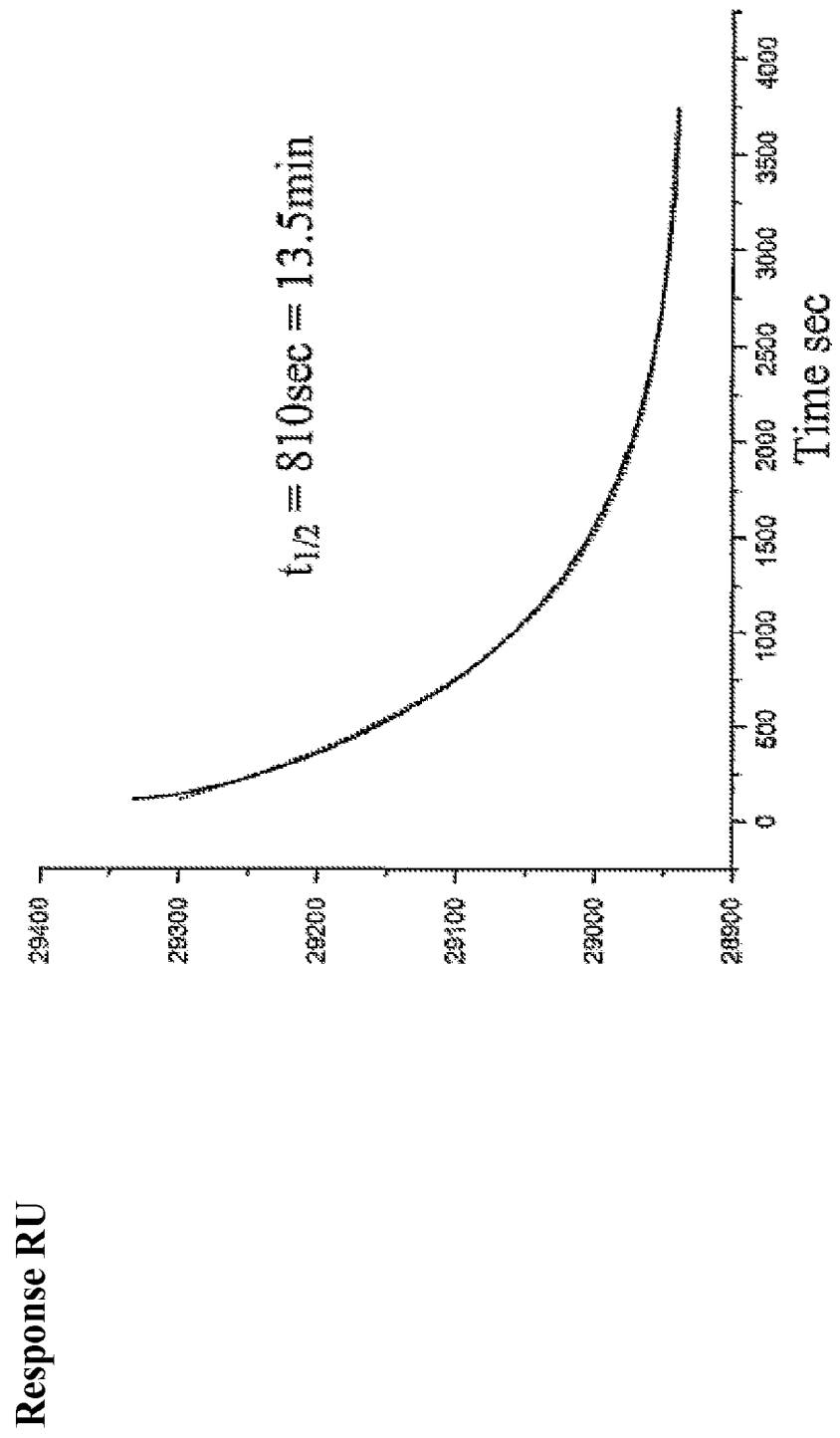

FIGS. 31A and 31B show Biacore plots of the interaction between a mutant soluble A6 TCR (Clone 1) and HLA-A2 Tax.

Figure 32A:
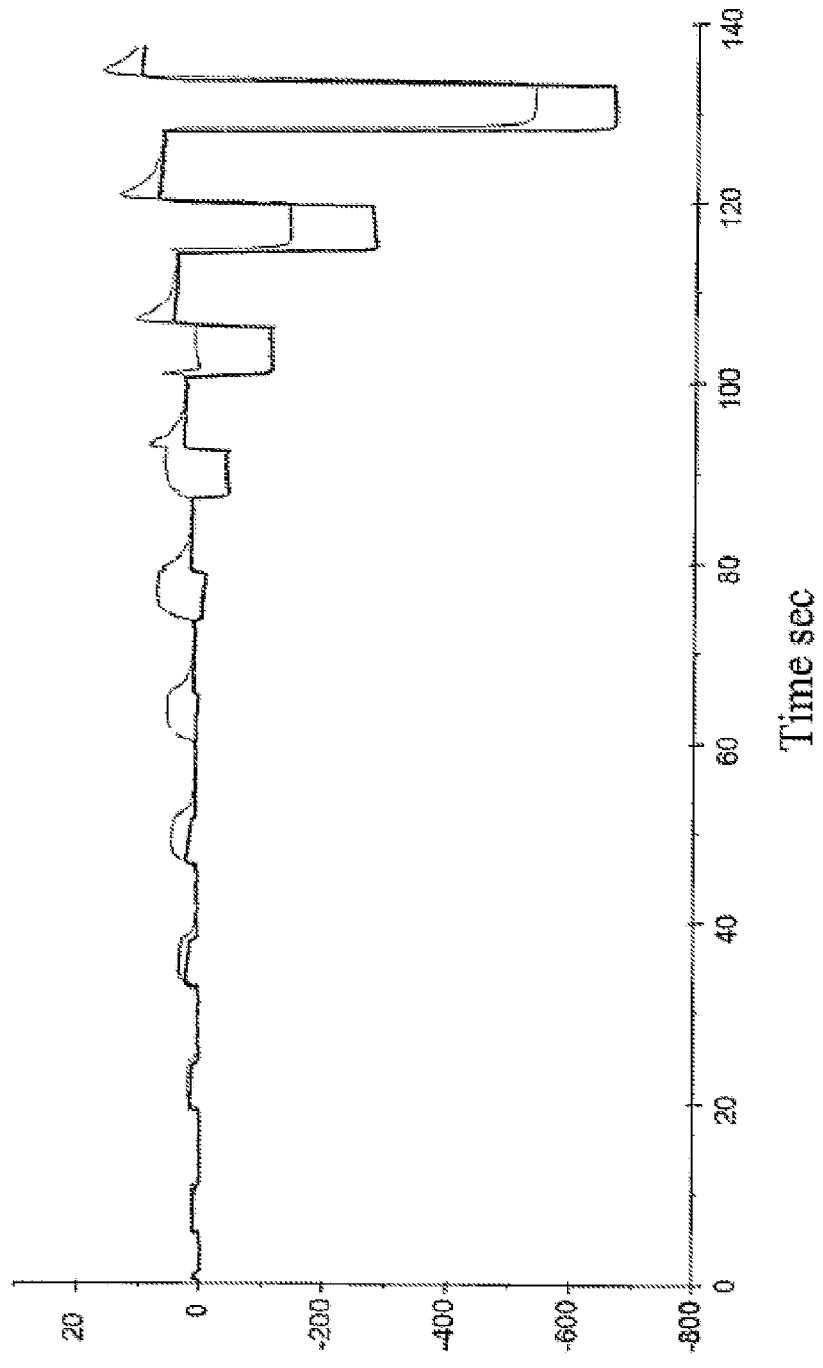
Figure 32B:
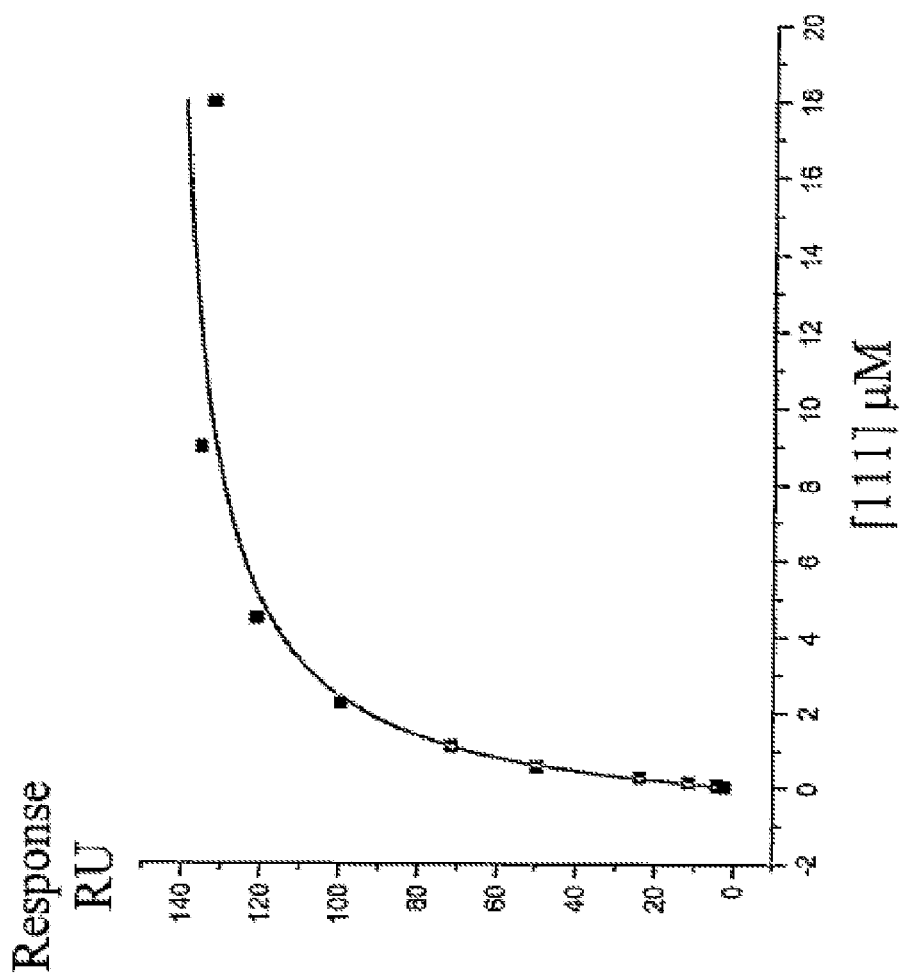

FIGS. 32A and 32B show Biacore plots of the interaction between a mutant soluble A6 TCR (Clone 111) and HLA-A2 Tax.

Figure 33A:
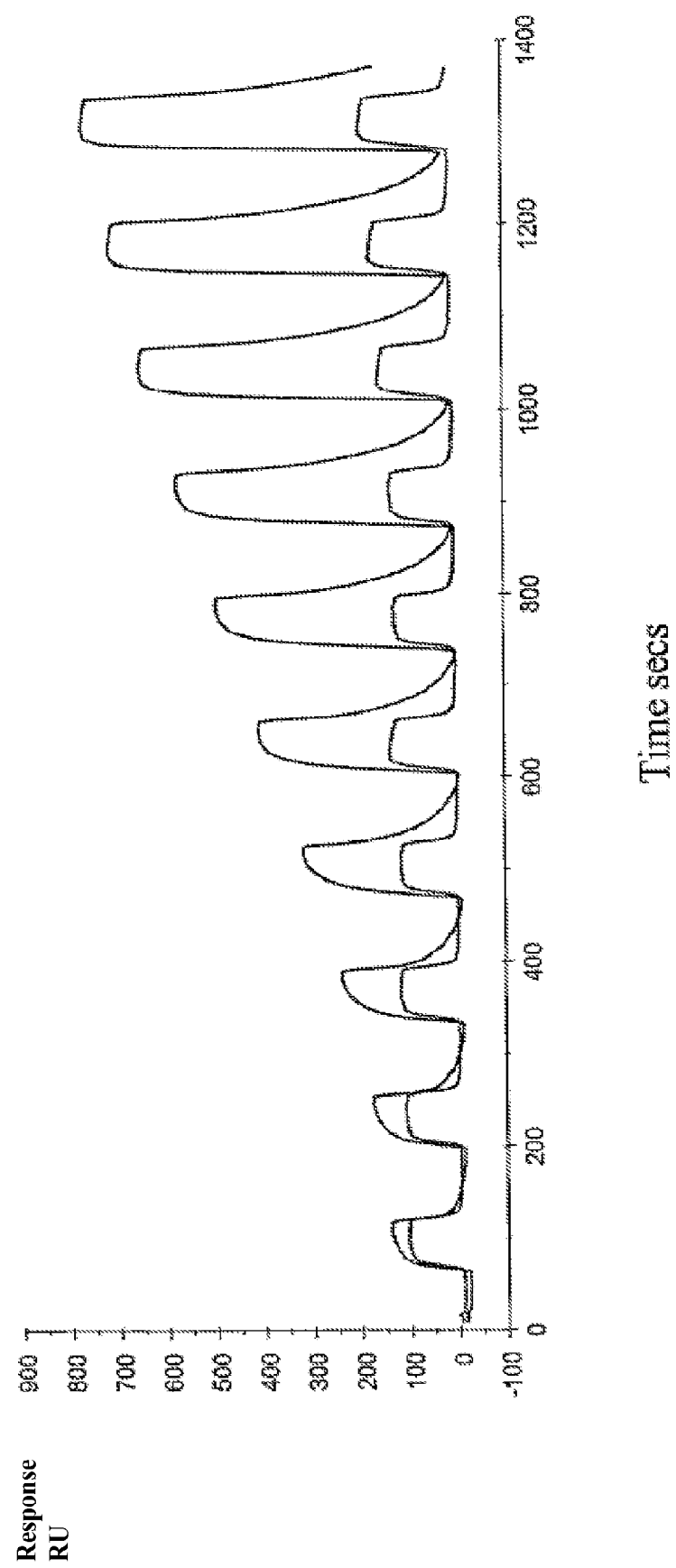
Figure 33B:
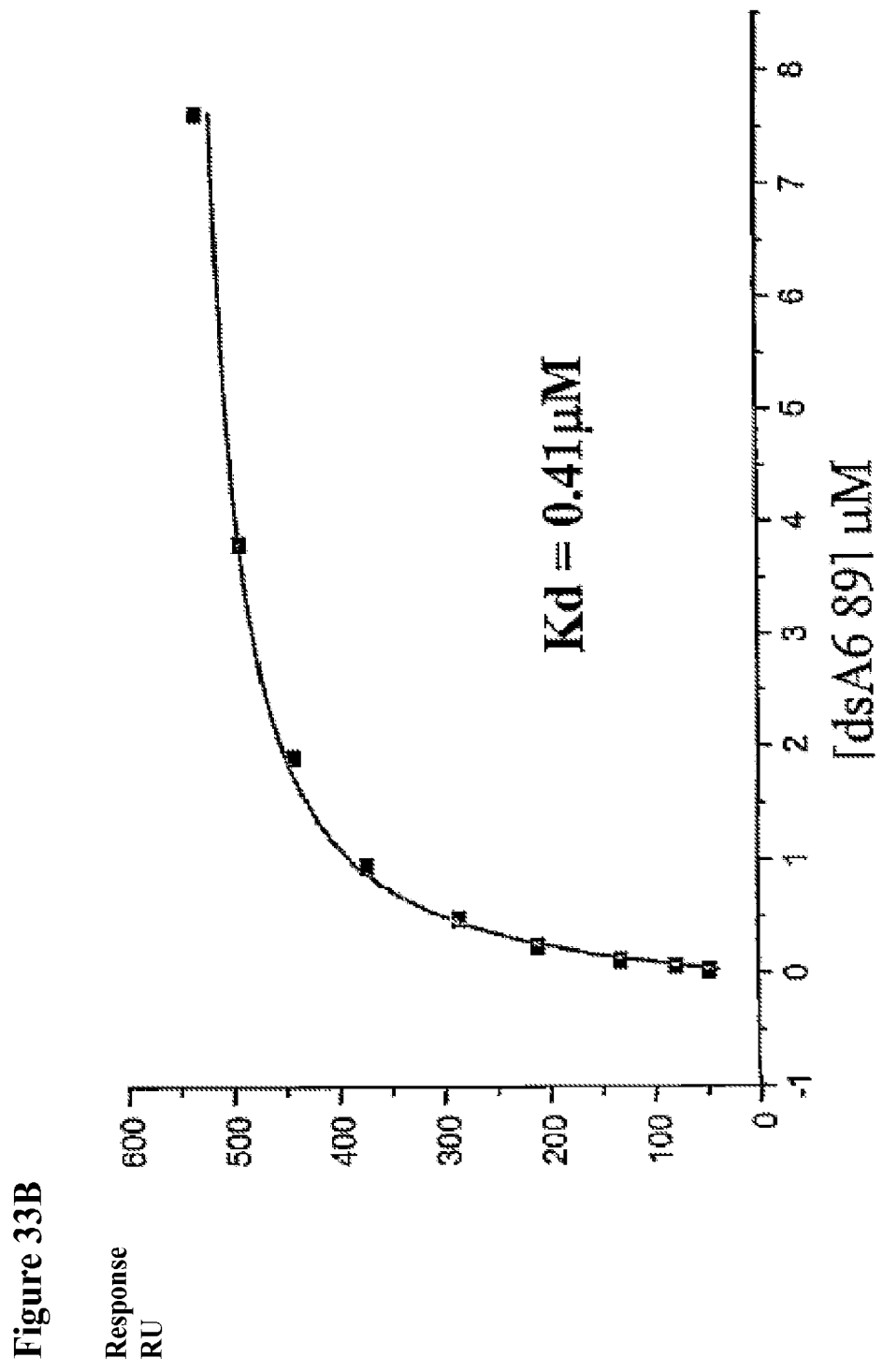

FIGS. 33A and 33B show Biacore plots of the interaction between a mutant soluble A6 TCR (Clone 89) and HLA-A2 Tax.

Figure 34:
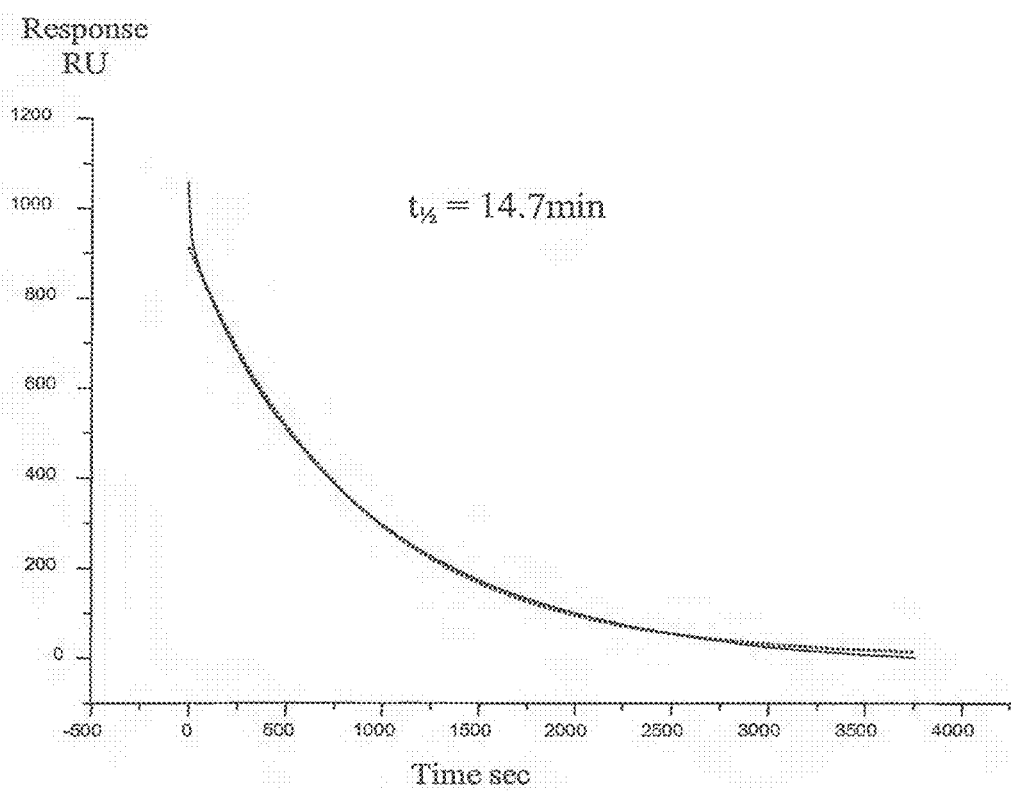

FIG. 34 shows a Biacore plot of the interaction between a mutant soluble A6 TCR (containing Clone 71 and Clone 134 mutations) and HLA-A2 Tax.

FIG. 35 shows a Biacore plot of the interaction between a mutant soluble A6 TCR (containing Clone 1 and βG102→A mutations) and HLA-A2 Tax.

Figure 36A:
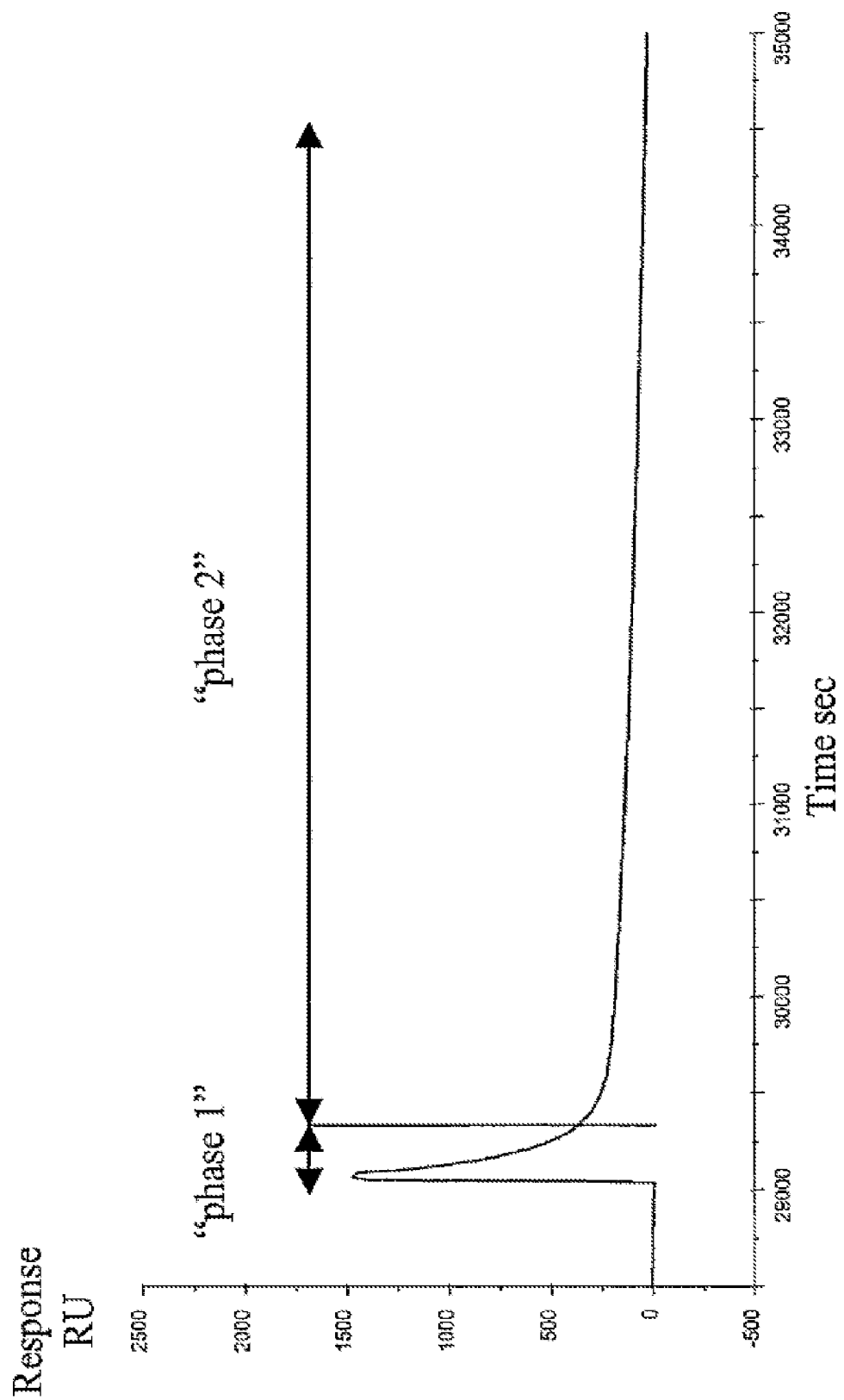
Figure 36C:
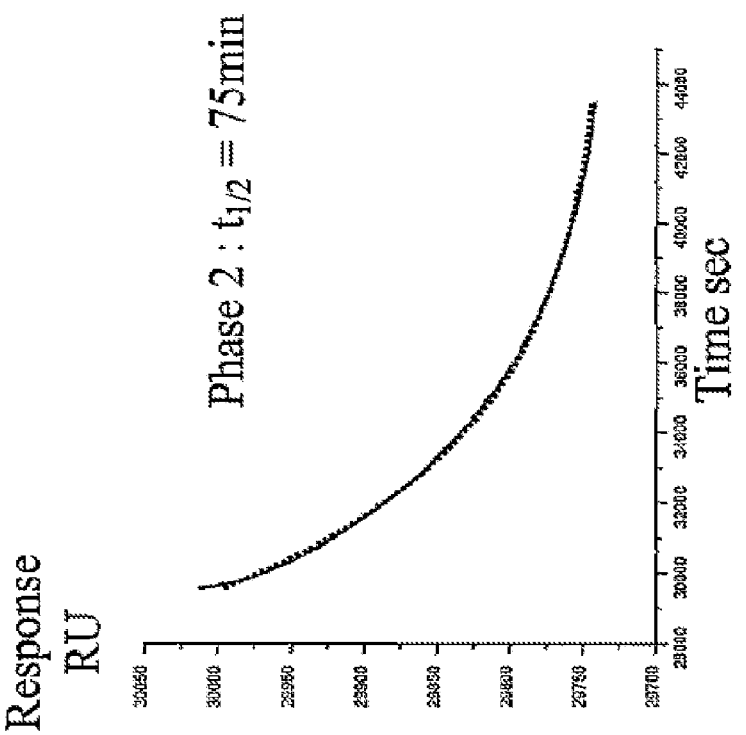
Figure 36B:
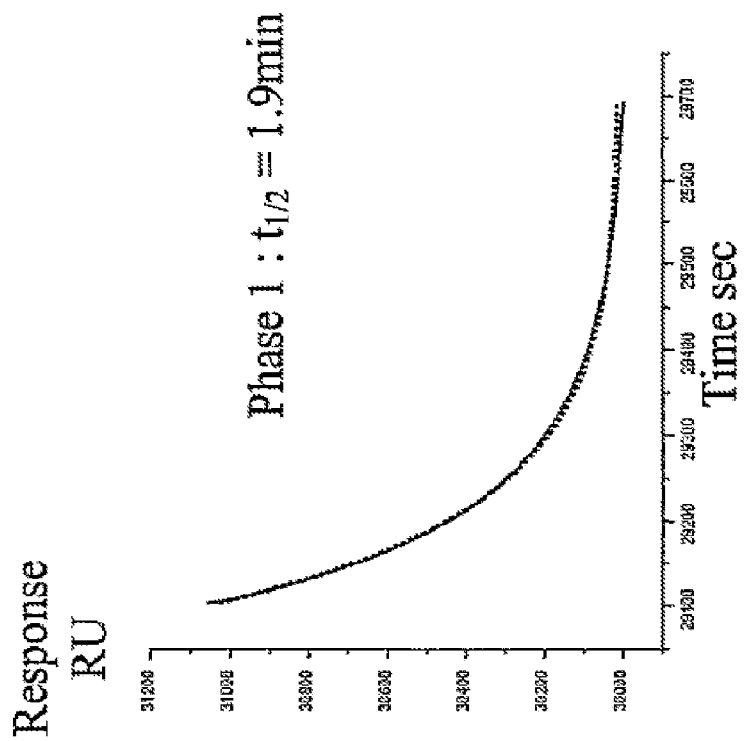

FIGS. 36A, 36B, and 36C show Biacore plots of the interaction between a mutant soluble A6 TCR (containing Clone 89 and Clone 134 mutations) and HLA-A2 Tax.

Figure 37A:
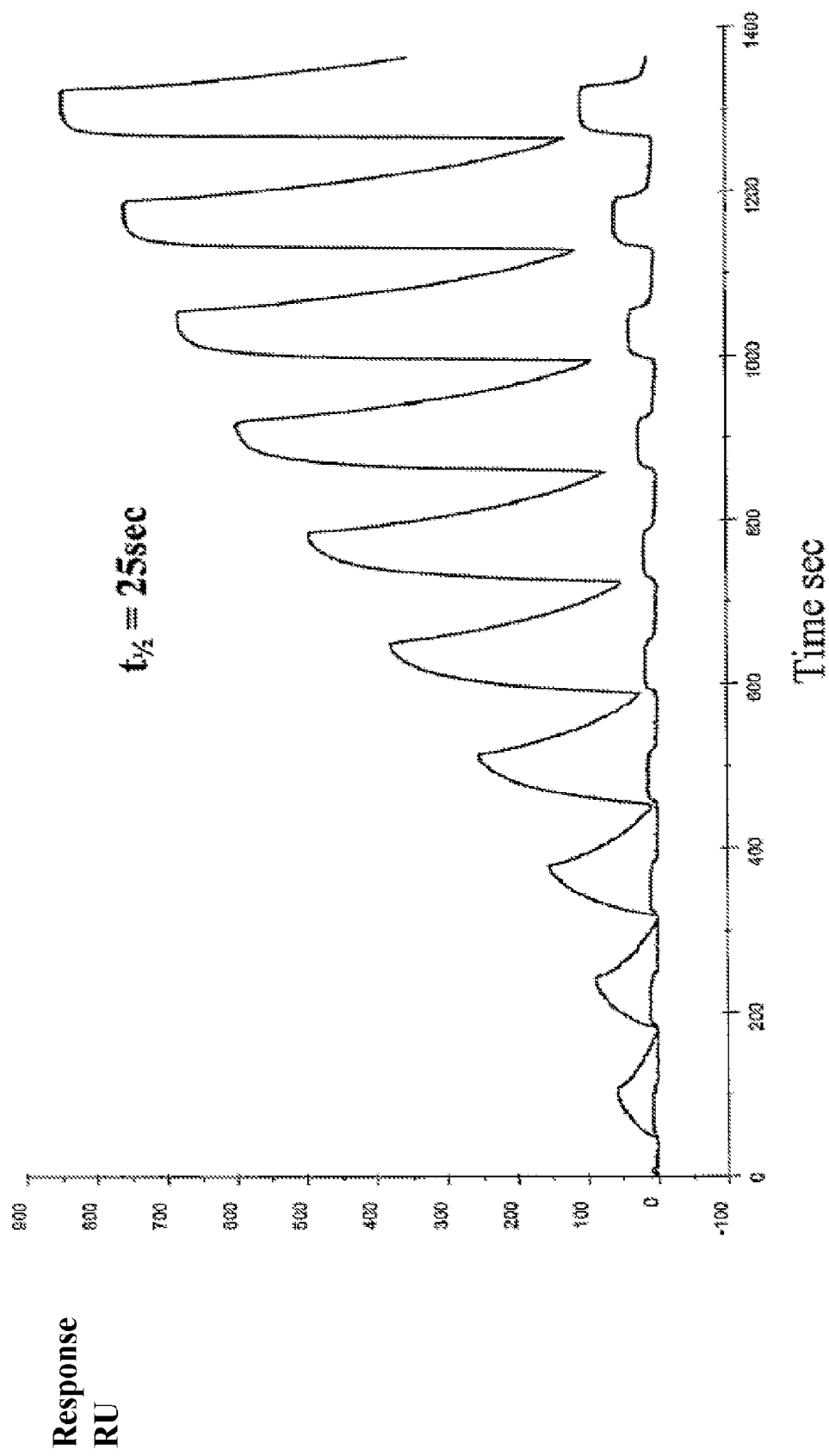
Figure 37B:
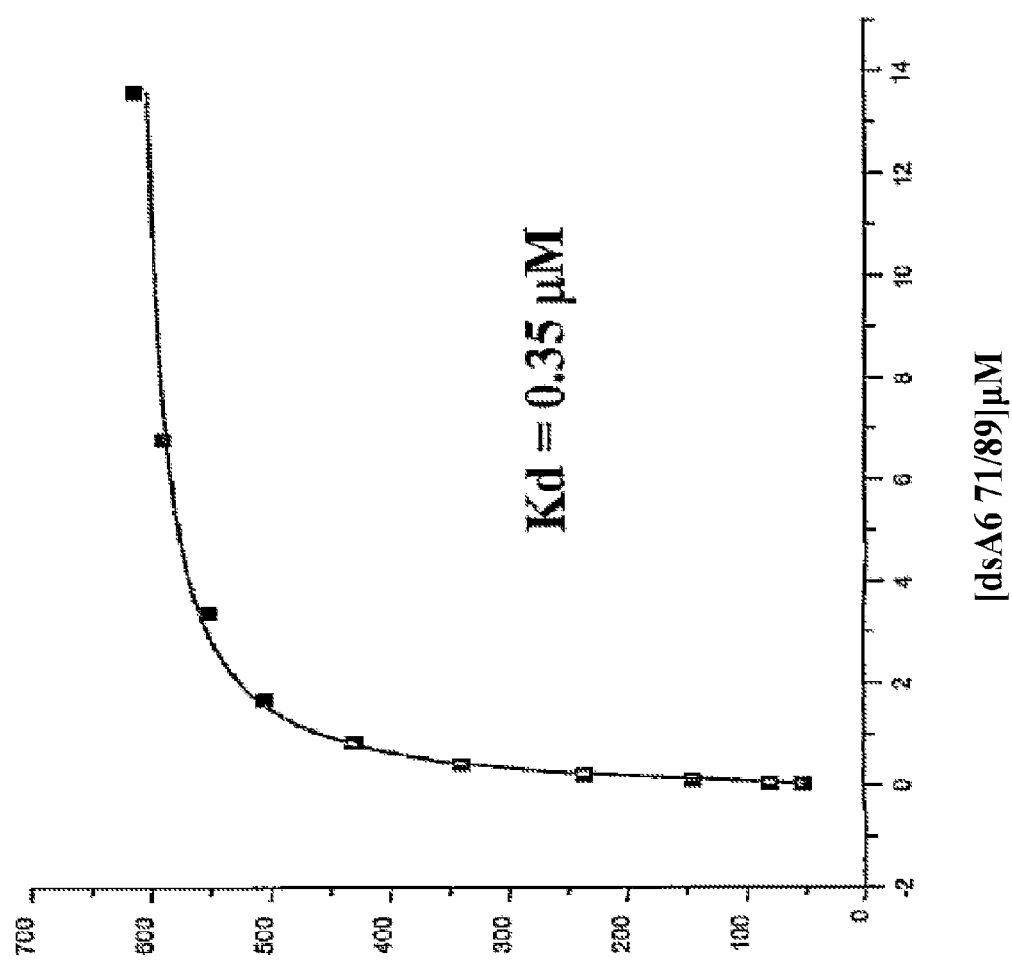

FIGS. 37A and 37B show Biacore plots of the interaction between a mutant soluble A6 TCR (containing Clone 71 and Clone 89 mutations) and HLA-A2 Tax.

FIGS. 38A-38E detail the β chain variable domain amino acid sequences of the following A6 TCR clones:

FIG. 38A, Wild-type, FIG. 38B, Clone 134, FIG. 38C, Clone 89, FIG. 38D, Clone 1 and FIG. 38E, Clone 111. The mutated residues are shown in bold, bracketed residues are alternative residues that may be present at a particular site.

Figure 39A:
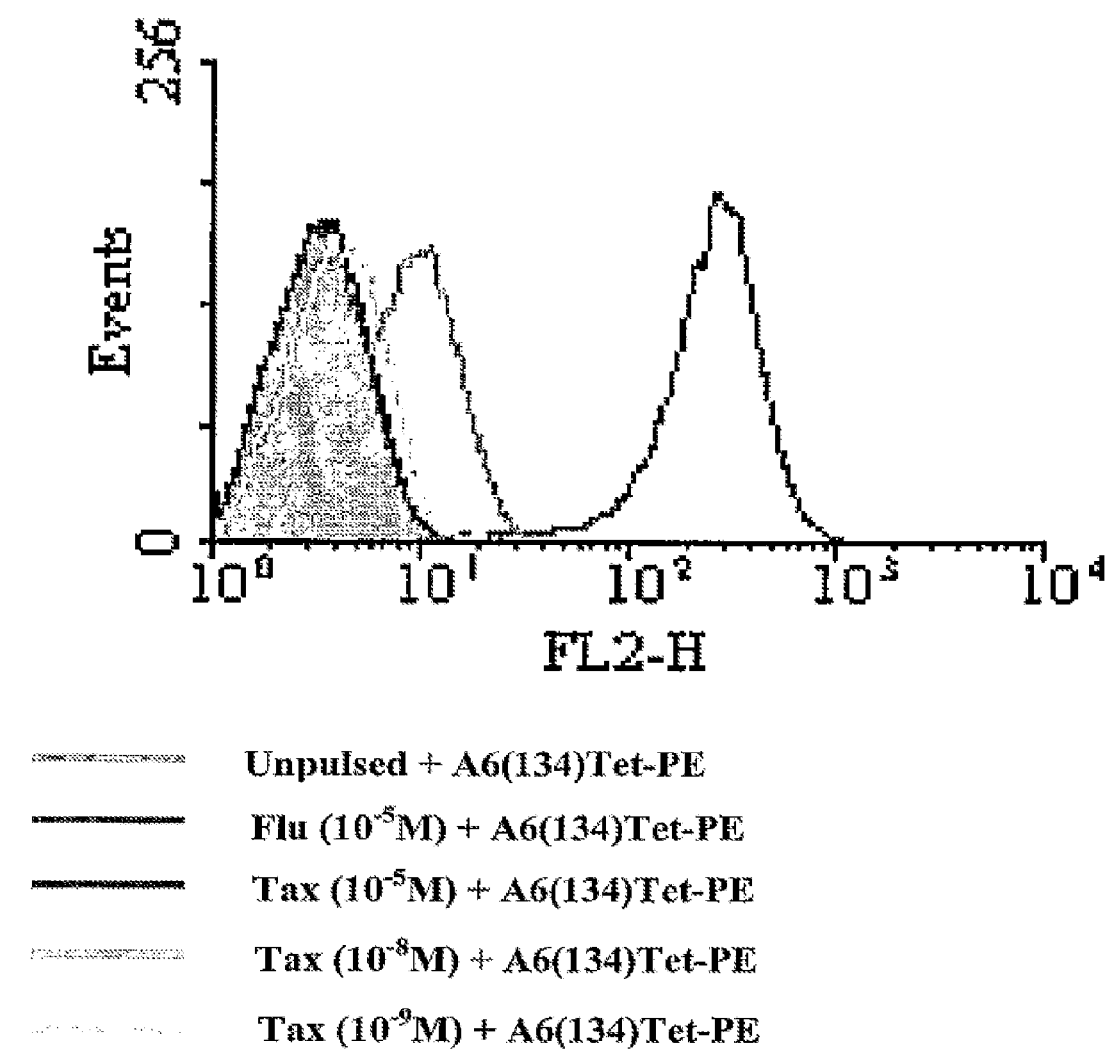
Figure 39B:
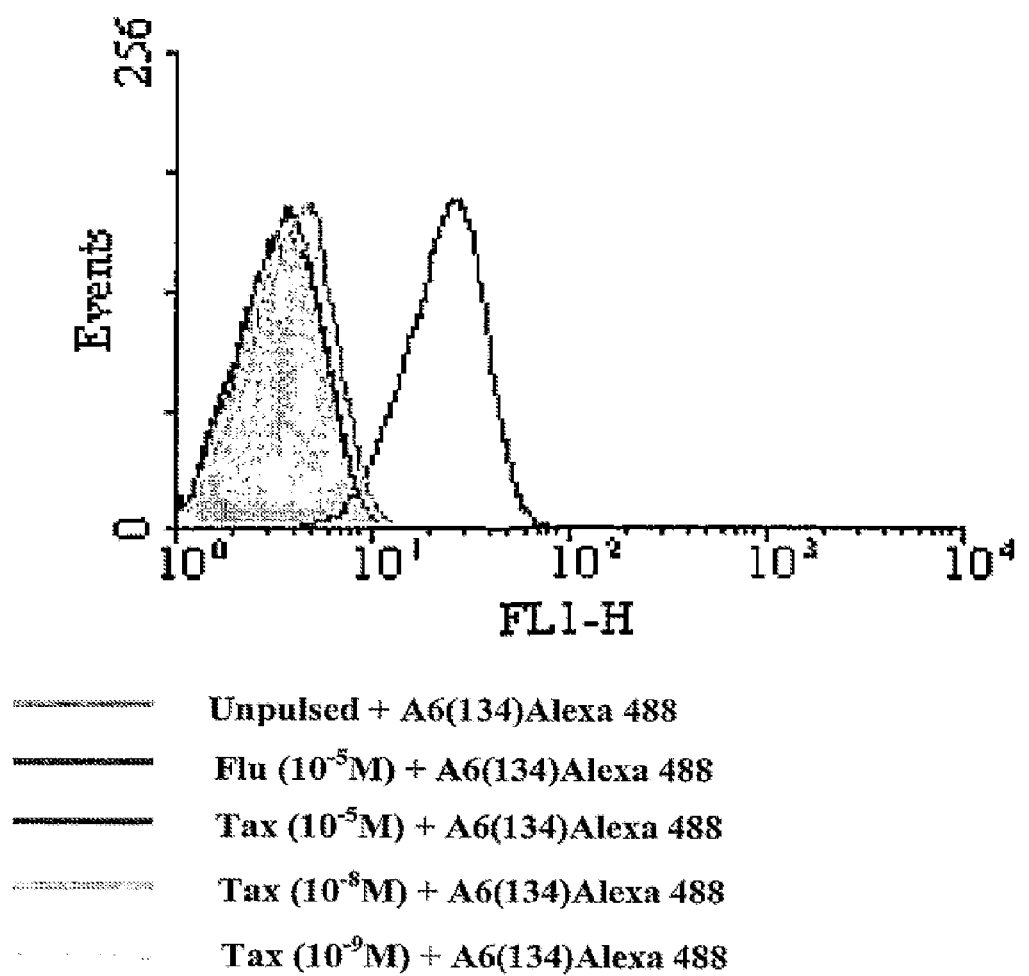

FIG. 39B illustrates specific staining of T2 cells by high affinity A6 TCR monomers.

FIGS. 39A AND 39B I

Example 1

Design of Primers and Mutagenesis of A6 Tax TCR α and β Chains to Introduce the Cysteine Residues Required for the Formation of a Novel Inter-Chain Disulphide Bond For mutating A6 Tax threonine 48 of exon 1 in TRAC*01 to cysteine, the following primers were designed (mutation shown in lower case):

```
                                         (SEQ ID 35)
    5'-C ACA GAC AAA tgT GTG CTA GAC AT (SEQ ID 36)
    5'-AT GTC TAG CAC Aca TTT GTC TGT G
```

For mutating A6 Tax serine 57 of exon 1 in both TRBC1*01 and TRBC2*01 to cysteine, the following primers were designed (mutation shown in lower case):

```
                                         (SEQ ID 37)
    5'-C AGT GGG GTC tGC ACA GAC CC (SEQ ID 38)
    5'-GG GTC TGT Gca GAC CCC ACT G
```

PCR Mutagenesis:

Expression plasmids containing the genes for the A6 Tax TCR α or β chain were mutated using the α-chain primers or the β-chain primers respectively, as follows:

100 ng of plasmid was mixed with 5 μl 10 mM dNTP, 25 μl 10xPfu-buffer (Stratagene), 10 units Pfu polymerase (Stratagene) and the final volume was adjusted to 240 μl with $H_2O$. 48 μl of this mix was supplemented with primers diluted to give a final concentration of 0.2 μM in 50 μl final reaction volume. After an initial denaturation step of 30 seconds at 95° C., the reaction mixture was subjected to 15 rounds of denaturation (95° C., 30 sec.), annealing (55° C., 60 sec.), and elongation (73° C., 8 min.) in a Hybaid PCR express PCR machine. The product was then digested for 5 hours at 37° C. with 10 units of DpnI restriction enzyme (New England Biolabs). 10 μl of the digested reaction was transformed into competent XL1-Blue bacteria and grown for 18 hours at 37° C. A single colony was picked and grown over night in 5 ml TYP+ampicillin (16 g/l Bacto-Tryptone, 16 g/l Yeast Extract, 5 g/l NaCl, 2.5 g/l $K_2HPO_4$, 100 mg/l Ampicillin). Plasmid DNA was purified on a Qiagen mini-prep column according to the manufacturer's instructions and the sequence was verified by automated sequencing at the sequencing facility of Department of Biochemistry, Oxford University. The respective mutated nucleic acid and amino acid sequences are shown in FIGS. 1a and 2a for the α chain and FIGS. 1b and 2b for the β chain.

Example 2

Figure 3:
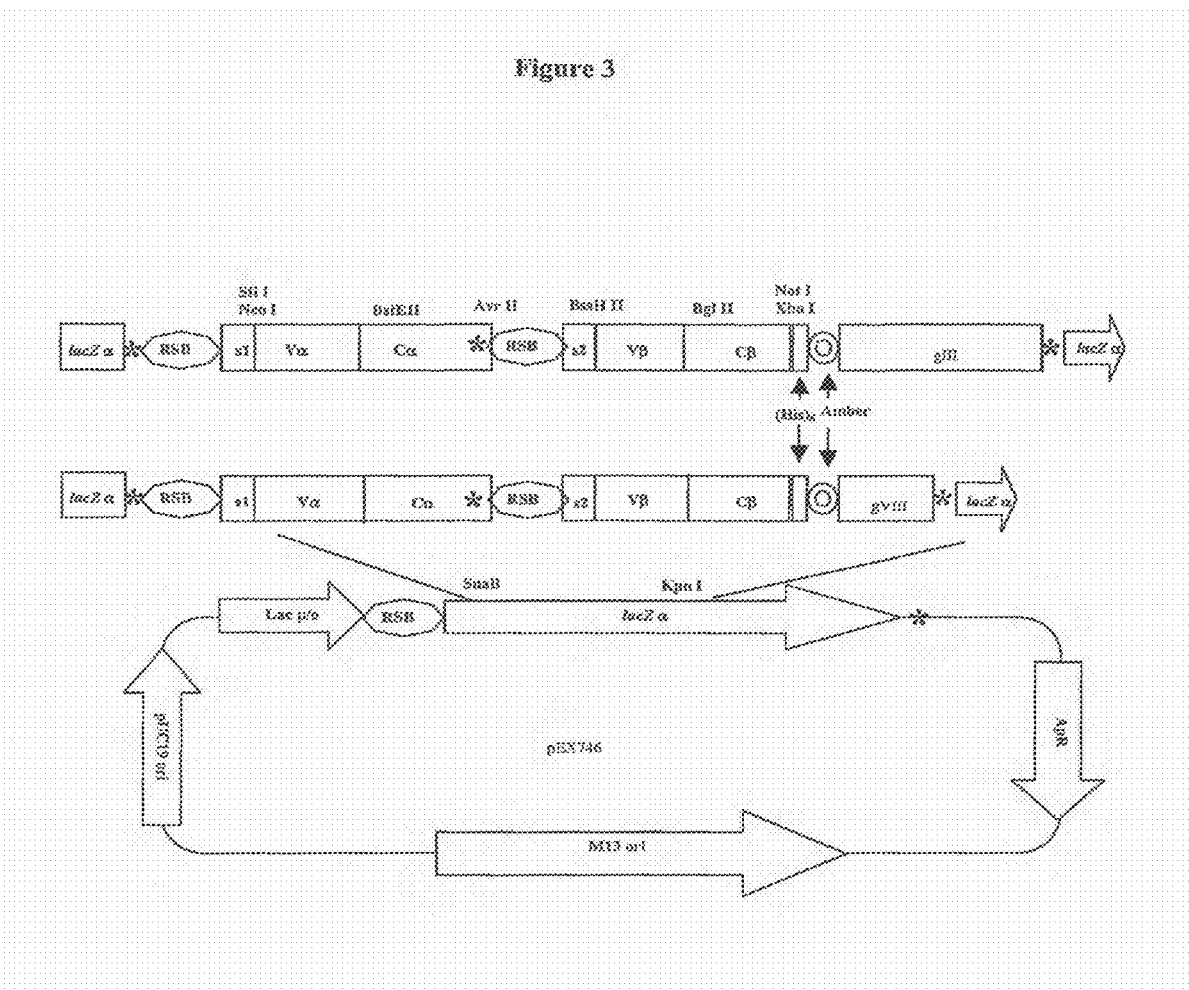
FIG. 3 Outlines the cloning of TCR α and β chains into phagemid vectors. The diagram describes a phage display vector. RSB is the ribosome-binding site. S1 or S2 are signal peptides for secretion of proteins into periplasm of *E. coli*. The * indicates translation stop codon. Either of the TCR α chain or β chain can be fused to phage coat protein, however in this diagram only TCR β chain is fused to phage coat protein.

Construction of Phage Display Vectors and Cloning of A6 TCR α and β Chains into the Phagemid Vectors In order to display a heterodimeric A6 TCR containing a non-native disulfide inter-chain bond on filamentous phage particles, phagemid vectors were constructed for expression of fusion proteins comprising the heterodimeric A6 TCR containing a non-native disulfide inter-chain bond with a phage coat protein. These vectors contain a pUC19 origin, an M13 origin, a bla (Ampicillin resistant) gene, Lac promoter/operator and a CAP-binding site. The design of these vectors is outlined in FIG. 3, which describes vectors encoding for both the A6 TCR β chain-gp3 or A6 TCR β chain-gp8 fusion proteins in addition to the soluble A6 TCR α chain β. The expression vectors containing the DNA sequences of the mutated A6 TCR α and β chains incorporating the additional cysteine residues required for the formation of a novel disulfide inter-chain bond prepared in Example 1 and as shown in FIGS. 1a and 1b were used as the source of the A6 TCR α and β chains for the production of a phagemid encoding this TCR. The complete DNA sequence of the phagemid construct (pEX746) utilised is given in FIG. 4.

The molecular cloning methods for constructing the vectors are described in "Molecular cloning: A laboratory manual, by J. Sambrook and D. W. Russell". Primers listed in table-1 are used for construction of the vectors. A example of the PCR programme is 1 cycle of 94° for 2 minutes, followed by 25 cycles of 94° for 5 seconds, 53° C. for 5 seconds and 72° C. for 90 seconds, followed by 1 cycles of 72° C. for 10 minutes, and then hold at 4° C. The Expand hifidelity Taq DNA polymerase is purchased from Roche.

TABLE 1

Primers used for construction of the A6 TCR phage display vectors

| Primer name | Sequence 5' to 3' |
| --- | --- |
| YOL1 | TAATAATACGTATAATAATATTCTATTTCAAG GAGACAGTC (SEQ ID 39) |
| YOL2 | CAATCCAGCGGCTGCCGTAGGCAATAGGTATT TCATTATGACTGTCTCCTTGAAATAG (SEQ ID 40) |
| YOL3 | CtaCGGCAGCCGCTGGATTGTTATTACTCGCG GCCCAGCCGGCCATGGCccag (SEQ ID 41) |
| YOL4 | GTTCTGCTCCACTTCCTTCTGGGCCATGGCCG GCTGGGCCG (SEQ ID 42) |
| YOL5 | CAGAAGGAAGTGGAGCAGAAC (SEQ ID 43) |
| YOL6 | CTTCTTAAAGAATTCTTAATTAACCTAGGTTA TTAGGAACTTTCTGGGCTGGGGAAG (SEQ ID 44) |
| YOL7 | GTTAATTAAGAATTCTTTAAGAAGGAGATATA CATATGAAAAAATTATTATTCGCAATTC (SEQ ID 45) |
| YOL8 | CGCGCTGTGAGAATAGAAAGGAACAACTAAAG GAATTGCGAATAATAATTTTTTCATATG (SEQ ID 46) |
| YOL9 | CTTTCTATTCTCACAGCGCGCAGGCTGGTGTC ACTCAGAC (SEQ ID 47) |
| YOL10 | ATGATGTCTAGATGCGGCCGCGTCTGCTCTAC CCCAGGCCTC (SEQ ID 48) |
| YOL11 | GCATCTAGACATCATCACCATCATCACTAGAC TGTTGAAAGTTGTTTAGCAAAAC (SEQ ID 49) |
| YOL12 | CTAGAGGGTACCTTATTAAGACTCCTTATTAC GCAGTATG (SEQ ID 50) |

Example 3

Expression of Fusions of Bacterial Coat Protein and Heterodimeric A6 TCR in E. coli In order to validate the construct made in Example 2, phage particles displaying the heterodimeric A6 TCR containing a non-native disulfide inter-chain bond were prepared using methods described previously for the generation of phage particles displaying antibody scFvs (Li et al, 2000, Journal of Immunological Methods 236: 133-146) with the following modifications. E. coli XL-1-Blue cells containing pEX746: A6 phagemid (i.e. the phagemid encoding the soluble A6 TCR α chain and an A6 TCR β chain fused to the phage gIII protein produced as described in Example 2) were used to inoculate 5 ml of Lbatg (Lennox L broth containing 100 m/ml of ampicillin, 12.5 μg/ml tetracycline and 2% glucose), and then the culture was incubated with shaking at 37° C. overnight (16 hours). 50 μl of the overnight culture was used to inoculate 5 ml of TYPatg (TYP is 16 g/l of peptone, 16 g/l of yeast extract, 5 g/l of NaCl and 2.5 g/l of $K_2HPO_4$), and then the culture was incubated with shaking at 37° C. until $OD_{600nm}$=0.8. Helper phage M13 K07 was added to the culture to the final concentration of $5 \times 10^9$ pfu/ml. The culture was then incubated at 37° C. stationary for thirty minutes and then with shaking at 200 rpm for further 30 minutes.

The medium of above culture was then changed to TYPak (TYP containing 100 μg/ml of ampicillin, 25 μg/ml of kanamycin), the culture was then incubated at 25° C. with shaking at 250 rpm for 36 to 48 hours. The culture was then centrifuged at 4° C. for 30 minutes at 4000 rpm. The supernatant was filtrated through a 0.45 μm syringe filter and stored at 4° C. for further concentration or analysis.

Figure 5:
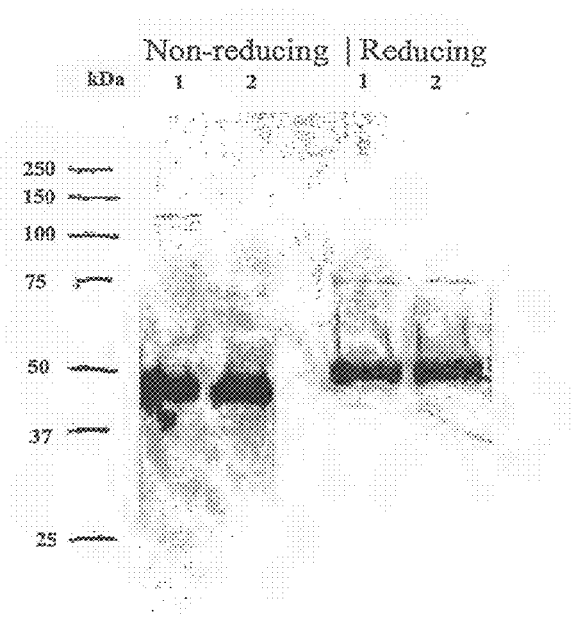
FIG. 5 expression of phage particle fusions of bacterial coat protein and heterodimeric A6 TCR in *E. coli*. Fusion proteins of heterodimeric A6 TCR::gIII are detected using western blotting. Phage particles are prepared from *E. coli* XL-1-Blue and concentrated with PEG/NaCl. The samples are loaded in reducing or non-reducing sample buffers. Lane 1 is the sample of clone 7 containing correct sequence, and lane 2 is the sample of clone 14 containing a deletion in the α-chain encoding gene. The heterodimeric A6 TCR:gIII fusion protein was detected at 125 kDa.

The fusion protein of filamentous coat protein and heterodimeric A6 TCR containing a non-native disulfide interchain bond was detected in the supernatant by western blotting. Approximately $10^{11}$ cfu phage particles were loaded on each lane of an SDS-PAGE gel in both reducing and non-reducing loading buffer. Separated proteins were primary-antibody probed with an anti-M13 gIII mAb, followed by a second antibody conjugated with Horseradish Peroxidase (HRP). The HRP activity was then detected with Opti-4CN substrate kit from Bio-Rad (FIG. 5). Theses data indicated that disulfide-bonded A6 TCR of clone 1 is fused with filamentous phage coat protein, gIII protein.

Example 4

Detection of Functional Heterodimeric A6 TCR Containing a Non-Native Disulfide Inter-Chain Bond on Filamentous Phage Particles The presence of functional (HLA-A2-tax binding) A6 TCR displayed on the phage particles was detected using a phage ELISA method.

TCR-Phage ELISA

Binding of the A6 TCR-displaying phage particles to immobilised peptide-MHC in ELISA is detected with primary rabbit anti-fd antisera (Sigma) followed by alkaline phosphatase (AP) conjugated anti-Rabbit mAb (Sigma). Non specific protein binding sites in the plates can be blocked with 2% MPBS or 3% BSA-PBS Materials and Reagents
1. Coating buffer, PBS
2. PBS: 138 mM NaCl, 2.7 mM KCl, 10 mM $Na_2HPO_4$, 2 mM $KH_2PO_4$
3. MPBS, 3% marvel-PBS
4. PBS-Tween: PBS, 0.1% Tween-20
5. Substrate solution, Sigma FAST pNPP, Cat# N2770

Figure 6:
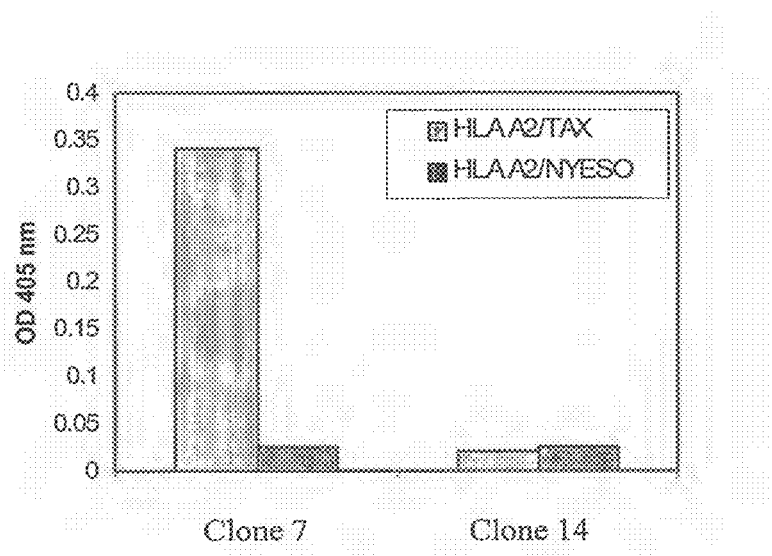
FIG. 6 illustrates ELISA detection of pMHC peptide complex binding activity of a heterodimeric A6 TCR displayed on phage. Clone 7 binds specifically to HLA A2-Tax complex. Clone 14 cannot bind to any pMHC, as no TCR is attached to the phage particles.

Method
1. Rinse NeutrAvidin coated wells twice with PBS.
2. Add 25 µl of biotin-HLA-A2 Tax or biotin-HLA-A2 NYESO in PBS at concentration of 10 µg/ml, and incubate at room temperature for 30 to 60 min.
3. Rinse the wells twice with PBS
4. Add 300 µA of 3% Marvel-PBS, and incubate at room temperature for 1 hr. Mix the TCR-phage suspension with 1 volume of 3% Marvel-PBS and incubate at room temperature.
5. Rinse the wells twice with PBS
6. Add 25 µl of the mixture of phage-A6 TCR/Marvel-PBS, incubate on ice for 1 hr
7. Rinse the wells three times with ice-cold PBStween, and three times with ice-cold PBS.
8. Add 25 µl of ice cold rabbit anti-fd antibody diluted 1:1000 in Marvel-PBS, and incubate on ice for 1 hr
9. Rinse the wells three times with ice-cold PBStween, and three times with ice-cold PBS.
10. Add 25 µl of ice cold anti-rabbit mAb-Ap conjugate diluted 1:50,000 in Marvel-PBS, and incubate on ice for 1 hr
11. Rinse the wells three times with ice-cold PBStween, and three times with ice-cold PBS.
12. Add 150 µl of Alkaline phosphatase yellow to each well and read the signal at 405 nm The results presented in FIG. 6 indicate clone 1 produced a phage particle displaying an A6 TCR that can bind specifically to its cognate pMHC. (HLA-A2 Tax)

Analysis of the DNA sequence of this displayed A6 TCR revealed the presence of an 'opal' stop codon in the TCR β chain not present in the corresponding sequence of the expression vector construct of Example 2. This codon is 'read-through' with low frequency by ribosomes of the *E. coli* strain utilised resulting in the insertion of a tryptophan residue at this site and a much-reduced overall level of full-length β chain expression. From this observation it was inferred that only cells expressing this mutated A6 TCR sequence had survived the culture rounds of Example 3, and that therefore the high levels of A6 TCR predicted to be expressed by the original expression vector were toxic to the host cells.

Example 5

Single-Chain TCR (scTCR) Ribosome Display

Construction of Ribosome Display scTCR Vectors for Use in Generation of Ribosome Display PCR Templates.

Figure 7A:
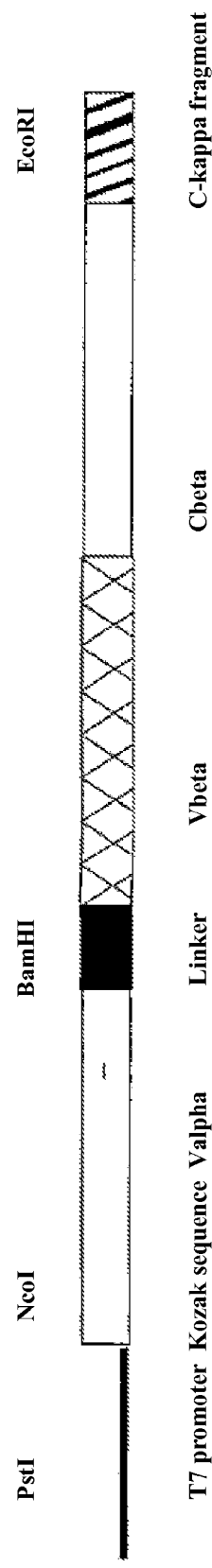
FIG. 7A is a schematic illustration of the single-chain A6 TCR-C-Kappa DNA ribosome display construct.

Ribosome display constructs were cloned into the readily available DNA plasmid pUC19 in order to generate an error free and stable DNA PCR template from which to conduct subsequent ribosome display experiments. Vector construction was undertaken in two steps so as to avoid the use of large oligonucleotide primers (with their associated error problems). The final A6 scTCR-C-Kappa DNA ribosome display construct is shown in a schematic form in FIG. 7a and both DNA and protein sequences are shown in FIG. 7b. This construct can be excised from pUC19 as a Pst1/EcoR1 double digest.

The molecular cloning methods for constructing the vectors are described in "Molecular cloning: A laboratory manual, by J. Sambrook and D. W. Russell". Primers listed in Table 2 are used for construction of the vectors. The PCR programme utilised was as follows—1 cycle of 94° C. for 2 minutes, followed by 25 cycles of 94° C. for 30 seconds, 55° C. for 20 seconds and 72° C. for 120 seconds, followed by 1 cycles of 72° C. for 5 minutes, and then hold at 4° C. The Pfu DNA polymerase is purchased from Strategene. Oligonucleotide primers used are described in table 2.

Construction of pUC19-T7—Step 1

The construction of pUC19-T7 is described below, the construction results in a pUC19 vector containing a T7 promoter region followed by a short space region and the an optimum eukaryotic Kozak sequence. This is an essential part of the ribosome display construct as it is required for the initiation of transcription of any attached sequence in rabbit reticulocyte lysates. Sequences for ribosome display such as the A6scTCR-Ckappa can be ligated into the pUC19-T7 vector between the Nco1 and EcoR1 restriction sites.

Equimolar amounts of the primer Rev-link and For-link were annealed by heating to 94° C. for 10 min and slowly cooling the reaction to room temperature. This results in the formation of a double stranded DNA complex that can be seen below.

```
                                               (SEQ ID 51)
5'AGCTGCAGCTAATACGACTCACTATAGGAACAGGCCACCATGG

CGTCGATTATGCTGAGTGATATCCTTGTCCGGTGGTACCCTAG 3'
```

The 5' region contains an overhanging sticky end complimentary to a HindIII restriction site whilst the 3' end contains a sticky end that is complimentary to a BamH1 restriction site.

The annealed oligonucleotides were ligated into Hind III/BamHI double-digested pUC19 which had been purified by agarose gel electrophoresis, excised and further purified with the Qiagen gel extraction kit. The ligations were transformed into *E. coli* XL1-BLUE. Individual pUC19-T7 clones were sequenced to confirm the presence of the correct sequence. The sequence is shown in FIG. 8.

Construction of A6scTCR-C-Kappa Vector—Step 2.

Construction of the single chain A6scTCR-C-Kappa DNA sequence requires the generation of three PCR fragments that must then be assembled into one A6scTCR-C-Kappa fragment. The fragments consist of (a.) the A6 TCR alpha chain variable region flanked by a Nco1 site in the 5' region and a section of Glycine Serine linker in the 3' region flanked by a BamH1 restriction site. This product was generated via a standard PCR of the vector pEX202 with the primers 45 and 50 (See Table 2). Fragment (b.) A6 TCR beta variable and constant region flanked by a BamH1 restriction site in the 5' region followed by a section of Glycine Serine linker. This product was generated via a standard PCR of the vector pEX207 with the primers 72 and 73 (See Table 2). Fragment (c.) Portion of a human C-kappa region generated by a standard PCR of the p147 vector with the primers 61-60 (See Table 2). All PCR products were run on a 1.6% TBE agarose gel and DNA bands of the correct size excised and purified using the Qiagen gel extraction kit.

Fragments (b.) and (c.) were fused by a standard overlap PCR via the complementarity in their primer sequences 73 and 61 (See Table 2). The PCR was carried out via the primers 72 and 60 (See Table 2). The PCR products were run on a 1.6% TBE agarose gel and DNA bands of the correct size excised and purified using the Qiagen gel extraction kit. This fragment is termed (d.).

Fragment (a.) was double digested with Nco1 and BamH1 whilst fragment (d.) was double digested with BamH1 and EcoR1. pUC19-T7 was double digested with Nco1 and EcoR1. All digested DNA products were run on a 1.2% TBE agarose gel and DNA bands of the correct size were excised and purified using the Qiagen gel extraction kit. The digested pUC19-T7, fragments (a.) and (d.) were ligated and transformed into *E. coli* XL1-BLUE. Transformants were sequenced to confirm the correct sequence. The sequence of the A6scTCR-C-Kappa ribosome display construct that was cloned into pUC19 is shown in FIG. 9 flanked by its Pst1 and EcoR1 sites.

TABLE 2

| Oligonucleotides used (Purchased from MWG). | |
|---|---|
| Rev-Link | 5'GATCCCATGGTGGCCTGTTCCTATAGTGAGT CGTATTAGCTCG (SEQ ID 52) |
| For-Link | 5'AGCTGCAGCTAATACGACTCACTATAGGAAC AGGCCACCATGG (SEQ ID 53) |
| 45-A6 | 5'CCACCATGGGCCAGAAGGAAGTGGAGCAGAA CTC (SEQ ID 54) |
| 7 A6-Beta(RT-PCR)(a) | 5'CGAGAGCCCGTAGAACTGGACTTG (SEQ ID 55) |
| 49-A6-BamH1-F | 5'GTGGATCCGGCGGTGGCGGGTCGAACGCTGG TGTCACTCAGACCCC (SEQ ID 56) |
| 50-A6-BamH1-R | 5'CCCGGATCCACCTCCGCCTGAACCGCCTCCAC CGGTGACCACAACCTGGGTCCCTC (SEQ ID 57) |
| 60-Kappa-rev EcoR1 | 5'CTGAGAATTCTTATGACTCTCCGCGGTTGAA GCTC (SEQ ID 58) |
| 61-Betac-Kappa-for1 | 5'TGACGAATTCTGACTCTCCGCGGTTGAAGCT C (SEQ ID 59) |
| 71 T7-Primer | 5'AGCTGCAGCTAATACGACTCACTATAGG (SEQ ID 60) |
| 72 A6-beta | 5'GGCCACCATGGGCAACGCTGGTGTCACTCAG ACCCC (SEQ ID 61) |
| 73-A6-cons-rev | 5'TGAACCGCCTCCACCGTCTGCTCTACCCCAG GCCTCGGCG (SEQ ID 62) |

TABLE 2-continued

| Oligonucleotides used (Purchased from MWG). | |
|---|---|
| 75 Kappa-rev | 5'TGACTCTCCGCGGTTGAAGCTC (SEQ ID 63) |

Demonstration of the Production of sc A6 TCR-C-Kappa by In Vitro Transcription Translation.

Preparation of scA6 TCR-C-Kappa PCR Product for In Vitro Transcription Translation Here we describe the synthesis of sc A6 TCR-C-Kappa via In vitro transcription translation in the presence of biotinylated lysine and its subsequent detection by western blotting and detection with alkaline phosphatase labelled streptavidin.

The sc A6 TCR-C-Kappa PCR product was prepared in a standard PCR reaction using the vector sc A6 TCR-C-Kappa as template and PCR primers 71 and 60. Primer 60 contains a stop codon to allow the release of the scTCR from the ribosome. Pfu polymerase (Strategene) was used for increased fidelity during PCR synthesis. The PCR products were run on a 1.6% TBE agarose gel and DNA bands of the correct size excised and purified using the Qiagen gel extraction kit.

The transcription translation reactions were carried out using the Ambion PROTEINscript II Linked transcription translation kit Cat 1280-1287 with 300 ng of the above described PCR product. Three transcription translation reactions were set up according to the manufactures protocol. The one modification was the addition of biotinylated lysine from the Transcend™ Non-Radioactive Translation Detection System.

Reaction 1 sc A6 TCR-C-Kappa 300 ng with 2 μl biotinylated lysine

Reaction 2 sc A6 TCR-C-Kappa 300 ng without 2 μl biotinylated lysine

Reaction 3 No DNA control with 2 μl biotinylated lysine.

Figure 10:
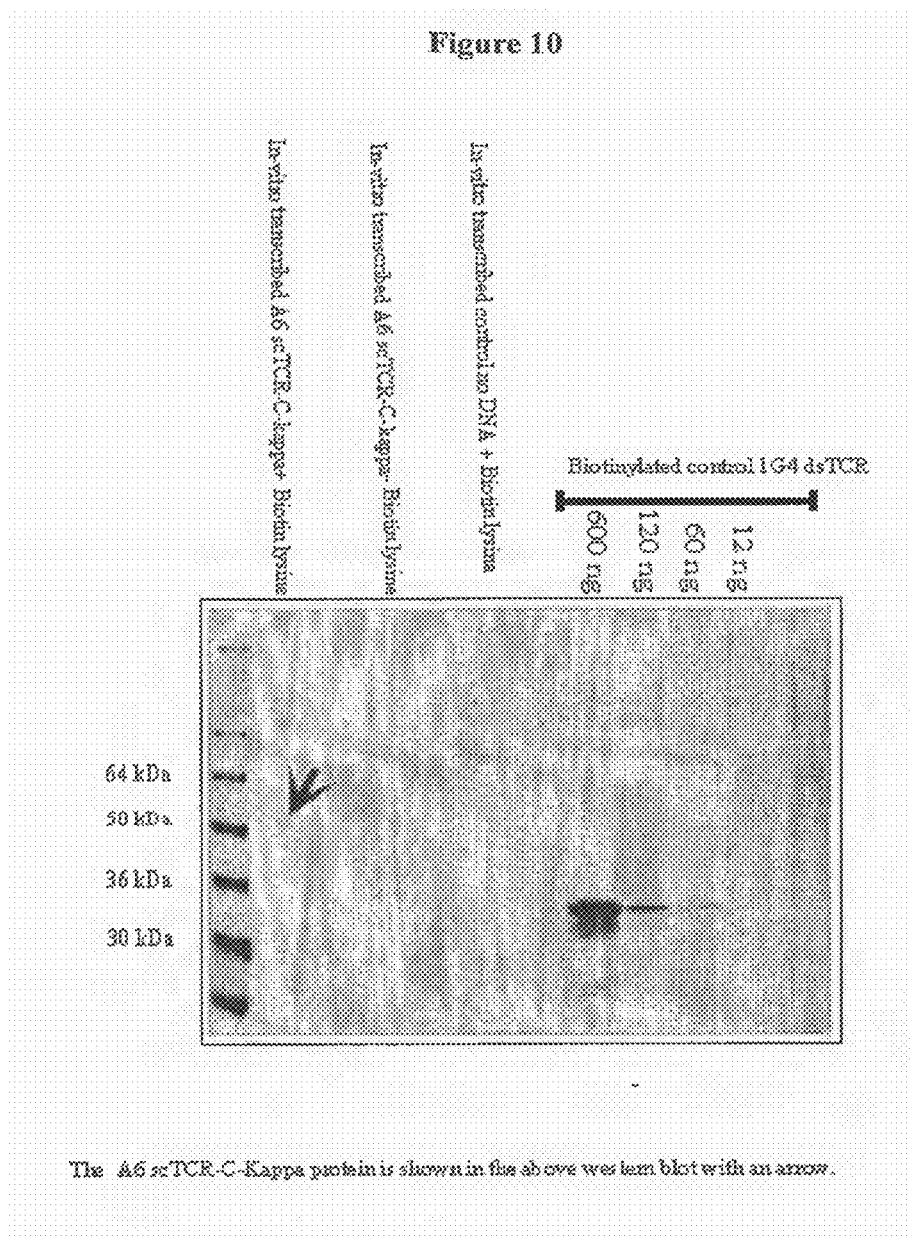
FIG. 10 Western blot showing the detection of in-vitro translated single-chain A6 TCR-C-Kappa using Ambion rabbit reticulocyte lysates.

Two microliters of each reaction was run on a 4-20% Novex gradient SDS-PAGE gel (Invitrogen). Additionally a number of dilutions of a control biotinylated TCR were also run. The gel was blotted and the proteins detected with streptavidin alkaline phosphatase and subsequently colometrically developed with Western Blue® Stabilized Substrate for Alkaline Phosphatase as described in the Transcend™ Non-Radioactive Translation Detection System protocol. The western blot is shown in FIG. 10.

In the no DNA control and A6scTCR-C-Kappa reaction without biotinylated lysine no band of approximately the correct size can be seen as expected whilst in the A6scTCR-C-Kappa reaction in the presence of biotinylated lysine a band of approximately the correct size can be seen. This demonstrates the synthesis of the sc A6 TCR-C-Kappa TCR by In vitro transcription translation.

Preparation of sc A6 TCR-C-Kappa Ribosome Display PCR Product.

The sc A6 TCR-C-Kappa PCR product was prepared in a standard PCR reaction using the vector A6scTCR-C-Kappa as template and PCR primers 71 and 75 (See Table 2). Primer 75 does not contain a stop codon. Pfu polymerase (Strategene) was used for increased fidelity during PCR synthesis. The PCR products were run on a 1.6% TBE agarose gel and DNA bands of the correct size were excised and purified using the Qiagen gel extraction kit.

Ribosome Display Process

Transcription and Translation of sc A6 TCR-C-Kappa

The transcription/translation reactions were carried out using the Ambion PROTEINscript II Linked transcription translation kit (Cat No. 1280-1287)

Transcription Reactions

The following transcription reactions were set up in Ambion 0.5 ml non stick tubes (Cat No. 12350).

| Contents | Tube 1 (Normal A6) | Tube 2 (Control) |
|---|---|---|
| Water | 4.53 µl | 5.7 µl |
| Template (PCR product) | Sc A6 TCR-C-Kappa PCR product 1.17 µl (300 ng) | No DNA |
| 5X transcription mix | 2 µl | 2 µl |
| Enzyme mix | 2 µl | 2 µl |
| Superasin Rnase inhibitor ambion | 0.3 µl | 0.3 µl |
| Final volume | 10 µl | 10 µl |

The tubes were incubated at 30° C. for 60 min on a PCR block with the hot lid off.

Translation Reactions

The following translation reactions were set up in Ambion 0.5 ml non stick tubes.

| Contents | 1 (Normal A6) | 2 (Control) |
|---|---|---|
| Reticulocyte Lysate | 105 µl | 105 µl |
| 25 mM Mg-Acetate | 3 µl | 3 µl |
| Translation Mix | 7.5 µl | 7.5 µl |
| Methionine | 7.5 µl | 7.5 µl |
| Water | 18 µl | 18 µl |
| Superasin Rnase inhibitor | 3 µl | 3 µl |
| Transcription reaction | 6 µl tube 1 above | 6 µl tube 2 above |

Each tube contains enough for 3×50 µl selections. The tubes were mixed and incubated at 30° C. for 60 min on a PCR block with the hot lid off. After 30 min 3 Unit of RQ1 Rnase free Dnase (Promega) was added to destroy the original DNA template in tube 1 and 3 Unit RQ1 Rnase free Dnase (Promega) in tube 2. After 60 min 18 µl of Heparin solution was added to translation reaction 2 and 18 µl of Heparin solution was added to translation reaction 1. Samples were stored on ice ready for selection against HLA-coated beads.

Coating of Magnetic Beads.

20 µl of resuspended Streptavidin Magnetic Particles (Roche Cat. No. 1641778) were transferred into a sterile Rnase free 1.5 ml eppendorf tube. The beads were immobilised with a Magnetic Particle Separator (Roche Cat. No. 1641794) and the supernatant was removed. The beads were then washed with 100 µl of Rnase free 1×PBS (10×PBS Ambion Cat No. 9624, Ambion H₂O Cat No. 9930) the beads were immobilised and the supernatant was removed. A total of 3 PBS washes were carried out.

The beads were resuspended in 20 µl of PBS and the contents split evenly between two tubes (10 µl each). One tube will be used to produce control-blocked beads and the other tubes to produce HLA-A2-Tax coated beads.

To the control beads tube 80 µl of BSA/Biotin solution was added and mixed. The BSA/Biotin solution was made up as follows. 10 µl of a 0.2M Tris base 0.1M Biotin solution was added to 990 µl of PBS 0.1% BSA (Ambion Ultrapure Cat No. 2616). Also 20 µl of Heparin solution (138 mg/ml Heparin (Sigma H-3393) in 1×PBS) was added and the solution mixed. The beads were incubated at room temperature for 1 hour with intermittent mixing. The beads were then washed three times with 100 µl of PBS and were resuspended in 10 µl of PBS, 0.1% BSA.

The HLA-TAX coated beads were prepared as follows. 40 µl of HLA-A2-Tax (1.15 mg/ml prepared as described in WO99/60120) was added to the 10 µl of beads and mixed. The beads were incubated at room temperature for 15 min and then 20 µl of BSA 50 mg/ml Ambion Cat 2616 and 20 µl of heparin solution (see above) were added and mixed. The beads were incubated for a further 45 min and then 20 µl of BSA/Biotin solution was added. The beads were then washed three times with 100 µl of PBS and were re-suspended in 10 µl of PBS, 0.1% BSA.

Panning with Magnetic Beads

The sc A6 TCR translation reaction was split into three 50 µl aliquots and each aliquot received either 2 µl of the following beads:

Control (no HLA)

HLA-A2-Tax

HLA-A2-Tax plus 10 µg soluble scA6 TCR

A control translation reaction was also carried out and split into three 50 µl aliquots and each aliquot received either 2 µl of the following beads Control (no HLA)

HLA-A2-Tax

HLA-A2-Tax plus 10 µg soluble sc A6 TCR

This gave a total of six tubes. The tubes were incubated on a PCR block at 5° C. for 60 min with intermittent mixing.

The beads were then washed three times with 100 µl ice cold buffer (PBS, 5 mM Mg-acetate, 0.2% Tween 20 (Sigma Rnase free). Each aliquot of beads were then re-suspended in 50 µl of 1×RQ1 Dnase digestion buffer containing 1 µl (40 U) of Superasin and 1 µl (1U) of RQ1 Dnase. The beads were incubated on a PCR block for 30 min at 30° C.

The beads were then washed three times with 100 µl ice cold buffer (PBS, 5 mM Mg-acetate, 0.2% Tween 20) and once with ice cold H₂O. The beads were re-suspended in 10 µl of Rnase free H₂O. The beads were then frozen ready for RT-PCR.

RT-PCR of sc A6 TCR-C-Kappa mRNA on Beads Rescued from the Ribosome Display Reactions.

The RT PCR reactions on the beads were carried out using the Titan one tube RT-PCR kit cat 1855476 as described in the manufacturers protocols. Two microliters of beads were added into each RT-PCR reaction along with the primers 45 and 7 and 0.3 µl of Superasin Rnase inhibitor.

For each RT-PCR reaction a second PCR only reaction was set up which differed only by the fact that no reverse transcriptase was present just Roche high fidelity polymerase. This second reaction served as a control for DNA contamination.

Additionally a RT-PCR positive control control was set up using 1 ng of the vector sc A6 TCR-C-Kappa.

The reactions were cycled as follows. An RT-PCR step was carried out by incubation of the samples at 50° C. for 30 min followed by the inactivation of the reverse transcriptase by incubation at 94° C. for 3 min on a PCR block.

The reactions were PCR cycles as follows for a total of 38 cycles:

94° C. 30 seconds

55° C. 20 seconds

68° C. 130 seconds.

The PCR reaction was finished by incubation at 72° C. for 4 minutes.

Great care was taken during all ribosome display steps to avoid Rnase contamination. The RT-PCR and PCR reactions were run on a 1.6% TBE agarose gel which can be seen in FIG. 11. Analysis of the gel shows that there is no DNA contamination and that all PCR products are derived from mRNA. The DNA band of the correct size in lane 2 demonstrates that ribosome displayed sc A6 TCR-C-Kappa was selected out by HLA-A2-Tax coated beads. Lane 3 shows that we can inhibit this specific selection of ribosome-displayed sc A6 TCR-C-Kappa by the addition of soluble sc A6 TCR. The significant reduction in the band intensity in lane 3 relative to the uninhibited sample in lane 2 demonstrates this. No binding of ribosome-displayed sc A6 TCR-C-Kappa could be shown against control non-HLA coated beads.

Example 6

Sequence Analysis of A6 TCR Clones Displayed on Phage Particles and Methods to Improve Display Characteristics After the construction of vectors for displaying A6 TCR on phage by PCR and molecular cloning, bacterial clones that can produce phage particles displaying A6 TCR were screened by phage ELISA as described in Example 4. Three different clones were identified that gave specific binding to HLA-A2-tax in the ELISA binding assay. These clones all contained mutations in the 'wild-type' A6 TCR DNA or in the associated regulatory sequences, which are described in the following table:

Functional Clones from Screening TCR A6 Displayed on Phage

| Name | Feature | |
|---|---|---|
| Clone 7 | The third ribosome-binding site, which is located in front of vβ gene, is mutated from AAGGAGA to AAGGGGA. | |
| Clone 9 | An opal codon is introduced in vβ CDR3. | Full DNA and amino acid sequence in FIGS. 12a & 12b |
| Clone 49 | An amber codon is introduced in vβ FR1. This mutation introduces a 'silent' mutation that does not affect the resulting amino acid sequence | Full DNA sequence in FIGS. 13a |

These clones all contained mutations that are likely to cause a reduction in the expression levels of the A6 TCR β chain. It was inferred that low expression clones were selected over high expression clones as a result of cell toxicity caused by high expression levels of TCR.

Example 7

Mutagenesis of A6 TCR CDR3 Regions

The CDR3 regions of the A6 TCR were targeted for the introduction of mutations to investigate the possibility of generating high affinity mutants.

Overlapping PCR was used to modify the sequence of α and β CDR3 regions to introduce two unique restriction sites Hind III for α chain, with oligos of YOL54, (SEQ ID 64)
5'CAGCTGGGGGAAGCTTCAGTTTGGAGCAG3'
and

YOL55, (SEQ ID 65)
5'CGCTCCAAACTGAAGCTTCCCCCAGCTG3',
and

Xho I for β chain, with oligos of YOL56

(SEQ ID 66)
5'GTACTTCTGGCCTCGAGGCCGGGACTAG3'
and

YOL57

(SEQ ID 67)
5'CTAGTCCCGGCCTCGAGGCACAGAAGTAC3'.

PCR was used to introduce mutations for affinity maturation. The A6 TCR clone 9 (incorporating an introduced opal codon in the β chain CDR3 sequence) was used as a source of template DNA, and TCR chains were amplified with the mutation primers (detailed in the following table) and YOL22 5'CATTTTCAGGGATAGCAAGC3' (SEQ ID 68) (β-chains) or YOL13 5'TCACACAGGAAACAGCTATG3' (SEQ ID 69) (α-chains).

| Primer name | Sequence 5' to 3' |
|---|---|
| Primers for introducing mutation at CDR3 of A6 β chain and α chain | |
| YOL59 | TGTGCCTCGAGGNNKNNKNNKNNKNNKNN NKCGACCAGAGCAGTACTTCG (SEQ ID 70) |
| YOL60 | TGTGCCTCGAGGCCGNNKNNKNNKNNKN NKNNKCCAGAGCAGTACTTCGGGC (SEQ ID 71) |
| YOL61 | TGTGCCTCGAGGCCGNNKNNKNNKNNKN NKNNKCGACCAGAGCAGTACTTCG (SEQ ID 72) |
| YOL62 | TGTGCCTCGAGGCCGNNKNNKNNKNNKN NKNNKGGAGGGCGACCAGAGCAG (SEQ ID 73) |
| YOL63 | TGTGCCTCGAGGCCGGGANNKNNKNNKN NKNNKNNKGGGCGACCAGAGCAGTAC (SEQ ID 74) |
| YOL68 | TGTGCCTCGAGGNNKNNKNNKNNKNNKN NKCCAGAGCAGTACTTCGggc (SEQ ID 75) |
| YOL69 | TGTGCCTCGAGGNNKNNKNNKNNKNNKN NKGAGCAGTACTTCGggccg (SEQ ID 76) |
| YOL70 | TGTGCCTCGAGGNNKNNKNNKNNKNNKN NKCAGTACTTCGggccgggc (SEQ ID 77) |
| YOL71 | TGTGCCTCGAGGccgNNKNNKNNKNNKg ggCGACCAGAGCAGTACTTCG (SEQ ID 78) |
| YOL58 | AAACTGAAGCTTMNNMNNMNNMNNMNNT GTAACGGCACAGAGGTAG (SEQ ID 79) |
| YOL72 | AAACTGAAGCTTMNNMNNgctgtcMNNT GTAACGGCACAGAGGTAG (SEQ ID 80) |
| YOL73 | AAACTGAAGCTTMNNMNNMNNgctgtcM NNTGTAACGGCACAGAGGTAG (SEQ ID 81) |

-continued

Primers for introducing mutation at CDR3 of A6 β chain and α chain

| Primer name | Sequence 5' to 3' |
|---|---|
| YOL74 | AAACTGAAGCTTMNNMNNgctgtcMNNA ACGGCACAGAGGTAG (SEQ ID 82) |

α-chain fragments were digested with Nco I and HindIII andre-purified using a Qiagen kit and vector was prepared by digesting clone 9 with Nco I and HindIII followed by gel purification using a Qiagen kit. β-chain fragments were digested with Xho I and Not I andre-purified using a Qiagen kit and vector was prepared by digesting clone 9 with Xho I and Not I followed by gel purification using a Qiagen kit. Purified inserts and vectors at 3:1 molar ratio were mixed with T4 ligase buffer, T4 ligase and nuclease-free water. The ligations were carried out at 16° C. water bath overnight. For each mutation-library, a total of 0.5 to 1 μg purified ligated products were electroporated into $E.\ coli$ TG1 at ratio of 0.2 μg DNA per 40 μl of electroporation-competent cells (Stratagen) following the protocols provided by the manufacturer. After electroporation, the cells were re-suspended immediately with 960 μl of SOC medium at 37° C. and plated on a 244 mm×244 mm tissue culture plate containing YTE (15 g Bacto-Agar, 8 g NaCl, 10 g Tryptone, 5 g Yeast Extract in liter) supplemented with 100 μg/ml ampicillin and 2% glucose. The plate was incubated at 30° C. over night. The cells were then scraped from the plates with 5 ml of DYT (16 g Trytone, 10 g Yeast extract and 5 g NaCl in liter, autoclaved at 125° C. for 15 minutes) supplemented with 15% glycerol.

In order to make phage particles displaying the A6 TCR, 500 ml of DYTag (DYT containing 100 μl/ml of ampicillin and 2% glucose) was inoculated with 500 to 1000 μl of the library stocks. The culture was grown until OD(600 nm) reached 0.5. 100 ml of the culture was infected with helper phage (M13 K07 (Invitrogen), or HYPER PHAGE (Progen Biotechnik, GmbH 69123 Heidelberg), and incubated at 37° C. water bath for 30 minutes. The medium was replaced with 100 ml of DYTak (DYT containing 100 μg/ml ampicillin and 25 μg/ml of kanamycin). The culture was then incubated with shaking at 300 rpm and 25° C. for 20 to 36 hours.

Example 8

Isolation of High Affinity A6 TCR Mutants

The isolation of high affinity A6 TCR mutants was carried out using two different methods.

The first method involves selecting phage particles displaying mutant A6 TCRs capable of binding to HLA-A2 Tax complex using Maxisorp immuno-tubes (Invitrogen) The immuno-tubes were coated with 1 to 2 ml 10 μg/ml streptavidin in PBS overnight at room temperature. The tubes were washed twice with PBS, and then 1 ml of biotinylated HLA-A2 Tax complex at 5 μg/ml in PBS was added and incubated at room temperature for 30 minutes. The rest of the protocol for selection of high affinity binders is as described previously (Li et al. (2000) *Journal of Immunological Methods* 236: 133-146), except for the following modifications. The selection was performed over three or four rounds. The concentrations of biotinylated HLA-A2 Tax complex were 5 μg/ml for the first round of selection, 0.5 μg/ml for the second, 0.05 μg/ml for the third and 0.005 μg/ml for the fourth round of selection. M13 K07 helper phage were used in rounds one and two, and hyper phage were used in subsequent rounds, for the selection.

The second method utilised was the selection of phage particles displaying mutant A6 TCRs capable of binding to HLA-A2 Tax complex in solution. Streptavidin-coated paramagnetic beads (Dynal M280) were pre-washed according to manufacturer's protocols. Phage particles, displaying mutated A6 TCR at a concentration of $10^{12}$ to $10^{13}$ cfu, were pre-mixed with biotinylated HLA-A2 Tax complex at concentrations of $2\times10^{-8}$M, $2\times10^{-9}$M, $2\times10^{-10}$ M and $2\times10^{-11}$M for first, second, third and fourth-round of selections respectively. The mixture of A6 TCR-displaying phage particles and HLA-A2 Tax complex was incubated for one hour at room temperature with gentle rotation, and A6 TCR-displaying phage particles bound to biotinylated HLA-A2 Tax complex were captured using 200 μl (round 1) or 50 μl (round 2, 3, and 4) of streptavidin-coated M280 magnetic beads. After capture of the phage particles, the beads were washed a total often times (three times in PBStween20, twice in PBStween 20 containing 2% skimmed milk powder, twice in PBS, once in PBS containing 2% skimmed milk powder, and twice in PBS) using a Dynal magnetic particle concentrator. After final wash, the beads were re-suspended in 1 ml of freshly prepared 100 mM triethylamine pH11.5, and incubated for 5 to 10 minutes at room temperature with gentle rotation.

Phage particles eluted from the beads were neutralized immediately with 300 μl of 1M tris-HCl pH7.0. Half of the eluate was used to infect 10 ml of $E.\ coli$ TG1 at OD(600 nm)=0.5 freshly prepared for the amplification of the selected phage particles according to the methods previously described (Li et al., (2000) *Journal of Immunological Methods* 236: 133-146).

After the third or fourth round of selection, 95 colonies were picked from the plates and used to inoculate 100 μl of DYTag in a 96-well microtiter plate. The culture was incubated at 37° C. with shaking overnight. 100 μl of DYTag was then sub-inoculated with 2 to 5 μl of the overnight cultures, and incubated at 37° C. with shaking for 2 to 3 hours or until the culture became cloudy. To infect the cells with helper phage, the culture was infected with 25 μl of DYTag containing $5\times10^9$ pfu helper phages, and incubated at 37° C. for 30 minutes. The medium was replaced with DYTak. The plates were incubated at 25° C. for 20 to 36 hours with shaking at 300 rpm. The cells were precipitated by centrifugation at 3000 g for 10 minutes at 4° C. Supernatants were used to screen for high affinity A6 TCR mutants by competitive phage ELISA as follows.

Nunc-Immuno Maxisorp wells coated with streptavidin were rinsed twice with PBS. 25 μl 5 μg/ml biotinylated HLA-A2-Tax complex was added to each well and these were incubated at room temperature for 30 to 60 minutes, and followed by two PBS rinses. Non-specific protein binding sites in the wells were blocked by the addition of 300 μl 3% skimmed milk in PBS followed by incubation at room temperature for 2 hours. In order to prepare phage particles displaying the heterodimric A6 TCR, phage particles were mixed with 3% skimmed milk in PBS containing 0, 20, and 200 nM HLA-A2-Tax, followed by incubated at room temperature for 1 hour. The phage is added to the wells coated with HLA-A2-Tax and incubated at room temperature for 1 hour, followed by 3 washes with PBS containing 0.1% tween 20 and then 3 washes with PBS. The bound TCR-displaying phage particles are detected with an anti-fd antibody (Sigma) as described in Example 4.

Several putative high affinity A6 TCR mutants were identified, and the CDR3 sequences are listed in the two following tables along with the corresponding wild-type sequences. Amber stop codons (X) were found in all β chain mutants and one α chain mutant.

A6 TCR β chain mutants

| clone | CDR3 sequence |
|---|---|
| Wild Type | GCCTCGAGGCCGGGACTAGCGGGAGGGCGACCAGAGCAGTAG (SEQ ID 83)<br>A S R P G L A G G R P E Q Y (SEQ ID 84) |
| 134 | GCCTCGAGGCCGGGGCTGATGAGTGCGTAGCCAGAGCAGTAC (SEQ ID 85)<br>A S R P G L M S A X P E Q Y (SEQ ID 86) |
| 86 | GCCTCGAGGCCGGGGCTGAGGTCGGCGTAGCCAGAGCAGTAC (SEQ ID 87)<br>A S R P G L R S A X P E Q Y (SEQ ID 88) |
| 87 | GCCTCGAGGCCGGGACTAGCGGGAGGGCGACCAGAGGCGTAG (SEQ ID 89)<br>A S R P G L A G G R P E A X (SEQ ID 90) |
| 89 | GCCTCGAGGCCGGGACTAGCGGGAGGGCGACCAGAGGATTAG (SEQ ID 91)<br>A S R P G L A G G R P E D X (SEQ ID 92) |
| 85 | GCCTCGAGGCCGGGACTAGCGGGAGGGCGACCAGATCAGTAG (SEQ ID 93)<br>A S R P G L A G G R P D Q X (SEQ ID 94) |
| 83 | GCCTCGAGGCCGGGTCTGTAGGCTGGGCGACCAGAGCAGTAC (SEQ ID 95)<br>A S R P G L X A G R P E Q Y (SEQ ID 96) |
| 1 | GCCTCGAGGCCGGGGCTGGTTCCGGGGCGACCAGAGCAGTAG (SEQ ID 97)<br>A S R P G L V P G R P E Q X (SEQ ID 98) |
| 2 | GCCTCGAGGCCGGGGCTTGTGTCTGCTTAGCCAGAGCAGTAC (SEQ ID 99)<br>A S R P G L V S A X P E Q Y (SEQ ID 100) |
| 111 | GCCTCGAGGCCGGGACTAGCGGGAGGGCGACCACATCCGTAG (SEQ ID 101)<br>A S R P G L A G G R P H P X (SEQ ID 102) |
| 125 | GCCTCGAGGCCGGGACTAGCGGGAGGGCGACCAGATGCGTAG (SEQ ID 103)<br>A S R P G L A G G R P D A X (SEQ ID 104) |
| 133 | GCCTCGAGGCCGGGTCTGATTAGTGCTTAGCCAGAGCAGTAC (SEQ ID 105)<br>A S R P G L I S A X P E Q Y (SEQ ID 106) |

A6 TCR α chain mutants

| Clone | CDR3 |
|---|---|
| Wild Type | GCCGTTACAACTGACAGCTGGGGGAAGCTTCAG (SEQ ID 107)<br>A V T T D S W G K L Q (SEQ ID 108) |
| 149 | GCCGTTACAACTGACAGCTGGGGGCCGCTTCAG (SEQ ID 109)<br>A V T T D S W G F L Q (SEQ ID 110) |
| 65 | GCCGTTACAACTGACAGCTGGGGGAAGATGCAG (SEQ ID 111)<br>A V T T D S W G K M Q (SEQ ID 112) |
| 66 | GCCGTTACAACTGACAGCTGGGGGAAGTTGCAT (SEQ ID 113)<br>A V T T D S W G L K H (SEQ ID 114) |
| 153 | GCCGTTACAACTGACAGCTGGGGGTAGCTTCAT (SEQ ID 115)<br>A V T T D S W G X L H (SEQ ID 116) |
| 71 | GCCGTTACAACTGACAGCTGGGGGGAGCTTCAT (SEQ ID 117)<br>A V T T D S W G E L H (SEQ ID 118) |
| 70 | GCCGTTACAACTGACAGCTGGGGGAGGCTGCAT (SEQ ID 119)<br>A V T T D S W G R L H (SEQ ID 120) |
| 121 | GCCGTTACAACTGACAGCTGGGGGCAGCTTCAT (SEQ ID 121)<br>A V T T D S W G Q L H (SEQ ID 122) |
| 117 | GCCGTTACAACTGACAGCTGGGGGAAGGTTCAT (SEQ ID 123)<br>A V T T D S W G K V H (SEQ ID 124) |
| 72 | GCCGTTACAACTGACAGCTGGGGGAAGGTGAAT (SEQ ID 125)<br>A V T T D S W G K V N (SEQ ID 126) |
| 150 | GCCGTTACAACTGACAGCTGGGGGAAGCTTCTG (SEQ ID 127)<br>A V T T D S W G K L L (SEQ ID 128) |

Example 9

Production of Soluble Heterodimeric A6 TCR with Non-Native Disulfide Bond Between Constant Regions, Containing CDR3 Mutations Phagemid DNA encoding the high affinity A6 TCR mutants identified in Example 8 was isolated from the relevant *E. coli* cells using a Mini-Prep kit (Quiagen, UK)

PCR amplification using the phagemid DNA as a target and the following primers was used to amplify the soluble TCR α and β chain DNA sequences.

```
A6 TCR alpha chain forward primer
                                        (SEQ ID 129)
ggaattc atcgatg cagaaggaagtggagcag
ClaT restriction site is underlined)

Universal TCR alpha chain reverse primer
                                        (SEQ ID 130)
gtacacggccgggtcagggtctggatatac
(EagI restriction site is underlined)

A6 beta chain forward primer
                                        (SEQ ID 131)
Tctctcattaatgaatgctggtgtcactcagacccc
(AseI restriction site is underlined)

Universal beta chain reverse primer
                                        (SEQ ID 132)
Tagaaaccggtggccaggcacaccagtgtggc
(AgeI restriction site is underlined)
```

In the case of the TCRchain a further PCR stitching was carried out to replace the amber stop codon in the CDR3 region with a codon encoding glutamic acid. When an amber stop codon is suppressed in *E. coli*, a glutamine residue is normally introduced instead of the translation being stopped. Therefore, when the amber codon-containing TCR is displayed on the surface of phage, it contains a glutamine residue in this position. However, when the TCR-β chain gene was transferred into the expression plasmid, a glutamic acid residue was used as an alternative to glutamine. The primers used for this PCR stitching were as follows.

```
YOL124
                                        (SEQ ID 133)
CTGCTCTGGTTCCGCACTC

YOL125
                                        (SEQ ID 134)
GAGTGCGGAACCAGAGCAG
```

The DNA sequence of the mutated soluble A6 TCR β chain was verified by automated sequencing (see FIG. 14a for the mutated A6 TCR β chain DNA sequence and 14b for the amino acid sequence encoded thereby). FIG. 14c shows the mutated A6 TCR β chain amino acid sequence without the glutamine to glutamic acid substitution, i.e. the sequence that was present in Clone 134 as isolated by phage-ELISA.

Theses A6 TCR α and β DNA sequences were then used to produce a soluble A6 TCR as described in WO 03/020763. Briefly, the two chains are expressed as inclusion bodies in separate *E. coli* cultures. The inclusion bodies are then isolated, de-natured and re-folded together in vitro.

Example 10

Figure 15:
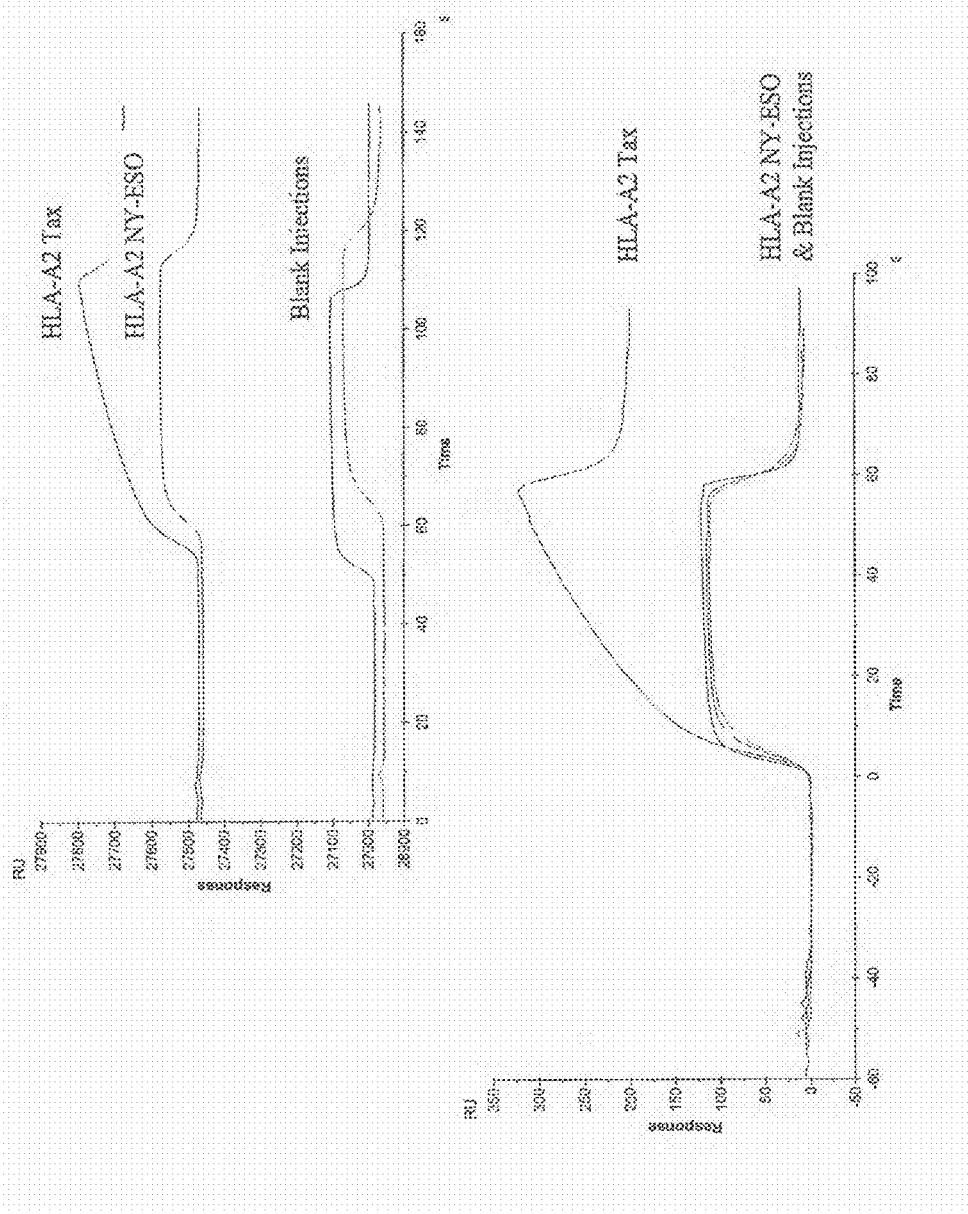
FIG. 15 BIAcore data for the binding of A6 TCR clone 134 to HLA-A2 Tax and HLA-A2 NY-ESO FIG. 16 BIAcore data used to determine $T_{OFF}$ for the binding of A6 TCR clone 134 to HLA-A2 Tax

BIAcore Surface Plasmon Resonance Characterisation of a High Affinity A6 TCR Binding to HLA-A2 Tax A surface plasmon resonance biosensor (BIAcore 3000™) was used to analyse the binding of the high affinity clone 134 A6 TCR (See FIGS. 15a & 15b for the full DNA and amino acid sequences of the mutated TCR β chain respectively) to the HLA-A2 Tax ligand. This was facilitated by producing pMHC complexes (described below) which were immobilised to a streptavidin-coated binding surface in a semi-oriented fashion, allowing efficient testing of the binding of a soluble T-cell receptor to up to four different pMHC (immobilised on separate flow cells) simultaneously. Manual injection of HLA complex allows the precise level of immobilised class I molecules to be manipulated easily.

Biotinylated class I HLA-A2 tax complexes were refolded in vitro from bacterially-expressed inclusion bodies containing the constituent subunit proteins and synthetic peptide, followed by purification and in vitro enzymatic biotinylation (O'Callaghan et al. (1999) *Anal. Biochem.* 266: 9-15). HLA-heavy chain was expressed with a C-terminal biotinylation tag which replaces the transmembrane and cytoplasmic domains of the protein in an appropriate construct. Inclusion body expression levels of ~75 mg/liter bacterial culture were obtained. The HLA light-chain or 2-microglobulin was also expressed as inclusion bodies in *E. coli* from an appropriate construct, at a level of ~500 mg/liter bacterial culture.

*E. coli* cells were lysed and inclusion bodies were purified to approximately 80% purity. Protein from inclusion bodies was denatured in 6 M guanidine-HCl, 50 mM Tris pH 8.1, 100 mM NaCl, 10 mM DTT, 10 mM EDTA, and was refolded at a concentration of 30 mg/liter heavy chain, 30 mg/liter 2 m into 0.4 M L-Arginine-HCl, 100 mM Tris pH 8.1, 3.7 mM cystamine, mM cysteamine, 4 mg/ml peptide (e.g. tax 11-19), by addition of a single pulse of denatured protein into refold buffer at <5° C. Refolding was allowed to reach completion at 4° C. for at least 1 hour.

Buffer was exchanged by dialysis in 10 volumes of 10 mM Tris pH 8.1. Two changes of buffer were necessary to reduce the ionic strength of the solution sufficiently. The protein solution was then filtered through a 1.5 µm cellulose acetate filter and loaded onto a POROS 50HQ anion exchange column (8 ml bed volume). Protein was eluted with a linear 0-500 mM NaCl gradient. HLA-A2-peptide complex eluted at approximately 250 mM NaCl, and peak fractions were collected, a cocktail of protease inhibitors (Calbiochem) was added and the fractions were chilled on ice.

Biotinylation tagged HLA-A2 complexes were buffer exchanged into 10 mM Tris pH 8.1, 5 mM NaCl using a Pharmacia fast desalting column equilibrated in the same buffer. Immediately upon elution, the protein-containing fractions were chilled on ice and protease inhibitor cocktail (Calbiochem) was added. Biotinylation reagents were then added: 1 mM biotin, 5 mM ATP (buffered to pH 8), 7.5 mM MgCl2, and 5 µg/ml BirA enzyme (purified according to O'Callaghan et al. (1999) Anal. Biochem. 266: 9-15). The mixture was then allowed to incubate at room temperature overnight.

Biotinylated HLA-A2 complexes were purified using gel filtration chromatography. A Pharmacia Superdex 75 HR 10/30 column was pre-equilibrated with filtered PBS and 1 ml of the biotinylation reaction mixture was loaded and the column was developed with PBS at 0.5 ml/min. Biotinylated HLA-A2 complexes eluted as a single peak at approximately 15 ml. Fractions containing protein were pooled, chilled on ice, and protease inhibitor cocktail was added. Protein concentration was determined using a Coomassie-binding assay (PerBio) and aliquots of biotinylated HLA-A2 complexes were stored frozen at −20° C. Streptavidin was immobilised by standard amine coupling methods.

The interactions between the high affinity A6 Tax TCR containing a novel inter-chain bond and the HLA-A2 Tax complex or an irrelevant HLA-A2 NY-ESO combination, the production of which is described above, were analysed on a BIAcore 3000™ surface plasmon resonance (SPR) biosensor. SPR measures changes in refractive index expressed in response units (RU) near a sensor surface within a small flow cell, a principle that can be used to detect receptor ligand interactions and to analyse their affinity and kinetic parameters. The probe flow cells were prepared by immobilising the individual HLA-A2 peptide complexes in separate flow cells via binding between the biotin cross linked onto β2 m and streptavidin which have been chemically cross linked to the activated surface of the flow cells. The assay was then performed by passing sTCR over the surfaces of the different flow cells at a constant flow rate, measuring the SPR response in doing so. Initially, the specificity of the interaction was verified by passing soluble A6 TCR at a constant flow rate of 5 μl min-1 over four different surfaces; one coated with ~1000 RU of HLA-A2 Tax complex, the second coated with ~1000 RU of HLA-A2 NY-ESO complex, and two blank flow cells coated only with streptavidin (see FIG. 15).

Figure 16:
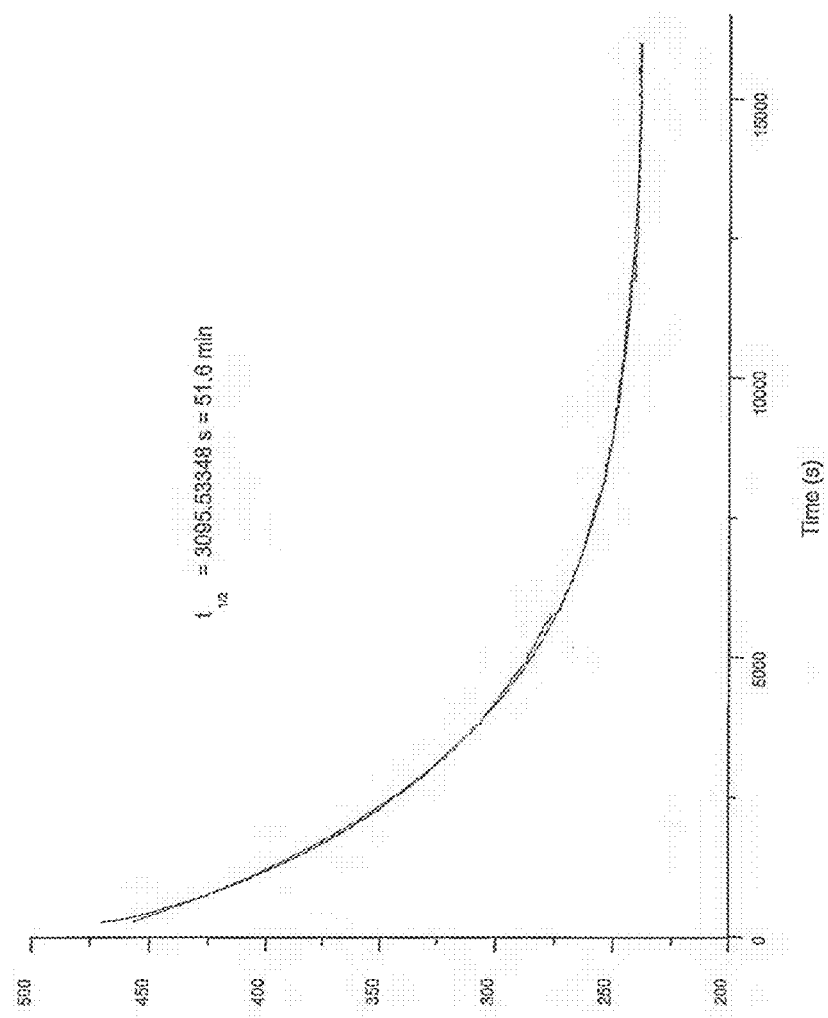

The increased affinity of the mutated soluble A6 TCR made calculation of the kd for the interaction of this moiety with the HLA-A2 Tax complex difficult. However, the half-life ($t_{1/2}$) for the interaction was calculated to be 51.6 minutes (see FIG. 16), which compares to a $t_{1/2}$ for the wild-type interaction of 7.2 seconds.

Example 11

Production of Vector Encoding a Soluble NY-ESO TCR Containing a Novel Disulphide Bond The β chain of the soluble A6 TCR prepared in Example 1 contains in the native sequence a BglII restriction site (AAGCTT) suitable for use as a ligation site.

PCR mutagenesis was carried as detailed below to introduce a BamH1 restriction site (GGATCC) into the α chain of soluble A6 TCR, 5' of the novel cysteine codon. The sequence described in FIG. 2a was used as a template for this mutagenesis. The following primers were used:

```
                                             (SEQ ID 135)
             |BamHI|
5'-ATATCCAGAACCCgGAtCCTGCCGTGTA-3'

(SEQ ID 136)
5'-TACACGGCAGGAaTCcGGGTTCTGGATAT-3'
```

100 ng of plasmid was mixed with 5 μl 10 mM dNTP, 25 μl 10 xPfu-buffer (Stratagene), 10 units Pfu polymerase (Stratagene) and the final volume was adjusted to 240 μl with H₂O. 48 μA of this mix was supplemented with primers diluted to give a final concentration of 0.2 μM in 50 μl final reaction volume. After an initial denaturation step of 30 seconds at 95° C., the reaction mixture was subjected to 15 rounds of denaturation (95° C., 30 sec.), annealing (55° C., 60 sec.), and elongation (73° C., 8 min.) in a Hybaid PCR express PCR machine. The product was then digested for 5 hours at 37° C. with 10 units of Dpnl restriction enzyme (New England Biolabs). 10 μl of the digested reaction was transformed into competent XL1-Blue bacteria and grown for 18 hours at 37° C. A single colony was picked and grown over night in 5 ml TYP+ampicillin (16 g/l Bacto-Tryptone, 16 g/l Yeast Extract, 5 g/l NaCl, 2.5 g/l K₂HPO₄, 100 mg/l Ampicillin). Plasmid DNA was purified on a Qiagen mini-prep column according to the manufacturer's instructions and the sequence was verified by automated sequencing at the sequencing facility of Department of Biochemistry, Oxford University.

cDNA encoding NY-ESO TCR was isolated from T cells according to known techniques. cDNA encoding NY-ESO TCR was produced by treatment of the mRNA with reverse transcriptase.

In order to produce vectors encoding a soluble NY-ESO TCR incorporating a novel disulphide bond, A6 TCR plasmids containing the α chain BamHI and β chain β chain restriction sites were used as templates. The following primers were used:

```
                                             (SEQ ID 137)
             |NdeI|
5'-GGAGATATACATATGCAGGAGGTGACACAG-3'

(SEQ ID 138)
5'-TACACGGCAGGATCCGGGTTCTGGATATT-3'
             |BamHI|

(SEQ ID 139)
             |NdeI|
5'-GGAGATATACATATGGGTGTCACTCAGACC-3'

(SEQ ID 140)
5'-CCCAAGCTTACTCTGCTCTACCCCAGGCCTCGGC-3'
     |BglII|
```

NY-ESO TCR α and β-chain constructs were obtained by PCR cloning as follows.

PCR reactions were performed using the primers as shown above, and templates containing the native NY-ESO TCR chains. The PCR products were restriction digested with the relevant restriction enzymes, and cloned into pGMT7 to obtain expression plasmids. The sequence of the plasmid inserts were confirmed by automated DNA sequencing. FIGS. 17a and 17b show the DNA sequence of the mutated NY-ESO TCR α and β chains respectively, and FIGS. 18a and 18b show the resulting amino acid sequences.

Example 12

Construction of Phage Display Vectors and Cloning of DNA Encoding NY-ESO TCR α and β chains into the phagemid vectors DNA encoding soluble NY-ESO TCR α and β chains incorporating novel cysteine codons to facilitate the formation of a non-native disulfide inter-chain bond, produced as described in Example 11 were incorporated into the phagemid vector pEX746 as follows.

The DNA encoding the two NY-ESO TCR chains were individually subjected to PCR in order to introduce cloning sites compatible with the pEX746 phagemid vector (containing DNA encoding A6 TCR clone 7) using the following primers:

```
For the NY-ESO TCR alpha chain
TRAV21
                                             (SEQ ID 141)
GCCGGCCATGGCCAAACAGGAGGTGACGCAGATTCCT YOL6
                                             (SEQ ID 142)
CTTCTTAAAGAATTCTTAATAACCTAGGTTATTAGGAACTTTCTGGGCTG

GGGAAG
```

-continued

For the NY-ESO TCR beta chain
TRBV6-1/2/3/5/6/7/8/9

(SEQ ID 143)
TCACAGCGCGCAGGCTGGTGTCACTCAGACCCCAAA

RT1
(SEQ ID 144)
CGAGAGCCCGTAGAACTGGACTTG

The molecular cloning methods for constructing the vectors are described in "Molecular cloning: A laboratory manual, by J. Sambrook and D. W. Russell". Primers listed in table-1 are used for construction of the vectors. A example of the PCR programme is 1 cycle of 94° C. for 2 minutes, followed by 25 cycles of 94° C. for 5 seconds, 53° C. for 5 seconds and 72° C. for 90 seconds, followed by 1 cycles of 72° C. for 10 minutes, and then hold at 4° C. The Expand hifidelity Taq DNA polymerase is purchased from Roche.

DNA encoding the clone 7 A6 TCR β chain was removed from pEX746 by digestion with restrictions enzymes BssHII and BglII. The correspondingly digested PCR DNA encoding the NY-ESO β chain was then substituted into the phagemid by ligation. The sequence of the cloning product was verified by automated sequencing.

Similarly, DNA encoding the clone 7 A6 TCR α chain was removed from pEX746 by digestion with restrictions enzymes Ncoi and AvrII. The correspondingly digested PCR DNA encoding the NY-ESO α chain was then substituted into the phagemid already containing DNA encoding the NY-ESO TCR β chain by ligation. The sequence of the cloning product was verified by automated sequencing.

FIGS. 19a and 19b detail respectively the DNA and amino acid sequence of the NY-ESO TCR α and β chain as well as surrounding relevant sequence incorporated in the phagemid (pEX746:NY-ESO). The sequence preceeding the NcoI site is the same as pEX746.

Example 13

Expression of Fusions of Bacterial Coat Protein and Heterodimeric NY-ESO TCR in E. coli Phage particles displaying the heterodimeric NY-ESO TCR containing a non-native disulfide inter-chain bond were prepared using methods described previously for the generation of phage particles displaying antibody scFvs (Li et al, 2000, Journal of Immunological Methods 236: 133-146) with the following modifications. E. coli TG 1 cells containing pEX746:NY-ESO phagemid (i.e. the phagemid encoding the soluble NY-ESO TCR α chain and an NY-ESO TCR β chain fused to the phage gIII protein produced as described in Example 12) were used to inoculate 10 ml of 2×TY (containing 100 µg/ml of ampicillin and 2% glucose), and then the culture was incubated with shaking at 37° C. overnight (16 hours). 50 µl of the overnight culture was used to inoculate 10 ml of 2×TY (containing 100 µg/ml of ampicillin and 2% glucose), and then the culture was incubated with shaking at 37° C. until $OD_{600nm}$=0.8. HYPERPHAGE Helper phage was added to the culture to the final concentration of $5 \times 10^9$ pfu/ml. The culture was then incubated at 37° C. stationary for thirty minutes and then with shaking at 200 rpm for further 30 minutes. The medium of above culture was then made up to 50 ml with 2×TY (containing 100 µg/ml of ampicillin and 25 µg/ml of kanamycin), the culture was then incubated at 25° C. with shaking at 250 rpm for 36 to 48 hours. The culture was then centrifuged at 4° C. for 30 minutes at 4000 rpm. The supernatant was filtrated through a 0.45 µm syringe filter and stored at 4° C. for further concentration. The supernatant was then concentrated by PEG precipitation and re-suspended in PBS at 10% of the original stored volume.

Example 14

Figure 20:
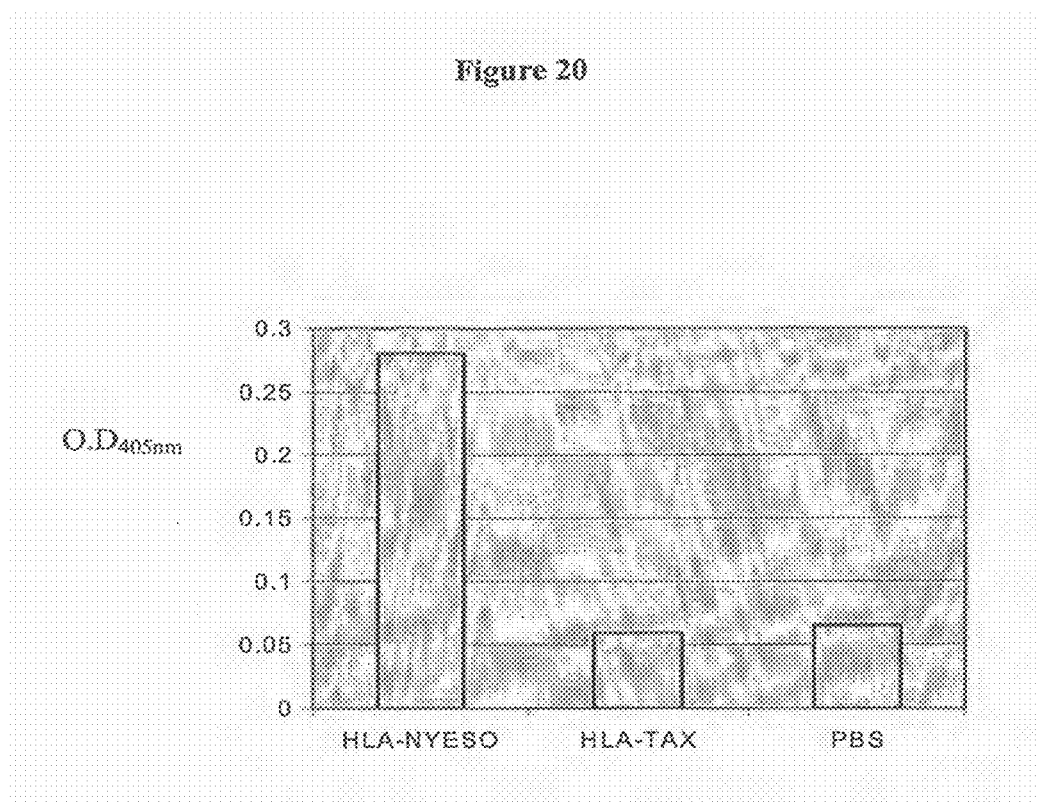
FIG. 20 shows the specific binding of phage particles displaying the NY-ESO TCR to HLA-A2-NY-ESO in a phage ELISA assay.

Detection of Functional Heterodimeric NY-ESO TCR Containing a Non-Native Disulfide Inter-Chain Bond on Filamentous Phage Particles The presence of functional (HLA-A2-NY-ESO binding) NY-ESO TCR displayed on the phage particles in the concentrated suspension prepared in Example 13 was detected using the phage ELISA methods described in Example 4. FIG. 20 shows the specific binding of phage particles displaying the NY-ESO TCR to HLA-A2-NY-ESO in a phage ELISA assay.

Example 15

Construction of Plasmids for Cellular Expression of HLA-DRA Genes

DNA sequences encoding the extracellular portion of HLA-DRA chains are amplified from eDNA isolated from the blood of a healthy human subject, using the polymerase chain reaction (PCR), with synthetic DNA primer pairs that are designed to include a Bgl II restriction site.

PCR mutagenesis is then used to add DNA encoding the Fos leucine zipper to the 3' end of the amplified sequencence.

DNA manipulations and cloning described above are carried out as described in Sambrook, J et al, (1989). Molecular Cloning—A Laboratory Manual. Second Edition. Cold Spring Harbor Laboratory Press, USA.

FIG. 21 provides the DNA sequence of the HLA-DR β chain ready for insertion into the bi-cistronic expression vector. This figure indicates the position of the codons encoding the Fos leucine zipper peptide and the biotinylation tag.

Amino acid numbering is based on the mouse sequence (Kabat, 1991, Sequences of Proteins of Immunological Interest, 5th edition, US Dept of Health & Human Services, Public Health Service, NIH, Bethesda, Md. 1-1137)

Figure 22D:
FIGS. 22A, B, C, and D show the DNA sequence of the pAcAB3 bi-cistronic vector used for the expression of Class II HLA-peptide complexes in Sf9 insect cells. The Bgl II restriction site (AGATCT) used to insert the HLA α chain and the BamHI restriction site (GGATCC) used to insert the HLA β chain are indicated by shading.

This DNA sequence is then inserted into a bi-cistronic baculovirus vector pAcAB3 (See FIG. 22 for the sequence of this vector) along with DNA encoding the corresponding Class II HLA β chain for expression in Sf9 insect cells. This vector can be used to express any Class II HLA-peptide complex in insect cells.

Example 16

Construction of Plasmids for Cellular Expression of HLA-DRB Wild Type and Mutant Genes DNA sequences encoding the extracellular portion of HLA-DRB chains are amplified from eDNA isolated from the blood of a healthy human subject, using the polymerase chain reaction (PCR), with synthetic DNA primer pairs that are designed to include a BamHI restriction site.

PCR mutagenesis is then used to add DNA encoding the Jun leucine zipper to the 3' end of the amplified sequence and DNA encoding the Flu HA peptide loaded by the HLA-DRI molecule to the 5' end of the sequence.

DNA manipulations and cloning described above are carried out as described in Sambrook, J et al, (1989). Molecular Cloning—A Laboratory Manual. Second Edition. Cold Spring Harbor Laboratory Press, USA.

FIG. 23 provides the DNA sequence of the HLA-DR β chain ready for insertion into the bi-cistronic expression vector. This figure indicates the position of the codons encoding the Jun leucine zipper peptide and the Flu HA peptide.

Amino acid numbering is based on the mouse sequence (Kabat, 1991, Sequences of Proteins of Immunological Interest, 5th edition, US Dept of Health & Human Services, Public Health Service, NIH, Bethesda, Md. 1-1137)

This DNA sequence is then inserted into a bi-cistronic baculovirus vector pAcAB3 (See FIG. 22 for the sequence of this vector) along with DNA encoding the corresponding Class II α chain for expression in Sf9 insect cells. This vector can be used to express any Class II HLA-peptide complex in insect cells.

Example 17

Expression and Refolding of Class II HLA-DR1—Flu HA Complexes

Class II MHC expression is carried out using the bi-cistronic expression vectors produced as described in Examples 15 and 16 containing the Class II HLA-DR1α and β chains and the Flu HA peptide. The expression and purification methods used are as described in (Gauthier (1998) PNAS USA 95 p11828-11833). Briefly, soluble HLA-DR1 is expressed in the baculovirus system by replacing the hydrophobic transmembrane regions and cytoplasmic segments of DR α and β chains with leucine zipper dimerization domains from the transcription factors Fos and Jun. In the expression construct, the required Class MHC-loaded Flu HA peptide sequence is covalently linked to the N terminus of the mature DR β chain and the DR α chain contains a biotinylation tag sequence to facilitate bifunctional ligand formation utilizing the biotin/strepavidin multimerisation methodology. The recombinant protein is secreted by Sf9 cells infected with the recombinant baculovirus, and purified by affinity chromatography. The protein is further purified by anion-exchange HPLC.

Example 18

Construction of Class I Soluble Peptide-HLA Molecules

In order to investigate further the specificity of the high affinity A6 TCR clone 134 the following soluble class I peptide-HLA molecules were produced:

```
HLA-A2-peptide
                                          (SEQ ID 23)
(LLGRNSFEV)

HLA-A2-peptide
                                          (SEQ ID 24)
(KLVALGINAV)

HLA-A2-peptide
                                          (SEQ ID 25)
(LLGDLFGV)

HLA-B8-peptide
                                          (SEQ ID 26)
(FLRGRAYGL)

HLA-B27-peptide
                                          (SEQ ID 27)
(HRCQAIRKK)

HLA-Cw6-peptide
                                          (SEQ ID 28)
(YRSGIIAVV)

HLA-A24-peptide
                                          (SEQ ID 29)
(VYGFVRACL)

HLA-A2-peptide
                                          (SEQ ID 30)
(ILAKFLHWL)

HLA-A2-peptide
                                          (SEQ ID 31)
(LTLGEFLKL)

HLA-A2-peptide
                                          (SEQ ID 33)
(GILGFVFTL)

HLA-A2-peptide
                                          (SEQ ID 34)
(SLYNTVAL)
```

These soluble peptide-HLAs were produced using the methods described in Example 10.

Example 19

B/Acore Surface Plasmon Resonance Measurement of the Specificity of Clone 134 high affinity A6 TCR binding to peptide-HLA A surface plasmon resonance biosensor (BIAcore 3000™) was used to analyse the binding specificitiy of the high affinity clone 134 A6 TCR. (See FIGS. 15a & 15b for the full DNA and amino acid sequences of the mutated TCR β chain respectively) This was carried out using the Class II HLA-DR1-peptide, produced as described in Examples 15-17, and the Class I peptide-HLA complexes listed in Example 18, produced using the methods detailed in Example 10. The following table lists the peptide-HLA complexes utilised:

```
1. HLA-A2-peptide
                                          (SEQ ID 23)
   (LLGRNSFEV)

2. HLA-A2-peptide
                                          (SEQ ID 24)
   (KLVALGINAV)

3. HLA-A2-peptide
                                          (SEQ ID 25)
   (LLGDLFGV)

4. HLA-B8-peptide
                                          (SEQ ID 26)
   (FLRGRAYGL)

5. HLA-B27-peptide
                                          (SEQ ID 27)
   (HRCQAIRKK)

6. HLA-Cw6-peptide
                                          (SEQ ID 28)
   (YRSGIIAVV)

7. HLA-A24-peptide
                                          (SEQ ID 29)
   (VYGFVRACL)
```

-continued

```
8. HLA-A2-peptide
                                         (SEQ ID 30)
   (ILAKFLHWL)

9. HLA-A2-peptide
                                         (SEQ ID 31)
   (LTLGEFLKL)

10. HLA-DR1-peptide
                                         (SEQ ID 32)
    (PKYVKQNTLKLA)

11. HLA-A2-peptide
                                         (SEQ ID 33)
    (GILGFVFTL)

12. HLA-A2-peptide
                                         (SEQ ID 34)
    (SLYNTVAL)
```

The above peptide HLAs were immobilised to streptavidin-coated binding surfaces in of the flow cells of a BIAcore 3000™ in a semi-oriented fashion.

The BIAcore 3000™ allows testing of the binding of the soluble T-cell receptor to up to four different pMHC (immobilised on separate flow cells) simultaneously. For this experiment three different HLA-peptides were immobilised in flowcells 2-4 and flowcell 1 was left blank as a control. Manual injection of HLA-peptide complexes allowed the precise level of immobilised molecules to be manipulated.

After the ability of the high affinity A6 TCR clone 134 to bind to the first 3 HLA-peptide complexes in the above list had been assessed the next three were immobilised onto these flowcells directly on top of the previous ones. This process was continued until the binding of the high affinity A6 TCR clone 134 to all 12 HLA-peptide complexes had been assessed.

Ten injections of 5 µl of the high affinity A6 TCR clone 134 were passed over each flowcell at 5 µl/min at concentrations ranging from 4.1 ng/ml to 2.1 mg/ml. (See FIGS. 24-28)

As a final control the high affinity A6 TCR clone 134 was passed over a flowcell containing immobilised HLA-A2 Tax (LLFGYPVYV) (SEQ ID 21), the cognate ligand for this TCR.

Specific binding of the high affinity A6 TCR clone 134 was only noted to its cognate ligand. (HLA-A2 Tax (LLFGYPVYV) (SEQ ID 21)) These data further demonstrate the specificity of the high affinity A6 TCR clone 134. (See FIGS. 24-28)

Example 20

Mutagenesis of NY-ESO TCR CDR3 Regions

The CDR3 regions of the NY-ESO TCR were targeted for the introduction of mutations to investigate the possibility of generating high affinity mutants. This was achieved using NY-ESO TCR-specific PCR primers in combination with methods substantially the same as those detailed in Example 7.

Example 21

Isolation of High Affinity A6 TCR Mutants

The isolation of high affinity NY-ESO TCR mutants was carried using out the first of the two methods described in Example 8.

A single high affinity NY-ESO TCR mutant was identified.

Example 22

Production of Soluble High Affinity Heterodimeric NY-ESO TCR with Non-Native Disulfide Bond Between Constant Regions, Containing Variable Region Mutations Phagemid DNA encoding the high affinity NY-ESO TCR mutant identified in Example 21 was isolated from the relevant *E. coli* cells using a Mini-Prep kit (Quiagen, UK)

PCR amplification using the phagemid DNA as a target and the following primers were used to amplify the mutated soluble NY-ESO TCR β chain variable region DNA sequence.

```
NY-ESO beta chain forward primer
                                        (SEQ ID 145)
Tctctcattaatgaatgctggtgtcactcagacccc
(AseI restriction site is underlined)

Universal beta chain reverse primer
                                        (SEQ ID 146)
Tagaaaccggtggccaggcacaccagtgtgg
(AgeI restriction site is underlined)
```

The PCR product was then digested with Age1/Ase1 and cloned into pEX821 (Produced as described in Example 11) cut with Nde/Age1.

The mutated NY-ESO TCR β chain DNA sequence amplified as described above, and the NY-ESO TCR α chain produced as described in Example 11 were then used to produce a soluble high affinity NY-ESO TCR as described in WO 03/020763. Briefly, the two chains are expressed as inclusion bodies in separate *E. coli* cultures. The inclusion bodies are then isolated, de-natured and re-folded together in vitro.

Example 23

BIAcore Surface Plasmon Resonance Characterisation of a High Affinity NY-ESO TCR Binding to HLA-A2 NY-ESO A surface plasmon resonance biosensor (Biacore 3000™) was used to analyse the binding of the high affinity NY-ESO TCR to the HLA-A2 NY-ESO ligand. This was facilitated by producing pMHC complexes (as described in Example 10) which were immobilised to a streptavidin-coated binding surface in a semi-oriented fashion, allowing efficient testing of the binding of a soluble T-cell receptor to up to four different pMHC (immobilised on separate flow cells) simultaneously. Manual injection of HLA complex allows the precise level of immobilised class I molecules to be manipulated easily.

The interactions between the high affinity NY-ESO TCR containing a novel inter-chain bond and the HLA-A2 NY-ESO complex or an irrelevant HLA-A2 Tax combination, the production of which is described in Example 10, were analysed on a Biacore 3000™ surface plasmon resonance (SPR) biosensor, again as described in Example 10.

The kd for the interaction of the soluble high affinity NY-ESO with the HLA-A2 NY-ESO was calculated to be 4.1 μm, (See FIGS. 29a and 29b) which compares to a kd of 15.7 μm for the wild-type interaction. (See FIGS. 30a and 30b)

Example 24

Production and Testing of Further High Affinity A6 TCRs

Soluble TCRs containing the following mutations corresponding to those identified in clones 89, 1, 111 and 71 (see Example 8) were produced using the methods detailed in Example 9. The binding of these soluble TCRs to HLA-A2 Tax was then assessed using the Biacore assay detailed in Example 10.

A6 TCR β chain mutants

| Clone | CDR3 sequence |
|---|---|
| Wild Type | GCCTCGAGGCCGGGACTAGCGGGAGGGCGACCAGAGCAGTAG (SEQ ID 83)<br>A S R P G L A G G R P E Q Y (SEQ ID 84) |
| 88 | GCCTCGAGGCCGGGACTAGCGGGAGGGCGACCAGAGGATTAG (SEQ ID 91)<br>A S R P G L A G G R P E D X (SEQ ID 92) |
| 1 | GCCTCGAGGCCGGGGCTGGTTCCGGGGCGACCAGAGCAGTAG (SEQ ID 97)<br>A S R P G L V P G R P E Q X (SEQ ID 98) |
| 111 | GCCTCGAGGAAGGGACTAGCGGGAGGGCGACCACATCCGTAG (SEQ ID 101)<br>A S R P G L A G G R P H P X (SEQ ID 102) |

A6 TCR α chain mutant

| Clone | CDR3 |
|---|---|
| Wild Type | GCCGTTACAACTGACAGCTGGGGAAGCTTCAG (SEQ ID 107)<br>A V T T D S W G K L Q (SEQ ID 108) |
| 71 | GCCGTTACAACTGACAGCTGGGGGGAGCTTCAT (SEQ ID 117)<br>A V T T D S W G E L H (SEQ ID 118) |

Combined mutations used as a basis for the production of mutated soluble A6 TCRs:

Clone 89 mutations+Clone 134 mutations
Clone 71 mutations+Clone 134 mutations
Clone 71 mutations+Clone 89 mutations
Clone 1 mutations+βG102→A mutation Results:

The following table compares the HLA-A2 Tax affinity of the above soluble mutated A6 TCRs to that obtained using a soluble A6 TCR containing unmutated variable regions. Note that the affinity of the highest affinity mutants is expressed as the half-life for the interaction. ($T_{1/2}$) These soluble mutant A6 TCRs exhibited higher affinity for HLA-A2 Tax than the unmutated soluble A6 TCR as demonstrated by their lower kd or longer $T_{1/2}$ for the interaction.

FIGS. 31-37 show the Biacore traces used to calculate the affinity for HLA-A2 Tax of these soluble mutated TCRs. FIGS. 38a-e show the amino acid sequence of the mutated A6 TCR chains.

| A6 TCR | Kd (μM) | $T_{1/2}$ (Secs) |
|---|---|---|
| Wild-type | 1.9 | 7 |
| Clone 1 | | 810 |
| Clone 89 | 0.41 | |
| Clone 111 | 1.18 | |
| Clone 71 | 1.37 | |
| Clone 89 + Clone 134 mutations | | 114 (phase 1)<br>4500 (phase 2) |
| Clone 71 + Clone 134 mutations | | 882 |
| Clone 71 + Clone 89 mutations | 0.35 | |
| Clone 1 + βG102→A mutation | | 738 |

Example 25

Cell Staining Using High Affinity A6 TCR Tetramers and Monomers

T2 antigen presenting cells were incubated with β2 m (3 μg/ml) pulsed with Tax peptide at a range of concentrations ($10^{-5}$-$10^{-9}$M) for 90 minutes at 37° C. Controls, also using T2 cells incubated with β2 m (3 μg/ml), were pulsed with $10^{-5}$M Flu peptide or incubated without peptide (unpulsed). After pulsing the cells were washed in serum-free RPMI and 2×105 cells were incubated with either strepavidin-linked high affinity Clone 134 A6 TCR tetramer labelled with phycoerythrin (PE). (Molecular probes, The Netherlands) (10 μg/ml) or high affinity Clone 134 A6 TCR monomers labelled with Alexa 488 (Molecular probes, The Netherlands) for 10 minutes at room temperature. After washing the cells, the binding of the labelled TCR tetramers and monomers was examined by flow cytometry using a FACSVantage SE (Becton Dickinson).

Results

As illustrated in FIG. 39A, specific staining of T2 cells by high affinity A6_TCR tetramers could be observed at Tax peptide concentrations of down to 10-9 M.

As illustrated in FIG. 39B, specific staining of T2 cells by high affinity A6 TCR monomers could be observed at Tax peptide concentrations of down to 10-8 M.

The invention claimed is:

1. A diverse library comprising a plurality of phage particles displaying on their surfaces dimeric T cell receptor (TCR) polypeptide pairs constituted by:
 a TCR α chain variable domain sequence fused to the N terminus of a TCR α chain constant domain extracellular sequence; and
 a TCR β chain variable domain sequence fused to the N terminus of a TCR β chain constant domain extracellular sequence,
 wherein the TCR α chain constant domain extracellular sequence and the TCR β chain constant domain extracellular sequence are linked by a disulfide bond between cysteine residues substituted for:
 Thr 48 of exon 1 of TRAC*01 at position 10 with reference to the position numbering of SEQ ID NO: 1 and Ser 57 of exon 1 of TRBC1 *01 or TRBC2*01 at position 10 with reference to the position numbering of SEQ ID NO: 5;
 Thr 45 of exon 1 of TRAC*01 at position 10 with reference to the position numbering of SEQ ID NO: 2 and Ser 77 of exon 1 of TRBC1 *01 or TRBC2*01 at position 10 with reference to the position numbering of SEQ ID NO: 6;
 Tyr 10 of exon 1 of TRAC*01 at position 10 with reference to the position numbering of SEQ ID NO: 3 and Ser 17 of exon 1 of TRBC1 *01 or TRBC2*01 at position 10 with reference to the position numbering of SEQ ID NO: 7;
 Thr 45 of exon 1 of TRAC*01 at position 10 with reference to the position numbering of SEQ ID NO: 2 and Asp 59 of exon 1 of TRBC1 *01 or TRBC2*01 at position 10 with reference to the position numbering of SEQ ID NO: 8; or
 Ser 15 of exon 1 of TRAC*01 at position 10 with reference to the position numbering of SEQ ID NO: 4 and Glu 15 of exon 1 of TRBC1 *01 or TRBC2*01 at position 10 with reference to the position numbering of SEQ ID NO: 9.

2. The diverse library of claim 1, wherein diversity resides in one or both of the TCR α variable domain and the TCR β variable domain.

3. A method for identifying T cell receptors with a specific characteristic, comprising steps of:
 subjecting the diverse library of claim 1 to a selection process which selects for the specific characteristic; and
 isolating a phage particle which displays a TCR having the specific characteristic.

4. The method of claim 3 wherein the specific characteristic is increased affinity for a TCR ligand.

5. The method of claim 3 further comprising a step of amplifying the phage particle which displays the TCR having the specific characteristic.

* * * * *

SEQUENCE LISTING

<160> NUMBER OF SEQ ID NOS: 181

<210> SEQ ID NO 1
<211> LENGTH: 20
<212> TYPE: PRT
<213> ORGANISM: Homo sapiens

<400> SEQUENCE: 1

Asp Ser Asp Val Tyr Ile Thr Asp Lys Thr Val Leu Asp Met Arg Ser
1               5                   10                  15

Met Asp Phe Lys
            20

<210> SEQ ID NO 2
<211> LENGTH: 20
<212> TYPE: PRT
<213> ORGANISM: Homo sapiens

<400> SEQUENCE: 2

Gln Ser Lys Asp Ser Asp Val Tyr Ile Thr Asp Lys Thr Val Leu Asp
1               5                   10                  15

Met Arg Ser Met
            20

<210> SEQ ID NO 3
<211> LENGTH: 20
<212> TYPE: PRT
<213> ORGANISM: Homo sapiens

<400> SEQUENCE: 3

Asp Ile Gln Asn Pro Asp Pro Ala Val Tyr Gln Leu Arg Asp Ser Lys
1               5                   10                  15

Ser Ser Asp Lys
            20

<210> SEQ ID NO 4
<211> LENGTH: 20
<212> TYPE: PRT
<213> ORGANISM: Homo sapiens

<400> SEQUENCE: 4

Asp Pro Ala Val Tyr Gln Leu Arg Asp Ser Lys Ser Ser Asp Lys Ser
1               5                   10                  15

Val Cys Leu Phe
            20

<210> SEQ ID NO 5
<211> LENGTH: 20
<212> TYPE: PRT
<213> ORGANISM: Homo sapiens

<400> SEQUENCE: 5

Asn Gly Lys Glu Val His Ser Gly Val Ser Thr Asp Pro Gln Pro Leu
1               5                   10                  15

Lys Glu Gln Pro
            20

<210> SEQ ID NO 6
<211> LENGTH: 20
<212> TYPE: PRT
<213> ORGANISM: Homo sapiens

<400> SEQUENCE: 6

```
Ala Leu Asn Asp Ser Arg Tyr Ala Leu Ser Ser Arg Leu Arg Val Ser
1               5                   10                  15

Ala Thr Phe Trp
            20

<210> SEQ ID NO 7
<211> LENGTH: 20
<212> TYPE: PRT
<213> ORGANISM: Homo sapiens

<400> SEQUENCE: 7

Pro Pro Glu Val Ala Val Phe Glu Pro Ser Glu Ala Glu Ile Ser His
1               5                   10                  15

Thr Gln Lys Ala
            20

<210> SEQ ID NO 8
<211> LENGTH: 20
<212> TYPE: PRT
<213> ORGANISM: Homo sapiens

<400> SEQUENCE: 8

Lys Glu Val His Ser Gly Val Ser Thr Asp Pro Gln Pro Leu Lys Glu
1               5                   10                  15

Gln Pro Ala Leu
            20

<210> SEQ ID NO 9
<211> LENGTH: 20
<212> TYPE: PRT
<213> ORGANISM: Homo sapiens

<400> SEQUENCE: 9

Val Phe Pro Pro Glu Val Ala Val Phe Glu Pro Ser Glu Ala Glu Ile
1               5                   10                  15

Ser His Thr Gln
            20

<210> SEQ ID NO 10
<211> LENGTH: 91
<212> TYPE: PRT
<213> ORGANISM: Mus musculus

<400> SEQUENCE: 10

Pro Tyr Ile Gln Asn Pro Glu Pro Ala Val Tyr Gln Leu Lys Asp Pro
1               5                   10                  15

Arg Ser Gln Asp Ser Thr Leu Cys Leu Phe Thr Asp Phe Asp Ser Gln
            20                  25                  30

Ile Asn Val Pro Lys Thr Met Glu Ser Gly Thr Phe Ile Thr Asp Lys
        35                  40                  45

Thr Val Leu Asp Met Lys Ala Met Asp Ser Lys Ser Asn Gly Ala Ile
    50                  55                  60

Ala Trp Ser Asn Gln Thr Ser Phe Thr Cys Gln Asp Ile Phe Lys Glu
65                  70                  75                  80

Thr Asn Ala Thr Tyr Pro Ser Ser Asp Val Pro
                85                  90

<210> SEQ ID NO 11
<211> LENGTH: 126
<212> TYPE: PRT
```

<213> ORGANISM: Mus musculus

<400> SEQUENCE: 11

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Arg Glu Val His Ser Gly Val Ser Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp
        115                 120                 125

<210> SEQ ID NO 12
<211> LENGTH: 20
<212> TYPE: PRT
<213> ORGANISM: Mus musculus

<400> SEQUENCE: 12

Glu Ser Gly Thr Phe Ile Thr Asp Lys Thr Val Leu Asp Met Lys Ala
1               5                   10                  15

Met Asp Ser Lys
            20

<210> SEQ ID NO 13
<211> LENGTH: 20
<212> TYPE: PRT
<213> ORGANISM: Mus musculus

<400> SEQUENCE: 13

Lys Thr Met Glu Ser Gly Thr Phe Ile Thr Asp Lys Thr Val Leu Asp
1               5                   10                  15

Met Lys Ala Met
            20

<210> SEQ ID NO 14
<211> LENGTH: 20
<212> TYPE: PRT
<213> ORGANISM: Mus musculus

<400> SEQUENCE: 14

Tyr Ile Gln Asn Pro Glu Pro Ala Val Tyr Gln Leu Lys Asp Pro Arg
1               5                   10                  15

Ser Gln Asp Ser
            20

<210> SEQ ID NO 15
<211> LENGTH: 20
<212> TYPE: PRT
<213> ORGANISM: Mus musculus

<400> SEQUENCE: 15

Ala Val Tyr Gln Leu Lys Asp Pro Arg Ser Gln Asp Ser Thr Leu Cys

-continued

```
1               5                   10                  15

Leu Phe Thr Asp
            20

<210> SEQ ID NO 16
<211> LENGTH: 20
<212> TYPE: PRT
<213> ORGANISM: Mus musculus

<400> SEQUENCE: 16

Asn Gly Arg Glu Val His Ser Gly Val Ser Thr Asp Pro Gln Ala Tyr
1               5                   10                  15

Lys Glu Ser Asn
            20

<210> SEQ ID NO 17
<211> LENGTH: 20
<212> TYPE: PRT
<213> ORGANISM: Mus musculus

<400> SEQUENCE: 17

Lys Glu Ser Asn Tyr Ser Tyr Cys Leu Ser Ser Arg Leu Arg Val Ser
1               5                   10                  15

Ala Thr Phe Trp
            20

<210> SEQ ID NO 18
<211> LENGTH: 20
<212> TYPE: PRT
<213> ORGANISM: Mus musculus

<400> SEQUENCE: 18

Pro Pro Lys Val Ser Leu Phe Glu Pro Ser Lys Ala Glu Ile Ala Asn
1               5                   10                  15

Lys Gln Lys Ala
            20

<210> SEQ ID NO 19
<211> LENGTH: 20
<212> TYPE: PRT
<213> ORGANISM: Mus musculus

<400> SEQUENCE: 19

Arg Glu Val His Ser Gly Val Ser Thr Asp Pro Gln Ala Tyr Lys Glu
1               5                   10                  15

Ser Asn Tyr Ser
            20

<210> SEQ ID NO 20
<211> LENGTH: 20
<212> TYPE: PRT
<213> ORGANISM: Mus musculus

<400> SEQUENCE: 20

Val Thr Pro Pro Lys Val Ser Leu Phe Glu Pro Ser Lys Ala Glu Ile
1               5                   10                  15

Ala Asn Lys Gln
            20

<210> SEQ ID NO 21
<211> LENGTH: 9
<212> TYPE: PRT
```

<213> ORGANISM: Artificial Sequence
<220> FEATURE:
<223> OTHER INFORMATION: HLA-A2 tax peptide

<400> SEQUENCE: 21

Leu Leu Phe Gly Tyr Pro Val Tyr Val
1               5

<210> SEQ ID NO 22
<211> LENGTH: 8
<212> TYPE: PRT
<213> ORGANISM: Artificial Sequence
<220> FEATURE:
<223> OTHER INFORMATION: HLA-A2 NY-ESO peptide

<400> SEQUENCE: 22

Ser Leu Leu Met Ile Thr Gln Cys
1               5

<210> SEQ ID NO 23
<211> LENGTH: 9
<212> TYPE: PRT
<213> ORGANISM: Artificial Sequence
<220> FEATURE:
<223> OTHER INFORMATION: HLA-A2 p53 peptide

<400> SEQUENCE: 23

Leu Leu Gly Arg Asn Ser Phe Glu Val
1               5

<210> SEQ ID NO 24
<211> LENGTH: 10
<212> TYPE: PRT
<213> ORGANISM: Artificial Sequence
<220> FEATURE:
<223> OTHER INFORMATION: HLA-A2 HCV N53-2 peptide

<400> SEQUENCE: 24

Lys Leu Val Ala Leu Gly Ile Asn Ala Val
1               5                   10

<210> SEQ ID NO 25
<211> LENGTH: 8
<212> TYPE: PRT
<213> ORGANISM: Artificial Sequence
<220> FEATURE:
<223> OTHER INFORMATION: HLA-A2 MDM-2 peptide

<400> SEQUENCE: 25

Leu Leu Gly Asp Leu Phe Gly Val
1               5

<210> SEQ ID NO 26
<211> LENGTH: 9
<212> TYPE: PRT
<213> ORGANISM: Artificial Sequence
<220> FEATURE:
<223> OTHER INFORMATION: HLA-B8 EBNA3A (325-333) peptide

<400> SEQUENCE: 26

Phe Leu Arg Gly Arg Ala Tyr Gly Leu
1               5

<210> SEQ ID NO 27
<211> LENGTH: 9
<212> TYPE: PRT
<213> ORGANISM: Artificial Sequence

```
<220> FEATURE:
<223> OTHER INFORMATION: HLA-B27 EBNA4A/3B (149-157) peptide

<400> SEQUENCE: 27

His Arg Cys Gln Ala Ile Arg Lys Lys
1               5

<210> SEQ ID NO 28
<211> LENGTH: 9
<212> TYPE: PRT
<213> ORGANISM: Artificial Sequence
<220> FEATURE:
<223> OTHER INFORMATION: HLA-Cw6 EBV peptide

<400> SEQUENCE: 28

Tyr Arg Ser Gly Ile Ile Ala Val Val
1               5

<210> SEQ ID NO 29
<211> LENGTH: 9
<212> TYPE: PRT
<213> ORGANISM: Artificial Sequence
<220> FEATURE:
<223> OTHER INFORMATION: HLA-A24 Telomerase-hTERT (461-469) peptide

<400> SEQUENCE: 29

Val Tyr Gly Phe Val Arg Ala Cys Leu
1               5

<210> SEQ ID NO 30
<211> LENGTH: 9
<212> TYPE: PRT
<213> ORGANISM: Artificial Sequence
<220> FEATURE:
<223> OTHER INFORMATION: HLA-A2 Telomerase-hTERT (540-548) peptide

<400> SEQUENCE: 30

Ile Leu Ala Lys Phe Leu His Trp Leu
1               5

<210> SEQ ID NO 31
<211> LENGTH: 9
<212> TYPE: PRT
<213> ORGANISM: Artificial Sequence
<220> FEATURE:
<223> OTHER INFORMATION: HLA-A2 Survivin (96-104) peptide

<400> SEQUENCE: 31

Leu Thr Leu Gly Glu Phe Leu Lys Leu
1               5

<210> SEQ ID NO 32
<211> LENGTH: 12
<212> TYPE: PRT
<213> ORGANISM: Artificial Sequence
<220> FEATURE:
<223> OTHER INFORMATION: HLA-DRA1 Flu HA (306-318) peptide

<400> SEQUENCE: 32

Pro Lys Tyr Val Lys Gln Asn Thr Leu Lys Leu Ala
1               5                   10

<210> SEQ ID NO 33
<211> LENGTH: 9
<212> TYPE: PRT
<213> ORGANISM: Artificial Sequence
<220> FEATURE:
```

<223> OTHER INFORMATION: HLA-A2 Flu MP (58-68) peptide

<400> SEQUENCE: 33

Gly Ile Leu Gly Phe Val Phe Thr Leu
1               5

<210> SEQ ID NO 34
<211> LENGTH: 9
<212> TYPE: PRT
<213> ORGANISM: Artificial Sequence
<220> FEATURE:
<223> OTHER INFORMATION: HLA-A2 HIV GAG (77-85) peptide

<400> SEQUENCE: 34

Ser Leu Tyr Asn Thr Val Ala Thr Leu
1               5

<210> SEQ ID NO 35
<211> LENGTH: 24
<212> TYPE: DNA
<213> ORGANISM: Artificial Sequence
<220> FEATURE:
<223> OTHER INFORMATION: Primer

<400> SEQUENCE: 35
cacagacaaa tgtgtgctag acat                                          24

<210> SEQ ID NO 36
<211> LENGTH: 24
<212> TYPE: DNA
<213> ORGANISM: Artificial Sequence
<220> FEATURE:
<223> OTHER INFORMATION: Primer

<400> SEQUENCE: 36
atgtctagca cacatttgtc tgtg                                          24

<210> SEQ ID NO 37
<211> LENGTH: 21
<212> TYPE: DNA
<213> ORGANISM: Artificial Sequence
<220> FEATURE:
<223> OTHER INFORMATION: Primer

<400> SEQUENCE: 37
cagtggggtc tgcacagacc c                                             21

<210> SEQ ID NO 38
<211> LENGTH: 21
<212> TYPE: DNA
<213> ORGANISM: Artificial Sequence
<220> FEATURE:
<223> OTHER INFORMATION: Primer

<400> SEQUENCE: 38
gggtctgtgc agacccccact g                                            21

<210> SEQ ID NO 39
<211> LENGTH: 41
<212> TYPE: DNA
<213> ORGANISM: Artificial Sequence
<220> FEATURE:
<223> OTHER INFORMATION: Primer

<400> SEQUENCE: 39
taataatacg tataataata ttctatttca aggagacagt c                       41

```
<210> SEQ ID NO 40
<211> LENGTH: 58
<212> TYPE: DNA
<213> ORGANISM: Artificial Sequence
<220> FEATURE:
<223> OTHER INFORMATION: Primer

<400> SEQUENCE: 40
caatccagcg gctgccgtag gcaataggta tttcattatg actgtctcct tgaaatag        58

<210> SEQ ID NO 41
<211> LENGTH: 53
<212> TYPE: DNA
<213> ORGANISM: Artificial Sequence
<220> FEATURE:
<223> OTHER INFORMATION: Primer

<400> SEQUENCE: 41
ctacggcagc cgctggattg ttattactcg cggcccagcc ggccatggcc cag            53

<210> SEQ ID NO 42
<211> LENGTH: 41
<212> TYPE: DNA
<213> ORGANISM: Artificial Sequence
<220> FEATURE:
<223> OTHER INFORMATION: Primer

<400> SEQUENCE: 42
gttctgctcc acttccttct gggccatggc cggctgggcc g                         41

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
cagaaggaag tggagcagaa c                                               21

<210> SEQ ID NO 44
<211> LENGTH: 57
<212> TYPE: DNA
<213> ORGANISM: Artificial Sequence
<220> FEATURE:
<223> OTHER INFORMATION: Primer

<400> SEQUENCE: 44
cttcttaaag aattcttaat taacctaggt tattaggaac tttctgggct ggggaag        57

<210> SEQ ID NO 45
<211> LENGTH: 60
<212> TYPE: DNA
<213> ORGANISM: Artificial Sequence
<220> FEATURE:
<223> OTHER INFORMATION: Primer

<400> SEQUENCE: 45
gttaattaag aattctttaa gaaggagata tacatatgaa aaaattatta ttcgcaattc     60

<210> SEQ ID NO 46
<211> LENGTH: 60
<212> TYPE: DNA
<213> ORGANISM: Artificial Sequence
<220> FEATURE:
```

<223> OTHER INFORMATION: Primer

<400> SEQUENCE: 46
cgcgctgtga aatagaaag gaacaactaa aggaattgcg aataataatt ttttcatatg    60

<210> SEQ ID NO 47
<211> LENGTH: 40
<212> TYPE: DNA
<213> ORGANISM: Artificial Sequence
<220> FEATURE:
<223> OTHER INFORMATION: Primer

<400> SEQUENCE: 47
ctttctattc tcacagcgcg caggctggtg tcactcagac    40

<210> SEQ ID NO 48
<211> LENGTH: 42
<212> TYPE: DNA
<213> ORGANISM: Artificial Sequence
<220> FEATURE:
<223> OTHER INFORMATION: Primer

<400> SEQUENCE: 48
atgatgtcta gatgcggccg cgtctgctct accccaggcc tc    42

<210> SEQ ID NO 49
<211> LENGTH: 55
<212> TYPE: DNA
<213> ORGANISM: Artificial Sequence
<220> FEATURE:
<223> OTHER INFORMATION: Primer

<400> SEQUENCE: 49
gcatctagac atcatcacca tcatcactag actgttgaaa gttgtttagc aaaac    55

<210> SEQ ID NO 50
<211> LENGTH: 40
<212> TYPE: DNA
<213> ORGANISM: Artificial Sequence
<220> FEATURE:
<223> OTHER INFORMATION: Primer

<400> SEQUENCE: 50
ctagagggta ccttattaag actccttatt acgcagtatg    40

<210> SEQ ID NO 51
<211> LENGTH: 43
<212> TYPE: DNA
<213> ORGANISM: Artificial Sequence
<220> FEATURE:
<223> OTHER INFORMATION: Primer

<400> SEQUENCE: 51
agctgcagct aatacgactc actataggaa caggccacca tgg    43

<210> SEQ ID NO 52
<211> LENGTH: 43
<212> TYPE: DNA
<213> ORGANISM: Artificial Sequence
<220> FEATURE:
<223> OTHER INFORMATION: Primer

<400> SEQUENCE: 52
gatcccatgg tggcctgttc ctatagtgag tcgtattagc tgc    43

```
<210> SEQ ID NO 53
<211> LENGTH: 43
<212> TYPE: DNA
<213> ORGANISM: Artificial Sequence
<220> FEATURE:
<223> OTHER INFORMATION: Primer

<400> SEQUENCE: 53
agctgcagct aatacgactc actataggaa caggccacca tgg                    43

<210> SEQ ID NO 54
<211> LENGTH: 34
<212> TYPE: DNA
<213> ORGANISM: Artificial Sequence
<220> FEATURE:
<223> OTHER INFORMATION: Primer

<400> SEQUENCE: 54
ccaccatggg ccagaaggaa gtggagcaga actc                              34

<210> SEQ ID NO 55
<211> LENGTH: 24
<212> TYPE: DNA
<213> ORGANISM: Artificial Sequence
<220> FEATURE:
<223> OTHER INFORMATION: Primer

<400> SEQUENCE: 55
cgagagcccg tagaactgga cttg                                         24

<210> SEQ ID NO 56
<211> LENGTH: 46
<212> TYPE: DNA
<213> ORGANISM: Artificial Sequence
<220> FEATURE:
<223> OTHER INFORMATION: Primer

<400> SEQUENCE: 56
gtggatccgg cggtggcggg tcgaacgctg gtgtcactca gacccc                 46

<210> SEQ ID NO 57
<211> LENGTH: 55
<212> TYPE: DNA
<213> ORGANISM: Artificial Sequence
<220> FEATURE:
<223> OTHER INFORMATION: Primer

<400> SEQUENCE: 57
ccggatccac ctccgcctga accgcctcca ccggtgacca caacctgggt ccctg       55

<210> SEQ ID NO 58
<211> LENGTH: 35
<212> TYPE: DNA
<213> ORGANISM: Artificial Sequence
<220> FEATURE:
<223> OTHER INFORMATION: Primer

<400> SEQUENCE: 58
ctgagaattc ttatgactct ccgcggttga agctc                             35

<210> SEQ ID NO 59
<211> LENGTH: 32
<212> TYPE: DNA
<213> ORGANISM: Artificial Sequence
<220> FEATURE:
<223> OTHER INFORMATION: Primer
```

```
<400> SEQUENCE: 59
tgacgaattc tgactctccg cggttgaagc tc                                32

<210> SEQ ID NO 60
<211> LENGTH: 28
<212> TYPE: DNA
<213> ORGANISM: Artificial Sequence
<220> FEATURE:
<223> OTHER INFORMATION: Primer

<400> SEQUENCE: 60
agctgcagct aatacgactc actatagg                                     28

<210> SEQ ID NO 61
<211> LENGTH: 36
<212> TYPE: DNA
<213> ORGANISM: Artificial Sequence
<220> FEATURE:
<223> OTHER INFORMATION: Primer

<400> SEQUENCE: 61
ggccaccatg ggcaacgctg gtgtcactca gacccc                            36

<210> SEQ ID NO 62
<211> LENGTH: 40
<212> TYPE: DNA
<213> ORGANISM: Artificial Sequence
<220> FEATURE:
<223> OTHER INFORMATION: Primer

<400> SEQUENCE: 62
tgaaccgcct ccaccgtctg ctctacccca ggcctcggcg                        40

<210> SEQ ID NO 63
<211> LENGTH: 22
<212> TYPE: DNA
<213> ORGANISM: Artificial Sequence
<220> FEATURE:
<223> OTHER INFORMATION: Primer

<400> SEQUENCE: 63
tgactctccg cggttgaagc tc                                           22

<210> SEQ ID NO 64
<211> LENGTH: 29
<212> TYPE: DNA
<213> ORGANISM: Artificial Sequence
<220> FEATURE:
<223> OTHER INFORMATION: Primer

<400> SEQUENCE: 64
cagctggggg aagcttcagt ttggagcag                                    29

<210> SEQ ID NO 65
<211> LENGTH: 29
<212> TYPE: DNA
<213> ORGANISM: Artificial Sequence
<220> FEATURE:
<223> OTHER INFORMATION: Primer

<400> SEQUENCE: 65
ctgctccaaa ctgaagcttc ccccagctg                                    29

<210> SEQ ID NO 66
<211> LENGTH: 29
```

```
<212> TYPE: DNA
<213> ORGANISM: Artificial Sequence
<220> FEATURE:
<223> OTHER INFORMATION: Primer

<400> SEQUENCE: 66
gtacttctgt gcctcgaggc cgggactag                                29

<210> SEQ ID NO 67
<211> LENGTH: 29
<212> TYPE: DNA
<213> ORGANISM: Artificial Sequence
<220> FEATURE:
<223> OTHER INFORMATION: Primer

<400> SEQUENCE: 67
ctagtcccgg cctcgaggca cagaagtac                                29

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
cattttcagg gatagcaagc                                          20

<210> SEQ ID NO 69
<211> LENGTH: 40
<212> TYPE: DNA
<213> ORGANISM: Artificial Sequence
<220> FEATURE:
<223> OTHER INFORMATION: Primer

<400> SEQUENCE: 69
tcacacagga aacagctatg tcacacagga aacagctatg                    40

<210> SEQ ID NO 70
<211> LENGTH: 49
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(49)
<223> OTHER INFORMATION: n is a or t or g or c; k is g or t

<400> SEQUENCE: 70
tgtgcctcga ggnnknnknn knnknnknnk cgaccagagc agtacttcg           49

<210> SEQ ID NO 71
<211> LENGTH: 52
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(52)
<223> OTHER INFORMATION: n is a or t or g or c; k is g or t

<400> SEQUENCE: 71
tgtgcctcga ggccgnnknn knnknnknnk nnkccagagc agtacttcgg gc       52

<210> SEQ ID NO 72
```

```
<211> LENGTH: 52
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(52)
<223> OTHER INFORMATION: n is a or t or g or c; k is g or t

<400> SEQUENCE: 72
tgtgcctcga ggccgnnknn knnknnknnk nnkcgaccag agcagtactt cg        52

<210> SEQ ID NO 73
<211> LENGTH: 51
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(51)
<223> OTHER INFORMATION: n is a or t or g or c; k is g or t

<400> SEQUENCE: 73
tgtgcctcga ggccgnnknn knnknnknnk nnkggagggc gaccagagca g         51

<210> SEQ ID NO 74
<211> LENGTH: 54
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(54)
<223> OTHER INFORMATION: n is a or t or g or c; k is g or t

<400> SEQUENCE: 74
tgtgcctcga ggccgggann knnknnknnk nnknnkgggc gaccagagca gtac      54

<210> SEQ ID NO 75
<211> LENGTH: 49
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(49)
<223> OTHER INFORMATION: n is a or t or g or c; k is g or t

<400> SEQUENCE: 75
tgtgcctcga ggnnknnknn knnknnknnk ccagagcagt acttcgggc            49

<210> SEQ ID NO 76
<211> LENGTH: 48
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(48)
<223> OTHER INFORMATION: n is a or t or g or c; k is g or t

<400> SEQUENCE: 76
tgtgcctcga ggnnknnknn knnknnknnk gagcagtact tcgggccg             48
```

-continued

```
<210> SEQ ID NO 77
<211> LENGTH: 48
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(48)
<223> OTHER INFORMATION: n is a or t or g or c; k is g or t

<400> SEQUENCE: 77
tgtgcctcga ggnnknnknn knnknnknnk cagtacttcg ggccgggc                    48

<210> SEQ ID NO 78
<211> LENGTH: 49
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(49)
<223> OTHER INFORMATION: n is a or t or g or c; k is g or t

<400> SEQUENCE: 78
tgtgcctcga ggccgnnknn knnknnkggg cgaccagagc agtacttcg                   49

<210> SEQ ID NO 79
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(46)
<223> OTHER INFORMATION: m is a or c; n is a or t or g or c

<400> SEQUENCE: 79
aaactgaagc ttmnnmnnmn nmnnmnntgt aacggcacag aggtag                      46

<210> SEQ ID NO 80
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(46)
<223> OTHER INFORMATION: m is a or c; n is a or t or g or c

<400> SEQUENCE: 80
aaactgaagc ttmnnmnnngc tgtcmnntgt aacggcacag aggtag                     46

<210> SEQ ID NO 81
<211> LENGTH: 49
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(49)
<223> OTHER INFORMATION: m is a or c; n is a or t or g or c

<400> SEQUENCE: 81
aaactgaagc ttmnnmnnmn ngctgtcmnn tgtaacggca cagaggtag                   49
```

```
<210> SEQ ID NO 82
<211> LENGTH: 43
<212> TYPE: DNA
<213> ORGANISM: Artificial Sequence
<220> FEATURE:
<223> OTHER INFORMATION: primer
<221> NAME/KEY: misc_feature
<222> LOCATION: (1)...(43)
<223> OTHER INFORMATION: n = A,T,C or G; m = A or C

<400> SEQUENCE: 82
aaactgaagc ttmnnmnngc tgtcmnnaac ggcacagagg tag            43

<210> SEQ ID NO 83
<211> LENGTH: 42
<212> TYPE: DNA
<213> ORGANISM: Homo sapiens

<400> SEQUENCE: 83
gcctcgaggc cgggactagc gggagggcga ccagagcagt ag             42

<210> SEQ ID NO 84
<211> LENGTH: 14
<212> TYPE: PRT
<213> ORGANISM: Homo sapiens

<400> SEQUENCE: 84

Ala Ser Arg Pro Gly Leu Ala Gly Gly Arg Pro Glu Gln Tyr
1               5                   10

<210> SEQ ID NO 85
<211> LENGTH: 42
<212> TYPE: DNA
<213> ORGANISM: Homo sapiens

<400> SEQUENCE: 85
gcctcgaggc cggggctgat gagtgcgtag ccagagcagt ac             42

<210> SEQ ID NO 86
<211> LENGTH: 14
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Xaa is an amino acid residue encoded by an
      amber codon

<400> SEQUENCE: 86

Ala Ser Arg Pro Gly Leu Met Ser Ala Xaa Pro Glu Gln Tyr
1               5                   10

<210> SEQ ID NO 87
<211> LENGTH: 42
<212> TYPE: DNA
<213> ORGANISM: Homo sapiens

<400> SEQUENCE: 87
gcctcgaggc cggggctgag gtcggcgtag ccagagcagt ac             42

<210> SEQ ID NO 88
<211> LENGTH: 14
<212> TYPE: PRT
<213> ORGANISM: Homo sapiens
<220> FEATURE:
<221> NAME/KEY: MISC_FEATURE
```

<222> LOCATION: (10)..(10)
<223> OTHER INFORMATION: Xaa is an amino acid residue encoded by an
     amber codon

<400> SEQUENCE: 88

Ala Ser Arg Pro Gly Leu Arg Ser Ala Xaa Pro Glu Gln Tyr
1               5                   10

<210> SEQ ID NO 89
<211> LENGTH: 42
<212> TYPE: DNA
<213> ORGANISM: Homo sapiens

<400> SEQUENCE: 89
gcctcgaggc cgggactagc gggagggcga ccagaggcgt ag                         42

<210> SEQ ID NO 90
<211> LENGTH: 14
<212> TYPE: PRT
<213> ORGANISM: Homo sapiens
<220> FEATURE:
<221> NAME/KEY: MISC_FEATURE
<222> LOCATION: (14)..(14)
<223> OTHER INFORMATION: Xaa is an amino acid residue encoded by an
     amber codon

<400> SEQUENCE: 90

Ala Ser Arg Pro Gly Leu Ala Gly Gly Arg Pro Glu Ala Xaa
1               5                   10

<210> SEQ ID NO 91
<211> LENGTH: 42
<212> TYPE: DNA
<213> ORGANISM: Homo sapiens

<400> SEQUENCE: 91
gcctcgaggc cgggactagc gggagggcga ccagaggatt ag                         42

<210> SEQ ID NO 92
<211> LENGTH: 14
<212> TYPE: PRT
<213> ORGANISM: Homo sapiens
<220> FEATURE:
<221> NAME/KEY: MISC_FEATURE
<222> LOCATION: (14)..(14)
<223> OTHER INFORMATION: Xaa is an amino acid residue encoded by an
     amber codon

<400> SEQUENCE: 92

Ala Ser Arg Pro Gly Leu Ala Gly Gly Arg Pro Glu Asp Xaa
1               5                   10

<210> SEQ ID NO 93
<211> LENGTH: 42
<212> TYPE: DNA
<213> ORGANISM: Homo sapiens

<400> SEQUENCE: 93
gcctcgaggc cgggactagc gggagggcga ccagatcagt ag                         42

<210> SEQ ID NO 94
<211> LENGTH: 14
<212> TYPE: PRT
<213> ORGANISM: Homo sapiens
<220> FEATURE:
<221> NAME/KEY: MISC_FEATURE
<222> LOCATION: (14)..(14)

```
<223> OTHER INFORMATION: Xaa is an amino acid residue encoded by an
      amber codon

<400> SEQUENCE: 94

Ala Ser Arg Pro Gly Leu Ala Gly Gly Arg Pro Asp Gln Xaa
1               5                   10

<210> SEQ ID NO 95
<211> LENGTH: 42
<212> TYPE: DNA
<213> ORGANISM: Homo sapiens

<400> SEQUENCE: 95
gcctcgaggc cgggtctgta ggctgggcga ccagagcagt ac                           42

<210> SEQ ID NO 96
<211> LENGTH: 14
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa is an amino acid residue encoded by an
      amber codon

<400> SEQUENCE: 96

Ala Ser Arg Pro Gly Leu Xaa Ala Gly Arg Pro Glu Gln Tyr
1               5                   10

<210> SEQ ID NO 97
<211> LENGTH: 42
<212> TYPE: DNA
<213> ORGANISM: Homo sapiens

<400> SEQUENCE: 97
gcctcgaggc cggggctggt tccggggcga ccagagcagt ag                           42

<210> SEQ ID NO 98
<211> LENGTH: 14
<212> TYPE: PRT
<213> ORGANISM: Homo sapiens
<220> FEATURE:
<221> NAME/KEY: MISC_FEATURE
<222> LOCATION: (14)..(14)
<223> OTHER INFORMATION: Xaa is an amino acid residue encoded by an
      amber codon

<400> SEQUENCE: 98

Ala Ser Arg Pro Gly Leu Val Pro Gly Arg Pro Glu Gln Xaa
1               5                   10

<210> SEQ ID NO 99
<211> LENGTH: 42
<212> TYPE: DNA
<213> ORGANISM: Homo sapiens

<400> SEQUENCE: 99
gcctcgaggc cggggcttgt gtctgcttag ccagagcagt ac                           42

<210> SEQ ID NO 100
<211> LENGTH: 14
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Xaa is an amino acid residue encoded by an
``` amber codon

<400> SEQUENCE: 100

Ala Ser Arg Pro Gly Leu Val Ser Ala Xaa Pro Glu Gln Tyr
1               5                   10

<210> SEQ ID NO 101
<211> LENGTH: 42
<212> TYPE: DNA
<213> ORGANISM: Homo sapiens

<400> SEQUENCE: 101
gcctcgaggc cgggactagc gggagggcga ccacatccgt ag                          42

<210> SEQ ID NO 102
<211> LENGTH: 14
<212> TYPE: PRT
<213> ORGANISM: Homo sapiens
<220> FEATURE:
<221> NAME/KEY: MISC_FEATURE
<222> LOCATION: (14)..(14)
<223> OTHER INFORMATION: Xaa is an amino acid residue encoded by an
      amber codon

<400> SEQUENCE: 102

Ala Ser Arg Pro Gly Leu Ala Gly Gly Arg Pro His Pro Xaa
1               5                   10

<210> SEQ ID NO 103
<211> LENGTH: 42
<212> TYPE: DNA
<213> ORGANISM: Homo sapiens

<400> SEQUENCE: 103
gcctcgaggc cgggactagc gggagggcga ccagatgcgt ag                          42

<210> SEQ ID NO 104
<211> LENGTH: 14
<212> TYPE: PRT
<213> ORGANISM: Homo sapiens
<220> FEATURE:
<221> NAME/KEY: MISC_FEATURE
<222> LOCATION: (14)..(14)
<223> OTHER INFORMATION: Xaa is an amino acid residue encoded by an
      amber codon

<400> SEQUENCE: 104

Ala Ser Arg Pro Gly Leu Ala Gly Gly Arg Pro Asp Ala Xaa
1               5                   10

<210> SEQ ID NO 105
<211> LENGTH: 42
<212> TYPE: DNA
<213> ORGANISM: Homo sapiens

<400> SEQUENCE: 105
gcctcgaggc cgggtctgat tagtgcttag ccagagcagt ac                          42

<210> SEQ ID NO 106
<211> LENGTH: 14
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Xaa is an amino acid residue encoded by an
      amber codon -continued

<400> SEQUENCE: 106

Ala Ser Arg Pro Gly Leu Ile Ser Ala Xaa Pro Glu Gln Tyr
1               5                   10

<210> SEQ ID NO 107
<211> LENGTH: 33
<212> TYPE: DNA
<213> ORGANISM: Homo sapiens

<400> SEQUENCE: 107
gccgttacaa ctgacagctg ggggaagctt cag                          33

<210> SEQ ID NO 108
<211> LENGTH: 11
<212> TYPE: PRT
<213> ORGANISM: Homo sapiens

<400> SEQUENCE: 108

Ala Val Thr Thr Asp Ser Trp Gly Lys Leu Gln
1               5                   10

<210> SEQ ID NO 109
<211> LENGTH: 33
<212> TYPE: DNA
<213> ORGANISM: Homo sapiens

<400> SEQUENCE: 109
gccgttacaa ctgacagctg ggggccgctt cag                          33

<210> SEQ ID NO 110
<211> LENGTH: 11
<212> TYPE: PRT
<213> ORGANISM: Artificial Sequence
<220> FEATURE:
<223> OTHER INFORMATION: CDR3 sequence in A6 TCR beta chain mutant

<400> SEQUENCE: 110

Ala Val Thr Thr Asp Ser Trp Gly Pro Leu Gln
1               5                   10

<210> SEQ ID NO 111
<211> LENGTH: 33
<212> TYPE: DNA
<213> ORGANISM: Homo sapiens

<400> SEQUENCE: 111
gccgttacaa ctgacagctg ggggaagatg cag                          33

<210> SEQ ID NO 112
<211> LENGTH: 11
<212> TYPE: PRT
<213> ORGANISM: Homo sapiens

<400> SEQUENCE: 112

Ala Val Thr Thr Asp Ser Trp Gly Lys Met Gln
1               5                   10

<210> SEQ ID NO 113
<211> LENGTH: 33
<212> TYPE: DNA
<213> ORGANISM: Homo sapiens

<400> SEQUENCE: 113

```
gccgttacaa ctgacagctg ggggaagttg cat                                    33
```

<210> SEQ ID NO 114
<211> LENGTH: 11
<212> TYPE: PRT
<213> ORGANISM: Homo sapiens

<400> SEQUENCE: 114

```
Ala Val Thr Thr Asp Ser Trp Gly Lys Leu His
1               5                   10
```

<210> SEQ ID NO 115
<211> LENGTH: 33
<212> TYPE: DNA
<213> ORGANISM: Homo sapiens

<400> SEQUENCE: 115

```
gccgttacaa ctgacagctg ggggtagctt cat                                    33
```

<210> SEQ ID NO 116
<211> LENGTH: 11
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: Xaa is an amino acid residue encoded by an
      amber codon

<400> SEQUENCE: 116

```
Ala Val Thr Thr Asp Ser Trp Gly Xaa Leu His
1               5                   10
```

<210> SEQ ID NO 117
<211> LENGTH: 33
<212> TYPE: DNA
<213> ORGANISM: Homo sapiens

<400> SEQUENCE: 117

```
gccgttacaa ctgacagctg gggggagctt cat                                    33
```

<210> SEQ ID NO 118
<211> LENGTH: 11
<212> TYPE: PRT
<213> ORGANISM: Homo sapiens

<400> SEQUENCE: 118

```
Ala Val Thr Thr Asp Ser Trp Gly Glu Leu His
1               5                   10
```

<210> SEQ ID NO 119
<211> LENGTH: 33
<212> TYPE: DNA
<213> ORGANISM: Artificial Sequence
<220> FEATURE:
<223> OTHER INFORMATION: CDR3 sequence in A6 TCR alpha chain mutant

<400> SEQUENCE: 119

```
gccgttacaa ctgacagctg ggggaggctg cat                                    33
```

<210> SEQ ID NO 120
<211> LENGTH: 11
<212> TYPE: PRT
<213> ORGANISM: Homo sapiens

<400> SEQUENCE: 120

Ala Val Thr Thr Asp Ser Trp Gly Arg Leu His
1               5                   10

<210> SEQ ID NO 121
<211> LENGTH: 33
<212> TYPE: DNA
<213> ORGANISM: Homo sapiens

<400> SEQUENCE: 121
gccgttacaa ctgacagctg ggggcagctt cat                              33

<210> SEQ ID NO 122
<211> LENGTH: 11
<212> TYPE: PRT
<213> ORGANISM: Homo sapiens

<400> SEQUENCE: 122

Ala Val Thr Thr Asp Ser Trp Gly Gln Leu His
1               5                   10

<210> SEQ ID NO 123
<211> LENGTH: 33
<212> TYPE: DNA
<213> ORGANISM: Homo sapiens

<400> SEQUENCE: 123
gccgttacaa ctgacagctg ggggaaggtt cat                              33

<210> SEQ ID NO 124
<211> LENGTH: 11
<212> TYPE: PRT
<213> ORGANISM: Homo sapiens

<400> SEQUENCE: 124

Ala Val Thr Thr Asp Ser Trp Gly Lys Val His
1               5                   10

<210> SEQ ID NO 125
<211> LENGTH: 33
<212> TYPE: DNA
<213> ORGANISM: Artificial Sequence
<220> FEATURE:
<223> OTHER INFORMATION: CDR3 sequence in A6 TCR alpha chain mutant

<400> SEQUENCE: 125
gccgttacaa ctgacagctg ggggaaggtg aat                              33

<210> SEQ ID NO 126
<211> LENGTH: 11
<212> TYPE: PRT
<213> ORGANISM: Homo sapiens

<400> SEQUENCE: 126

Ala Val Thr Thr Asp Ser Trp Gly Lys Val Asn
1               5                   10

<210> SEQ ID NO 127
<211> LENGTH: 33
<212> TYPE: DNA
<213> ORGANISM: Homo sapiens

<400> SEQUENCE: 127
gccgttacaa ctgacagctg ggggaagctt ctg                              33

<210> SEQ ID NO 128
<211> LENGTH: 11
<212> TYPE: PRT
<213> ORGANISM: Homo sapiens

<400> SEQUENCE: 128

Ala Val Thr Thr Asp Ser Trp Gly Lys Leu Leu
1               5                   10

<210> SEQ ID NO 129
<211> LENGTH: 32
<212> TYPE: DNA
<213> ORGANISM: Artificial sequence
<220> FEATURE:
<223> OTHER INFORMATION: Primer

<400> SEQUENCE: 129
ggaattcatc gatgcagaag gaagtggagc ag                                    32

<210> SEQ ID NO 130
<211> LENGTH: 31
<212> TYPE: DNA
<213> ORGANISM: Artificial sequence
<220> FEATURE:
<223> OTHER INFORMATION: Primer

<400> SEQUENCE: 130
gtacacggcc gggtcagggt tctggatata c                                     31

<210> SEQ ID NO 131
<211> LENGTH: 36
<212> TYPE: DNA
<213> ORGANISM: Artificial sequence
<220> FEATURE:
<223> OTHER INFORMATION: Primer

<400> SEQUENCE: 131
tctctcatta atgaatgctg gtgtcactca gacccc                                36

<210> SEQ ID NO 132
<211> LENGTH: 32
<212> TYPE: DNA
<213> ORGANISM: Artificial sequence
<220> FEATURE:
<223> OTHER INFORMATION: Primer

<400> SEQUENCE: 132
tagaaaccgg tggccaggca caccagtgtg gc                                    32

<210> SEQ ID NO 133
<211> LENGTH: 19
<212> TYPE: DNA
<213> ORGANISM: Artificial Sequence
<220> FEATURE:
<223> OTHER INFORMATION: primer

<400> SEQUENCE: 133
ctgctctggt tccgcactc                                                   19

<210> SEQ ID NO 134
<211> LENGTH: 19
<212> TYPE: DNA
<213> ORGANISM: Artificial sequence
<220> FEATURE:
<223> OTHER INFORMATION: Primer

```
<400> SEQUENCE: 134
gagtgcggaa ccagagcag                                             19

<210> SEQ ID NO 135
<211> LENGTH: 28
<212> TYPE: DNA
<213> ORGANISM: Artificial sequence
<220> FEATURE:
<223> OTHER INFORMATION: Primer

<400> SEQUENCE: 135
atatccagaa cccggatcct gccgtgta                                   28

<210> SEQ ID NO 136
<211> LENGTH: 29
<212> TYPE: DNA
<213> ORGANISM: Artificial sequence
<220> FEATURE:
<223> OTHER INFORMATION: Primer

<400> SEQUENCE: 136
tacacggcag gaatccgggt tctggatat                                  29

<210> SEQ ID NO 137
<211> LENGTH: 30
<212> TYPE: DNA
<213> ORGANISM: Artificial sequence
<220> FEATURE:
<223> OTHER INFORMATION: Primer

<400> SEQUENCE: 137
ggagatatac atatgcagga ggtgacacag                                 30

<210> SEQ ID NO 138
<211> LENGTH: 29
<212> TYPE: DNA
<213> ORGANISM: Artificial sequence
<220> FEATURE:
<223> OTHER INFORMATION: Primer

<400> SEQUENCE: 138
tacacggcag gatccgggtt ctggatatt                                  29

<210> SEQ ID NO 139
<211> LENGTH: 30
<212> TYPE: DNA
<213> ORGANISM: Artificial sequence
<220> FEATURE:
<223> OTHER INFORMATION: Primer

<400> SEQUENCE: 139
ggagatatac atatgggtgt cactcagacc                                 30

<210> SEQ ID NO 140
<211> LENGTH: 34
<212> TYPE: DNA
<213> ORGANISM: Artificial sequence
<220> FEATURE:
<223> OTHER INFORMATION: Primer

<400> SEQUENCE: 140
cccaagctta gtctgctcta ccccaggcct cggc                            34

<210> SEQ ID NO 141
<211> LENGTH: 37
```

```
<212> TYPE: DNA
<213> ORGANISM: Artificial sequence
<220> FEATURE:
<223> OTHER INFORMATION: Primer

<400> SEQUENCE: 141
gccggccatg gccaaacagg aggtgacgca gattcct                              37

<210> SEQ ID NO 142
<211> LENGTH: 57
<212> TYPE: DNA
<213> ORGANISM: Artificial sequence
<220> FEATURE:
<223> OTHER INFORMATION: Primer

<400> SEQUENCE: 142
cttcttaaag aattcttaat taacctaggt tattaggaac tttctgggct ggggaag        57

<210> SEQ ID NO 143
<211> LENGTH: 36
<212> TYPE: DNA
<213> ORGANISM: Artificial sequence
<220> FEATURE:
<223> OTHER INFORMATION: Primer

<400> SEQUENCE: 143
tcacagcgcg caggctggtg tcactcagac cccaaa                               36

<210> SEQ ID NO 144
<211> LENGTH: 24
<212> TYPE: DNA
<213> ORGANISM: Artificial sequence
<220> FEATURE:
<223> OTHER INFORMATION: Primer

<400> SEQUENCE: 144
cgagagcccg tagaactgga cttg                                            24

<210> SEQ ID NO 145
<211> LENGTH: 36
<212> TYPE: DNA
<213> ORGANISM: Artificial sequence
<220> FEATURE:
<223> OTHER INFORMATION: Primer

<400> SEQUENCE: 145
tctctcatta atgaatgctg gtgtcactca gacccc                               36

<210> SEQ ID NO 146
<211> LENGTH: 31
<212> TYPE: DNA
<213> ORGANISM: Artificial Sequence
<220> FEATURE:
<223> OTHER INFORMATION: primer

<400> SEQUENCE: 146
tagaaaccgg tggccaggca caccagtgtg g                                    31

<210> SEQ ID NO 147
<211> LENGTH: 621
<212> TYPE: DNA
<213> ORGANISM: Homo sapiens

<400> SEQUENCE: 147
atgcagaagg aagtggagca gaactctgga cccctcagtg ttccagaggg agccattgcc    60
```

```
tctctcaact gcacttacag tgaccgaggt tcccagtcct tcttctggta cagacaatat      120
tctgggaaaa gccctgagtt gataatgtcc atatactcca atggtgacaa agaagatgga      180
aggtttacag cacagctcaa taaagccagc cagtatgttt ctctgctcat cagagactcc      240
cagcccagtg attcagccac ctacctctgt gccgttacaa ctgacagctg ggggaaattg      300
cagtttggag cagggaccca ggttgtggtc accccagata tccagaaccc tgaccctgcc      360
gtgtaccagc tgagagactc taaatccagt gacaagtctg tctgcctatt caccgatttt      420
gattctcaaa caaatgtgtc acaaagtaag gattctgatg tgtatatcac agacaaatgt      480
gtgctagaca tgaggtctat ggacttcaag agcaacagtg ctgtggcctg agcaacaaa       540 tctgactttg catgtgcaaa cgccttcaac aacagcatta ttccagaaga caccttcttc      600
cccagcccag aaagttccta a                                                621
```

<210> SEQ ID NO 148
<211> LENGTH: 741
<212> TYPE: DNA
<213> ORGANISM: Homo sapiens

<400> SEQUENCE: 148

```
atgaacgctg gtgtcactca gaccccaaaa ttccaggtcc tgaagacagg acagagcatg       60
acactgcagt gtgcccagga tatgaaccat gaatacatgt cctggtatcg acaagaccca      120
ggcatggggc tgaggctgat tcattactca gttggtgctg gtatcactga ccaaggagaa      180
gtccccaatg ctacaatgt ctccagatca accacagagg atttcccgct caggctgctg       240
tcggctgctc cctcccagac atctgtgtac ttctgtgcca gcaggccggg actagcggga      300
gggcgaccag agcagtactt cgggccgggc accaggctca cggtcacaga ggacctgaaa      360
aacgtgttcc caccccgagt cgctgtgttt gagccatcag aagcagagat ctcccacacc      420
caaaaggcca cactggtgtg cctggccaca ggcttctacc ccgaccacgt ggagctgagc      480
tggtgggtga atgggaagga ggtgcacagt ggggtctgca cagacccgca gcccctcaag      540
gagcagcccg ccctcaatga ctccagatac gctctgagca gccgcctgag ggtctcggcc      600
accttctggc aggacccccg caaccacttc cgctgtcaag tccagttcta cgggctctcg      660
gagaatgacg agtggaccca ggatagggcc aaacccgtca cccagatcgt cagcgccgag      720
gcctggggta gagcagacta a                                                741
```

<210> SEQ ID NO 149
<211> LENGTH: 206
<212> TYPE: PRT
<213> ORGANISM: Homo sapiens

<400> SEQUENCE: 149

```
Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
                20                  25                  30

Ser Phe Phe Trp Tyr Arg Gln Tyr Ser Gly Lys Ser Pro Glu Leu Ile
            35                  40                  45

Met Ser Ile Tyr Ser Asn Gly Asp Lys Glu Asp Gly Arg Phe Thr Ala
        50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Val Thr Asp Ser
                85                  90                  95
```

```
Trp Gly Lys Leu Gln Phe Gly Ala Gly Thr Gln Val Val Thr Pro
                100                 105                 110

Asp Ile Gln Asn Pro Asp Pro Ala Val Tyr Gln Leu Arg Asp Ser Lys
            115                 120                 125

Ser Ser Asp Lys Ser Val Cys Leu Phe Thr Asp Phe Asp Ser Gln Thr
    130                 135                 140

Asn Val Ser Gln Ser Lys Asp Ser Asp Val Tyr Ile Thr Asp Lys Cys
145                 150                 155                 160

Val Leu Asp Met Arg Ser Met Asp Phe Lys Ser Asn Ser Ala Val Ala
                165                 170                 175

Trp Ser Asn Lys Ser Asp Phe Ala Cys Ala Asn Ala Phe Asn Asn Ser
            180                 185                 190

Ile Ile Pro Glu Asp Thr Phe Phe Pro Ser Pro Glu Ser Ser
        195                 200                 205

<210> SEQ ID NO 150
<211> LENGTH: 246
<212> TYPE: PRT
<213> ORGANISM: Homo sapiens

<400> SEQUENCE: 150

Met Asn Ala Gly Val Thr Gln Thr Pro Lys Phe Gln Val Leu Lys Thr
1               5                   10                  15

Gly Gln Ser Met Thr Leu Gln Cys Ala Gln Asp Met Asn His Glu Tyr
            20                  25                  30

Met Ser Trp Tyr Arg Gln Asp Pro Gly Met Gly Leu Arg Leu Ile His
        35                  40                  45

Tyr Ser Val Gly Ala Gly Ile Thr Asp Gln Gly Glu Val Pro Asn Gly
    50                  55                  60

Tyr Asn Val Ser Arg Ser Thr Thr Glu Asp Phe Pro Leu Arg Leu Leu
65                  70                  75                  80

Ser Ala Ala Pro Ser Gln Thr Ser Val Tyr Phe Cys Ala Ser Arg Pro
                85                  90                  95

Gly Leu Ala Gly Gly Arg Pro Glu Gln Tyr Phe Gly Pro Gly Thr Arg
            100                 105                 110

Leu Thr Val Thr Glu Asp Leu Lys Asn Val Phe Pro Pro Glu Val Ala
        115                 120                 125

Val Phe Glu Pro Ser Glu Ala Glu Ile Ser His Thr Gln Lys Ala Thr
    130                 135                 140

Leu Val Cys Leu Ala Thr Gly Phe Tyr Pro Asp His Val Glu Leu Ser
145                 150                 155                 160

Trp Trp Val Asn Gly Lys Glu Val His Ser Gly Val Cys Thr Asp Pro
                165                 170                 175

Gln Pro Leu Lys Glu Gln Pro Ala Leu Asn Asp Ser Arg Tyr Ala Leu
            180                 185                 190

Ser Ser Arg Leu Arg Val Ser Ala Thr Phe Trp Gln Asp Pro Arg Asn
        195                 200                 205

His Phe Arg Cys Gln Val Gln Phe Tyr Gly Leu Ser Glu Asn Asp Glu
    210                 215                 220

Trp Thr Gln Asp Arg Ala Lys Pro Val Thr Gln Ile Val Ser Ala Glu
225                 230                 235                 240

Ala Trp Gly Arg Ala Asp
                245
```

<210> SEQ ID NO 151
<211> LENGTH: 5495
<212> TYPE: DNA
<213> ORGANISM: Artificial sequence
<220> FEATURE:
<223> OTHER INFORMATION: Phagemid vector pEX746:A6

<400> SEQUENCE: 151

| | | | | | |
|---|---|---|---|---|---|
| gttaactacg | tcaggtggca | cttttcgggg | aaatgtgcgc | ggaaccccta | tttgtttatt | 60 |
| tttctaaata | cattcaaata | tgtatccgct | catgagacaa | taaccctgat | aaatgcttca | 120 |
| ataatattga | aaaggaaga | gtatgagtat | tcaacatttc | cgtgtcgccc | ttattccctt | 180 |
| ttttgcggca | ttttgccttc | ctgttttttgc | tcacccagaa | acgctggtga | agtaaaaga | 240 |
| tgctgaagat | cagttgggtg | cacgagtggg | ttacatcgaa | ctggatctca | acagcggtaa | 300 |
| gatccttgag | agttttcgcc | ccgaagaacg | ttctccaatg | atgagcactt | ttaaagttct | 360 |
| gctatgtggc | gcggtattat | cccgtgttga | cgccgggcaa | gagcaactcg | gtcgccgcat | 420 |
| acactattct | cagaatgact | tggttgagta | ctcaccagtc | acagaaaagc | atcttacgga | 480 |
| tggcatgaca | gtaagagaat | tatgcagtgc | tgccataacc | atgagtgata | acactgcggc | 540 |
| caacttactt | ctgacaacga | tcggaggacc | gaaggagcta | accgcttttt | tgcacaacat | 600 |
| gggggatcat | gtaactcgcc | ttgatcgttg | ggaaccggag | ctgaatgaag | ccataccaaa | 660 |
| cgacgagcgt | gacaccacga | tgcctgtagc | aatggcaaca | acgttgcgca | aactattaac | 720 |
| tggcgaacta | cttactctag | cttcccggca | acaattaata | gactggatgg | aggcggataa | 780 |
| agttgcagga | ccacttctgc | gctcggccct | tccggctggc | tggtttattg | ctgataaatc | 840 |
| tggagccggt | gagcgtgggt | ctcgcggtat | cattgcagca | ctggggccag | atggtaagcc | 900 |
| ctcccgtatc | gtagttatct | acacgacggg | gagtcaggca | actatggatg | aacgaaatag | 960 |
| acagatcgct | gagataggtg | cctcactgat | taagcattgg | taactgtcag | accaagttta | 1020 |
| ctcatatata | ctttagattg | atttaccccg | gttgataatc | agaaaagccc | caaaaacagg | 1080 |
| aagattgtat | aagcaaatat | ttaaattgta | aacgttaata | ttttgttaaa | attcgcgtta | 1140 |
| aatttttgtt | aaatcagctc | attttttaac | caataggccg | aaatcggcaa | aatcccttat | 1200 |
| aaatcaaaag | aatagcccga | gatagggttg | agtgttgttc | cagtttggaa | caagagtcca | 1260 |
| ctattaaaga | acgtggactc | caacgtcaaa | gggcgaaaaa | ccgtctatca | gggcgatggc | 1320 |
| ccactacgtg | aaccatcacc | caaatcaagt | tttttgggt | cgaggtgccg | taaagcacta | 1380 |
| aatcggaacc | ctaaagggag | cccccgattt | agagcttgac | ggggaaagcg | aacgtggcga | 1440 |
| gaaaggaagg | gaagaaagcg | aaaggagcgg | gcgctagggc | gctggcaagt | gtagcggtca | 1500 |
| cgctgcgcgt | aaccaccaca | cccgccgcgc | ttaatgcgcc | gctacagggc | gcgtaaaagg | 1560 |
| atctaggtga | agatcctttt | tgataatctc | atgaccaaaa | tcccttaacg | tgagttttcg | 1620 |
| ttccactgag | cgtcagaccc | cgtagaaaag | atcaaaggat | cttcttgaga | tccttttttt | 1680 |
| ctgcgcgtaa | tctgctgctt | gcaaacaaaa | aaaccaccgc | taccagcggt | ggtttgtttg | 1740 |
| ccggatcaag | agctaccaac | tctttttccg | aaggtaactg | gcttcagcag | agcgcagata | 1800 |
| ccaaatactg | ttcttctagt | gtagccgtag | ttaggccacc | acttcaagaa | ctctgtagca | 1860 |
| ccgcctacat | acctcgctct | gctaatcctg | ttaccagtgg | ctgctgccag | tggcgataag | 1920 |
| tcgtgtctta | ccgggttgga | ctcaagacga | tagttaccgg | ataaggcgca | gcggtcgggc | 1980 |
| tgaacggggg | gttcgtgcac | acagcccagc | ttggagcgaa | cgacctacac | cgaactgaga | 2040 |
| tacctacagc | gtgagctatg | agaaagcgcc | acgcttcccg | aagggagaaa | ggcggacagg | 2100 |

-continued

```
tatccggtaa gcggcagggt cggaacagga gagcgcacga gggagcttcc agggggaaac    2160
gcctggtatc tttatagtcc tgtcgggttt cgccacctct gacttgagcg tcgattttg     2220 tgatgctcgt caggggggcg gagcctatgg aaaaacgcca gcaacgcggc cttttacgg     2280 ttcctggcct tttgctggcc ttttgctcac atgtaatgtg agttagctca ctcattaggc    2340
accccaggct ttacacttta tgcttccggc tcgtatgttg tgtggaattg tgagcggata    2400
acaatttcac acaggaaaca gctatgacca tgattacgcc aagctacgta taataatatt    2460
ctatttcaag gagacagtca taatgaaata cctattgcct acggcagccg ctggattgtt    2520
attactcgcg gcccagccgg ccatggccca aaggaagtg agcagaact ctggacccct      2580 cagtgttcca gagggagcca ttgcctctct caactgcact tacagtgacc gaggttccca    2640
gtccttcttc tggtacagac aatattctgg gaaaagccct gagttgataa tgtccatata    2700
ctccaatggt gacaaagaag atggaaggtt tacagcacag ctcaataaag ccagccagta    2760
tgtttctctg ctcatcagag actcccagcc cagtgattca gccacctacc tctgtgccgt    2820
tacaactgac agctggggga aattgcagtt tggagcaggg acccaggttg tggtcaccc     2880 agatatccag aaccctgacc ctgccgtgta ccagctgaga gactctaaat ccagtgacaa    2940
gtctgtctgc ctattcaccg attttgattc tcaaacaaat gtgtcacaaa gtaaggattc    3000
tgatgtgtat atcacagaca aatgtgtgct agacatgagg tctatggact caagagcaa    3060 cagtgctgtg gcctggagca acaaatctga ctttgcatgt gcaaacgcct tcaacaacag    3120
cattattcca gaagacacct tcttccccag cccagaaagt tcctaataac ctaggttaat    3180
taagaattct ttaagaagga gatatacata tgaaaaaatt attattcgca attcctttag    3240
ttgttccttt ctattctcac agcgcgcagg ctggtgtcac tcagaccca aaattccagg     3300 tcctgaagac aggacagagc atgacactgc agtgtgccca ggatatgaac catgaataca    3360
tgtcctggta tcgacaagac ccaggcatgg ggctgaggct gattcattac tcagttggtg    3420
ctggtatcac tgaccaagga gaagtcccca atggctacaa tgtctccaga tcaaccacag    3480
aggatttccc gctcaggctg ctgtcggctg ctccctccca gacatctgtg tacttctgtg    3540
ccagcaggcc gggactagcg ggagggcgac cagagcagta cttcgggccg gcaccaggc    3600 tcacggtcac agaggacctg aaaaacgtgt cccacccga ggtcgctgtg tttgagccat     3660
cagaagcaga gatctcccac acccaaaagg ccacactggt gtgcctggcc acaggcttct    3720
accccgacca cgtggagctg agctggtggg tgaatgggaa ggaggtgcac agtgggggtct    3780 gcacagaccc gcagcccctc aaggagcagc ccgcccctcaa tgactccaga tacgctctga    3840
gcagccgcct gagggtctcg gccaccttct ggcaggaccc ccgcaaccac ttccgctgtc    3900
aagtccagtt ctacgggctc tcggagaatg acgagtggac ccaggatagg gccaaacccg    3960
tcacccagat cgtcagcgcc gaggcctggg gtagagcaga cgcggccgca tctagacatc    4020
atcaccatca tcactagact gttgaaagtt gtttagcaaa accccataca gaaaattcat    4080
ttactaacgt ctggaaagac gacaaaactt tagatcgtta cgctaactat gagggttgtc    4140
tgtggaatgc tacaggcgtt gtagtttgta ctggtgacga aactcagtgt tacggtacat    4200
gggttcctat tgggcttgct atccctgaaa atgagggtgg tggctctgag ggtgcggtt     4260 ctgagggtgg cggttctgag ggtggcggta ctaaacctcc tgagtacggt gatacaccta    4320
ttccgggcta tacttatatc aaccctctcg acggcactta ccgcctggt actgagcaaa     4380 accccgctaa tcctaatcct tctcttgagg agtctcagcc tcttaatact ttcatgtttc    4440
agaataatag gttccgaaat aggcagggg cattaactgt ttatacgggc actgttactc     4500
```

```
aaggcactga ccccgttaaa acttattacc agtacactcc tgtatcatca aaagccatgt    4560
atgacgctta ctggaacggt aaattcagag actgcgcttt ccattctggc tttaatgagg    4620
atccattcgt ttgtgaatat caaggccaat cgtctgacct gcctcaacct cctgtcaatg    4680
ctggcggcgg ctctggtggt ggttctggtg gcggctctga gggtggtggc tctgagggtg    4740
gcggttctga gggtggcggc tctgagggag gcggttccgg tggtggctct ggttccggtg    4800
attttgatta tgaaaagatg gcaaacgcta ataaggggc tatgaccgaa atgccgatgt    4860
aaaacgcgct acagtctgac gctaaaggca aacttgattc tgtcgctact gattacggtg    4920
ctgctatcga tggtttcatt ggtgacgttt ccggccttgc taatggtaat ggtgctactg    4980
gtgattttgc tggctctaat cccaaatgg ctcaagtcgg tgacggtgat aattcacctt    5040
taatgaataa tttccgtcaa tatttacctt ccctccctca atcggttgaa tgtcgccctt    5100
ttgtctttag cgctggtaaa ccatatgaat tttctattga ttgtgacaaa ataaacttat    5160
tccgtggtgt ctttgcgttt cttttatatg ttgccacctt tatgtatgta ttttctacgt    5220
ttgctaacat actgcgtaat aaggagtctt aataaggtac cctctagtca aggcctatag    5280
tgagtcgtat tacggactgg ccgtcgtttt acaacgtcgt gactgggaaa accctggcgt    5340
tacccaactt aatcgccttg cagcacatcc cctttcgcc agctggcgta atagcgaaga    5400
ggcccgcacc gatcgccctt cccaacagtt gcgcagcctg aatggcgaat ggcgcttcgc    5460
ttggtaataa agcccgcttc ggcgggcttt ttttt                               5495

<210> SEQ ID NO 152
<211> LENGTH: 1303
<212> TYPE: DNA
<213> ORGANISM: Artificial sequence
<220> FEATURE:
<223> OTHER INFORMATION: A6 TCR-C-Kappa Ribosome display construct

<400> SEQUENCE: 152
agctgcagct aatacgactc actataggaa caggccacca tgggccagaa ggaagtggag      60
cagaactctg gacccctcag tgttccagag ggagccattg cctctctcaa ctgcacttac     120
agtgaccgag gttcccagtc cttcttctgg tacagacaat attctgggaa agccctgag      180 ttgataatgt ccatatactc caatggtgac aaagaagatg gaaggtttac agcacagctc     240
aataaagcca gccagtatgt ttctctgctc atcagagact cccagcccag tgattcagcc     300
acctacctct gtgccgttac aactgacagc tgggggaaat tgcagtttgg agcagggacc     360
caggttgtgt tcaccggtgg aggcggttca ggcggaggtg gatccggcgg tggcgggtcg     420
aacgctggtg tcactcagac cccaaaattc caggtcctga agacaggaca gagcatgaca     480
ctgcagtgtg cccaggatat gaaccatgaa tacatgtcct ggtatcgaca agacccaggc     540
atggggctga ggctgattca ttactcagtt ggtgctggta tcactgacca aggagaagtc     600
cccaatggct acaatgtctc cagatcaacc acagaggatt tcccgctcag gctgctgtcg     660
gctgctccct cccagacatc tgtgtacttc tgtgccagca ggccgggact agcggagggg     720
cgaccagagc agtacttcgg gccgggcacc aggctcacgg tcacagagga cctgaaaaac     780
gtgttcccac cgaggtcgc tgtgtttgag ccatcagaag cagagatctc cacacccaa      840 aaggccacac tggtgtgcct ggccacaggc ttctacccg accacgtgga gctgagctgg     900
tgggtgaatg gaaggaggt gcacagtggg gtcagcacag acccgcagcc cctcaaggag     960
cagcccgccc tcaatgactc cagatacgct ctgagcagcc gcctgagggt ctcggccacc    1020
```

```
ttctggcagg accccgcaa ccacttccgc tgtcaagtcc agttctacgg gctctcggag   1080
aatgacgagt ggacccagga tagggccaaa cccgtcaccc agatcgtcag cgccgaggcc   1140
tggggtagag cagacggtgg aggcggttca ctcagcagca ccctgacgct gagcaaagca   1200
gactacgaga acacaaagt ctacgcctgc gaagtcaccc atcagggcct gagttcgccc   1260
gtcacaaaga gcttcaaccg cggagagtca taagaattct cag                     1303
```

<210> SEQ ID NO 153
<211> LENGTH: 416
<212> TYPE: PRT
<213> ORGANISM: Artificial sequence
<220> FEATURE:
<223> OTHER INFORMATION: A6 TCR-C-Kappa ribosome display construct AA
      sequence

<400> SEQUENCE: 153

```
Met Gly Gln Lys Glu Val Glu Gln Asn Ser Gly Pro Leu Ser Val Pro
1               5                   10                  15

Glu Gly Ala Ile Ala Ser Leu Asn Cys Thr Tyr Ser Asp Arg Gly Ser
            20                  25                  30

Gln Ser Phe Phe Trp Tyr Arg Gln Tyr Ser Gly Lys Ser Pro Glu Leu
        35                  40                  45

Ile Met Ser Ile Tyr Ser Asn Gly Asp Lys Glu Asp Gly Arg Phe Thr
    50                  55                  60

Ala Gln Leu Asn Lys Ala Ser Gln Tyr Val Ser Leu Leu Ile Arg Asp
65                  70                  75                  80

Ser Pro Ser Asp Ser Ala Thr Tyr Leu Cys Ala Val Thr Thr Asp Ser
                85                  90                  95

Trp Gly Lys Leu Gln Phe Gly Ala Gly Thr Gln Val Val Val Thr Gly
            100                 105                 110

Gly Gly Gly Ser Gly Gly Gly Ser Gly Gly Gly Ser Asn Ala
        115                 120                 125

Gly Val Thr Gln Thr Pro Lys Phe Gln Val Leu Lys Thr Gly Gln Ser
    130                 135                 140

Met Thr Leu Gln Cys Ala Gln Asp Met Asn His Glu Tyr Met Ser Trp
145                 150                 155                 160

Tyr Arg Gln Asp Pro Gly Met Gly Leu Arg Leu Ile His Tyr Ser Val
                165                 170                 175

Gly Ala Gly Ile Thr Asp Gln Gly Glu Val Pro Asn Gly Tyr Asn Val
            180                 185                 190

Ser Arg Ser Thr Thr Glu Asp Phe Pro Leu Arg Leu Leu Ser Ala Ala
        195                 200                 205

Pro Ser Gln Thr Ser Val Tyr Phe Cys Ala Ser Arg Pro Gly Leu Ala
    210                 215                 220

Gly Gly Arg Pro Glu Gln Tyr Phe Gly Pro Gly Thr Arg Leu Thr Val
225                 230                 235                 240

Thr Glu Asp Leu Lys Asn Val Phe Pro Pro Glu Val Ala Val Phe Glu
                245                 250                 255

Pro Ser Glu Ala Glu Ile Ser His Thr Gln Lys Ala Thr Leu Val Cys
            260                 265                 270

Leu Ala Thr Gly Phe Tyr Pro Asp His Val Glu Leu Ser Trp Trp Val
        275                 280                 285

Asn Gly Lys Glu Val His Ser Gly Val Ser Thr Asp Pro Gln Pro Leu
    290                 295                 300

Lys Glu Gln Pro Ala Leu Asn Asp Ser Arg Tyr Ala Leu Ser Ser Arg
```

```
                305                 310                 315                 320
Leu Arg Val Ser Ala Thr Phe Trp Gln Asp Pro Arg Asn His Phe Arg
                    325                 330                 335

Cys Gln Val Gln Phe Tyr Gly Leu Ser Glu Asn Asp Glu Trp Thr Gln
                    340                 345                 350

Asp Arg Ala Lys Pro Val Thr Gln Ile Val Ser Ala Glu Ala Trp Gly
                    355                 360                 365

Arg Ala Asp Gly Gly Gly Ser Leu Ser Ser Thr Leu Thr Leu Ser
        370                 375                 380

Lys Ala Asp Tyr Glu Lys His Lys Val Tyr Ala Cys Glu Val Thr His
385                 390                 395                 400

Gln Gly Leu Ser Ser Pro Val Thr Lys Ser Phe Asn Arg Gly Glu Ser
                    405                 410                 415

<210> SEQ ID NO 154
<211> LENGTH: 2699
<212> TYPE: DNA
<213> ORGANISM: Artificial sequence
<220> FEATURE:
<223> OTHER INFORMATION: pUC19-T7 vector

<400> SEQUENCE: 154
ctgctttccc ggagcactat gcggataaaa atatccaatt acagtactat tattaccaaa      60
gaatctgcag tccaccgtga aaagcccctt tacacgcgcc ttggggataa acaaataaaa     120
agatttatgt aagtttatac ataggcgagt actctgttat tgggactatt tacgaagtta     180
ttataacttt ttccttctca tactcataag ttgtaaaggc acagcgggaa taagggaaaa     240
aacgccgtaa aacggaagga caaaaacgag tgggtctttg cgaccacttt cattttctac     300
gacttctagt caacccacgt gctcacccaa tgtagcttga cctagagttg tcgccattct     360
aggaactctc aaaagcgggg cttcttgcaa aaggttacta ctcgtgaaaa tttcaagacg     420
atacaccgcg ccataatagg cataactgc ggcccgttct cgttgagcca gcggcgtatg      480
tgataagagt cttactgaac caactcatga gtggtcagtg tcttttcgta gaatgcctac     540
cgtactgtca ttctcttaat acgtcacgac ggtattggta ctcactattg tgacgccggt     600
tgaatgaaga ctgttgctag cctcctggct tcctcgattg gcgaaaaaac gtgttgtacc     660
ccctagtaca ttgagcggaa ctagcaaccc ttggcctcga cttacttcgg tatggttttgc    720 tgctcgcact gtggtgctac ggacatcgtt accgttgttg caacgcgttt gataattgac     780
cgcttgatga atgagatcga agggccgttg ttaattatct gacctacctc cgcctatttc     840
aacgtcctgg tgaagacgcg agccgggaag gccgaccgac caaataacga ctatttagac     900
ctcggccact cgcacccaga gcgccatagt aacgtcgtga ccccggtcta ccattcggga     960
gggcatagca tcaatagatg tgctgccct cagtccgttg atacctactt gctttatctg     1020
tctagcgact ctatccacgg agtgactaat tcgtaaccat tgacagtctg gttcaaatga     1080
gtatatatga aatctaacta aattttgaag taaaaattaa attttcctag atccacttct    1140
aggaaaaact attagagtac tggttttagg gaattgcact caaaagcaag gtgactcgca    1200 gtctgggggca tcttttctag tttcctagaa gaactctagg aaaaaagac gcgcattaga   1260 cgacgaacgt ttgttttttt ggtggcgatg gtcgccacca aacaaacggc ctagttctcg     1320
atggttgaga aaaaggcttc cattgaccga agtcgtctcg cgtctatggt ttatgacagg    1380
aagatcacat cggcatcaat ccggtggtga agttcttgag acatcgtggc ggatgtatgg    1440
agcgagacga ttaggacaat ggtcaccgac gacggtcacc gctattcagc acagaatggc   1500
```

```
ccaacctgag ttctgctatc aatggcctat tccgcgtcgc cagcccgact tgccccccaa    1560
gcacgtgtgt cgggtcgaac ctcgcttgct ggatgtggct tgactctatg gatgtcgcac    1620
tcgatactct ttcgcggtgc gaagggcttc cctctttccg cctgtccata ggccattcgc    1680
cgtcccagcc ttgtcctctc gcgtgctccc tcgaaggtcc ccctttgcgg accatagaaa    1740
tatcaggaca gcccaaagcg gtggagactg aactcgcagc taaaaacact acgagcagtc    1800
cccccgcctc ggatacccttt tgcggtcgt tgcgccggaa aaatgccaag gaccggaaaa    1860
cgaccggaaa acgagtgtac aagaaaggac gcaatagggg actaagacac ctattggcat    1920
aatggcggaa actcactcga ctatggcgag cggcgtcggc ttgctggctc gcgtcgctca    1980
gtcactcgct ccttcgcctt ctcgcgggtt atgcgtttgg cggagagggg cgcgcaaccg    2040
gctaagtaat tacgtcgacc gtgctgtcca aagggctgac cttttcgcccg tcactcgcgt    2100 tgcgttaatt acactcaatc gagtgagtaa tccgtggggt ccgaaatgtg aaatacgaag    2160
gccgagcata caacacacct taacactcgc ctattgttaa agtgtgtcct ttgtcgatac    2220
tggtactaat gcggttcgac gtcgattatg ctgagtgata tccttgtccg gtggtaccct    2280
aggggcccat ggctcgagct taagtgaccg gcagcaaaat gttgcagcac tgacccttttt    2340 gggaccgcaa tgggttgaat tagcggaacg tcgtgtaggg ggaaagcggt cgaccgcatt    2400
atcgcttctc cgggcgtggc tagcgggaag ggttgtcaac gcgtcggact taccgcttac    2460
cgcggactac gccataaaag aggaatgcgt agacacgcca taaagtgtgg cgtataccac    2520
gtgagagtca tgttagacga gactacgcgc tatcaattcg gtcggggctg tgggcggttg    2580
tgggcgactg cgcgggactg cccgaacaga cgagggccgt aggcgaatgt ctgttcgaca    2640
ctggcagagg ccctcgacgt acacagtctc caaaagtggc agtagtggct ttgcgcgct    2699

<210> SEQ ID NO 155
<211> LENGTH: 1262
<212> TYPE: DNA
<213> ORGANISM: Artificial sequence
<220> FEATURE:
<223> OTHER INFORMATION: scA6 TCR-C-Kappa construct

<400> SEQUENCE: 155
ccatgggcca gaaggaagtg gagcagaact ctggaccccct cagtgttcca gagggagcca     60
ttgcctctct caactgcact tacagtgacc gaggttccca gtccttcttc tggtacagac    120
aatattctgg gaaagcccct gagttgataa tgtccatata ctccaatggt gacaaagaag    180
atggaaggtt tacagcacag ctcaataaag ccagccagta tgtttctctg ctcatcagag    240
actcccagcc cagtgattca gccacctacc tctgtgccgt tacaactgac agctggggga    300
aattgcagtt tggagcaggg acccaggttg tggtcaccgg tggaggcggt tcaggcggag    360
gtggatccgg cggtggcggg tcgaacgctg gtgtcactca gacccccaaaa ttccaggtcc    420 tgaagacagg acagagcatg acactgcagt gtgcccagga tatgaaccat gaatacatgt    480
cctggtatcg acaagaccca ggcatgggc tgaggctgat tcattactca gttggtgctg    540
gtatcactga ccaaggagaa gtccccaatg gctacaatgt ctccagatca accacagagg    600
atttcccgct caggctgctg tcggctgctc cctcccagac atctgtgtac ttctgtgcca    660
gcaggccggg actagcggga gggcgaccag agcagtactt cgggccgggc accaggctca    720
cggtcacaga ggacctgaaa aacgtgttcc cacccgaggt cgctgtgttt gagccatcag    780
aagcagagat ctcccacacc caaaaggcca cactggtgtg cctggccaca ggcttctacc    840
```

```
ccgaccacgt ggagctgagc tggtgggtga atgggaagga ggtgcacagt ggggtcagca    900
cagacccgca gcccctcaag gagcagcccg ccctcaatga ctccagatac gctctgagca    960
gccgcctgag ggtctcggcc accttctggc aggaccccg caaccacttc cgctgtcaag    1020
tccagttcta cgggctctcg gagaatgacg agtggaccca gatagggcc aaacccgtca    1080 cccagatcgt cagcgccgag gctggggta gagcagacgg tggaggcggt tcactcagca    1140
gcaccctgac gctgagcaaa gcagactacg agaaacacaa agtctacgcc tgcgaagtca    1200
cccatcaggg cctgagttcg cccgtcacaa agagcttcaa ccgcggagag tcataagaat    1260
tc                                                                   1262
```

<210> SEQ ID NO 156
<211> LENGTH: 732
<212> TYPE: DNA
<213> ORGANISM: Homo sapiens

<400> SEQUENCE: 156

```
gctggtgtca ctcagacccc aaaattccag gtcctgaaga caggacagag catgacactg     60
cagtgtgccc aggatatgaa ccatgaatac atgtcctggt atcgacaaga cccaggcatg    120
gggctgaggc tgattcatta ctcagttggt gctggtatca ctgaccaagg agaagtcccc    180
aatggctaca atgtctccag atcaaccaca gaggatttcc cgctcaggct gctgtcggct    240
gctccctccc agacatctgt gtacttctgt gccagcaggc cgggactagc gggagggtga    300
ccagagcagt acttcgggcc gggcaccagg ctcacggtca cagaggacct gaaaaacgtg    360
ttcccacccg aggtcgctgt gtttgagcca tcagaagcag agatctccca cacccaaaag    420
gccacactgg tgtgcctggc cacaggcttc taccccgacc acgtggagct gagctggtgg    480
gtgaatggga aggaggtgca cagtggggtc tgcacagacc cgcagcccct caaggagcag    540
cccgccctca atgactccag atacgctctg agcagccgcc tgagggtctc ggccaccttc    600
tggcaggacc ccgcaaccac ttccgctgt caagtccagt tctacgggct ctcggagaat    660
gacgagtgga cccaggatag ggccaaaccc gtcacccaga tcgtcagcgc cgaggcctgg    720
ggtagagcag ac                                                        732
```

<210> SEQ ID NO 157
<211> LENGTH: 244
<212> TYPE: PRT
<213> ORGANISM: Homo sapiens
<220> FEATURE:
<221> NAME/KEY: MISC_FEATURE
<222> LOCATION: (100)..(100)
<223> OTHER INFORMATION: Xaa is an amino acid residue encoded by an opal codon

<400> SEQUENCE: 157

```
Ala Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Ile Thr Asp Gln Gly Glu Val Pro Asn Gly Tyr Asn
    50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Arg Pro Gly Leu
```

```
                    85                  90                  95
Ala Gly Gly Xaa Pro Glu Gln Tyr Phe Gly Pro Gly Thr Arg Leu Thr
                100                 105                 110

Val Thr Glu Asp Leu Lys Asn Val Phe Pro Pro Glu Val Ala Val Phe
            115                 120                 125

Glu Pro Ser Glu Ala Glu Ile Ser His Thr Gln Lys Ala Thr Leu Val
130                 135                 140

Cys Leu Ala Thr Gly Phe Tyr Pro Asp His Val Glu Leu Ser Trp Trp
145                 150                 155                 160

Val Asn Gly Lys Glu Val His Ser Gly Val Cys Thr Asp Pro Gln Pro
                165                 170                 175

Leu Lys Glu Gln Pro Ala Leu Asn Asp Ser Arg Tyr Ala Leu Ser Ser
            180                 185                 190

Arg Leu Arg Val Ser Ala Thr Phe Trp Gln Asp Pro Arg Asn His Phe
        195                 200                 205

Arg Cys Gln Val Gln Phe Tyr Gly Leu Ser Glu Asn Asp Glu Trp Thr
    210                 215                 220

Gln Asp Arg Ala Lys Pro Val Thr Gln Ile Val Ser Ala Glu Ala Trp
225                 230                 235                 240

Gly Arg Ala Asp
```

```
<210> SEQ ID NO 158
<211> LENGTH: 732
<212> TYPE: DNA
<213> ORGANISM: Homo sapiens

<400> SEQUENCE: 158
gctggtgtca ctcagacccc aaaattccag gtcctgaaga caggacagag catgacactg      60
tagtgtgccc aggatatgaa ccatgaatac atgtcctggt atcgacaaga cccaggcatg     120
gggctgaggc tgattcatta ctcagttggt gctggtatca ctgaccaagg agaagtcccc     180
aatggctaca atgtctccag atcaaccaca gaggatttcc cgctcaggct gctgtcggct     240
gctccctccc agacatctgt gtacttctgt gccagcaggc cgggactagc gggagggcga     300
ccagagcagt acttcgggcc gggcaccagg ctcacggtca cagaggacct gaaaaacgtg     360
ttcccacccg aggtcgctgt gtttgagcca tcagaagcag agatctccca cacccaaaag     420
gccacactgg tgtgcctggc cacaggcttc taccccgacc acgtggagct gagctggtgg     480
gtgaatggga aggaggtgca cagtggggtc tgcacagacc cgcagcccct caaggagcag     540
cccgccctca tgactccaga tacgctctg agcagccgcc tgagggtctc ggccaccttc     600
tggcaggacc ccgcaacca cttccgctgt caagtccagt tctacgggct ctcggagaat     660
gacgagtgga cccaggatag gccaaaccc gtcacccaga tcgtcagcgc cgaggcctgg     720
ggtagagcag ac                                                         732

<210> SEQ ID NO 159
<211> LENGTH: 745
<212> TYPE: DNA
<213> ORGANISM: Homo sapiens

<400> SEQUENCE: 159
gctggtgtca ctcagacccc aaaattccag gtcctgaaga caggacagag catgacactg      60
cagtgtgccc aggatatgaa ccatgaatac atgtcctggt atcgacaaga cccaggcatg     120
gggctgaggc tgattcatta ctcagttggt gctggtatca ctgaccaagg agaagtcccc     180
```

-continued

```
aatggctaca atgtctccag atcaaccaca gaggatttcc cgctcaggct gctgtcggct    240
gctccctccc agacatctgt gtacttctgt gcctcgaggc cggggctgat gagtgcggaa    300
ccagagcagt acttcgggcc gggcaccagg ctcacggtca cagaggacct gaaaaacgtg    360
ttcccacccg aggtcgctgt gtttgagcca tcagaagcag agatctccca cacccaaaag    420
gccacactgg tgtgcctggc caccggtttc taccccgacc acgtggagct gagctggtgg    480
gtgaatggga aggaggtgca cagtggggtc tgcacagacc cgcagcccct caaggagcag    540
cccgccctca tgactccag atacgctctg agcagccgcc tgagggtctc ggccaccttc    600
tggcaggacc cccgcaacca cttccgctgt caagtccagt tctacgggct ctcggagaat    660
gacgagtgga cccaggatag gccaaaccc gtcacccaga tcgtcagcgc cgaggcctgg    720
ggtagagcag actaagcttg aattc                                         745
```

<210> SEQ ID NO 160
<211> LENGTH: 246
<212> TYPE: PRT
<213> ORGANISM: Homo sapiens

<400> SEQUENCE: 160

```
Met Asn Ala Gly Val Thr Gln Thr Pro Lys Phe Gln Val Leu Lys Thr
1               5                   10                  15
Gly Gln Ser Met Thr Leu Gln Cys Ala Gln Asp Met Asn His Glu Tyr
            20                  25                  30
Met Ser Trp Tyr Arg Gln Asp Pro Gly Met Gly Leu Arg Leu Ile His
        35                  40                  45
Tyr Ser Val Gly Ala Gly Ile Thr Asp Gln Gly Glu Val Pro Asn Gly
    50                  55                  60
Tyr Asn Val Ser Arg Ser Thr Thr Glu Asp Phe Pro Leu Arg Leu Leu
65                  70                  75                  80
Ser Ala Ala Pro Ser Gln Thr Ser Val Tyr Phe Cys Ala Ser Arg Pro
                85                  90                  95
Gly Leu Met Ser Ala Glu Pro Glu Gln Tyr Phe Gly Pro Gly Thr Arg
            100                 105                 110
Leu Thr Val Thr Glu Asp Leu Lys Asn Val Phe Pro Pro Glu Val Ala
        115                 120                 125
Val Phe Glu Pro Ser Glu Ala Glu Ile Ser His Thr Gln Lys Ala Thr
    130                 135                 140
Leu Val Cys Leu Ala Thr Gly Phe Tyr Pro Asp His Val Glu Leu Ser
145                 150                 155                 160
Trp Trp Val Asn Gly Lys Glu Val His Ser Gly Val Cys Thr Asp Pro
                165                 170                 175
Gln Pro Leu Lys Glu Gln Pro Ala Leu Asn Asp Ser Arg Tyr Ala Leu
            180                 185                 190
Ser Ser Arg Leu Arg Val Ser Ala Thr Phe Trp Gln Asp Pro Arg Asn
        195                 200                 205
His Phe Arg Cys Gln Val Gln Phe Tyr Gly Leu Ser Glu Asn Asp Glu
    210                 215                 220
Trp Thr Gln Asp Arg Ala Lys Pro Val Thr Gln Ile Val Ser Ala Glu
225                 230                 235                 240
Ala Trp Gly Arg Ala Asp
                245
```

<210> SEQ ID NO 161
<211> LENGTH: 244

<212> TYPE: PRT
<213> ORGANISM: Homo sapiens

<400> SEQUENCE: 161

```
Ala Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Ile Thr Asp Gln Gly Glu Val Pro Asn Gly Tyr Asn
    50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Arg Pro Gly Leu
                85                  90                  95

Met Ser Ala Gln Pro Glu Gln Tyr Phe Gly Pro Gly Thr Arg Leu Thr
            100                 105                 110

Val Thr Glu Asp Leu Lys Asn Val Phe Pro Pro Glu Val Ala Val Phe
        115                 120                 125

Glu Pro Ser Glu Ala Glu Ile Ser His Thr Gln Lys Ala Thr Leu Val
    130                 135                 140

Cys Leu Ala Thr Gly Phe Tyr Pro Asp His Val Glu Leu Ser Trp Trp
145                 150                 155                 160

Val Asn Gly Lys Glu Val His Ser Gly Val Cys Thr Asp Pro Gln Pro
                165                 170                 175

Leu Lys Glu Gln Pro Ala Leu Asn Asp Ser Arg Tyr Ala Leu Ser Ser
            180                 185                 190

Arg Leu Arg Val Ser Ala Thr Phe Trp Gln Asp Pro Arg Asn His Phe
        195                 200                 205

Arg Cys Gln Val Gln Phe Tyr Gly Leu Ser Glu Asn Asp Glu Trp Thr
    210                 215                 220

Gln Asp Arg Ala Lys Pro Val Thr Gln Ile Val Ser Ala Glu Ala Trp
225                 230                 235                 240

Gly Arg Ala Asp
```

<210> SEQ ID NO 162
<211> LENGTH: 627
<212> TYPE: DNA
<213> ORGANISM: Homo sapiens

<400> SEQUENCE: 162

| | | | | | |
|---|---|---|---|---|---|
| atgcaggagg | tgacacagat | tcctgcagct | ctgagtgtcc | cagaaggaga | aaacttggtt | 60 |
| ctcaactgca | gtttcactga | tagcgctatt | tacaacctcc | agtggtttag | gcaggaccct | 120 |
| gggaaaggtc | tcacatctct | gttgcttatt | cagtcaagtc | agagagagca | aacaagtgga | 180 |
| agacttaatg | cctcgctgga | taaatcatca | ggacgtagta | ctttatacat | tgcagcttct | 240 |
| cagcctggtg | actcagccac | ctacctctgt | gctgtgaggc | cacatcagg | aggaagctac | 300 |
| atacctacat | ttggaagagg | aaccagcctt | attgttcatc | cgtatatcca | gaaccctgac | 360 |
| cctgccgtgt | accagctgag | agactctaaa | tccagtgaca | agtctgtctg | cctattcacc | 420 |
| gattttgatt | ctcaaacaaa | tgtgtcacaa | agtaaggatt | ctgatgtgta | tatcacagac | 480 |
| aaatgtgtgc | tagacatgag | gtctatggac | ttcaagagca | cagtgctgt | ggcctggagc | 540 |
| aacaaatctg | actttgcatg | tgcaaacgcc | ttcaacaaca | gcattattcc | agaagacacc | 600 |

```
ttcttcccca gcccagaaag ttcctaa                                          627
```

<210> SEQ ID NO 163
<211> LENGTH: 729
<212> TYPE: DNA
<213> ORGANISM: Homo sapiens

<400> SEQUENCE: 163

```
atgggtgtca ctcagacccc aaaattccag gtcctgaaga caggacagag catgacactg      60
cagtgtgccc aggatatgaa ccatgaatac atgtcctggt atcgacaaga cccaggcatg     120
gggctgaggc tgattcatta ctcagttggt gctggtatca ctgaccaagg agaagtcccc     180
aatggctaca atgtctccag atcaaccaca gaggatttcc cgctcaggct gctgtcggct     240
gctccctccc agacatctgt gtacttctgt gccagcagtt acgtcgggaa caccggggag     300
ctgttttttg gagaaggctc taggctgacc gtactggagg acctgaaaaa cgtgttccca     360
cccgaggtcg ctgtgtttga gccatcagaa gcagagatct cccacaccca aaaggccaca     420
ctggtgtgcc tggccacagg cttctacccc gaccacgtgg agctgagctg gtgggtgaat     480
gggaaggagg tgcacagtgg ggtctgcaca gacccgcagc ccctcaagga gcagcccgcc     540
ctcaatgact ccagatacgc tctgagcagc cgcctgaggg tctcggccac cttctggcag     600
gaccccgcga accacttccg ctgtcaagtc cagttctacg ggctctcgga gaatgacgag     660
tggacccagg ataggggccaa acccgtcacc cagatcgtca gcgccgaggc ctggggtaga     720
gcagactaa                                                             729
```

<210> SEQ ID NO 164
<211> LENGTH: 208
<212> TYPE: PRT
<213> ORGANISM: Homo sapiens

<400> SEQUENCE: 164

```
Met Gln Glu Val Thr Gln Ile Pro Ala Ala Leu Ser Val Pro Glu Gly
  1               5                  10                  15

Glu Asn Leu Val Leu Asn Cys Ser Phe Thr Asp Ser Ala Ile Tyr Asn
             20                  25                  30

Leu Gln Trp Phe Arg Gln Asp Pro Gly Lys Gly Leu Thr Ser Leu Leu
         35                  40                  45

Leu Ile Gln Ser Ser Gln Arg Glu Gln Thr Ser Gly Arg Leu Asn Ala
     50                  55                  60

Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Thr Ser
                 85                  90                  95

Gly Gly Ser Tyr Ile Pro Thr Phe Gly Arg Gly Thr Ser Leu Ile Val
                100                 105                 110

His Pro Tyr Ile Gln Asn Pro Asp Pro Ala Val Tyr Gln Leu Arg Asp
            115                 120                 125

Ser Lys Ser Ser Asp Lys Ser Val Cys Leu Phe Thr Asp Phe Asp Ser
        130                 135                 140

Gln Thr Asn Val Ser Gln Ser Lys Asp Ser Asp Val Tyr Ile Thr Asp
145                 150                 155                 160

Lys Cys Val Leu Asp Met Arg Ser Met Asp Phe Lys Ser Asn Ser Ala
                165                 170                 175

Val Ala Trp Ser Asn Lys Ser Asp Phe Ala Cys Ala Asn Ala Phe Asn
```

```
                    180                 185                 190
Asn Ser Ile Ile Pro Glu Asp Thr Phe Phe Pro Ser Pro Glu Ser Ser
            195                 200                 205

<210> SEQ ID NO 165
<211> LENGTH: 242
<212> TYPE: PRT
<213> ORGANISM: Homo sapiens

<400> SEQUENCE: 165

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Ile Thr Asp Gln Gly Glu Val Pro Asn Gly Tyr Asn
    50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Tyr Val Gly
                85                  90                  95

Asn Thr Gly Glu Leu Phe Phe Gly Glu Gly Ser Arg Leu Thr Val Leu
            100                 105                 110

Glu Asp Leu Lys Asn Val Phe Pro Pro Glu Val Ala Val Phe Glu Pro
        115                 120                 125

Ser Glu Ala Glu Ile Ser His Thr Gln Lys Ala Thr Leu Val Cys Leu
    130                 135                 140

Ala Thr Gly Phe Tyr Pro Asp His Val Glu Leu Ser Trp Trp Val Asn
145                 150                 155                 160

Gly Lys Glu Val His Ser Gly Val Cys Thr Asp Pro Gln Pro Leu Lys
                165                 170                 175

Glu Gln Pro Ala Leu Asn Asp Ser Arg Tyr Ala Leu Ser Ser Arg Leu
            180                 185                 190

Arg Val Ser Ala Thr Phe Trp Gln Asp Pro Arg Asn His Phe Arg Cys
        195                 200                 205

Gln Val Gln Phe Tyr Gly Leu Ser Glu Asn Asp Glu Trp Thr Gln Asp
    210                 215                 220

Arg Ala Lys Pro Val Thr Gln Ile Val Ser Ala Glu Ala Trp Gly Arg
225                 230                 235                 240

Ala Asp

<210> SEQ ID NO 166
<211> LENGTH: 3466
<212> TYPE: DNA
<213> ORGANISM: Artificial sequence
<220> FEATURE:
<223> OTHER INFORMATION: pEX746:NY-ESO phagemid

<400> SEQUENCE: 166
ttcctggcct tttgctggcc ttttgctcac atgtaatgtg agttagctca aaggaccgga      60
aaacgaccgg aaaacgagtg tacattacac tcaatcgagt ctcattaggc accccaggct     120
ttacacttta tgcttccggc tcgtatgttg gagtaatccg tggggtccga aatgtgaaat     180
acgaaggccg agcatacaac tgtggaattg tgagcggata caatttcac acaggaaaca      240 gctatgacca acaccttaac actcgcctat tgttaaagtg tgtcctttgt cgatactggt     300
```

```
tgattacgcc aagctacgta cttaagtatt ctatttcaag gagacagtca actaatgcgg    360
ttcgatgcat gaattcataa gataaagttc ctctgtcagt taatgaaata cctattgcct    420
acggcagccg ctggattgtt attactcgcg attactttat ggataacgga tgccgtcggc    480
gacctaacaa taatgagcgc gcccagccgg ccatggccaa acaggaggtg acgcagattc    540
ctgcagctct cgggtcggcc ggtaccggtt tgtcctccac tgcgtctaag gacgtcgaga    600
gagtgtccca gaaggagaaa acttggttct caactgcagt tcactgata ctcacagggt     660 cttcctcttt tgaaccaaga gttgacgtca aagtgactat gcgctattta caacctccag    720
tggtttaggc aggaccctgg gaaaggtctc cgcgataaat gttggaggtc accaaatccg    780
tcctgggacc ctttccagag acatctctgt tgcttattca gtcaagtcag agagagcaaa    840
caagtggaag tgtagagaca acgaataagt cagttcagtc tctctcgttt gttccccttc    900
acttaatgcc tcgctggata aatcatcagg acgtagtact ttatacattg tgaattacgg    960
agcgacctat ttagtagtcc tgcatcatga aatatgtaac cagcttctca gcctggtgac    1020
tcagccacct acctctgtgc tgtgaggccc gtcgaagagt cggaccactg agtcggtgga    1080
tggagacacg acactccggg acatcaggag gaagctacat acctacattt ggaagaggaa    1140
ccagccttat tgtagtcctc cttcgatgta tggatgtaaa ccttctcctt ggtcggaata    1200
tgttcatccg tatatccaga acccggatcc tgccgtgtac cagctgagag acaagtaggc    1260
atataggtct tgggcctagg acggcacatg gtcgactctc actctaaatc cagtgacaag    1320
tctgtctgcc tattcaccga ttttgattct tgagatttag gtcactgttc agacagacgg    1380
ataagtggct aaaactaaga caaacaaatg tgtcacaaag taaggattct gatgtgtata    1440
tcacagacaa gtttgtttac acagtgtttc attcctaaga ctacacatat agtgtctgtt    1500
atgtgtgcta gacatgaggt ctatggactt caagagcaac agtgctgtgg tacacacgat    1560
ctgtactcca gatacctgaa gttctcgttg tcacgacacc cctggagcaa caaatctgac    1620
tttgcatgtg caaacgcctt caacaacagc ggaccctcgt gtttagactg aaacgtacac    1680
gtttgcggaa gttgttgtcg attattccag aagacacctt cttccccagc ccagaaagtt    1740
cctaataacc taataaggtc ttctgtggaa gaagggggtcg ggtctttcaa ggattattgg    1800
taggttaatt aagaattctt taagaagggg atatacatat gaaaaaatta atccaattaa    1860
ttcttaagaa attcttcccc tatatgtata cttttttaat ttattcgcaa ttccttagt     1920 tgttcctttc tattctcaca gcgcgcaggc aataagcgtt aaggaaatca acaaggaaag    1980
ataagagtgt cgcgcgtccg tggtgtcact cagaccccaa aattccaggt cctgaagaca    2040
ggacagagca accacagtga gtctggggtt ttaaggtcca ggacttctgt cctgtctcgt    2100
tgacactgca gtgtgcccag gatatgaacc atgaatacat gtcctggtat actgtgacgt    2160
cacacgggtc ctatacttgg tacttatgta caggaccata cgacaagacc caggcatggg    2220
gctgaggctg attcattact cagttggtgc gctgttctgg gtccgtaccc cgactccgac    2280
taagtaatga gtcaaccacg tggtatcact gaccaaggag aagtccccaa tggctacaat    2340
gtctccagat accatagtga ctggttcctc ttcaggggtt accgatgtta cagaggtcta    2400
caaccacaga ggatttcccg ctcaggctgc tgtcggctgc tccctcccag gttggtgtct    2460
cctaaagggc gagtccgacg acagccgacg agggagggtc acatctgtgt acttctgtgc    2520
cagcagttac gtcgggaaca ccggggagct tgtagacaca tgaagacacg gtcgtcaatg    2580
cagcccttgt ggcccctcga gttttttgga gaaggctcta ggctgaccgt actggaggac    2640
```

```
ctgaaaaacg caaaaaacct cttccgagat ccgactggca tgacctcctg gacttttgc    2700 tgttcccacc cgaggtcgct gtgtttgagc catcagaagc agagatctcc acaagggtgg    2760
gctccagcga cacaaactcg gtagtcttcg tctctagagg cacacccaaa aggccacact    2820
ggtgtgcctg gccacaggct tctaccccga gtgtgggttt tccggtgtga ccacacggac    2880
cggtgtccga agatggggct ccacgtggag ctgagctggt gggtgaatgg aaggaggtg    2940 cacagtgggg ggtgcacctc gactcgacca cccacttacc cttcctccac gtgtcacccc    3000
tctgcacaga cccgcagccc ctcaaggagc agcccgccct caatgactcc agacgtgtct    3060
gggcgtcggg gagttcctcg tcgggcggga gttactgagg agatacgctc tgagcagccg    3120
cctgagggtc tcggccacct tctggcagga tctatgcgag actcgtcggc ggactcccag    3180
agccggtgga agaccgtcct cccccgcaac cacttccgct gtcaagtcca gttctacggg    3240
ctctcggaga gggggcgttg gtgaaggcga cagttcaggt caagatgccc gagagcctct    3300
atgacgagtg gacccaggat agggccaaac ccgtcaccca gatcgtcagc tactgctcac    3360
ctgggtccta tcccggtttg ggcagtgggt ctagcagtcg gccgaggcct ggggtagagc    3420
agacgcggcc gcacggctcc ggaccccatc tcgtctgcgc cggcgt             3466
```

<210> SEQ ID NO 167
<211> LENGTH: 494
<212> TYPE: PRT
<213> ORGANISM: Artificial sequence
<220> FEATURE:
<223> OTHER INFORMATION: amino acid sequence encoded by pEX746:NY-ESO

<400> SEQUENCE: 167

```
Lys Tyr Leu Leu Pro Thr Ala Ala Gly Leu Leu Leu Leu Ala Ala
1               5                   10                  15

Gln Pro Ala Met Ala Lys Gln Glu Val Thr Gln Ile Pro Ala Ala Leu
            20                  25                  30

Ser Val Pro Glu Gly Glu Asn Leu Val Leu Asn Cys Ser Phe Thr Asp
        35                  40                  45

Ser Ala Ile Tyr Asn Leu Gln Trp Phe Arg Gln Asp Pro Gly Lys Gly
    50                  55                  60

Leu Thr Ser Leu Leu Leu Ile Gln Ser Ser Gln Arg Glu Gln Thr Ser
65                  70                  75                  80

Gly Arg Leu Asn Ala Ser Leu Asp Lys Ser Ser Gly Arg Ser Thr Leu
                85                  90                  95

Tyr Ile Ala Ala Ser Gln Pro Gly Asp Ser Ala Thr Tyr Leu Cys Ala
            100                 105                 110

Val Arg Pro Thr Ser Gly Gly Ser Tyr Ile Pro Thr Phe Gly Arg Gly
        115                 120                 125

Thr Ser Leu Ile Val His Pro Tyr Ile Gln Asn Pro Asp Pro Ala Val
    130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Cys Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
    210                 215                 220
```

-continued

Ser Pro Glu Ser Ser Met Lys Lys Leu Leu Phe Ala Ile Pro Leu Val
225                 230                 235                 240

Val Pro Phe Tyr Ser His Ser Ala Gln Ala Gly Val Thr Gln Thr Pro
            245                 250                 255

Lys Phe Gln Val Leu Lys Thr Gly Gln Ser Met Thr Leu Gln Cys Ala
        260                 265                 270

Gln Asp Met Asn His Glu Tyr Met Ser Trp Tyr Arg Gln Asp Pro Gly
    275                 280                 285

Met Gly Leu Arg Leu Ile His Tyr Ser Val Gly Ala Gly Ile Thr Asp
290                 295                 300

Gln Gly Glu Val Pro Asn Gly Tyr Asn Val Ser Arg Ser Thr Thr Glu
305                 310                 315                 320

Asp Phe Pro Leu Arg Leu Leu Ser Ala Ala Pro Ser Gln Thr Ser Val
            325                 330                 335

Tyr Phe Cys Ala Ser Ser Tyr Val Gly Asn Thr Gly Glu Leu Phe Phe
            340                 345                 350

Gly Glu Gly Ser Arg Leu Thr Val Leu Glu Asp Leu Lys Asn Val Phe
        355                 360                 365

Pro Pro Glu Val Ala Val Phe Glu Pro Ser Glu Ala Glu Ile Ser His
    370                 375                 380

Thr Gln Lys Ala Thr Leu Val Cys Leu Ala Thr Gly Phe Tyr Pro Asp
385                 390                 395                 400

His Val Glu Leu Ser Trp Trp Val Asn Gly Lys Glu Val His Ser Gly
                405                 410                 415

Val Cys Thr Asp Pro Gln Pro Leu Lys Glu Gln Pro Ala Leu Asn Asp
            420                 425                 430

Ser Arg Tyr Ala Leu Ser Ser Arg Leu Arg Val Ser Ala Thr Phe Trp
        435                 440                 445

Gln Asp Pro Arg Asn His Phe Arg Cys Gln Val Gln Phe Tyr Gly Leu
    450                 455                 460

Ser Glu Asn Asp Glu Trp Thr Gln Asp Arg Ala Lys Pro Val Thr Gln
465                 470                 475                 480

Ile Val Ser Ala Glu Ala Trp Gly Arg Ala Asp Ala Ala Ala
                485                 490

<210> SEQ ID NO 168
<211> LENGTH: 854
<212> TYPE: DNA
<213> ORGANISM: Artificial sequence
<220> FEATURE:
<223> OTHER INFORMATION: HLA-DR1 alpha chain fused to Fos dimerisation
      sequence

<400> SEQUENCE: 168
ggatccatgg ccataagtgg agtccctgtg ctaggatttt tcatcatagc tgtgctgatg      60
agcgctcagg aatcatgggc tatcaaagaa gaacatgtga tcatccaggc cgagttctat     120
ctgaatcctg accaatcagg cgagtttatg tttgactttg atggtgatga gattttccat     180
gtggatatgg caaagaagga gacggtctgg cggcttgaag aatttggacg atttgccagc     240
tttgaggctc aaggtgcatt ggccaacata gctgtggaca agccaacct ggaaatcatg      300 acaaagcgct ccaactatac tccgatcacc aatgtacctc cagaggtaac tgtgctcacg     360
aacagccctg tggaactgag agagcccaac gtcctcatct gtttcatcga caagttcacc     420
ccaccagtgg tcaatgtcac gtggcttcga aatggaaaac tgtcaccac aggagtgtca     480

| | |
|---|---|
| gagacagtct tcctgcccag ggaagaccac cttttccgca agttccacta tctcccttc | 540 |
| ctgccctcaa ctgaggacgt ttacgactgc agggtggagc actggggctt ggatgagcct | 600 |
| cttctcaagc actgggagtt tgatgctcca agccctctcc cagagactac agagaacgtg | 660 |
| gatggggtc tgactgatac actccaagcg gagacagatc aacttgaaga caagaagtct | 720 |
| gcgttgcaga ccgagattgc caatctactg aaagagaagg aaaaactaga gttcatcctg | 780 |
| gcagcttacg gatctggtgg tggtctgaac gatattttg aagctcagaa atcgaatgg | 840 |
| catgagtagg atcc | 854 |

<210> SEQ ID NO 169
<211> LENGTH: 10096
<212> TYPE: DNA
<213> ORGANISM: Artificial sequence
<220> FEATURE:
<223> OTHER INFORMATION: pAcAB3 bi-cistronic vector

<400> SEQUENCE: 169

| | |
|---|---|
| aattctactc gtaaagcgag ttgaaggatc atatttagtt gcgtttatga gataagattg | 60 |
| aaagcacgtg taaaatgttt cccgcgcgtt ggcacaacta tttacaatgc ggccaagtta | 120 |
| taaaagattc taatctgata tgttttaaaa cacctttgcg gcccgagttg tttgcgtacg | 180 |
| tgactagcga agaagatgtg tggaccgcag aacagatagt aaaacaaaac cctagtattg | 240 |
| gagcaataat cgatttaacc aacacgtcta aatattatga tggtgtgcat tttttgcggg | 300 |
| cgggcctgtt atacaaaaaa attcaagtac ctggccagac tttgccgcct gaaagcatag | 360 |
| ttcaagaatt tattgacacg gtaaagaat ttacagaaaa gtgtcccggc atgttggtgg | 420 |
| gcgtgcactg cacacacggt attaatcgca ccggttacat ggtgtgcaga tatttaatgc | 480 |
| acaccctggg tattgcgccg caggaagcca tagatagatt cgaaaaagcc agaggtcaca | 540 |
| aaattgaaag acaaaattac gttcaagatt tattaattta attaatatta tttgcattct | 600 |
| ttaacaaata ctttatccta ttttcaaatt gttgcgcttc ttccagcgaa ccaaaactat | 660 |
| gcttcgcttg ctccgtttag cttgtagccg atcagtggcg ttgttccaat cgacggtagg | 720 |
| attaggccgg atattctcca ccacaatgtt ggcaacgttg atgttacgtt tatgcttttg | 780 |
| gttttccacg tacgtctttt ggccggtaat agccgtaaac gtagtgccgt cgcgcgtcac | 840 |
| gcacaacacc ggatgtttgc gcttgtccgc ggggtattga accgcgcgat ccgacaaatc | 900 |
| caccactttg gcaactaaat cggtgacctg cgcgtctttt ttctgcatta tttcgtcttt | 960 |
| cttttgcatg gttcctgga agccggtgta catgcggttt agatcagtca tgacgcgcgt | 1020 |
| gacctgcaaa tctttggcct cgatctgctt gtccttgatg gcaacgatgc gttcaataaa | 1080 |
| ctcttgtttt ttaacaagtt cctcggtttt ttgcgccacc accgcttgca gcgcgtttgt | 1140 |
| gtgctcggtg aatgtcgcaa tcagcttagt caccaactgt ttgctctcct cctcccgttg | 1200 |
| tttgatcgcg ggatcgtact tgccggtgca gagcacttga ggaattactt cttctaaaag | 1260 |
| ccattcttgt aattctatgg cgtaaggcaa tttggacttc ataatcagct gaatcacgcc | 1320 |
| ggatttagta atgagcactg tatgcggctg caaatacagc gggtcgcccc ttttcacgac | 1380 |
| gctgttagag gtagggcccc cattttggat ggtctgctca ataacgattt gtatttatt | 1440 |
| gtctacatga acacgtatag ctttatcaca aactgtatat tttaaactgt tagcgacgtc | 1500 |
| cttggccacg aaccggacct gttggtcgcg ctctagcacg taccgcaggt tgaacgtatc | 1560 |
| ttctccaaat ttaaattctc caattttaac gcgagccatt ttgatacacg tgtgtcgatt | 1620 |
| ttgcaacaac tattgttttt taacgcaaac taaacttatt gtggtaagca ataattaaat | 1680 |

-continued

```
atgggggaac atgcgccgct acaacactcg tcgttatgaa cgcagacggc gccggtctcg    1740
gcgcaagcgg ctaaaacgtg ttgcgcgttc aacgcggcaa acatcgcaaa agccaatagt    1800
acagttttga tttgcatatt aacggcgatt ttttaaatta tcttatttaa taaatagtta    1860
tgacgcctac aactccccgc ccgcgttgac tcgctgcacc tcgagcagtt cgttgacgcc    1920
ttcctccgtg tggccgaaca cgtcgagcgg gtggtcgatg accagcggcg tgccgcacgc    1980
gacgcacaag tatctgtaca ccgaatgatc gtcgggcgaa ggcacgtcgg cctccaagtg    2040
gcaatattgg caaattcgaa aatatataca gttgggttgt ttgcgcatat ctatcgtggc    2100
gttgggcatg tacgtccgaa cgttgatttg catgcaagcc gaaattaaat cattgcgatt    2160
agtgcgatta aaacgttgta catcctcgct tttaatcatg ccgtcgatta atcgcgcaa     2220
tcgagtcaag tgatcaaagt gtggaataat gttttctttg tattcccgag tcaagcgcag    2280
cgcgtatttt aacaaactag ccatcttgta agttagtttc atttaatgca actttatcca    2340
ataatatatt atgtatcgca cgtcaagaat taacaatgcg cccgttgtcg catctcaaca    2400
cgactatgat agagatcaaa taaagcgcga attaaatagc ttgcgacgca acgtgcacga    2460
tctgtgcacg cgttccggca cgagctttga ttgtaataag tttttacgaa gcgatgacat    2520
gacccccgta gtgacaacga tcacgcccaa aagaactgcc gactacaaaa ttaccgagta    2580
tgtcggtgac gttaaaacta ttaagccatc caatcgaccg ttagtcgaat caggaccgct    2640
ggtgcgagaa gccgcgaagt atggcgaatg catcgtataa cgtgtggagt ccgctcatta    2700
gagcgtcatg tttagacaag aaagctacat atttaattga tcccgatgat tttattgata    2760
aattgaccct aactccatac acggtattct acaatggcgg ggttttggtc aaaatttccg    2820
gactgcgatt gtacatgctg ttaacggctc cgcccactat taatgaaatt aaaaattcca    2880
attttaaaaa acgcagcaag agaaacattt gtatgaaaga atgcgtagaa ggaaagaaaa    2940
atgtcgtcga catgctgaac aacaagatta atatgcctcc gtgtataaaa aaatattga    3000
acgatttgaa agaaaacaat gtaccgcgcg gcggtatgta caggaagagg tttatactaa    3060
actgttacat tgcaaacgtg gtttcgtgtg ccaagtgtga aaaccgatgt ttaatcaagg    3120
ctctgacgca tttctacaac cacgactcca agtgtgtggg tgaagtcatg catcttttaa    3180
tcaaatccca agatgtgtat aaaccaccaa actgccaaaa aatgaaaact gtcgacaagc    3240
tctgtccgtt tgctggcaac tgcaagggtc tcaatcctat ttgtaattat tgaataataa    3300
aacaattata aatgctaaat ttgttttttta ttaacgatac aaaccaaacg caacaagaac    3360
atttgtagta ttatctataa ttgaaaacgc gtagttataa tcgctgaggt aatatttaaa    3420
atcattttca aatgattcac agttaatttg cgacaatata attttatttt cacataaact    3480
agacgccttg tcgtcttctt cttcgtattc cttctctttt tcattttttct cctcataaaa    3540
attaacatag ttattatcgt atccatatat gtatctatcg tatagagtaa attttttgtt    3600
gtcataaata tatatgtctt ttttaatggg gtgtatagta ccgctgcgca tagttttttct    3660
gtaatttaca acagtgctat tttctggtag ttcttcggag tgtgttgctt taattattaa    3720
atttatataa tcaatgaatt tgggatcgtc ggttttgtac aatatgttgc cggcatagta    3780
cgcagcttct tctagttcaa ttacaccatt ttttagcagc accggattaa cataactttc    3840
caaaatgttg tacgaaccgt taaacaaaaa cagttcacct cccttttcta tactattgtc    3900
tgcgagcagt tgtttgttgt taaaaataac agcatttgta atgagacgca caaactaata    3960
tcacaaactg gaaatgtcta tcaatatata gttgctgatg atccagcatg ataagataca    4020
```

```
ttgatgagtt tggacaaacc acaactagaa tgcagtgaaa aaaatgcttt atttgtgaaa    4080
tttgtgatgc tattgcttta tttgtaacca ttataagctg caataaacaa gttccgagtt    4140
tgtcagaaag cagaccaaac agcggttgga ataatagcga gaacagagaa atagcggcaa    4200
aaataatacc cgtatcactt tgctgatat ggttgatgtc atgtagccaa atcgggaaaa     4260
acgggaagta ggctcccatg ataaaaagt aaaagaaaaa gaataaaccg aacatccaaa     4320
agtttgtgtt ttttaaatag tacataatgg atttccttac gcgaaatacg ggcagacatg    4380
gcctgcccgg ttattattat ttttgacacc agaccaactg gtaatggtag cgaccggcgc    4440
tcagctggaa ttcagatctg tgattgtaaa taaaatgtaa tttacagtat agtattttaa    4500
ttaatataca aatgatttga taataattct tatttaacta taatatattg tgttgggttg    4560
aattaaaggt cccggcatcc tcaaatgcat aatttcatag tccccttgt tgtaagtgat     4620
gcgtatttct gaatctttgt aaaatagcac acaagactcc aacgcgtttg gcgttttatt    4680
ttcttgctcg actctagttt attaggcctc tagagatccg tatttatagg ttttttttatt   4740
acaaaactgt tacgaaaaca gtaaaatact tatttatttg cgagatggtt atcattttaa    4800
ttatctccat gatccaataa acctagaata aagggcccga cctttaattc aacccaacac    4860
aatatattat agttaaataa gaattattat caaatcattt gtatattaat taaaatacta    4920
tactgtaaat tacattttat ttacaatcac agatcccggg gatccggtta ttagtacatt    4980
tattaagcgc tagattctgt gcgttgttga tttacagaca attgttgtac gtattttaat    5040
aattcattaa atttataatc tttagggtgg tatgttagag cgaaaatcaa atgattttca    5100
gcgtctttat atctgaattt aaatattaaa tcctcaatag atttgtaaaa taggtttcga    5160
ttagtttcaa acaagggttg ttttttccgaa ccgatggctg gactatctaa tggattttcg    5220
ctcaacgcca caaaacttgc caaatcttgt agcagcaatc tagctttgtc gatattcgtt    5280
tgtgttttgt tttgtaataa aggttcgacg tcgttcaaaa tattatgcgc ttttgtatt     5340
cttttcatcac tgtcgttagt gtacaattga ctcgacgtaa acacgttaaa taaagcttgg    5400
acatatttaa catcgggcgt gttagcttta ttaggccgat tatcgtcgtc gtcccaaccc    5460
tcgtcgttag aagttgcttc cgaagacgat tttgccatag ccacacgacg cctattaatt    5520
gtgtcggcta acacgtccgc gatcaaattt gtagttgagc ttttttggaat tatttctgat   5580
tgcgggcgtt tttgggcggg tttcaatcta actgtgcccg attttaattc agacaacacg    5640
ttagaaagcg atggtgcagg cggtggtaac atttcagacg gcaaatctac taatggcggc    5700
ggtggtggag ctgatgataa atctaccatc ggtggaggcg caggcgggc tggcggcgga     5760
ggcggaggcg gaggtggtgg cggtgatgca gacggcggtt taggctcaaa tgtctcttta    5820
ggcaacacag tcggcacctc aactattgta ctggtttcgg gcgccgtttt tggtttgacc    5880
ggtctgagac gagtgcgatt tttttcgttt ctaatagctt ccaacaattg ttgtctgtcg    5940
tctaaaggtg cagcgggttg aggttccgtc ggcattggtg gagcgggcgg caattcagac    6000
atcgatggtg gtgtggtgg tggaggcgct ggaatgttag gcacgggaga aggtggtggc     6060
ggcggtgccg ccggtataat ttgttctggt ttagtttgtt cgcgcacgat tgtgggcacc    6120
ggcgcaggcg ccgctggctg cacaacggaa ggtcgtctgc ttcgaggcag cgcttggggt    6180
ggtggcaatt caatattata attggaatac aaatcgtaaa aatctgctat aagcattgta    6240
atttcgctat cgtttaccgt gccgatattt aacaaccgct caatgtaagc aattgtattg    6300
taaagagatt gtctcaagct cggatcgatc ccgcacgccg ataacaagcc ttttcatttt    6360
tactacagca ttgtagtggc gagacacttc gctgtcgtcg acgtacatgt atgctttgtt    6420
```

```
gtcaaaaacg tcgttggcaa gctttaaaat atttaaaaga acatctctgt tcagcaccac    6480
tgtgttgtcg taaatgttgt ttttgataat ttgcgcttcc gcagtatcga cacgttcaaa    6540
aaattgatgc gcatcaattt tgttgttcct attattgaat aaataagatt gtacagattc    6600
atatctacga ttcgtcatgg ccaccacaaa tgctacgctg caaacgctgg tacaatttta    6660
cgaaaactgc aaaaacgtca aaactcggta taaaataatc aacgggcgct ttggcaaaat    6720
atctatttta tcgcacaagc ccactagcaa attgtatttg cagaaaacaa tttcggcgca    6780
caattttaac gctgacgaaa taaaagttca ccagttaatg agcgaccacc caaattttat    6840
aaaaatctat tttaatcacg gttccatcaa caaccaagtg atcgtgatgg actacattga    6900
ctgtcccgat ttatttgaaa cactacaaat taaaggcgag cttcgtacc  aacttgttag    6960 caatattatt agacagctgt gtgaagcgct caacgatttg cacaagcaca atttcataca    7020
caacgacata aaactcgaaa atgtcttata tttcgaagca cttgatcgcg tgtatgtttg    7080
cgattacgga ttgtgcaaac acgaaaaactc acttagcgtg cacgacggca cgttggagta    7140
ttttagtccg gaaaaaattc gacacacaac tatgcacgtt tcgtttgact ggtacgcggc    7200
gtgttaacat acaagttgct aaccggcggc cgacacccat ttgaaaaaag cgaagacgaa    7260
atgttggact tgaatagcat gaagcgtcgt cagcaataca atgacattgg cgttttaaaa    7320
cacgttcgta acgttaacgc tcgtgacttt gtgtactgcc taacaagata caacatagat    7380
tgtagactca caaattacaa acaaattata aaacatgagt ttttgtcgta aaaatgccac    7440
ttgttttacg agtagaattc ccagcttggc actggccgtc gttttacaac gtcgtgactg    7500
ggaaaaccct ggcgttaccc aacttaatcg ccttgcagca catccccctt tcgccagctg    7560
gcgtaatagc gaagaggccc gcaccgatcg cccttcccaa cagttgcgca gcctgaatgg    7620
cgaatggcgc ctgatgcggt attttctcct tacgcatctg tgcggtattt cacaccgcat    7680
atggtgcact ctcagtacaa tctgctctga tgccgcatag ttaagccagc ccgacaccc    7740 gccaacaccc gctgacgcgc cctgacgggc ttgtctgctc ccggcatccg cttacagaca    7800
agctgtgacc gtctccggga gctgcatgtg tcagaggttt tcaccgtcat caccgaaacg    7860
cgcggacgaa agggcctcgt gatacgccta ttttataggg ttaatgtcat gataataatg    7920
gtttcttaga cgtcaggtgg cacttttcgg ggaaatgtgc gcggaacccc tatttgttta    7980
tttttctaaa tacattcaaa tatgtatccg ctcatgagac aataaccctg ataaatgctt    8040
caataatatt gaaaaaggaa gagtatgagt attcaacatt tccgtgtcgc ccttattccc    8100
ttttttgcgg cattttgcct tcctgttttt gctcacccag aaacgctggt gaaagtaaaa    8160
gatgctgaag atcagttggg tgcacgagtg ggttacatcg aactggatct caacagcggt    8220
aagatccttg agagttttcg ccccgaagaa cgttttccaa tgatgagcac ttttaaagtt    8280
ctgctatgtg gcgcggtatt atcccgtatt gacgccgggc aagagcaact cggtcgccgc    8340
atacactatt ctcagaatga cttggttgag tactcaccag tcacagaaaa gcatcttacg    8400
gatggcatga cagtaagaga attatgcagt gctgccataa ccatgagtga taacactgcg    8460
gccaacttac ttctgacaac gatcggagga ccgaaggagc taaccgcttt tttgcacaac    8520 atggggatc atgtaactcg ccttgatcgt tgggaaccgg agctgaatga agccatacca    8580
aacgacgagc gtgacaccac gatgcctgta gcaatggcaa caacgttgcg caaactatta    8640
actggcgaac tacttactct agcttcccgg caacaattaa tagactggat ggaggcggat    8700
aaagttgcag gaccacttct gcgctcggcc cttccggctg ctggtttat  tgctgataaa    8760
```

|  |  |
|---|---|
| tctggagccg gtgagcgtgg gtctcgcggt atcattgcag cactggggcc agatggtaag | 8820 |
| ccctcccgta tcgtagttat ctacacgacg gggagtcagg caactatgga tgaacgaaat | 8880 |
| agacagatcg ctgagatagg tgcctcactg attaagcatt ggtaactgtc agaccaagtt | 8940 |
| tactcatata tactttagat tgatttaaaa cttcattttt aatttaaaag gatctaggtg | 9000 |
| aagatccttt ttgataatct catgaccaaa atcccttaac gtgagttttc gttccactga | 9060 |
| gcgtcagacc ccgtagaaaa gatcaaagga tcttcttgag atcctttttt tctgcgcgta | 9120 |
| atctgctgct tgcaaacaaa aaaaccaccg ctaccagcgg tggtttgttt gccggatcaa | 9180 |
| gagctaccaa ctcttttttcc gaaggtaact ggcttcagca gagcgcagat accaaatact | 9240 |
| gtccttctag tgtagccgta gttaggccac cacttcaaga actctgtagc accgcctaca | 9300 |
| tacctcgctc tgctaatcct gttaccagtg gctgctgcca gtggcgataa gtcgtgtctt | 9360 |
| accgggttgg actcaagacg atagttaccg gataaggcgc agcggtcggg ctgaacgggg | 9420 |
| ggttcgtgca cacagcccag cttggagcga acgacctaca ccgaactgag atacctacag | 9480 |
| cgtgagcatt gagaaagcgc cacgcttccc gaagggagaa aggcggacag gtatccggta | 9540 |
| agcggcaggg tcggaacagg agagcgcacg agggagcttc cagggggaaa cgcctggtat | 9600 |
| ctttatagtc ctgtcgggtt tcgccacctc tgacttgagc gtcgattttt gtgatgctcg | 9660 |
| tcagggggc ggagcctatg gaaaaacgcc agcaacgcgg cctttttacg gttcctggcc | 9720 |
| ttttgctggc cttttgctca catgttcttt cctgcgttat cccctgattc tgtggataac | 9780 |
| cgtattaccg cctttgagtg agctgatacc gctcgccgca gccgaacgac cgagcgcagc | 9840 |
| gagtcagtga gcgaggaagc ggaagagcgc ccaatacgca aaccgcctct ccccgcgcgt | 9900 |
| tggccgattc attaatgcag ctggcacgac aggtttcccg actggaaagc gggcagtgag | 9960 |
| cgcaacgcaa ttaatgtgag ttagctcact cattaggcac cccaggcttt acactttatg | 10020 |
| cttccggctc gtatgttgtg tggaattgtg agcggataac aatttcacac aggaaacagc | 10080 |
| tatgaccatg attacg | 10096 |

<210> SEQ ID NO 170
<211> LENGTH: 941
<212> TYPE: DNA
<213> ORGANISM: Artificial sequence
<220> FEATURE:
<223> OTHER INFORMATION: peptide-HLA-DR1 fused to Jun dimersiation
      sequence

<400> SEQUENCE: 170

|  |  |
|---|---|
| ggtaccggat ccagcatggt gtgtctgaag ctccctggag gctcctgcat gacagcgctg | 60 |
| acagtgacac tgatggtgct gagctcccca ctggctttgt ccggagacac cggacctaag | 120 |
| tacgtcaagc agaacacact gaaactggct tccggtggcg gatctctagt ccacgcggt | 180 |
| agtggaggcg gtggttccgg agacacgcgt ccacgtttct tgtggcagct taagtttgaa | 240 |
| tgtcattct tcaatgggac ggagcgggtg cggttgctgg aaagatgcat ctataaccaa | 300 |
| gaggagtccg tgcgcttcga cagcgacgtg ggggagtacc gggcggtgac ggagctgggg | 360 |
| cggcctgatg ccgagtactg gaacagccag aaggacctcc tggagcagag gcgggccgcg | 420 |
| gtggacacct actgcagaca caactacggg gttggtgaga gcttcacagt gcagcggcga | 480 |
| gttgagccta aggtgactgt gtatccttca aagacccagc ccctgcagca ccacaacctc | 540 |
| ctggtctgct ctgtgagtgg tttctatcca ggcagcattg aagtcaggtg gttccggaac | 600 |
| ggccaggaag agaaggctgg ggtggtgtcc acaggcctga tccagaatgg agattggacc | 660 |

```
ttccagaccc tgqtgatgct ggaaacagtt cctcggagtg gagaggttta cacctgccaa    720
gtggagcacc caagtgtgac gagccctctc acagtggaat ggagagcacg gtctgaatct    780
gcacagagca aggtcgacgg aggcggtggg ggtagaatcg cccggctgga ggaaaaagtg    840
aaaaccttga agctcagaa  ctcggagctg gcgtccacgg ccaacatgct cagggaacag    900
gtggcacagc ttaaacagaa agtcatgaac tactaggatc c                        941
```

<210> SEQ ID NO 171
<211> LENGTH: 116
<212> TYPE: PRT
<213> ORGANISM: Homo sapiens

<400> SEQUENCE: 171

Met Asn Ala Gly Val Thr Gln Thr Pro Lys Phe Gln Val Leu Lys Thr
1               5                   10                  15

Gly Gln Ser Met Thr Leu Gln Cys Ala Gln Asp Met Asn His Glu Tyr
            20                  25                  30

Met Ser Trp Tyr Arg Gln Asp Pro Gly Met Gly Leu Arg Leu Ile His
        35                  40                  45

Tyr Ser Val Gly Ala Gly Ile Thr Asp Gln Gly Glu Val Pro Asn Gly
50                  55                  60

Tyr Asn Val Ser Arg Ser Thr Thr Glu Asp Phe Pro Leu Arg Leu Leu
65                  70                  75                  80

Ser Ala Ala Pro Ser Gln Thr Ser Val Tyr Phe Cys Ala Ser Arg Pro
                85                  90                  95

Gly Leu Ala Gly Gly Arg Pro Glu Gln Tyr Phe Gly Pro Gly Thr Arg
            100                 105                 110

Leu Thr Val Thr
            115

<210> SEQ ID NO 172
<211> LENGTH: 116
<212> TYPE: PRT
<213> ORGANISM: Homo sapiens
<220> FEATURE:
<221> NAME/KEY: MISC_FEATURE
<222> LOCATION: (102)..(102)
<223> OTHER INFORMATION: Xaa is Glu, Gln, or Arg

<400> SEQUENCE: 172

Met Asn Ala Gly Val Thr Gln Thr Pro Lys Phe Gln Val Leu Lys Thr
1               5                   10                  15

Gly Gln Ser Met Thr Leu Gln Cys Ala Gln Asp Met Asn His Glu Tyr
            20                  25                  30

Met Ser Trp Tyr Arg Gln Asp Pro Gly Met Gly Leu Arg Leu Ile His
        35                  40                  45

Tyr Ser Val Gly Ala Gly Ile Thr Asp Gln Gly Glu Val Pro Asn Gly
50                  55                  60

Tyr Asn Val Ser Arg Ser Thr Thr Glu Asp Phe Pro Leu Arg Leu Leu
65                  70                  75                  80

Ser Ala Ala Pro Ser Gln Thr Ser Val Tyr Phe Cys Ala Ser Arg Pro
                85                  90                  95

Gly Leu Met Ser Ala Xaa Pro Glu Gln Tyr Phe Gly Pro Gly Thr Arg
            100                 105                 110

Leu Thr Val Thr
            115

<210> SEQ ID NO 173
<211> LENGTH: 117
<212> TYPE: PRT
<213> ORGANISM: Homo sapiens

<400> SEQUENCE: 173

Met Asn Ala Gly Val Thr Gln Thr Pro Lys Phe Gln Val Leu Lys Thr
1               5                   10                  15

Gly Gln Ser Met Thr Leu Gln Cys Ala Gln Asp Met Asn His Glu Tyr
            20                  25                  30

Met Ser Trp Tyr Arg Gln Asp Pro Gly Met Gly Leu Arg Leu Ile His
        35                  40                  45

Tyr Ser Val Gly Ala Gly Ile Thr Asp Gln Gly Glu Val Pro Asn Gly
    50                  55                  60

Tyr Asn Val Ser Arg Ser Thr Thr Glu Asp Phe Pro Leu Arg Leu Leu
65                  70                  75                  80

Ser Ala Ala Pro Ser Gln Thr Ser Val Tyr Phe Cys Ala Ser Arg Pro
                85                  90                  95

Gly Leu Ala Gly Gly Arg Pro Glu Asp Gln Tyr Phe Gly Pro Gly Thr
            100                 105                 110

Arg Leu Thr Val Thr
        115

<210> SEQ ID NO 174
<211> LENGTH: 116
<212> TYPE: PRT
<213> ORGANISM: Homo sapiens

<400> SEQUENCE: 174

Met Asn Ala Gly Val Thr Gln Thr Pro Lys Phe Gln Val Leu Lys Thr
1               5                   10                  15

Gly Gln Ser Met Thr Leu Gln Cys Ala Gln Asp Met Asn His Glu Tyr
            20                  25                  30

Met Ser Trp Tyr Arg Gln Asp Pro Gly Met Gly Leu Arg Leu Ile His
        35                  40                  45

Tyr Ser Val Gly Ala Gly Ile Thr Asp Gln Gly Glu Val Pro Asn Gly
    50                  55                  60

Tyr Asn Val Ser Arg Ser Thr Thr Glu Asp Phe Pro Leu Arg Leu Leu
65                  70                  75                  80

Ser Ala Ala Pro Ser Gln Thr Ser Val Tyr Phe Cys Ala Ser Arg Pro
                85                  90                  95

Gly Leu Val Pro Gly Arg Pro Glu Gln Gln Phe Gly Pro Gly Thr Arg
            100                 105                 110

Leu Thr Val Thr
        115

<210> SEQ ID NO 175
<211> LENGTH: 116
<212> TYPE: PRT
<213> ORGANISM: Homo sapiens

<400> SEQUENCE: 175

Met Asn Ala Gly Val Thr Gln Thr Pro Lys Phe Gln Val Leu Lys Thr
1               5                   10                  15

Gly Gln Ser Met Thr Leu Gln Cys Ala Gln Asp Met Asn His Glu Tyr
            20                  25                  30

Met Ser Trp Tyr Arg Gln Asp Pro Gly Met Gly Leu Arg Leu Ile His
        35                  40                  45

Tyr Ser Val Gly Ala Gly Ile Thr Asp Gln Gly Glu Val Pro Asn Gly
 50                  55                  60

Tyr Asn Val Ser Arg Ser Thr Thr Glu Asp Phe Pro Leu Arg Leu Leu
 65                  70                  75                  80

Ser Ala Ala Pro Ser Gln Thr Ser Val Tyr Phe Cys Ala Ser Arg Pro
                 85                  90                  95

Gly Leu Ala Gly Gly Arg Pro His Pro Gln Phe Gly Pro Gly Thr Arg
            100                 105                 110

Leu Thr Val Thr
        115

<210> SEQ ID NO 176
<211> LENGTH: 30
<212> TYPE: PRT
<213> ORGANISM: Artificial sequence
<220> FEATURE:
<223> OTHER INFORMATION: scTCR Linker

<400> SEQUENCE: 176

Pro Gly Gly Gly Ser Gly Gly Gly Ser Gly Gly Gly Ser Gly
1               5                   10                  15

Gly Gly Gly Ser Gly Gly Gly Ser Gly Gly Gly Gly Pro
            20                  25                  30

<210> SEQ ID NO 177
<211> LENGTH: 35
<212> TYPE: PRT
<213> ORGANISM: Artificial sequence
<220> FEATURE:
<223> OTHER INFORMATION: scTCR Linker

<400> SEQUENCE: 177

Pro Gly Gly Gly Ser Gly Gly Gly Ser Gly Gly Gly Ser Gly
1               5                   10                  15

Gly Gly Ser Gly Gly Gly Ser Gly Gly Gly Ser Gly Gly
            20                  25                  30

Gly Gly Pro
        35

<210> SEQ ID NO 178
<211> LENGTH: 4
<212> TYPE: PRT
<213> ORGANISM: Homo sapiens

<400> SEQUENCE: 178

Ala Gly Gly Ala
1

<210> SEQ ID NO 179
<211> LENGTH: 4
<212> TYPE: PRT
<213> ORGANISM: Homo sapiens

<400> SEQUENCE: 179

Ala Gly Gly Gly
1

<210> SEQ ID NO 180
<211> LENGTH: 7
<212> TYPE: PRT
<213> ORGANISM: Homo sapiens

```
<400> SEQUENCE: 180

Ala Ala Gly Gly Ala Gly Ala
1               5

<210> SEQ ID NO 181
<211> LENGTH: 7
<212> TYPE: PRT
<213> ORGANISM: Homo Sapiens

<400> SEQUENCE: 181

Ala Ala Gly Gly Gly Gly Ala
1               5
```